(12) United States Patent
Cywin et al.

(10) Patent No.: US 6,974,870 B2
(45) Date of Patent: Dec. 13, 2005

(54) SUBSTITUTED 3-AMINO-THIENO [2,3-B] PYRIDINE-2-CARBOXYLIC ACID AMIDE COMPOUNDS AND PROCESSES FOR PREPARING AND THEIR USES

(75) Inventors: Charles L. Cywin, Bethel, CT (US); Can Mao, New Milford, CT (US); Jonathan Emeigh, Danbury, CT (US); Roman Wolfgang Fleck, Greenwich, CT (US); Ming-Hong Hao, Ridgefield, CT (US); Eugene Hickey, Danbury, CT (US); Weimin Liu, Sandy Hook, CT (US); Daniel Richard Marshall, Norwalk, CT (US); Tina Morwick, New Milford, CT (US); Peter Nemoto, Southbury, CT (US); Ronald John Sorcek, Bethel, CT (US); Sanxing Sun, Danbury, CT (US); Jiang-Ping Wu, Danbury, CT (US); Erick Young, Danbury, CT (US); Darren DiSalvo, New Milford, CT (US); John Ginn, New Milford, CT (US); Pier Cirillo, Woodbury, CT (US)

(73) Assignee: Boehringer Ingelheim Phamaceuticals, Inc., Ridgefield, CT (US)

(*) Notice: Subject to any disclaimer, the term of this patent is extended or adjusted under 35 U.S.C. 154(b) by 0 days.

(21) Appl. No.: 10/730,172

(22) Filed: Dec. 6, 2003

(65) Prior Publication Data
US 2004/0180922 A1 Sep. 16, 2004

Related U.S. Application Data

(63) Continuation of application No. 10/453,175, filed on Jun. 3, 2003.
(60) Provisional application No. 60/386,312, filed on Jun. 6, 2002.

(51) Int. Cl.[7] .................. C07D 495/04; A61K 31/4365; A61K 31/497; A61K 31/5377
(52) U.S. Cl. .................. 546/114; 514/218; 514/211.15; 514/217.04; 514/233.8; 514/253.04; 514/255.05; 514/256; 514/228.2; 514/301; 540/492; 540/544; 540/575; 540/597; 544/58.2; 544/60; 544/127; 544/33; 544/362; 544/405
(58) Field of Search .................. 546/114; 544/58.2, 544/60, 127, 333, 362, 405; 540/492, 544, 575, 597; 514/301, 218, 211.15, 217.04, 233.8, 253.04, 255.05, 256, 228.2

(56) References Cited

U.S. PATENT DOCUMENTS 5,656,638 A 8/1997 Gaeta et al.
6,232,320 B1 5/2001 Stewart et al.
6,313,301 B1 11/2001 Miki et al.
6,579,882 B2 6/2003 Stewart et al.

2001/0020030 A1 9/2001 Stewart et al.

FOREIGN PATENT DOCUMENTS

WO  WO 92/03427      3/1992
WO  WO 00/61586     10/2000
WO  WO 00/75145 A1  12/2000
WO  WO 01/30774 A1   5/2001
WO  WO 01/58890 A1   8/2001
WO  WO 01/68648 A1   9/2001
WO  WO 03/037886 A2  5/2003
WO  WO 01/00610 A1   1/2004

OTHER PUBLICATIONS

Sharanin et al. Zhurnal Organischeskoi Khimii (1996), 32(8): 1251–1255.*
Albert S. Baldwin, Jr., The NF–kB and IkB Proteins: New Discoveries and Insights, Annu. Rev. Immunol. 1996, 14: 649–681.
Toshiki Murata, et al, Discovery of Novel and Selective IKK–B Serine–Threonine Protein Kinase Inhibitors. Part 1, Bioorganic & Medicinal Chem Letters, 2003 13:913–918 Elsevier Science Ltd.
XP–002254095 Abstract, "Synthesis of Novel Heterocyclic Compounds for Antitumor and Radioprotective Activities".
M.–M. Ghorab, et al., "Synthesis of Novel Heterocyclic Compounds for Antitumor and Radioprotective Activities", Phosphorus, Sulfur, and Silicon, 1998 vol. 134/135, pp 447–462.
XP–002254099 Abstract, "Use of benzo– and pyrido–furan or –thiophene cpds.—as hypercalcaemia agents for treating osteoporosis".
XP–002254097 Abstract, "Synthesis and Antimicrobial Evaluation of Several New Pyridine, Thienopyridine and Pyridothienopyrazole Derivatives".
F.A. Attaby, et al., "Synthesis and Antimicrobial Evaluation of Several New Pyridine, Thienopyridine and Pyridothienopyrazole Derivatives", Phosphorus, Sulfur, and Silicone, 1999, vol. 149, pp 49–64.

(Continued)

Primary Examiner—Evelyn Mei Huang
(74) Attorney, Agent, or Firm—Michael Morris; Mary-Ellen Devlin; David A. Dow

(57) ABSTRACT

Disclosed are compounds of formula (I):

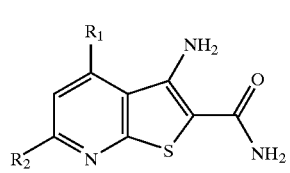

wherein $R_1$ and $R_2$ are defined herein, which are useful as inhibitors of the kinase activity of the IκB kinase (IKK) complex. The compounds are therefore useful in the treatment of IKK mediated diseases including autoimmune diseases inflammatory diseases and cancer. Also disclosed are pharmaceutical compositions comprising these compounds and processes for preparing these compounds.

5 Claims, No Drawings

OTHER PUBLICATIONS

E.I. Kaigorodova, et al., "Synthesis of Substituted 2-Alkyl(Aryl)Thio-3-Cyanopyridines and 3-Aminothieno[2,3-b] Pyridines", Chem. Heterocyclic Compounds, vol. 32, No. 10, pp 1234–1238 1996.

G. Wagner, et al., "Synthese neuer prim., sek. und tert. 3-Amino-thieno[2,3-b]pyridin-2-car-bonsaureamide auf verschiedenen Wegen", vol. 45, 1990, pp 102–109.

* cited by examiner

SUBSTITUTED 3-AMINO-THIENO [2,3-B] PYRIDINE-2-CARBOXYLIC ACID AMIDE COMPOUNDS AND PROCESSES FOR PREPARING AND THEIR USES

APPLICATION DATA

This application is a continuation in part of U.S. nonprovisional application No 10,453,175 filed Jun. 3, 2003 under 35 U.S.C 120 which claims benefit to U.S. provisional application No. 60/386,312 filed Jun. 6, 2002.

TECHNICAL FIELD OF THE INVENTION

This invention relates to substituted 3-amino-thieno[2,3-b]pyridine-2-carboxylic acid amide compounds useful as inhibitors of the kinase activity of the IκB kinase (IKK) complex. The compounds are therefore useful in the treatment of IKK-mediated diseases including autoimmune diseases, inflammatory diseases and cancer. The invention also relates to processes for preparing such compounds and pharmaceutical compositions comprising them.

BACKGROUND OF THE INVENTION

NF-κB or nuclear factor κB is a transcription factor that induces the expression of a large number of pro-inflammatory and anti-apoptotic genes. These include cytokines such as IL-1, IL-2, TNF-α and IL-6, chemokines including IL-8 and RANTES, as well as other pro-inflammatory molecules including COX-2 and cell adhesion molecules such as ICAM-1, VCAM-1, and E-selectin. The NF-κB family includes homo- and heterodimeric transcription factors composed of members of the Rel family (see for example P. A. Baeurle and D. Baltimore, *Cell,* 1996, 87, 13). Under resting conditions, NF-κB is present in the cytosol of cells as a complex with IκB. The IκB family of proteins serve as inhibitors of NF-κB, interfering with the function of its nuclear localization signal (see for example U. Siebenlist et al., *Ann. Rev. Cell Biol.,* 1994, 10, 405). Upon disruption of the IκB-NF-κB complex following cell activation, NF-κB translocates to the nucleus and activates gene transcription. Disruption of the IκB-NF-κB complex and subsequent activation of NF-κB is initiated by degradation of IκB.

Upon cellular activation by a variety of pro-inflammatory stimuli including IL-1, TNF-α and LPS (bacterial lipopolysaccharide), two specific serine residues of IκB are phosphorylated. Upon phosphorylation, IκB undergoes polyubiquination and subsequent degradation by the 26S proteasome (see for example V. J. Palombella et al., *Cell,* 1994, 78, 773), freeing NF-κB to translocate to the nucleus. The phosphorylation of IκB is carried out by the IκB kinases (see for example a review by M. Karin and M. Delhase, *Seminars in Immunology,* 2000, 12, 85). The traditional IKK complex includes at least three subunits, IKKα (also called IKK-1), IKKβ (or IKK-2) and IKKγ (or NEMO), although other relevant complexes involving IKKα and IKKβ may exist. IKKα and IKKβ are both catalytic subunits while IKKγ is believed to be a regulatory subunit. Both IKKα and IKKβ can phosphorylate IκB. For the purposes of this document, the terms IKK or IKK complex refers to any complex that has kinase activity derived from IKKα and/or IKKβ subunits.

In vivo, activation of IKK occurs upon phosphorylation of its catalytic subunit. Both IKKα and IKKβ can be phosphorylated on serine residues, S177 and S181 of the activation loop in the case of IKKβ, and S176 and S180 of the activation loop for IKKα. An IKKβ mutant having alanines in place of serines at 177 and 181 prevented IKKβ phosphorylation and subsequent activation of the IKK complex by TNFα, IL-1 and other upstream activators. These results support a key role for IKKβ in phosphorylation of IκB following proinflammatory stimulation.

Studies in which the NF-κB pathway has been inhibited in cells and animals support the concept that inhibition of the phosphorylation of IκB is a viable approach to treatment of inflammatory, autoimmune and other diseases. In these studies, NF-κB activation was prevented by expression of a non-degradable version of the IκB protein. Expression of this inhibitor in synovial cells derived from rheumatoid arthritis patients reduced the expression of TNF-α, IL-6, IL-1 β and IL-8 while the anti-inflammatory molecules IL-10, IL-1ra and IL-11 were not affected. Matrix metalloproteinases (MMP1 and MMP3) were also down-regulated (J. Bonderson et al., *Proc. Natl. Acad. Sci. U.S.A.,* 1999, 96, 5668). Transgenic expression of the IκB inhibitor in T cells caused a significant reduction in the severity and onset of collagen-induced arthritis in mice (R. Seetharaman et al., *J. Immunol.* 1999, 163, 1577). These experiments indicate that suppression of NF-κB in the diseased joint could reduce both the severity and progression of RA. In primary intestinal epithelial cells, the NF-κB inhibitor blocked the expression of IL-1, IL-8, iNOS and COX-2, mediators that are up-regulated during the course of inflammatory bowel disease (C. Jubin et al., *J. Immunol.,* 1998, 160, 410). Expression of this inhibitor in certain tumor cells enhances killing of these cells by chemotherapeutic reagents (A. A. Beg and D. Baltimore, *Science,* 1996, 274, 782).

Analysis of biopsies from lungs of patients with chronic obstructive pulmonary disease (COPD) found an increased expression of NF-κB that correlated with disease severity (A. Di Stefano et al., *Eur. Resp. J.,* 2002, 1, 437). Inhibition of NF-κB activation with inhibitors of IKK-β was among the anti-inflammatory approaches reported to be potentially useful in the treatment of COPD (P. J. Barnes, *Nature Rev. Drug Disc.,* 2002, 1, 437). Likewise, inhibition of NF-κB activity has been mentioned as a therapeutic approach for asthma (A. Pahl and I. Szelenyi, *Infl. Res.,* 2002, 51, 273).

A recent review describes the essential role of inflammatory mediators in the development cardiovascular disease. The inflammatory mediators and the cells that they recruit are reported to play a key role in the development of fatty streaks and plaques that lead to atherosclerosis. In addition they are reported to play a key role in subsequent degradation of the fibrous cap that forms over the plaque, leading to rupture and clot formation. If the clot grows large enough it can lead to myocardial infarction or stroke. Thus, anti-inflammatory drugs that can inhibit the production of these mediators and subsequent recruitment and activation of these cells may be beneficial in treatment of these diseases (P. Libby, *Scientific American,* 2002, 46).

A number of studies indicate that activation of NF-κB also plays a key role in the pathogenesis and development of cancer (see for example reviews by B. Haefnier, *Drug Disc. Today,* 2002, 7, 653 and M. Karin et al., *Nat. Rev. Cancer,* 2002, 2, 301). Studies have shown that cells in which NF-κB is constitutively active are resistant to apoptosis. This can contribute to carcinogenesis by preventing cell death in cells that have undergone chromosomal changes or damage. In addition tumor cells with constitutively active NF-κB are resistant to anti-cancer therapies including chemotherapy and radiation. Further studies have linked activated NF-κB to a variety of lymphoid-, myeloid- and epithelial-derived malignancies including leukemia, lymphomas and breast, gastric, colorectal, lung, and pancreatic cancers. Thus it is suggested that inhibitors of NF-κB, including inhibitors of IKKα and IKKβ, may be useful either alone or in combination with other anti-cancer therapies in treating cancer.

Collectively, the studies described above provide support that inhibition of NF-κB function through inhibition of IKK may be a useful therapeutic approach to treatment of autoimmune and inflammatory disease, cardiovascular disease and cancer.

Studies have also been done in mice with targeted disruption of the IKKβ gene. Knockout of the IKKβ gene resulted in embryonic lethality due to apoptosis of hepatocytes. However, fibroblasts from the IKKβ knockouts did not undergo IKK and NF-κB activation upon stimulation with IL-1 or TNFα (Q. Li et al., *Science*, 1999, 284, 321), supporting a key role for IKKβ in and NF-κB activation following inflammatory stimuli.

A conditional knockout was generated by expressing a liver-specific inducible dominant negative IκBα transgene (I. Lavon et al., *Nature Medicine*, 2000, 6, 573). These mice were viable with no signs of liver dysfunction even after one year but they did have impaired immune function. This study supports the idea that inhibition of IKKβ can result in immune suppression without damage to the liver.

IKKα knock-out mice died shortly after birth and displayed a variety of skeletal defects and skin abnormalities. Fibroblast and thymocytes from these mice showed normal IKK activation and IκB degradation in response to TNFα, IL-1 or LPS (Y. Hu et al., *Science*, 1999, 284, 316; K. Takeda et al., *Science*, 1999, 284, 313). Recent studies with knock-out and knock-in mice have revealed distinct roles for IKKα in development and cell signaling. In contrast to the studies with IKKα knock-out mice, mice having a kinase inactive version of IKKα knocked in are viable and fertile, indicating that the perinatal lethality and abnormalities seen in the IKKα knock-out mice are not due to the lack of kinase activity. However, these mice do have defects in B cell maturation and development of secondary lymphoid organs (U. Senftleben et al., *Science*, 2001, 293, 1495). This phenotype appears to be due to a defect in processing of the NF-κB2/p100 protein to p52, the DNA binding form of this member of the Rel family of transcription factors. In turn, this leads to a defect in the activation of a subset of NF-κB target genes in B cells. In addition, other studies with these same mice have shown that IKKα kinase activity is required for NF-κB activation in the mammary epithelium during pregnancy (Cao, Y., et. al., *Cell*, 2001, 107, 763). This pathway is specifically activated through the TNF receptor family member RANK, requires phosphorylation of the canonical IKK substrate IκBα, and culminates in induction of the cell cycle regulatory gene Cyclin D1.

These studies indicate that an inhibitor of IKKα kinase activity may be useful in treating diseases associated with inappropriate B cell activation such as lupus (O. T. Chan et al., *Immunological Rev.*, 1999, 169, 107) and rheumatoid arthritis (A. Gause and C. Borek, *Biodrugs*, 2001, 15, 73). In addition, an inhibitor of IKKα may be useful in the treatment of breast cancer since NF-κB is constitutively active in a number of breast tumors and many of these tumors depend on Cyclin D1 for proliferation.

Some inhibitors of IKKβ have been reported. WO 01/58890 and WO 03/037886 describes heteoaromatic carboxamide derivatives as inhibitors of IKKβ. WO 01/68648 describes substituted β-carbolines having IKKβ inhibiting activity. Substituted indoles having IKKβ inhibitory activity are reported in WO 01/30774. WO 01/00610 describes substituted benzimidazoles having NF-κB inhibitory activity. Aspirin and salicylate have been reported to bind to and inhibit IKKβ (M. Yin et al., *Nature*, 1998, 396, 77).

Substituted thienopyridines having cell adhesion inhibiting activity are reported in U.S. 2001/0020030 A1 and A. O. Stewart et al., *J. Med. Chem.*, 2001, 44, 988. Thienopyridines exhibiting gonadotropin releasing hormone antagonizing activity are reported in U.S. Pat. No. 6,313,301. Substituted thienopyridines described as telomerase inhibitors are disclosed in U.S. Pat. No. 5,656,638.

A number of 4,6-disubstituted thieno[2,3-b]pyridine-2-carboxylic acid amides have been described in the chemical literature. Examples include 3-amino-4,6-dimethyl-thieno[2,3-b]pyridine-2-carboxylic acid amide, 3-amino-6-methyl-thieno[2,3-b]pyridine-2,4-dicarboxylic acid diamide, 3-amino-4-methyl-6-phenyl-thieno[2,3-b]-pyridine-2-carboxamide, 3-amino-6-methyl-4-phenyl-thieno[2,3-b]pyridine-2-carboxylic acid amide, 3-amino-6-(4-bromo-phenyl)-4-methyl-thieno[2,3-b]pyridine-2-carboxylic acid amide, 3-amino-4-(4-bromo-phenyl)-6-methyl-thieno[2,3-b]pyridine-2-carboxylic acid amide, 3-amino-6-methyl-thieno[2,3-b]pyridine-2,4-dicarboxylic acid 2-amide-4-butylamide, 3-amino-6-furan-2-yl-4-phenyl-thieno[2,3-b]pyridine-2-carboxylic acid amide, 3-amino-6-furan-2-yl-4-pyridin-3-yl-thieno[2,3-b]pyridine-2-carboxylic acid amide, 3-amino-4-(4-chloro-phenyl)-6-phenyl-thieno[2,3-b]pyridine-2-carboxylic acid amide, 3-amino-4-(4-fluoro-phenyl)-6-furan-2-yl-thieno[2,3-b]pyridine-2-carboxylic acid amide, 3-amino-4-(4-chloro-phenyl)-6-furan-2-yl-thieno[2,3-b]pyridine-2-carboxylic acid amide, 3-amino-4-(4-bromo-phenyl)-6-furan-2-yl-thieno[2,3-b]pyridine-2-carboxylic acid amide, 3-amino-4,6-bis-(4-chloro-phenyl)-thieno[2,3-b]pyridine-2-carboxylic acid amide, 3-amino-6-naphth-2-yl-4-pyridin-3-yl-thieno[2,3-b]pyridine-2-carboxylic acid amide, 3-amino-6-methyl-thieno[2,3-b]pyridine-2,4-dicarboxylic acid 2-amide-4-(2-hydroxyethyl)amide, 3-amino-6-methyl-4-piperidin-1-yl-thieno[2,3-b]-pyridine-2-carboxamide and 3-amino-4-methyl-6-hydroxy-thieno[2,3-b]-pyridine-2-carboxamide reported as intermediates for synthesis of tricyclic heterocycles and evaluated for anti-allergic activity (G. Wagner et al., *Pharmazie*, 1990, 45, 102).

Other examples includes 3-amino-4,6-diphenyl-thieno[2,3-b]pyridine-2-carboxylic acid amide (A. M. Shestopalov et al., *J. Org. Chem. USSR*, (Engl. Transl.) 1984, 20, 1382), 3-amino-6-methyl-4-pyridin-4-yl-thieno[2,3-b]pyridine-2-carboxylic acid amide and 3-amino-6-methyl-4-pyridin-3-yl-thieno[2,3-b]pyridine-2-carboxylic acid amide (G. Wagner et al., *Pharmazie*, 1993, 48, 514), 3-amino-4-methoxymethyl-6-methyl-thieno[2,3-b]pyridine-2-carboxylic acid amide (E. I. Kaigorodova et al., *Chem. Heterocycl. Compd.* (Engl. Transl.), 1996, 32, 1234), 3-amino-6-phenyl-4-thiophen-2-yl-thieno[2,3-b]pyridine-2-carboxylic acid amide, 3-amino-4-furan-2-yl-6-methyl-thieno[2,3-b]pyridine-2-carboxylic acid amide, 3-amino-4-(4-chloro-phenyl)-6-methyl-thieno[2,3-b]pyridine-2-carboxylic acid amide and 3-amino-4-furan-2-yl-6-phenyl-thieno[2,3-b]pyridine-2-carboxylic acid amide (F. A. Attaby, *Phosphorus, Sulfur, Silicon Relat. Elem.*, 1998, 139, 1), 3-amino-6-(4-chloro-phenyl)-4-thiophen-2-yl-thieno[2,3-b]pyridine-2-carboxylic acid amide (Y. Sharanin et al., *J. Org. Chem. USSR*, (Engl. Transl.) 1996, 32, 1207), 3-amino-6-phenyl-4-pyridin-3-yl-thieno[2,3-b]pyridine-2-carboxylic acid amide (A. Krauze, *Eur. J. Med. Chem. Chim. Ther.*, 1999, 34, 301) and 3-amino-6-thiophen-2-yl-4-trifluoromethyl-thieno[2,3-b]pyridine-2-carboxylic acid amide (M. I. Abdel-Monem et al., *Pharmazie*, 2001, 56, 41).

In no case are these compounds described as having the ability to inhibit IKKα or IKKβ.

SUMMARY OF THE INVENTION

It is therefore an object of this invention to provide novel compounds according to the following formula (I):

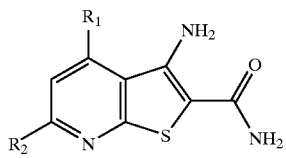

wherein the variables $R_1$ and $R_2$ are described herein which inhibit IKK. It is a further object of the invention to provide methods for treating diseases and pathological conditions exacerbated by IKK such as, but not limited to autoimmune diseases, inflammatory diseases and cancer. It is yet a further object of the invention to provide novel processes for preparation of the above-mentioned novel compounds.

DETAILED DESCRIPTION OF THE INVENTION

A first aspect of the invention comprises a method of treating an inflammatory or autoimmune condition by administration of certain novel and known molecules of the formula (I):

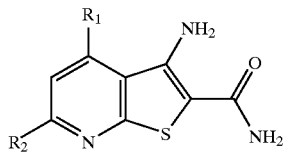

wherein:

$R_1$ is
(a) phenyl or heteroaryl selected from furanyl, thienyl, pyridyl, pyrrolyl, imidazolyl and benzofuranyl, optionally substituted with one to two $R_3$,
(b) heterocyclyl selected from 1-piperidinyl, 1-piperazinyl, 1-pyrrolidinyl and 4-morpholinyl, optionally substituted with one to two groups selected from $C_{1-6}$alkyl, —$CO_2C_{1-5}$alkyl, phenyl, benzyl, —OH and —C(O)heteroaryl, wherein the heteroaryl is selected from furanyl, thienyl, pyridyl and pyrrolyl,
(c) $R_6(CH_2)_mO$—,
(d) $R_6OCH_2$—,
(e) $R_6(CH_2)_mNH$—,
(f) $R_6(CH_2)_p(CH=CH)_m$— or pyridyl$(CH_2)_p(CH=CH)$m-
(g) $C_{1-6}$alkyl, optionally partially of fully halogenated and optionally substituted with one to two $R_9$,
(h) $C_{3-6}$cycloalkyl
(i) $C_{1-8}$alkoxy, optionally partially of fully halogenated and optionally substituted with one to two $R_9$,
(j) $C_{1-8}$alkylS(O)$_n$—, optionally partially of fully halogenated and optionally substituted with one to two $R_9$,
(k) —$N(R_4)(R_5)$, or
(l) —C(O)NHR', wherein R' is $R_6$, pyridyl or —$CH_3$;
$R_2$ is
(a) $C_{1-6}$alkyl, optionally partially or fully halogenated and optionally substituted with one to two $R_{10}$,
(b) $C_{1-6}$alkoxy, optionally partially or fully halogenated and optionally substituted with one to two $R_{10}$,
(c) $C_{1-6}$alkylamino, optionally partially or fully halogenated and optionally substituted with one to two $R_{10}$,
(d) $C_{1-6}$alkylthio, optionally partially or fully halogenated and optionally substituted with one to two $R_{10}$,
(e) heterocyclyl$(CH_2)_m$— wherein said heterocycle is selected from piperidinyl, piperazinyl, morpholinyl, azepanyl, pyrrolidinyl, 1,4-diazacycloheptanyl, azepanyl, 2,5-diazabicyclo[2.2.1]heptanyl, oxazepanyl and thiomorpholino and is optionally substituted with one to three $R_7$,
(f) heterocyclylCH$_2$O— wherein the heterocyclyl is selected from 1-piperidinyl, 1-piperazinyl, 4-morpholinyl and 1-pyrrolidinyl, optionally substituted with $C_{1-6}$alkyl,
(g) phenyl, optionally substituted with one to three $R_3$,
(h) —$N(R_4)(R_5)$,
(i) heteroaryl selected from furanyl, thienyl, imidazolyl, pyridyl and pyrrolyl, or
(j) —H;
$R_3$ is chosen from $C_{1-6}$alkyl, $C_{1-6}$alkoxy, hydroxy$C_{1-6}$alkyl, halogen, —CN, —$CO_2H$, —$CO_2C_{1-6}$alkyl, —S(O)$_n$C$_{1-6}$alkyl, —$NO_2$, —OH, —$CF_3$, —$N(R_4)(R_5)$, —NHC(O)NHC$_{1-6}$alkyl, —C(O)N(R$_4$)(R$_5$) and phenyl optionally substituted with halogen, $C_{1-6}$alkyl, —CN or $C_{1-6}$alkoxy;
$R_4$ and $R_5$ are independently selected from H, $C_{1-6}$alkyl, —$C_{0-3}$alkylC$_{3-6}$cycloalkyl, —$C_{0-3}$alkylheteroaryl, —$C_{0-3}$alkylheterocyclyl, —$C_{0-3}$alkylphenyl($R_6$),-2-methylcyclohexyl, —C(O)C$_{1-6}$alkyl, —SO$_2$C$_{1-6}$alkyl, phenyl, pyridyl, piperidinyl, phenylethyl optionally substituted with hydroxymethyl, (CH$_3$)$_3$COC(O)—, —CH$_2$CO$_2$Me, —C$_{1-6}$alkylOH, —C$_{1-6}$alkylNMe$_2$, or alternatively R4 and R5 with the atom to which they are attached can be fused together to form a heterocyclic ring which may be substituted with an OH group;
$R_6$ is a phenyl group optionally substituted with one to three groups selected from halogen, $C_{1-6}$alkyl, —CN, —$CO_2C_{1-6}$alkyl, —$CO_2H$, —C(O)NR$_4$R$_5$, —CH$_2$N(R$_4$)(R$_5$), —SO$_2$N(R$_4$)(R$_5$),
—NHSO$_2$C$_{1-6}$alkyl, —SO$_2$C$_{1-6}$alkyl, —$NO_2$, —OH, —$NH_2$, —$CF_3$, OCF$_2$, OCF$_3$, OBenzyl, $C_{1-6}$alkoxy, a heteroaryl group which may be further substituted by an $R_4$ group, phenyl, a heterocyclic group, or alternatively when R6 is phenyl two of its adjacent carbon atoms may be bridged by an —OCH$_2$O— or an —OCF$_2$O— group, or $R_6$ is $C_{3-6}$cycloalkyl, —CH$_2$OH, naphthalene-2-yl, naphthalene-1-yl or 2-thienyl;
$R_7$ is selected from —OH, —CN, oxo, —$CO_2C_{1-6}$alkyl, —$CO_2H$, —C(O)N(R$_4$)(R$_5$), —N(R$_4$)(R$_5$), —CH$_2$N(R$_4$)(R$_5$), —CH$_2$OH, $C_{1-6}$alkyl, —CO$_2$benzyl, hydroxyC$_{1-6}$alkyl, —C(O)C$_{1-6}$alkylN(R$_4$)(R$_5$), —NHCO$_2$C$_{1-6}$alkyl, —NHC(O)N(R$_4$)(R$_5$), —S(O)$_n$C$_{1-6}$alkyl, (CH$_3$)$_3$COC(O)—, phenyl, pyridyl, H$_2$NCH(R$_8$)C (O)—, HO(CH$_2$)$_m$CH$_2$CH(NH$_2$)C(O)—, R$_6$(CH2)nCH(OH)CH$_2$NH—, R$_6$XCH$_2$CH(OH)CH$_2$NH— wherein X=O or N, —NHCH$_2$CH(OH)C(O)N(R$_4$)(R$_5$), NHCH$_2$C(O)N(R$_4$)(R$_5$), and —C(O)heterocyclyl, wherein said heterocyclyl is selected from piperidinyl, piperazinyl, morpholinyl and pyrrolidinyl, or $R_7$ is 2-hydroxyethylamino, methylcarbamimidoyl, hydroxyimino, hydrozinocarbonyl, sulfamoyl, methanesulfonylamino, methylsulfonylhydrazino, 2-hydroxypropylamino, 2-hydroxy-2-methylpropylamino, 2,3-dihydroxypropylamino, 2-hydroxy-1-methylethylamino, carbamoylmethylamino, N'-phenylhydrazinocarbonyl or toluene-4-sulfonylamino;
$R_8$ is selected from $C_{1-6}$alkyl, —(CH$_2$)$_{1-4}$NH$_2$, phenyl or benzyl;

$R_9$ is selected from oxo, —OH, —NR$_4$R$_5$, —CO$_2$H and C$_{1-6}$alkoxy;
$R_{10}$ is selected from oxo, —OH, —N(R$_4$)(R$_5$), C$_{1-6}$alkoxy, —C(O)C$_{1-6}$alkyl, —C(O)N(R$_4$)(R$_5$), R$_6$, and heteroaryl selected from furanyl, thienyl, imidazolyl, pyridyl, indolyl and pyrrolyl;
m is 0 or 1;
n is 0, 1 or 2; and
p is 0, 1, 2 or 3.

A second aspect of the invention comprises compounds of the formula (I):

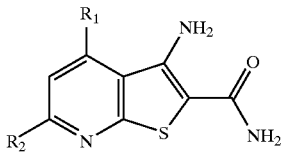

wherein:
$R_1$ is
- (a) phenyl or heteroaryl selected from furanyl, thienyl, pyridyl, pyrrolyl, imidazolyl and benzofuranyl, optionally substituted with one to two R$_3$,
- (b) heterocyclyl selected from 1-piperidinyl, 1-piperazinyl, 1-pyrrolidinyl and 4-morpholinyl, optionally substituted with one to two groups selected from C$_{1-6}$alkyl, —CO$_2$C$_{1-5}$alkyl, phenyl, benzyl, —OH and —C(O)heteroaryl, wherein the heteroaryl is selected from furanyl, thienyl, pyridyl and pyrrolyl,
- (c) R$_6$(CH$_2$)$_m$O—,
- (d) R$_6$OCH$_2$—,
- (e) R$_6$(CH$_2$)$_m$NH—,
- (f) R$_6$(CH$_2$)$_p$(CH=CH)$_m$— or pyridyl(CH$_2$)p(CH=CH)m-
- (g) C$_{1-6}$alkyl, optionally partially of fully halogenated and optionally substituted with one to two R$_9$,
- (h) C$_{3-6}$ cycloalkyl
- (i) C$_{1-8}$alkoxy, optionally partially of fully halogenated and optionally substituted with one to two R$_9$,
- (j) C$_{1-8}$alkylS(O)$_n$—, optionally partially of fully halogenated and optionally substituted with one to two R$_9$,
- (k) —N(R$_4$)(R$_5$), or
- (l) —C(O)NHR', wherein R' is R$_6$, pyridyl or —CH$_3$;
$R_2$ is
- (a) C$_{1-6}$alkyl, optionally partially or fully halogenated and optionally substituted with one to two R$_{10}$,
- (b) C$_{1-6}$alkoxy, optionally partially or fully halogenated and optionally substituted with one to two R$_{10}$,
- (c) C$_{1-6}$alkylamino, optionally partially or fully halogenated and optionally substituted with one to two R$_{10}$,
- (d) C$_{1-6}$alkylthio, optionally partially or fully halogenated and optionally substituted with one to two R$_{10}$,
- (e) heterocyclyl(CH$_2$)$_m$— wherein said heterocycle is selected from piperidinyl, piperazinyl, morpholinyl, azepanyl, pyrrolidinyl, 1,4-diazacycloheptanyl, azepanyl, 2,5-diazabicyclo[2.2.1]heptanyl, oxazepanyl and thiomorpholino and is optionally substituted with one to three R$_7$,
- (f) heterocyclylCH$_2$O— wherein the heterocyclyl is selected from 1-piperidinyl, 1-piperazinyl, 4-morpholinyl and 1-pyrrolidinyl, optionally substituted with C$_{1-6}$alkyl,
- (g) phenyl, optionally substituted with one to three R$_3$,
- (h) —N(R$_4$)(R$_5$),
- (i) heteroaryl selected from furanyl, thienyl, imidazolyl, pyridyl and pyrrolyl, or
- (j) —H;
$R_3$ is chosen from C$_{1-6}$alkyl, C$_{1-6}$alkoxy, hydroxyC$_{1-6}$alkyl, halogen, —CN, —CO$_2$H, —CO$_2$C$_{1-6}$alkyl, —S(O)$_n$C$_{1-6}$alkyl, —NO$_2$, —OH, —CF$_3$, —N(R$_4$)(R$_5$), —NHC(O)NHC$_{1-6}$alkyl, —C(O)N(R$_4$)(R$_5$) and phenyl optionally substituted with halogen, C$_{1-6}$alkyl, —CN or C$_{1-6}$alkoxy;
$R_4$ and $R_5$ are independently selected from H, C$_{1-6}$alkyl, —C$_{0-3}$alkylC$_{3-6}$cycloalkyl, —C$_{0-3}$alkylheteroaryl selected from the list consisiting of benzothiophenyl, furanyl, tetrazolyl, pyridyl , —C$_{0-3}$alkylheterocyclyl selected from the list consisting of piperdinyl and morpholinyl, —C$_{0-3}$alkylphenyl(R$_6$),-2-methylcyclohexyl, —C(O)C$_{1-6}$alkyl, —SO$_2$C$_{1-6}$alkyl, phenyl, pyridyl, piperidinyl, phenylethyl optionally substituted with hydroxymethyl, (CH$_3$)$_3$COC(O)—, —CH$_2$CO$_2$Me, —C$_{1-6}$alkylOH, —C$_{1-6}$alkylNMe$_2$, or alternatively R4 and R5 with the atom to which they are attached can be fused together to form a heterocyclic ring which may be substituted with an OH group;
$R_6$ is a phenyl group optionally substituted with one to three groups selected from halogen, C$_{1-6}$alkyl, —CN, —CO$_2$C$_{1-6}$alkyl, —CO$_2$H, —C(O)NR$_4$R$_5$, —CH$_2$N(R$_4$)(R$_5$), —SO$_2$N(R$_4$)(R$_5$), —NHSO$_2$C$_{1-6}$alkyl, —SO$_2$C$_{1-6}$alkyl, —NO$_2$, —OH, —NH$_2$, —CF$_3$, OCF$_2$, OCF$_3$, OBenzyl, C$_{1-6}$alkoxy, a heteroaryl group selected from the list consisiting of pyridyl, pyrazine, imidazolyl and thiazolyl which may be further substituted by an R$_4$ group, phenyl, a heterocyclic group, or alternatively when R6 is phenyl two of its adjacent carbon atoms may be bridged by an —OCH$_2$O— or an —OCF$_2$O— group, or R$_6$ is C$_{3-6}$cycloalkyl, —CH$_2$OH, naphthalene-2-yl, naphthalene-1-yl or 2-thienyl;
$R_7$ is selected from —OH, —CN, oxo, —CO$_2$C$_{1-6}$alkyl, —CO$_2$H, —C(O)N(R$_4$)(R$_5$), —N(R$_4$)(R$_5$), —CH$_2$N(R$_4$)(R$_5$), —CH$_2$OH, C$_{1-6}$alkyl, —CO$_2$benzyl, hydroxyC$_{1-6}$alkyl, —C(O)C$_{1-6}$alkylN(R$_4$)(R$_5$), —NHCO$_2$C$_{1-6}$alkyl, —NHC(O)N(R$_4$)(R$_5$), —S(O)$_n$C$_{1-6}$alkyl, (CH$_3$)$_3$COC(O)—, phenyl, pyridyl, H$_2$NCH(R$_8$)C(O)—, HO(CH$_2$)$_m$CH$_2$CH(NH$_2$)C(O)—, R$_6$(CH2)nCH(OH)CH$_2$NH—, R$_6$XCH$_2$CH(OH)CH$_2$NH— wherein X=O or N, —NHCH$_2$CH(OH)C(O)N(R$_4$)(R$_5$), NHCH$_2$C(O)N(R$_4$)(R$_5$), and —C(O)heterocyclyl, wherein said heterocyclyl is selected from piperidinyl, piperazinyl, morpholinyl and pyrrolidinyl, or R$_7$ is 2-hydroxyethylamino, methylcarbamimidoyl, hydroxyimino, hydrozinocarbonyl, sulfamoyl, methanesulfonylamino, methylsulfonylhydrazino, 2-hydroxypropylamino, 2-hydroxy-2-methylpropylamino, 2,3-dihydroxypropylamino, 2-hydroxy-1-methylethylamino, carbamoylmethylamino, N'-phenylhydrazinocarbonyl or toluene-4-sulfonylamino;
$R_8$ is selected from C$_{1-6}$alkyl, —(CH$_2$)$_{1-4}$NH$_2$, phenyl or benzyl;
$R_9$ is selected from oxo, —OH, —NR$_4$R$_5$, —CO$_2$H and C$_{1-6}$alkoxy;
$R_{10}$ is selected from oxo, —OH, —N(R$_4$)(R$_5$), C$_{1-6}$alkoxy, —C(O)C$_{1-6}$alkyl, —C(O)N(R$_4$)(R$_5$), R$_6$, and heteroaryl selected from furanyl, thienyl, imidazolyl, pyridyl, indolyl and pyrrolyl;
m is 0 or 1;
n is 0, 1 or 2; and
p is 0, 1, 2 or 3.

A third aspect of the invention comprises compounds of formula (I) above:
wherein:
$R_1$ is
- (a) phenyl or heteroaryl selected from furanyl, thienyl, pyridyl, pyrrolyl, imidazolyl and benzofuranyl, optionally substituted with one to two $R_3$,
- (b) heterocyclyl selected from 1-piperidinyl, 1-piperazinyl, 1-pyrrolidinyl and 4-morpholinyl, optionally substituted with one to two groups selected from $C_{1-6}$alkyl, —$CO_2C_{1-5}$alkyl, phenyl, benzyl, —OH and —C(O)heteroaryl, wherein the heteroaryl is selected from furanyl, thienyl, pyridyl and pyrrolyl,
- (c) $R_6(CH_2)_mO$—,
- (d) $R_6OCH_2$—,
- (e) $R_6(CH_2)_mNH$—,
- (f) $R_6(CH_2)p(CH=CH)_m$— or pyridyl$(CH_2)_p(CH=CH)_m$-
- (g) $C_{1-6}$alkyl, optionally partially of fully halogenated and optionally substituted with one to two $R_9$,
- (h) $C_{3-6}$ cycloalkyl
- (i) $C_{1-8}$alkoxy, optionally partially of fully halogenated and optionally substituted with one to two $R_9$,
- (j) $C_{1-8}$alkylS(O)$_n$—, optionally partially of fully halogenated and optionally substituted with one to two $R_9$,
- (k) —N($R_4$)($R_5$), or
- (l) —C(O)NHR', wherein R' is $R_6$, pyridyl or —$CH_3$;

$R_2$ is
- (a) heterocyclyl$(CH_2)_m$— wherein said heterocycle is selected from piperidinyl, piperazinyl, morpholinyl, azepanyl, pyrrolidinyl, 1,4-diazacycloheptanyl, azepanyl, 2,5-diazabicyclo[2.2.1]heptanyl, oxazepanyl and thiomorpholino and is optionally substituted with one to three $R_7$,
- (b) heterocyclylCH$_2$O— wherein the heterocyclyl is selected from 1-piperidinyl, 1-piperazinyl, 4-morpholinyl and 1-pyrrolidinyl, optionally substituted with $C_{1-6}$alkyl,
- (c) phenyl, optionally substituted with one to three $R_3$,
- (d) heteroaryl selected from furanyl, thienyl, imidazolyl, pyridyl and pyrrolyl, or $R_3$ is chosen from $C_{1-6}$alkyl, $C_{1-6}$alkoxy, hydroxy$C_{1-6}$alkyl, halogen, —CN, —$CO_2H$, —$CO_2C_{1-6}$alkyl, —S(O)$_nC_{1-6}$alkyl, —$NO_2$, —OH, —$CF_3$, —N($R_4$)($R_5$), —NHC(O)NHC$_{1-6}$alkyl, —C(O)N($R_4$)($R_5$) and phenyl optionally substituted with halogen, $C_{1-6}$alkyl, —CN or $C_{1-6}$alkoxy;

$R_4$ and $R_5$ are independently selected from H, $C_{1-6}$alkyl, —$C_{0-3}$alkyl$C_{3-6}$cycloalkyl, —$C_{0-3}$alkylheteroaryl selected from the list consisiting of benzothiophenyl, furanyl, tetrazolyl, pyridyl, —$C_{0-3}$alkylheterocyclyl selected from the list consisting of piperdinyl and morpholinyl, —$C_{0-3}$alkylphenyl($R_6$),-2-methylcyclohexyl, —C(O)$C_{1-6}$alkyl, —$SO_2C_{1-6}$alkyl, phenyl, pyridyl, piperidinyl, phenylethyl optionally substituted with hydroxymethyl, $(CH_3)_3COC(O)$—, —$CH_2CO_2Me$, —$C_{1-6}$alkylOH, —$C_{1-6}$alkylNMe$_2$, or alternatively R4 and R5 with the atom to which they are attached can be fused together to form a heterocyclic ring which may be substituted with an OH group;

$R_6$ is a phenyl group optionally substituted with one to three groups selected from halogen, $C_{1-6}$alkyl, —CN, —$CO_2C_{1-6}$alkyl, —$CO_2H$, —C(O)NR$_4$R$_5$, —$CH_2N(R_4)(R_5)$, —$SO_2N(R_4)(R_5)$, —$NHSO_2C_{1-6}$alkyl, —$SO_2C_{1-6}$alkyl, —$NO_2$, —OH, —$NH_2$, —$CF_3$, OCF$_2$, OCF$_3$, OBenzyl, $C_{1-6}$alkoxy, a heteroaryl group selected from the list consisting of pyridyl, pyrazinyl, imidazolyl and thiazolyl which may be further substituted by an $R_4$ group, phenyl, a heterocyclic group, or alternatively when R6 is phenyl two of its adjacent carbon atoms may be bridged by a an —OCH$_2$O— or an —OCF$_2$O— group, or $R_6$ is $C_{3-6}$cycloalkyl, —CH$_2$OH, naphthalene-2-yl, naphthalene-1-yl or 2-thienyl;

$R_7$ is selected from—OH, —CN, oxo, —$CO_2C_{1-6}$alkyl, —$CO_2H$, —C(O)N($R_4$)($R_5$), —N($R_4$)($R_5$), —CH$_2$N($R_4$)($R_5$), —CH$_2$OH, $C_{1-6}$alkyl, —$CO_2$benzyl, hydroxy$C_{1-6}$alkyl, —C(O)$C_{1-6}$alkylN($R_4$)($R_5$), —NHCO$_2C_{1-6}$alkyl, —NHC(O)N($R_4$)($R_5$), —S(O)$_nC_{1-6}$alkyl, $(CH_3)_3COC(O)$—, phenyl, pyridyl, H$_2$NCH($R_8$)C(O)—, HO(CH$_2$)$_m$CH$_2$CH(NH$_2$)C(O)—, $R_6$(CH2)nCH(OH)CH$_2$NH—, $R_6$XCH$_2$CH(OH)CH$_2$NH— wherein X=O or N, —NHCH$_2$CH(OH)C(O)N($R_4$)($R_5$), NHCH$_2$C(O)N($R_4$)($R_5$), and —C(O)heterocyclyl, wherein said heterocyclyl is selected from piperidinyl, piperazinyl, morpholinyl and pyrrolidinyl, or $R_7$ is 2-hydroxyethylamino, methylcarbamimidoyl, hydroxyimino, hydrozinocarbonyl, sulfamoyl, methanesulfonylamino, methylsulfonylhydrazino, 2-hydroxypropylamino, 2-hydroxy-2-methylpropylamino, 2,3-dihydroxypropylamino, 2-hydroxy-1-methylethylamino, carbamoylmethylamino, N'-phenylhydrazinocarbonyl or toluene-4-sulfonylamino;

$R_8$ is selected from $C_{1-6}$alkyl, —$(CH_2)_{1-4}NNH_2$, phenyl or benzyl;

$R_9$ is selected from oxo, —OH, —NR$_4$R$_5$, —$CO_2H$ and $C_{1-6}$alkoxy;

$R_{10}$ is selected from oxo, —OH, —N($R_4$)($R_5$), $C_{1-6}$alkoxy, —C(O)$C_{1-6}$alkyl, —C(O)N($R_4$)($R_5$), $R_6$, and heteroaryl selected from furanyl, thienyl, imidazolyl, pyridyl, indolyl and pyrrolyl;

m is 0 or 1;
n is 0, 1 or 2; and
p is 0, 1, 2 or 3.

A fourth aspect of the invention comprises a method of treating an inflammatory or autoimmune condition by administration of certain novel and known molecules of the formula (I) above wherein:
$R_1$ is
- (a) phenyl or heteroaryl selected from furanyl, thienyl, pyridyl, pyrrolyl, imidazolyl and benzofuranyl, optionally substituted with one to two $R_3$,
- (b) heterocyclyl selected from 1-piperidinyl, 1-piperazinyl, 1-pyrrolidinyl and 4-morpholinyl, optionally substituted with one to two groups selected from $C_{1-6}$alkyl, —$CO_2C_{1-5}$alkyl, phenyl, benzyl, —OH and —C(O)heteroaryl, wherein the heteroaryl is selected from furanyl, thienyl, pyridyl and pyrrolyl,
- (c) $R_6(CH_2)_mO$—,
- (d) $R_6OCH_2$—,
- (e) $R_6(CH_2)_mNH$—,
- (f) $R_6(CH_2)_p(CH=CH)_m$— or pyridyl$(CH_2)p(CH=CH)_m$—
- (g) $C_{1-6}$alkyl, optionally partially of fully halogenated and optionally substituted with one to two $R_9$,
- (h) $C_{3-6}$ cycloalkyl
- (i) $C_{1-8}$alkoxy, optionally partially of fully halogenated and optionally substituted with one to two $R_9$,
- (j) $C_{1-8}$alkylS(O)$_n$—, optionally partially of fully halogenated and optionally substituted with one to two $R_9$, (k) —N(R$_4$)(R$_5$), or (l) —C(O)NHR', wherein R' is R$_6$, pyridyl or —CH$_3$;

R$_2$ is heterocyclyl(CH$_2$)$_m$— wherein said heterocycle is selected from piperidinyl, optionally substituted with one to three R$_7$, R$_3$ is chosen from C$_{1-6}$alkyl, C$_{1-6}$alkoxy, hydroxyC$_{1-6}$alkyl, halogen, —CN, —CO$_2$H, —CO$_2$C$_{1-6}$alkyl, —S(O)$_n$C$_{1-6}$alkyl, —NO$_2$, —OH, —CF$_3$, —N(R$_4$)(R$_5$), —NHC(O)NHC$_{1-6}$alkyl, —C(O)N(R$_4$)(R$_5$) and phenyl optionally substituted with halogen, C$_{1-6}$alkyl, —CN or C$_{1-6}$alkoxy;

R$_4$ and R$_5$ are independently selected from H, —C$_{0-3}$alkylheteroaryl, —C$_{0-3}$alkylheterocyclyl, —C$_{0-3}$alkylphenyl(R$_6$),-2-methylcyclohexyl, —C(O)C$_{1-6}$alkyl, —SO$_2$C$_{1-6}$alkyl, phenyl, pyridyl, piperidinyl, phenylethyl optionally substituted with hydroxymethyl, (CH$_3$)$_3$COC(O)—, —CH$_2$CO$_2$Me, —C$_{1-6}$alkylOH, —C$_{1-6}$alkylNMe$_2$, or alternatively R$_4$ and R$_5$ with the atom to which they are attached can be fused together to form a heterocyclic ring which may be substituted with an OH group, provided that R$_4$ or R$_5$ are not methyl or benzyl and R$_4$ and R$_5$ are not both H;

R$_6$ is a phenyl group substituted with one to three groups selected from —CN, —CO$_2$H, —CH$_2$N(R$_4$)(R$_5$),—SO$_2$N(R$_4$)(R$_5$), —C(O)NR$_4$R$_5$, C$_{1-6}$alkyl, NHSO$_2$C$_{1-6}$alkyl, —SO$_2$C$_{1-6}$alkyl, —CF$_3$, OCF$_2$, OCF$_3$, OBenzyl, C$_{2-6}$alkoxy, a heteroaryl group selected from the list consisting of pyridyl, pyrazinyl, imidazolyl and thiazolyl which may be further substituted by an R$_4$ group, phenyl, a heterocyclic group, or alternatively when R6 is phenyl two of its adjacent carbon atoms may be bridged by an —OCH$_2$O— or an —OCF$_2$O— group;

R$_7$ is selected from R$_6$(CH$_2$)nCH(OH)CH$_2$NH—, R$_6$XCH$_2$CH(OH)CH$_2$NH— wherein X=O;

R$_9$ is selected from oxo, —OH, —NR$_4$R$_5$, —CO$_2$H and C$_{1-6}$alkoxy;

R$_{10}$ is selected from oxo, —OH, —N(R$_4$)(R$_5$), C$_{1-6}$alkoxy, —C(O)C$_{1-6}$alkyl, —C(O)N(R$_4$)(R$_5$), R$_6$, and heteroaryl selected from furanyl, thienyl, imidazolyl, pyridyl, indolyl and pyrrolyl;

m is 0 or 1;

n is 0, 1 or 2; and p is 0, 1, 2 or 3.

A fifth embodiment of the invention provides for compounds of formula 1 wherein

R$_1$ is (a) R$_6$(CH$_2$)$_p$(CH=CH)$_m$— or pyridyl(CH$_2$)p(CH=CH)m-

(b) C$_{3-6}$ cycloalkyl,

R$_2$ is (a) heterocyclyl(CH$_2$)$_m$— wherein said heterocycle is selected from piperidinyl, piperazinyl, morpholinyl, azepanyl, pyrrolidinyl, 1,4-diazacycloheptanyl, azepanyl, 2,5-diazabicyclo[2.2.1]heptanyl, oxazepanyl and thiomorpholino and is optionally substituted with one to three R$_7$, (b) heterocyclylCH$_2$O— wherein the heterocyclyl is selected from 1-piperidinyl, 1-piperazinyl, 4-morpholinyl and 1-pyrrolidinyl, optionally substituted with C$_{1-6}$alkyl, (c) phenyl, optionally substituted with one to three R$_3$, (d) heteroaryl selected from furanyl, thienyl, imidazolyl, pyridyl and pyrrolyl, or R$_3$ is chosen from C$_{1-6}$alkyl, C$_{1-6}$alkoxy, hydroxyC$_{1-6}$alkyl, halogen, —CN, —CO$_2$H, —CO$_2$C$_{1-6}$alkyl, —S(O)$_n$C$_{1-6}$alkyl, —NO$_2$, —OH, —CF$_3$, —N(R$_4$)(R$_5$), —NHC(O)NHC$_{1-6}$alkyl, —C(O)N(R$_4$)(R$_5$) and phenyl optionally substituted with halogen, C$_{1-6}$alkyl, —CN or C$_{1-6}$alkoxy;

R$_4$ and R$_5$ are independently selected from H, C$_{1-6}$alkyl, —C$_{0-3}$alkylC$_{3-6}$cycloalkyl, —C$_{0-3}$alkylheteroaryl selected from the list consisiting of benzothiophenyl, furanyl, tetrazolyl, pyridyl, —C$_{0-3}$alkylheterocyclyl selected from the list consisting of piperdinyl and morpholinyl, —C$_{0-3}$alkylphenyl(R$_6$),-2-methylcyclohexyl, —C(O)C$_{1-6}$alkyl, —SO$_2$C$_{1-6}$alkyl, phenyl, pyridyl, piperidinyl, phenylethyl optionally substituted with hydroxymethyl, (CH$_3$)$_3$COC(O)—, —CH$_2$CO$_2$Me, —C$_{1-6}$alkylOH, —C$_{1-6}$alkylNMe$_2$, or alternatively R4 and R5 with the atom to which they are attached can be fused together to form a heterocyclic ring which may be substituted with an OH group;

R$_6$ is a phenyl group optionally substituted with one to three groups selected from halogen, C$_{1-6}$alkyl, —CN, —CO$_2$C$_{1-6}$alkyl, —CO$_2$H, —C(O)NR$_4$R$_5$, —CH$_2$N(R$_4$)(R$_5$), —SO$_2$N(R$_4$)(R$_5$), —NHSO$_2$C$_{1-6}$alkyl, —SO$_2$C$_{1-6}$alkyl, —NO$_2$, —OH, —NH$_2$, —CF$_3$, OCF$_2$, OCF$_3$, OBenzyl, C$_{1-6}$alkoxy, a heteroaryl group selected from the list consisiting of pyridyl, pyrazinyl, imidazolyl and thiazolyl which may be further substituted by an R$_4$ group, phenyl, a heterocyclic group, or alternatively when R6 is phenyl two of its adjacent carbon atoms may be bridged by a an —OCH$_2$O— or an —OCF$_2$O— group, or R$_6$ is C$_{3-6}$cycloalkyl, —CH$_2$OH, naphthalene-2-yl, naphthalene-1-yl or 2-thienyl;

R$_7$ is selected from —OH, —CN, oxo, —CO$_2$C$_{1-6}$alkyl, —CO$_2$H, —C(O)N(R$_4$)(R$_5$), —N(R$_4$)(R$_5$), —CH$_2$N(R$_4$)(R$_5$), —CH$_2$OH, C$_{1-6}$alkyl, —CO$_2$benzyl, hydroxyC$_{1-6}$alkyl, —C(O)C$_{1-6}$alkylN(R$_4$)(R$_5$), —NHCO$_2$C$_{1-6}$alkyl, —NHC(O)N(R$_4$)(R$_5$), —S(O)$_n$C$_{1-6}$alkyl, (CH$_3$)$_3$COC(O)—, phenyl, pyridyl, H$_2$NCH(R$_8$)C(O)—, HO(CH$_2$)$_m$CH$_2$CH(NH$_2$)C(O)—, R$_6$(CH2)nCH(OH)CH$_2$NH—, R$_6$XCH$_2$CH(OH)CH$_2$NH— wherein X=O or N, —NHCH$_2$CH(OH)C(O)N(R$_4$)(R$_5$), NHCH$_2$C(O)N(R$_4$)(R$_5$), and —C(O)heterocyclyl, wherein said heterocyclyl is selected from piperidinyl, piperazinyl, morpholinyl and pyrrolidinyl, or R$_7$ is 2-hydroxyethylamino, methylcarbamimidoyl, hydroxyimino, hydrozinocarbonyl, sulfamoyl, methanesulfonylamino, methylsulfonylhydrazino, 2-hydroxypropylamino, 2-hydroxy-2-methylpropylamino, 2,3-dihydroxypropylamino, 2-hydroxy-1-methylethylamino, carbamoylmethylamino, N'-phenylhydrazinocarbonyl or toluene-4-sulfonylamino;

R$_8$ is selected from C$_{1-6}$alkyl, —(CH$_2$)$_{1-4}$NH$_2$, phenyl or benzyl;

R$_9$ is selected from oxo, —OH, —NR$_4$R$_5$, —CO$_2$H and C$_{1-6}$alkoxy;

R$_{10}$ is selected from oxo, —OH, —N(R$_4$)(R$_5$), C$_{1-6}$alkoxy, —C(O)C$_{1-6}$alkyl, —C(O)N(R$_4$)(R$_5$), R$_6$, and heteroaryl selected from furanyl, thienyl, imidazolyl, pyridyl, indolyl and pyrrolyl;

m is 0 or 1;

n is 0, 1 or 2; and p is 0, 1, 2 or 3.

For all the compounds disclosed in this application, in the event the nomenclature is in conflict with the structure, it shall be understood that the compound is defined by the structure.

In another embodiment of the invention, there are provided the following compound of Table I:

3-Amino-6-{4-[2-(4-carbamoyl-phenyl)-2-hydroxy-ethylamino]-piperidin-1-yl}-4-propyl-thieno[2,3-b]pyridine-2-carboxylic acid amide

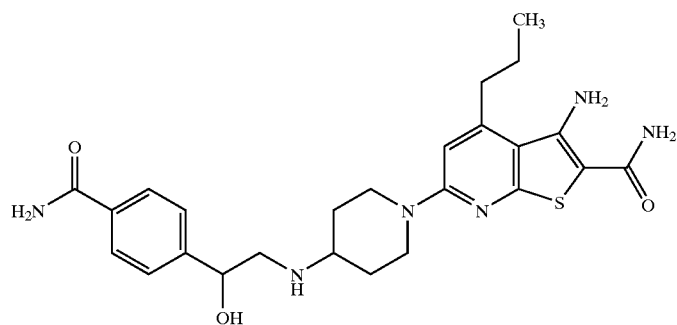

3-Amino-6-{4-[2-hydroxy-2-(4-methylcarbamoyl-phenyl)-ethylamino]-piperidin-1-yl}-4-propyl-thieno[2,3-b]pyridine-2-carboxylic acid amide

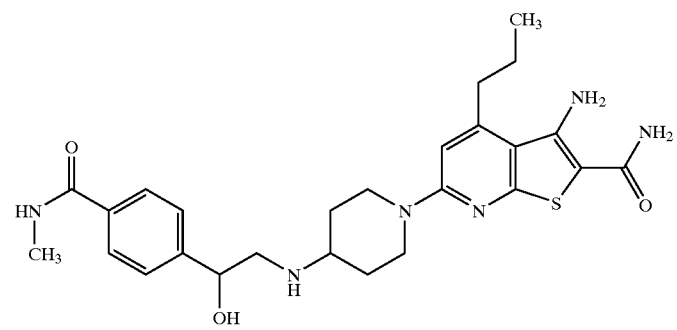

3-Amino-6-{4-[2-(4-dimethylcarbamoyl-phenyl)-2-hydroxy-ethylamino]-piperidin-1-yl}-4-propyl-thieno[2,3-b]pyridine-2-carboxylic acid amide

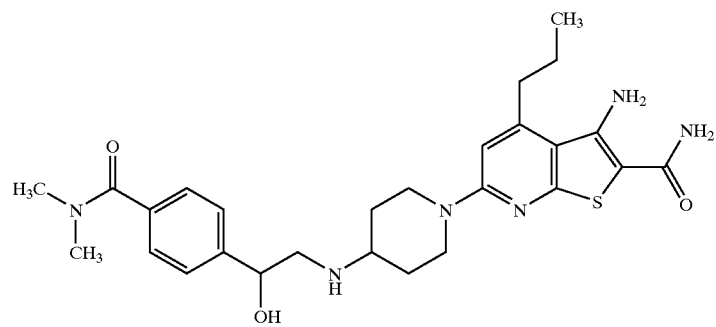

3-Amino-6-{4-[2-(4-benzylcarbamoyl-phenyl)-2-hydroxy-ethylamino]-piperidin-1-yl}-4-propyl-thieno[2,3-b]pyridine-2-carboxylic acid amide

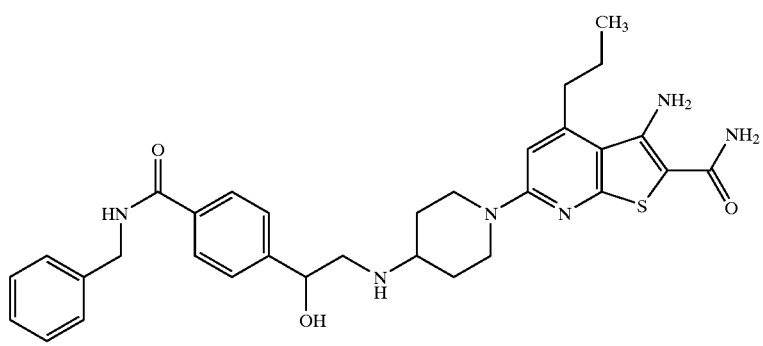

-continued

3-Amino-6-{4-[2-(3-carbamoyl-phenyl)-2-hydroxy-ethylamino]-piperidin-1-yl}-4-propyl-thieno[2,3-b]pyridine-2-carboxylic acid amide

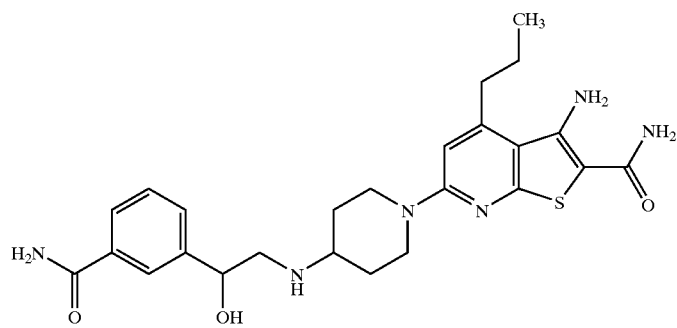

3-Amino-6-(4-{2-[4-(cyclopropylmethyl-carbamoyl)-phenyl]-2-hydroxy-ethylamino}-piperidin-1-yl)-4-propyl-thieno[2,3-b]pyridine-2-carboxylic acid amide

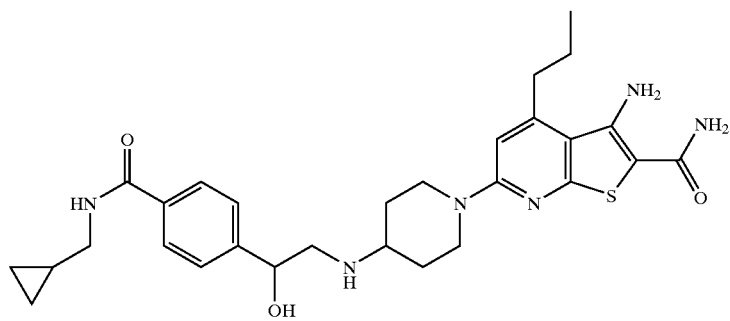

3-Amino-6-(4-{2-[4-(cyclohexylmethyl-carbamoyl)-phenyl]-2-hydroxy-ethylamino}-piperidin-1-yl)-4-propyl-thieno[2,3-b]pyridine-2-carboxylic acid amide

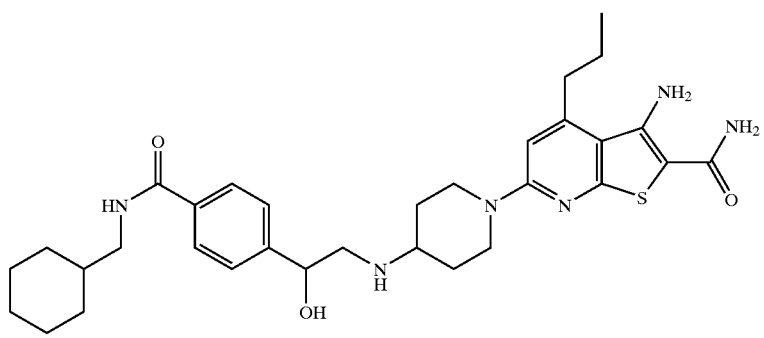

3-Amino-6-(4-{2-hydroxy-2-[4-(2-methyl-cyclohexylcarbamoyl)-phenyl]-ethylamino}-piperidin-1-yl)-4-propyl-thieno[2,3-b]pyridine-2-carboxylic acid amide

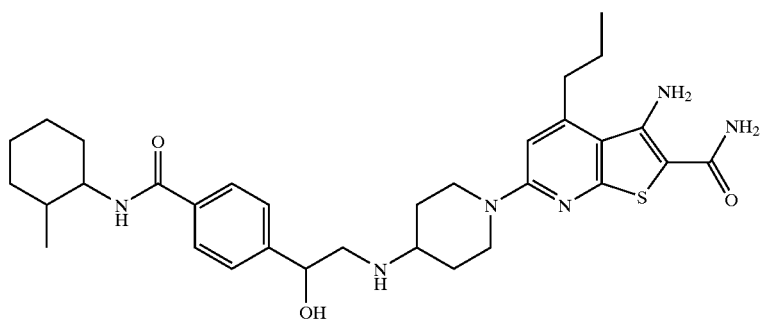

3-Amino-6-(4-{2-hydroxy-2-[4-(1-methyl-1-phenyl-ethylcarbamoyl)-phenyl]-ethylamino}-piperidin-1-yl)-4-propyl-thieno[2,3-b]pyridine-2-carboxylic acid amide

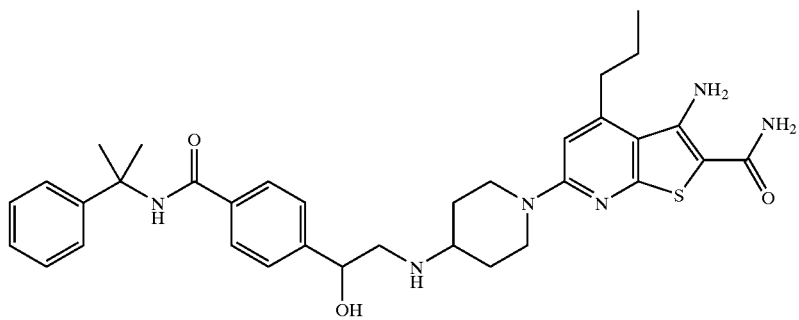

3-Amino-6-{4-[2-hydroxy-2-(4-phenethylcarbamoyl-phenyl)-ethylamino]-piperidin-1-yl}-4-propyl-thieno[2,3-b]pyridine-2-carboxylic acid amide

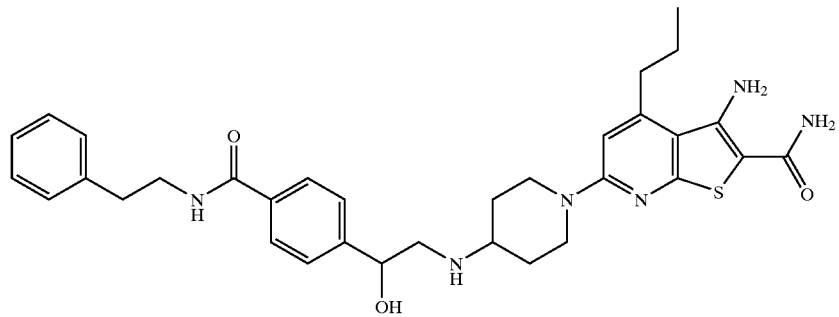

3-Amino-6-(4-{2-[4-(2-dimethylamino-ethylcarbamoyl)-phenyl]-2-hydroxy-ethylamino}-piperidin-1-yl)-4-propyl-thieno[2,3-b]pyridine-2-carboxylic acid amide

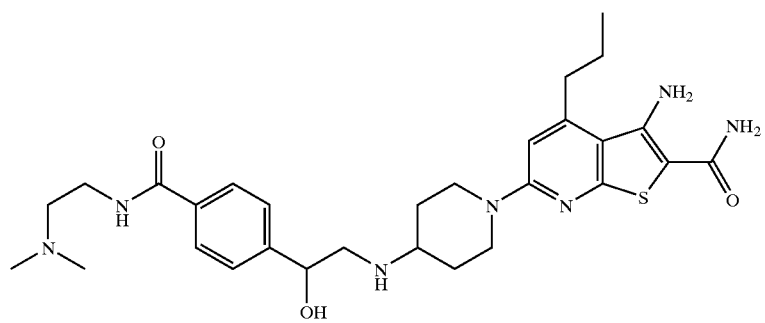

3-Amino-6-(4-{2-hydroxy-2-[4-(3-nitro-benzylcarbamoyl)-phenyl]-ethylamino}-piperidin-1-yl)-4-propyl-thieno[2,3-b]pyridine-2-carboxylic acid amide

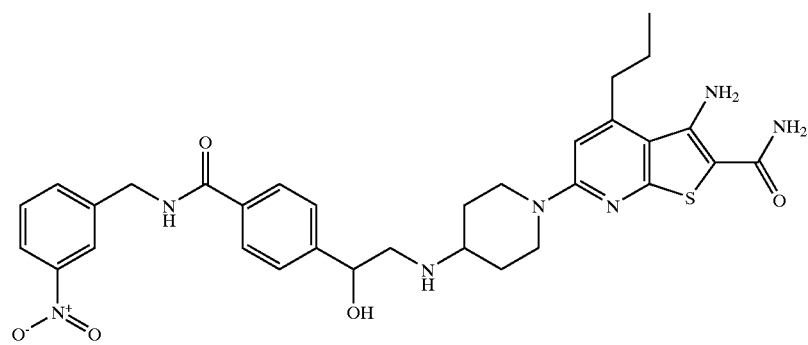

3-Amino-6-(4-{2-hydroxy-2-[4-(3-methoxy-benzylcarbamoyl)-phenyl]-ethylamino}-piperidin-1-yl)-4-propyl-thieno[2,3-b]pyridine-2-carboxylic acid amide

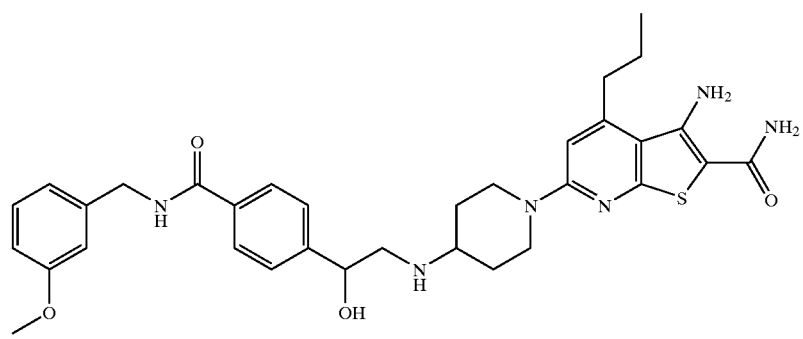

| | |
|---|---|
| 3-Amino-6-(4-{2-[4-(3-chloro-benzylcarbamoyl)-phenyl]-2-hydroxy-ethylamino}-piperidin-1-yl)-4-propyl-thieno[2,3-b]pyridine-2-carboxylic acid amide | 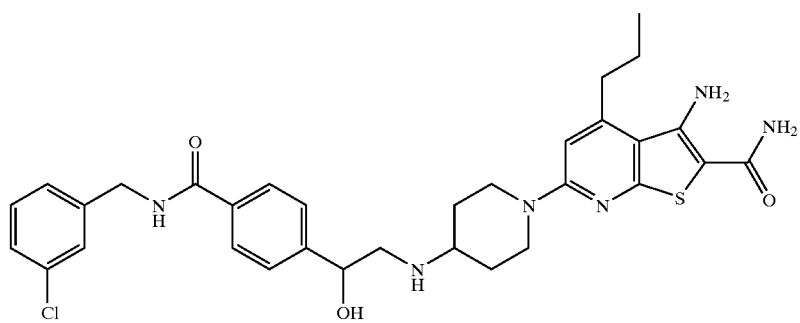 |
| 3-Amino-6-(4-{2-hydroxy-2-[4-(4-hydroxy-piperidine-1-carbonyl)-phenyl]-ethylamino}-piperidin-1-yl)-4-propyl-thieno[2,3-b]pyridine-2-carboxylic acid amide | 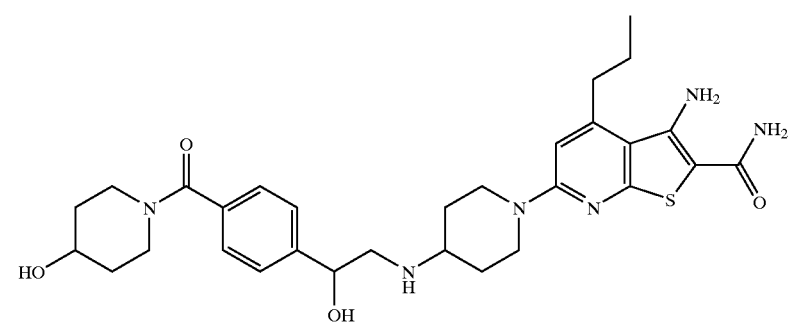 |
| 3-Amino-6-{4-[2-hydroxy-2-(4-isobutylcarbamoyl-phenyl)-ethylamino]-piperidin-1-yl}-4-propyl-thieno[2,3-b]pyridine-2-carboxylic acid amide | 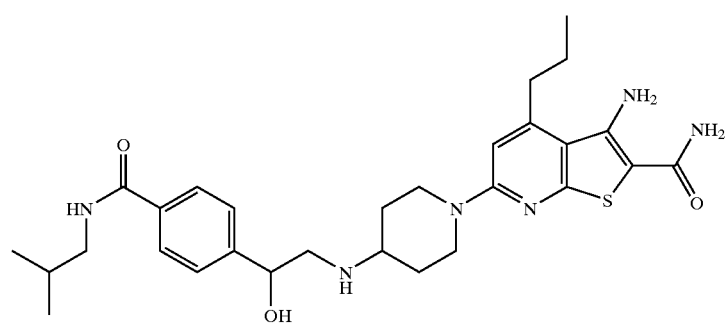 |
| 3-Amino-6-[4-(2-(4-[(benzo[b]thiophen-2-ylmethyl)-carbamoyl]-phenyl}-2-hydroxy-ethylamino)-piperidin-1-yl]-4-propyl-thieno[2,3-b]pyridine-2-carboxylic acid amide | 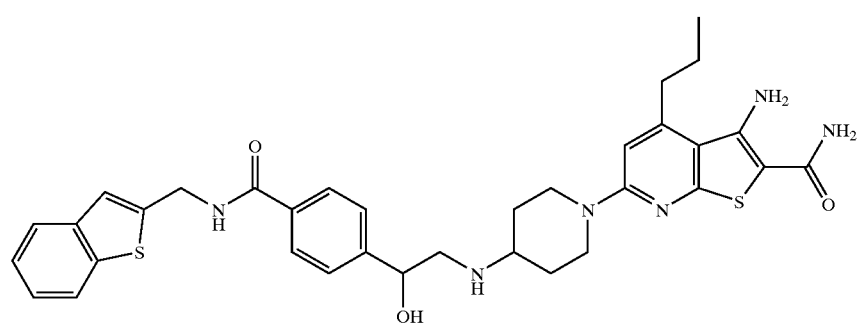 |
| 3-Amino-6-(4-{2-hydroxy-2-[4-((S)-1-hydroxymethyl-2-phenyl-ethylcarbamoyl)-phenyl]-ethylamino}-piperidin-1-yl)-4-propyl-thieno[2,3-b]pyridine-2-carboxylic acid amide | 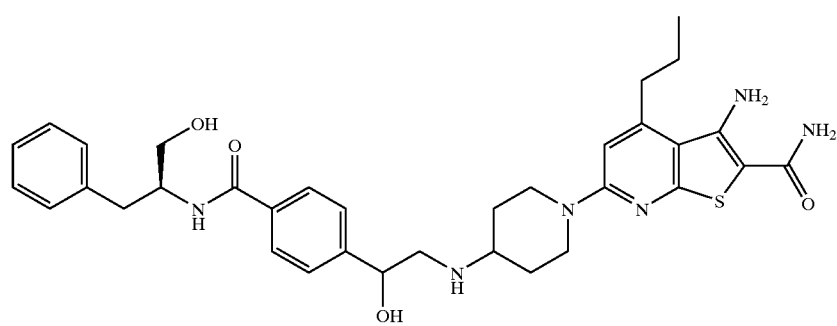 |

| | |
|---|---|
| 3-Amino-6-(4-{2-hydroxy-2-[4-((R)-1-hydroxymethyl-2-phenyl-ethylcarbamoyl)-phenyl]-ethylamino}-piperidin-1-yl)-4-propyl-thieno[2,3-b]pyridine-2-carboxylic acid amide | 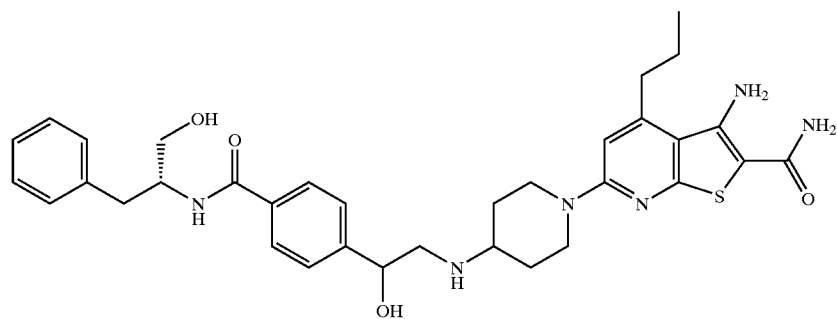 |
| 3-Amino-6-(4-{2-hydroxy-2-[4-(3-hydroxy-propylcarbamoyl)-phenyl]-ethylamino}-piperidin-1-yl)-4-propyl-thieno[2,3-b]pyridine-2-carboxylic acid amide | 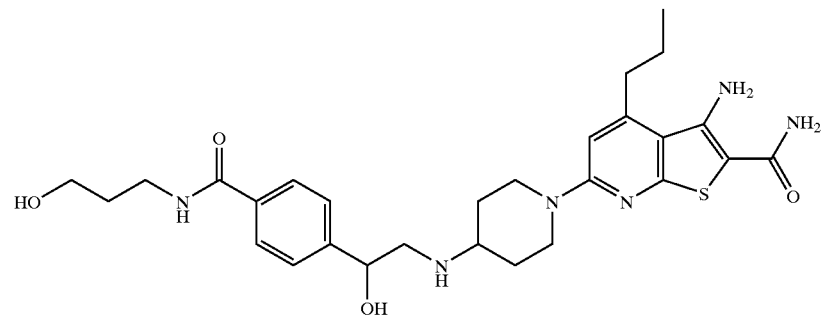 |
| (4-{2-[1-(3-Amino-2-carbamoyl-4-propyl-thieno[2,3-b]pyridin-6-yl)-piperidin-4-ylamino]-1-hydroxy-ethyl}-benzoylamino)-acetic acid methyl ester | 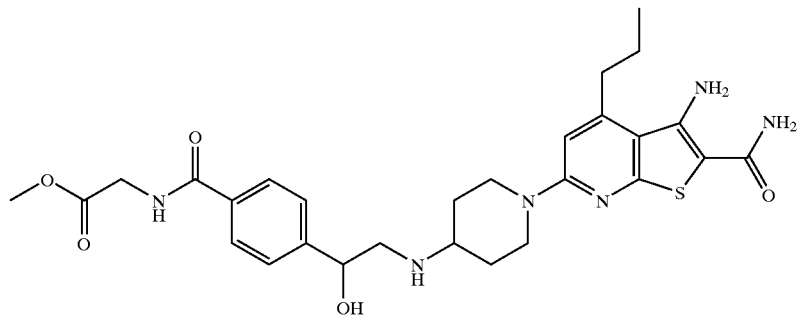 |
| 3-Amino-6-(4-{2-hydroxy-2-[4-(morpholine-4-carbonyl)-phenyl]-ethylamino}-piperidin-1-yl)-4-propyl-thieno[2,3-b]pyridine-2-carboxylic acid amide | 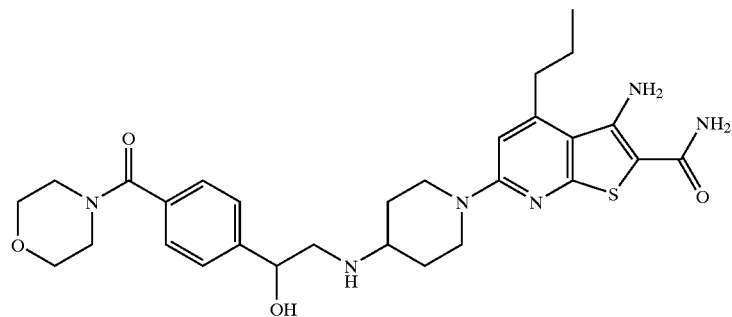 |

| | |
|---|---|
| 3-Amino-6-(4-{2-hydroxy-2-[4-(3-trifluoromethyl-benzylcarbamoyl)-phenyl]-ethylamino}-piperidin-1-yl)-4-propyl-thieno[2,3-b]pyridine-2-carboxylic acid amide | 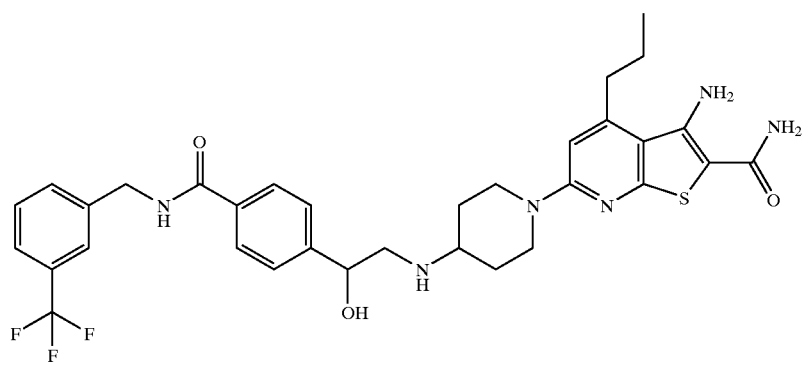 |
| 3-Amino-6-(4-{2-[4-(3-carbamoyl-benzylcarbamoyl)-phenyl]-2-hydroxy-ethylamino}-piperidin-1-yl)-4-propyl-thieno[2,3-b]pyridine-2-carboxylic acid amide | 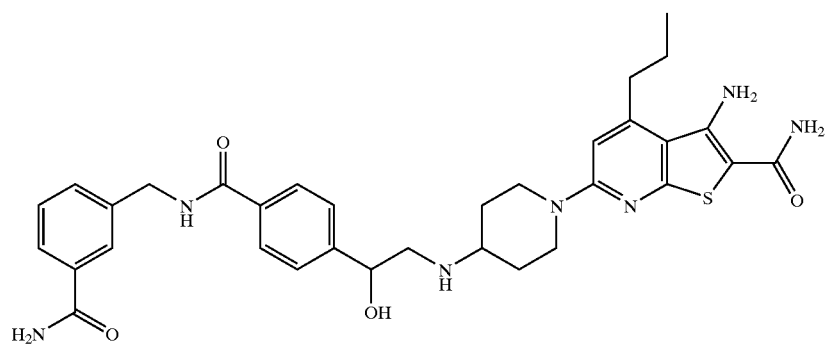 |
| 3-Amino-6-[4-(2-{4-[(furan-2-ylmethyl)-carbamoyl]-phenyl}-2-hydroxy-ethylamino)-piperidin-1-yl]-4-propyl-thieno[2,3-b]pyridine-2-carboxylic acid amide | 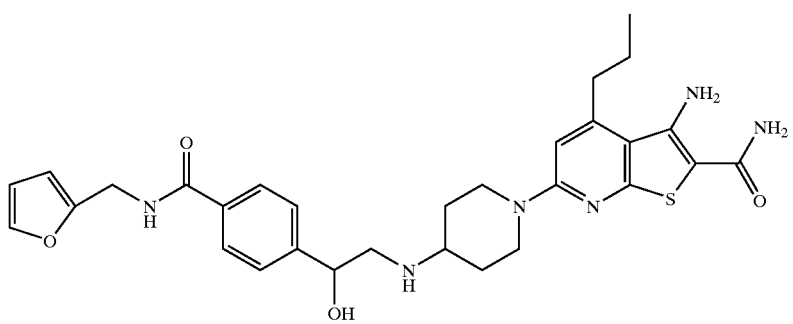 |
| 3-Amino-6-[4-(2-hydroxy-2-{4-[(pyridin-3-ylmethyl)-carbamoyl]-phenyl}-ethylamino)-piperidin-1-yl]-4-propyl-thieno[2,3-b]pyridine-2-carboxylic acid amide | 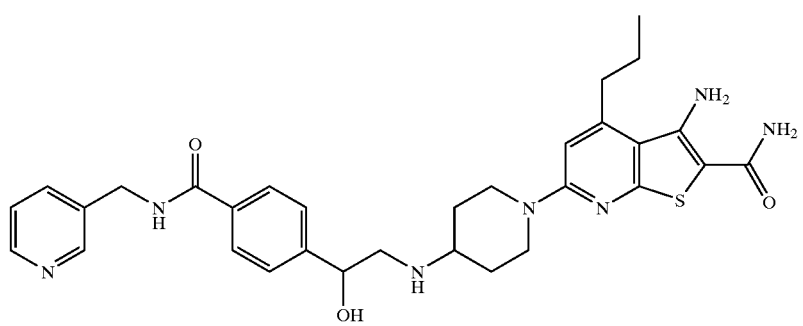 | and pharmaceutically acceptable salts, esters, tautomers, individual isomers, and mixtures of isomers thereof.

In another embodiment of the invention there are provided the following compounds of Table II:

| | |
|---|---|
| 3-Amino-6-[4-(2-hydroxy-2-phenyl-ethylamino)-piperidin-1-yl]-4-propyl-thieno[2,3-b]pyridine-2-carboxylic acid amide | 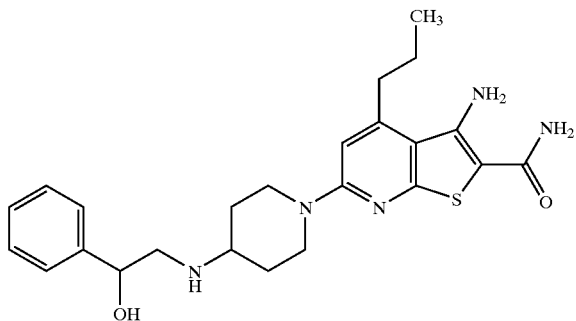 |
| 3-Amino-6-[4-((S)-2-hydroxy-2-phenyl-ethylamino)-piperidin-1-yl]-4-propyl-thieno[2,3-b]pyridine-2-carboxylic acid amide | 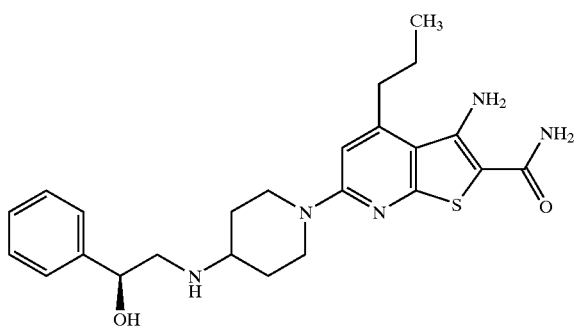 |
| 3-Amino-6-[4-((R)-2-hydroxy-2-phenyl-ethylamino)-piperidin-1-yl]-4-propyl-thieno[2,3-b]pyridine-2-carboxylic acid amide | 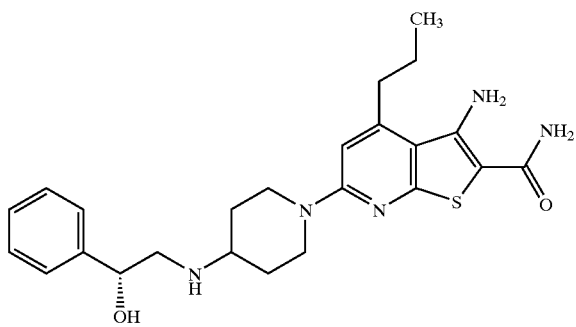 |
| 3-Amino-6-{4-[2-hydroxy-2-(4-nitro-phenyl)-ethylamino]-piperidin-1-yl}-4-propyl-thieno[2,3-b]pyridine-2-carboxylic acid amide | 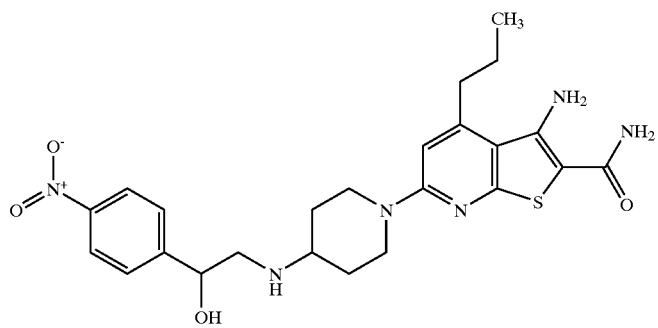 |

-continued

3-Amino-6-{4-[2-hydroxy-2-(3-hydroxy-phenyl)-ethylamino]-piperidin-1-yl}-4-propyl-thieno[2,3-b]pyridine-2-carboxylic acid amide

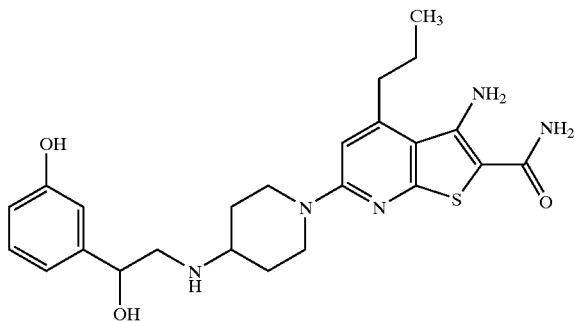

3-Amino-6-{4-[2-hydroxy-2-(4-hydroxy-phenyl)-ethylamino]-piperidin-1-yl}-4-propyl-thieno[2,3-b]pyridine-2-carboxylic acid amide

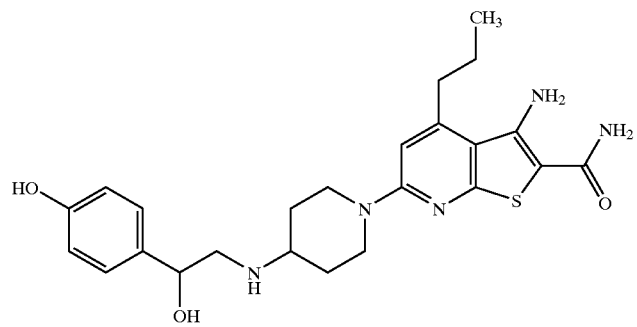

3-Amino-6-{4-[2-(4-amino-phenyl)-2-hydroxy-ethylamino]-piperidin-1-yl}-4-propyl-thieno[2,3-b]pyridine-2-carboxylic acid amide

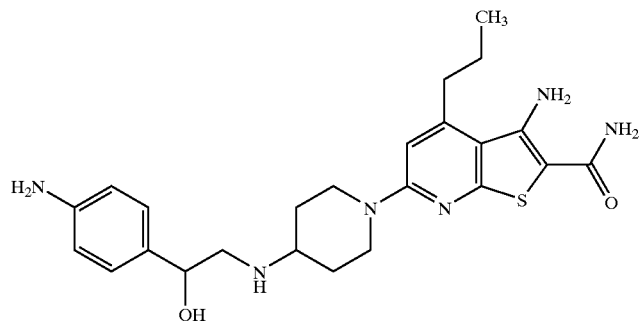

3-Amino-6-{4-[2-hydroxy-2-(4-methoxy-phenyl)-ethylamino]-piperidin-1-yl}-4-propyl-thieno[2,3-b]pyridine-2-carboxylic acid amide

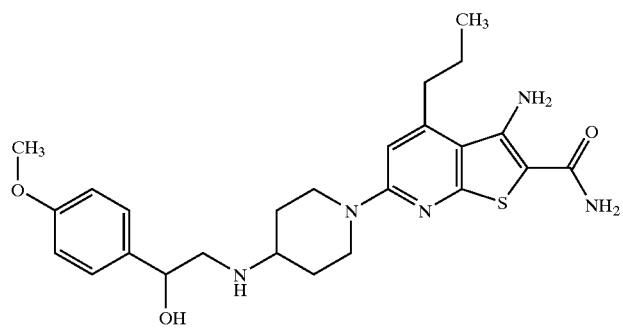

-continued

3-Amino-6-{4-[2-(4-chloro-phenyl)-2-hydroxy-ethylamino]-piperidin-1-yl}-4-propyl-thieno[2,3-b]pyridine-2-carboxylic acid amide

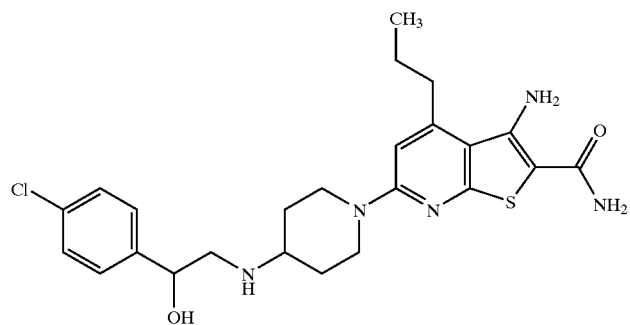

4-{2-[1-(3-Amino-2-carbamoyl-4-propyl-thieno[2,3-b]pyridin-6-yl)-piperidin-4-ylamino]-1-hydroxy-ethyl}-benzoic acid methyl ester

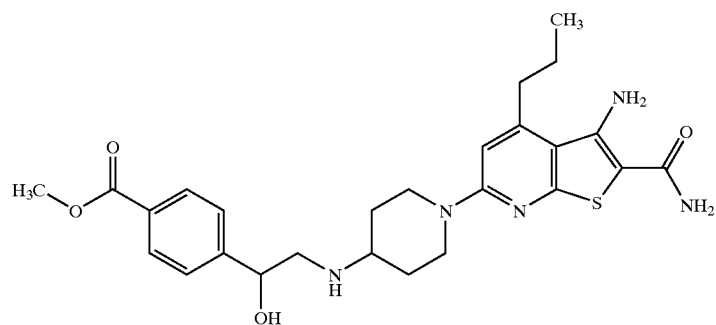

3-Amino-6-[4-(2-hydroxy-2-naphthalen-2-yl-ethylamino)-piperidin-1-yl]-4-propyl-thieno[2,3-b]pyridine-2-carboxylic acid amide

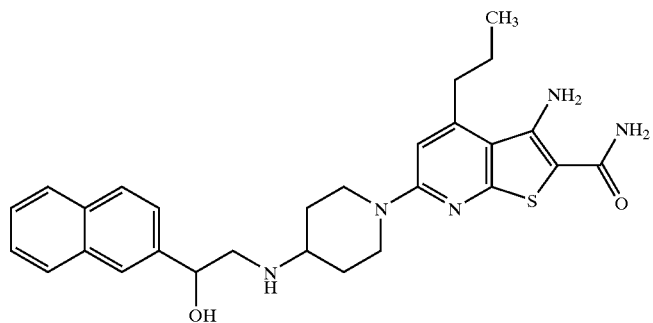

3-Amino-6-[4-(2-hydroxy-2-naphthalen-1-yl-ethylamino)-piperidin-1-yl]-4-propyl-thieno[2,3-b]pyridine-2-carboxylic acid amide

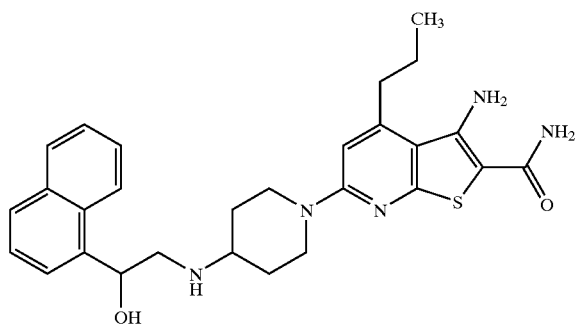

3-{2-[1-(3-Amino-2-carbamoyl-4-propyl-thieno[2,3-b]pyridin-6-yl)-piperidin-4-ylamino]-1-hydroxy-ethyl}-benzoic acid methyl ester

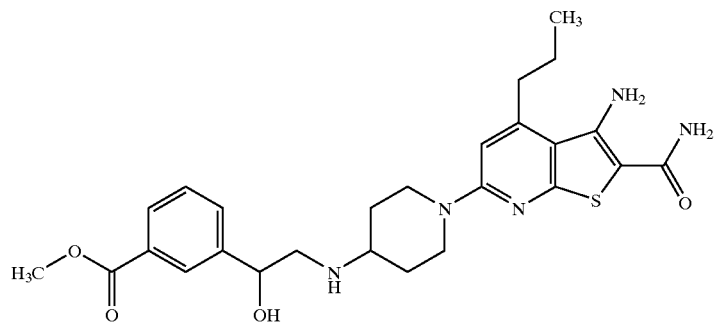

4-{2-[1-(3-Amino-2-carbamoyl-4-propyl-thieno[2,3-b]pyridin-6-yl)-piperidin-4-ylamino]-1-hydroxy-ethyl}-benzoic acid

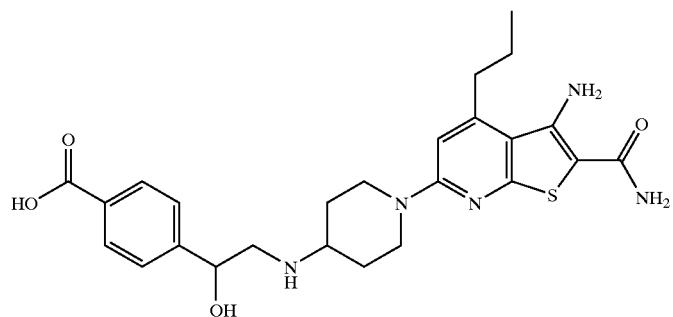

3-Amino-6-{4-[2-(4-benzylsulfamoyl-phenyl)-2-hydroxy-ethylamino]-piperidin-1-yl}-4-propyl-thieno[2,3-b]pyridine-2-carboxylic acid amide

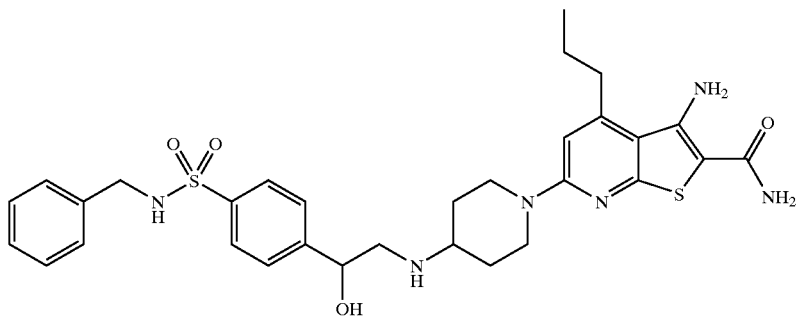

3-Amino-6-{4-[2-(4-cyano-phenyl)-2-hydroxy-ethylamino]-piperidin-1-yl}-4-propyl-thieno[2,3-b]pyridine-2-carboxylic acid amide

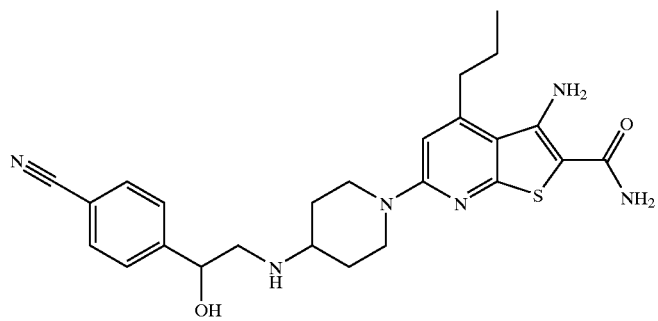

3-Amino-6-{4-[2-hydroxy-2-(4-methanesulfonylamino-phenyl)-ethylamino]-piperidin-1-yl}-4-propyl-thieno[2,3-b]pyridine-2-carboxylic acid amide

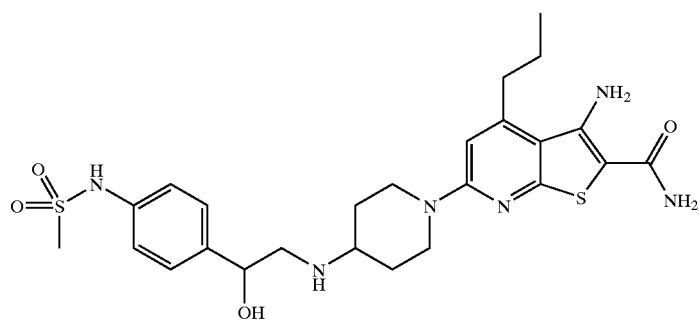

-continued

3-Amino-6-{4-[2-(4-fluoro-phenyl)-2-hydroxy-ethylamino]-piperidin-1-yl}-4-propyl-thieno[2,3-b]pyridine-2-carboxylic acid amide

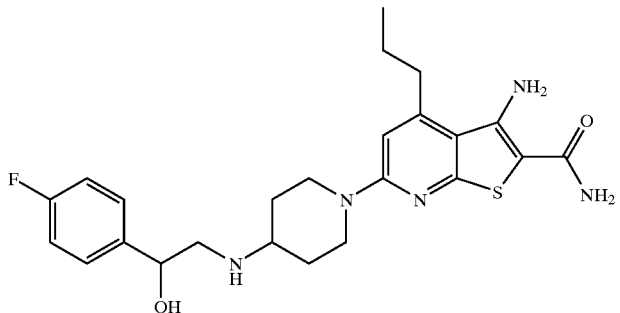

3-Amino-6-{4-[2-(2-fluoro-phenyl)-2-hydroxy-ethylamino]-piperidin-1-yl}-4-propyl-thieno[2,3-b]pyridine-2-carboxylic acid amide

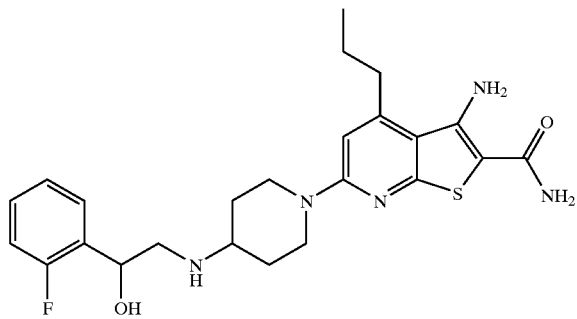

3-Amino-6-{4-[2-(3,4-difluoro-phenyl)-2-hydroxy-ethylamino]-piperidin-1-yl}-4-propyl-thieno[2,3-b]pyridine-2-carboxylic acid amide

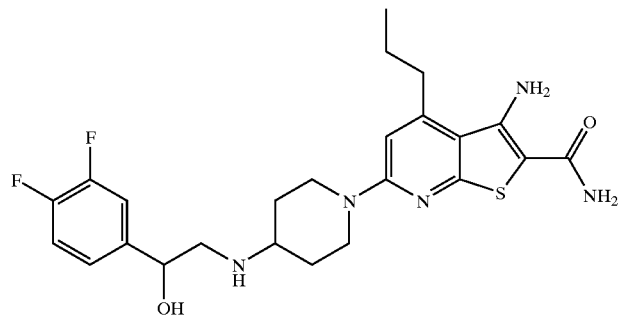

3-Amino-6-{4-[2-(3-cyano-phenyl)-2-hydroxy-ethylamino]-piperidin-1-yl}-4-propyl-thieno[2,3-b]pyridine-2-carboxylic acid amide

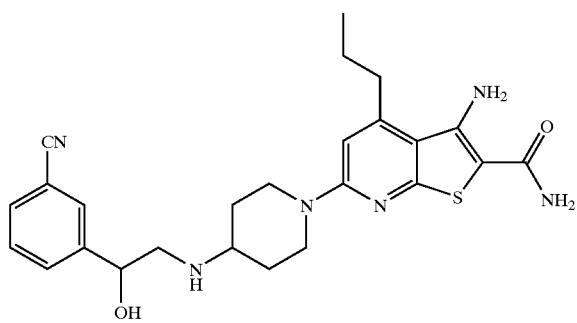

3-Amino-6-{4-[2-(4-difluoromethoxy-phenyl)-2-hydroxy-ethylamino]-piperidin-1-yl}-4-propyl-thieno[2,3-b]pyridine-2-carboxylic acid amide

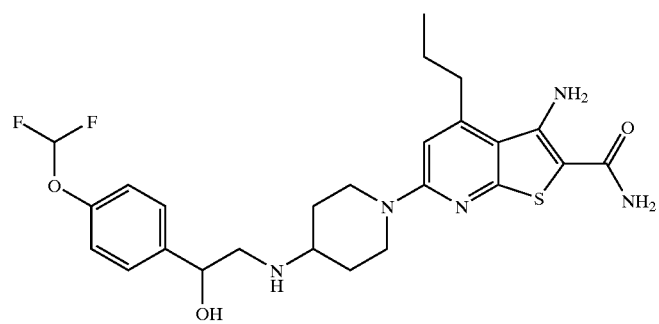

3-Amino-6-{4-[2-hydroxy-2-(4-trifluoromethoxy-phenyl)-ethylamino]-piperidin-1-yl}-4-propyl-thieno[2,3-b]pyridine-2-carboxylic acid amide

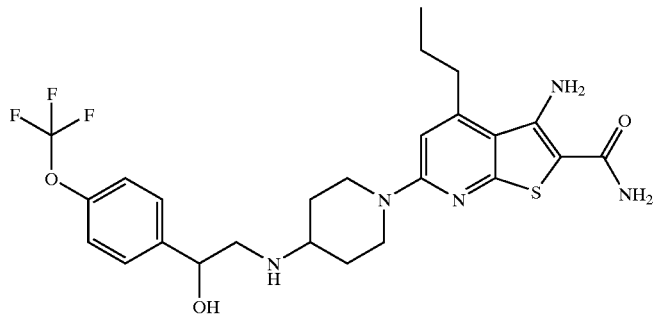

3-Amino-6-{4-[2-(3,5-difluoro-phenyl)-2-hydroxy-ethylamino]-piperidin-1-yl}-4-propyl-thieno[2,3-b]pyridine-2-carboxylic acid amide

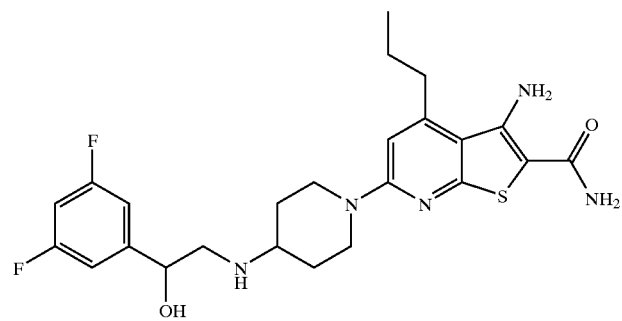

3-Amino-6-{4-[2-(4-dimethylaminomethyl-phenyl)-2-hydroxy-ethylamino]-piperidin-1-yl}-4-propyl-thieno[2,3-b]pyridine-2-carboxylic acid amide

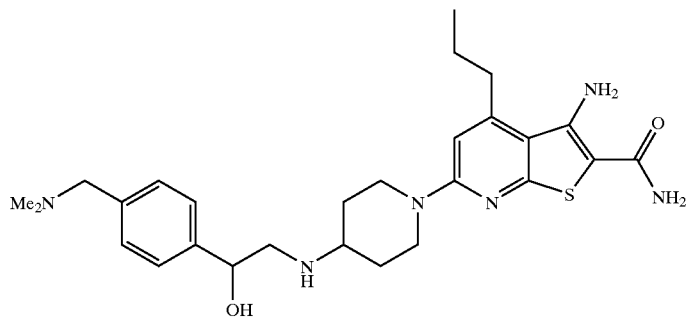

3-Amino-6-{4-[2-hydroxy-2-(4-methylaminomethyl-phenyl)-ethylamino]-piperidin-1-yl}-4-propyl-thieno[2,3-b]pyridine-2-carboxylic acid amide

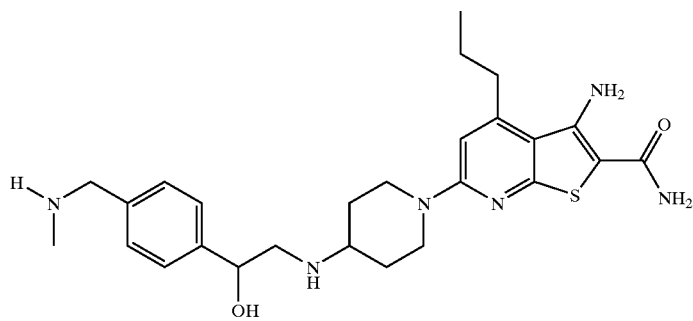

-continued

3-Amino-6-[4-(2-benzo[1,3]dioxol-5-yl-2-hydroxy-ethylamino)-piperidin-1-yl]-4-propyl-thieno[2,3-b]pyridine-2-carboxylic acid amide

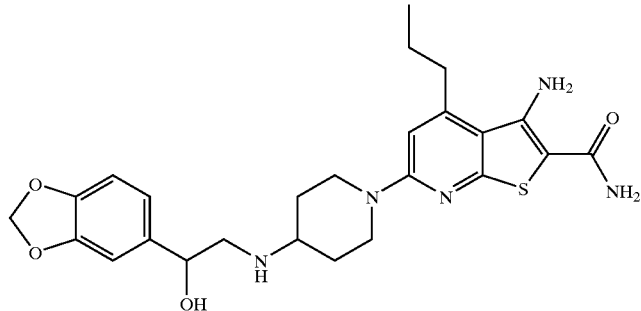

and pharmaceutically acceptable salts, esters, tautomers, individual isomers, and mixtures of isomers thereof.

In another embodiment the invention provides for the compounds of Table III

3-Amino-6-{4-[2-hydroxy-2-(4-morpholin-4-yl-phenyl)-ethylamino]-piperidin-1-yl}-4-propyl-thieno[2,3-b]pyridine-2-carboxylic acid amide

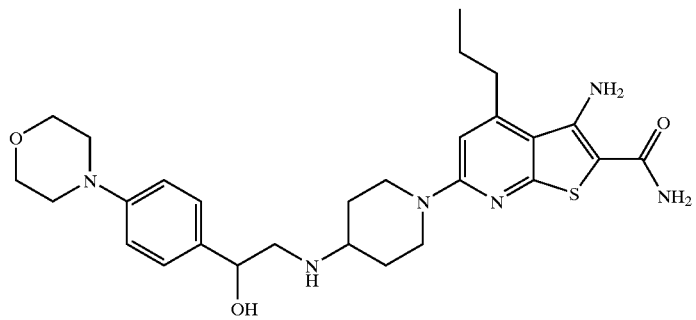

3-Amino-6-[4-(2-biphenyl-4-yl-2-hydroxy-ethylamino)-piperidin-1-yl]-4-propyl-thieno[2,3-b]pyridine-2-carboxylic acid amide

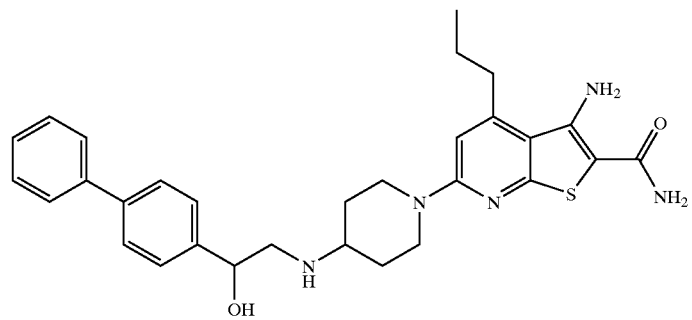

3-Amino-6-{4-[2-hydroxy-2-(4-pyridin-2-yl-phenyl)-ethylamino]-piperidin-1-yl}-4-propyl-thieno[2,3-b]pyridine-2-carboxylic acid amide

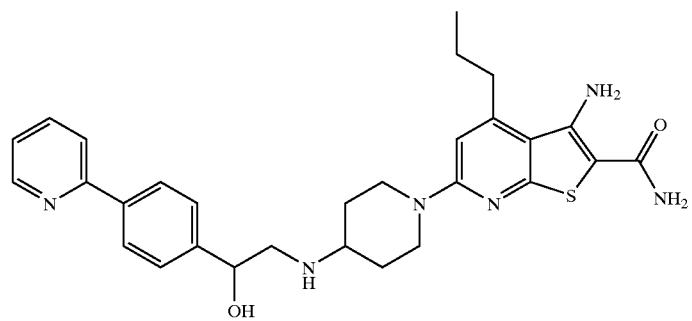

-continued

3-Amino-6-{4-[2-hydroxy-2-(4-pyridin-3-yl-phenyl)-ethylamino]-piperidin-1-yl}-4-propyl-thieno[2,3-b]pyridine-2-carboxylic acid amide

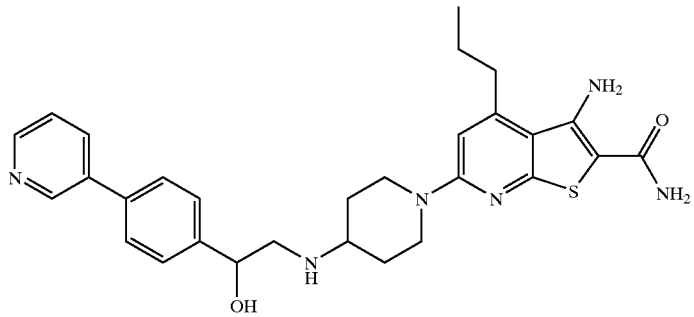

3-Amino-6-{4-[2-hydroxy-2-(4-pyridin-4-yl-phenyl)-ethylamino]-piperidin-1-yl}-4-propyl-thieno[2,3-b]pyridine-2-carboxylic acid amide

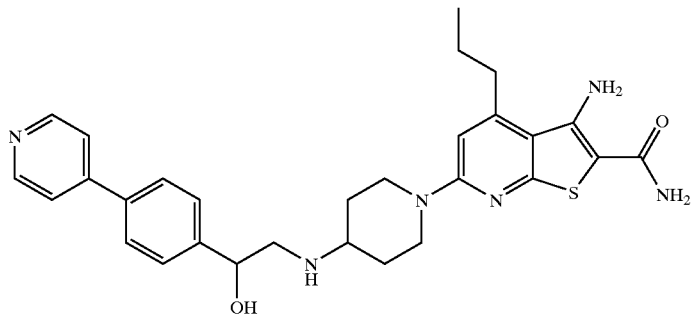

3-Amino-6-{4-[2-hydroxy-2-(3-pyridin-2-yl-phenyl)-ethylamino]-piperidin-1-yl}-4-propyl-thieno[2,3-b]pyridine-2-carboxylic acid amide

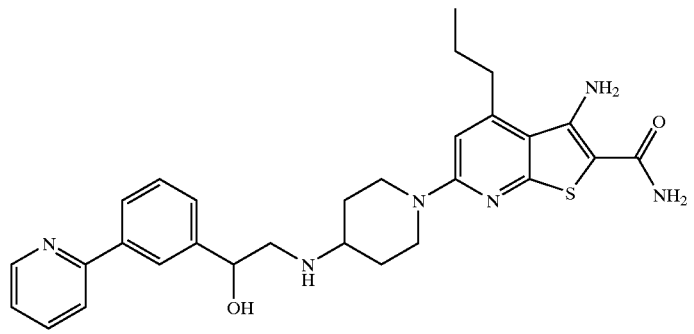

3-Amino-6-{4-[2-hydroxy-2-(4-pyrazin-2-yl-phenyl)-ethylamino]-piperidin-1-yl}-4-propyl-thieno[2,3-b]pyridine-2-carboxylic acid amide

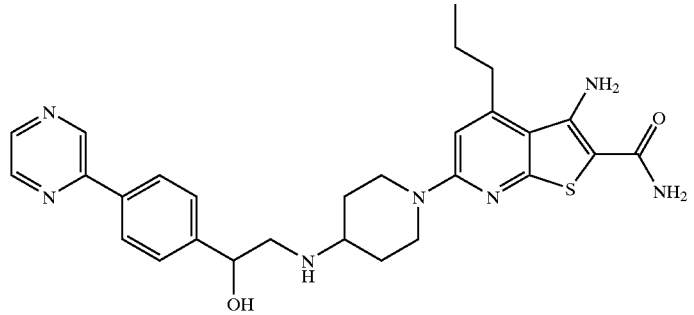

3-Amino-6-{4-[2-hydroxy-2-(4-pyrimidin-5-yl-phenyl)-ethylamino]-piperidin-1-yl}-4-propyl-thieno[2,3-b]pyridine-2-carboxylic acid amide

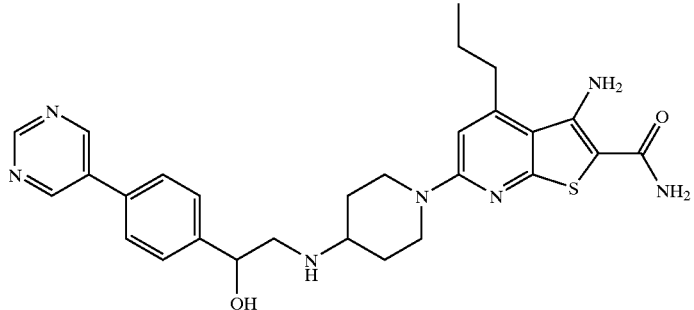

3-Amino-6-{4-[2-hydroxy-2-(4-imidazol-1-yl-phenyl)-ethylamino]-piperidin-1-yl}-4-propyl-thieno[2,3-b]pyridine-2-carboxylic acid amide

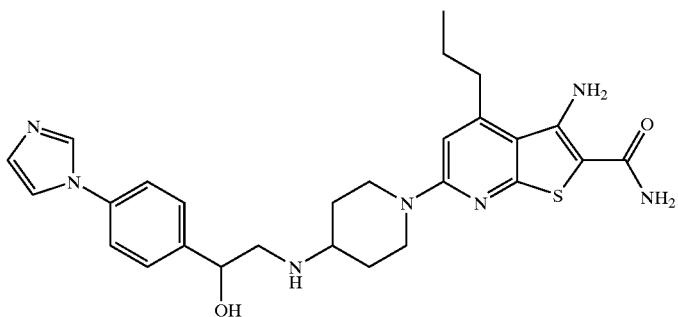

3-Amino-6-{4-[2-hydroxy-2-(4-thiazol-2-yl-phenyl)-ethylamino]-piperidin-1-yl}-4-propyl-thieno[2,3-b]pyridine-2-carboxylic acid amide

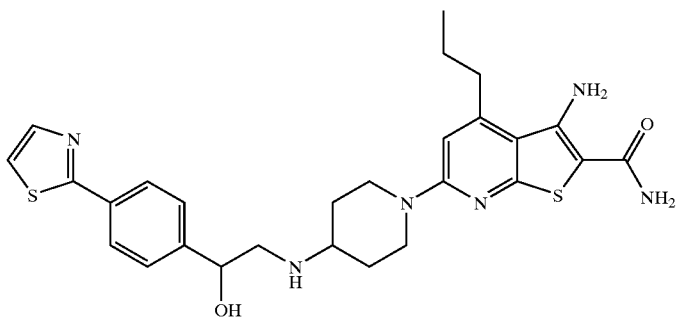

3-Amino-6-(4-{2-hydroxy-2-[4-(1-methyl-1H-imidazol-2-yl)-phenyl]-ethylamino}-piperidin-1-yl)-4-propyl-thieno[2,3-b]pyridine-2-carboxylic acid amide

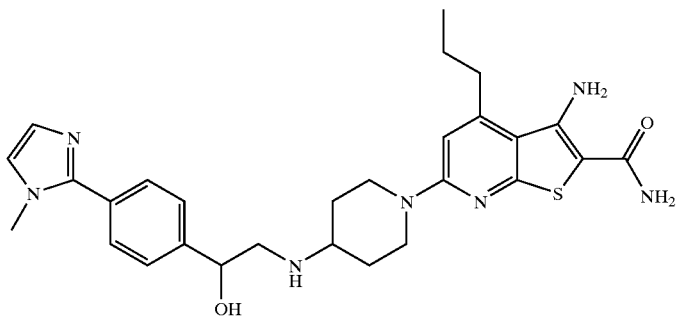

3-Amino-6-(4-{2-[4-(1-benzyl-1H-imidazol-2-yl)-phenyl]-2-hydroxy-ethylamino}-piperidin-1-yl)-4-propyl-thieno[2,3-b]pyridine-2-carboxylic acid amide

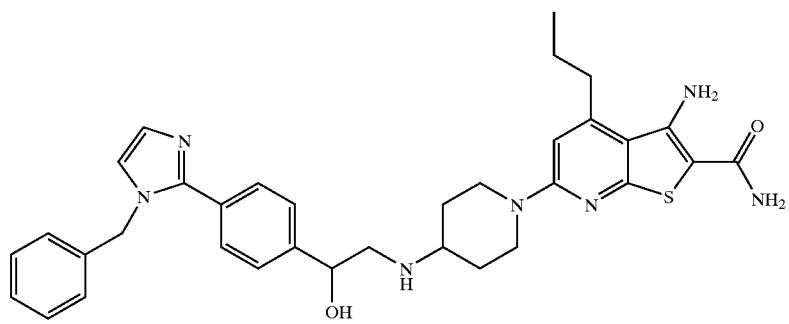

and pharmaceutically acceptable salts, esters, tautomers, individual isomers, and mixtures of isomers thereof.

Another embodiment of invention provides the compounds of Table IV:

| Name | Structure |
|---|---|
| 3-Amino-6-(4-hydroxy-piperidin-1-yl)-4-propyl-thieno[2,3-b]pyridine-2-carboxylic acid amide | 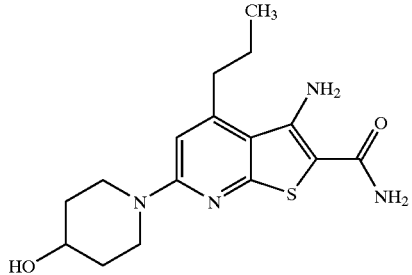 |
| 3-Amino-6-(4-carbamoyl-piperidin-1-yl)-4-propyl-thieno[2,3-b]pyridine-2-carboxylic acid amide | 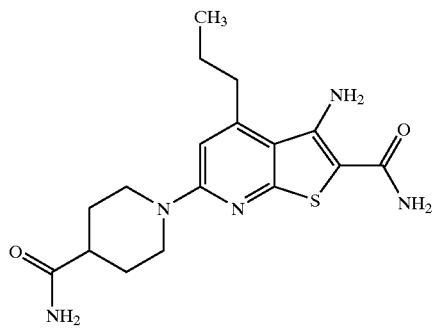 |
| 3-Amino-6-(4-methyl-piperazin-1-yl)-4-propyl-thieno[2,3-b]pyridine-2-carboxylic acid amide | 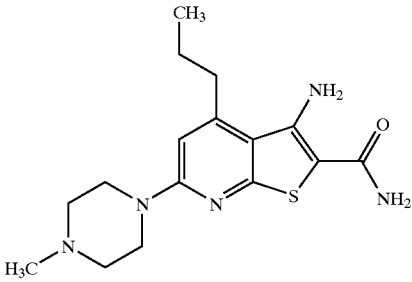 |
| 3-Amino-6-piperazin-1-yl-4-propyl-thieno[2,3-b]pyridine-2-carboxylic acid amide | 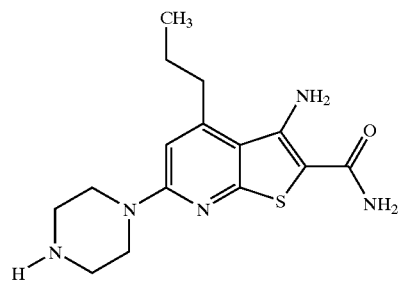 |
| 3-Amino-6-(4-methanesulfonyl-piperazin-1-yl)-4-propyl-thieno[2,3-b]pyridine-2-carboxylic acid amide | 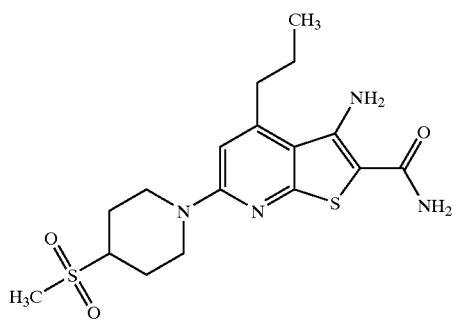 |

-continued

| Name | Structure |
|---|---|
| 3-Amino-6-(3-hydroxy-piperidin-1-yl)-4-propyl-thieno[2,3-b]pyridine-2-carboxylic acid amide | 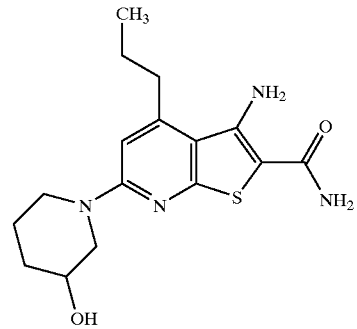 |
| 3-Amino-6-(4-amino-piperidin-1-yl)-4-propyl-thieno[2,3-b]pyridine-2-carboxylic acid amide | 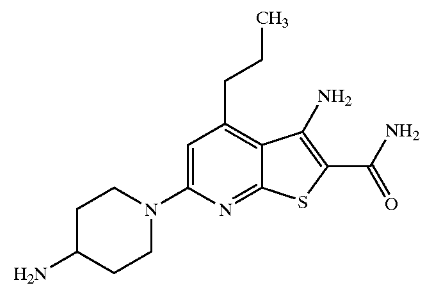 |
| 3-Amino-6-[4-(2-amino-ethanoyl)-piperazin-1-yl]-4-propyl-thieno[2,3-b]pyridine-2-carboxylic acid amide | 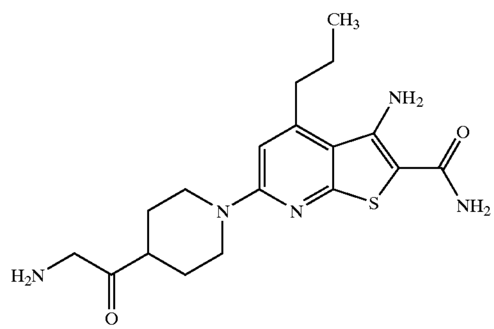 |
| 3-Amino-6-(4-oxo-piperidin-1-yl)-4-propyl-thieno[2,3-b]pyridine-2-carboxylic acid amide | 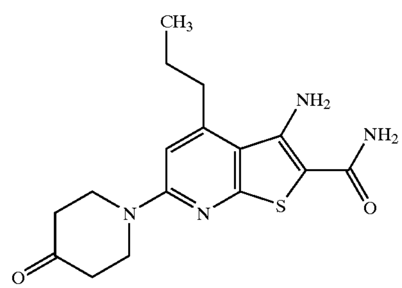 |
| 3-Amino-6-(4-carbamoyl-piperazin-1-yl)-4-propyl-thieno[2,3-b]pyridine-2-carboxylic acid amide | 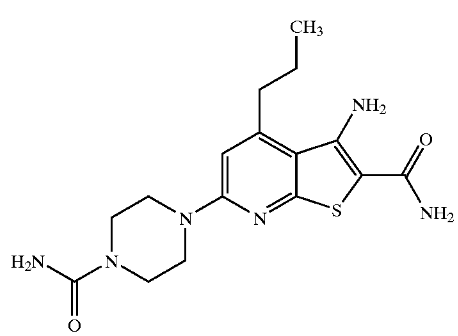 |

-continued
| Name | Structure |
|---|---|
| 3-Amino-6-((S)-3-amino-pyrrolidin-1-yl)-4-propyl-thieno[2,3-b]pyridine-2-carboxylic acid amide | 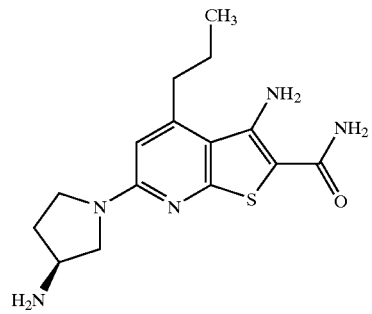 |
| 3-Amino-6-((R)-3-amino-pyrrolidin-1-yl)-4-propyl-thieno[2,3-b]pyridine-2-carboxylic acid amide | 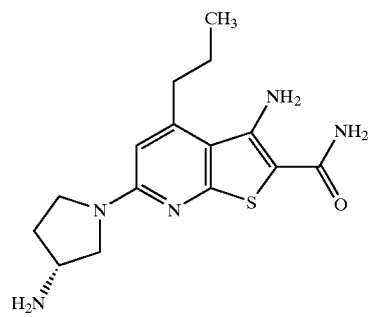 |
| 3-Amino-6-(4-amino-4-cyano-piperidin-1-yl)-4-propyl-thieno[2,3-b]pyridine-2-carboxylic acid amide | 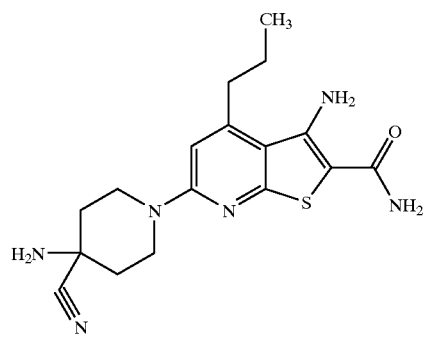 |
| 4-(3-Amino-2-carbamoyl-4-propyl-thieno[2,3-b]pyridin-6-yl)-piperazine-2-carboxylic acid methyl ester | 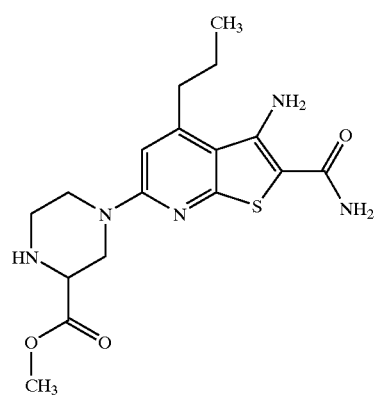 |

-continued

| Name | Structure |
|---|---|
| 3-Amino-6-[4-(4-amino-butanoyl)-piperazin-1-yl]-4-propyl-thieno[2,3-b]pyridine-2-carboxylic acid amide | 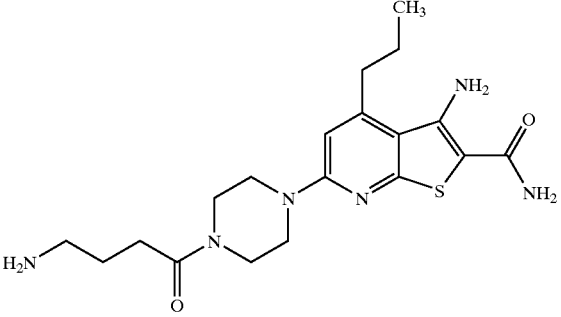 |
| 3-Amino-6-[4-((R)-2-amino-propanoyl)-piperazin-1-yl]-4-propyl-thieno[2,3-b]pyridine-2-carboxylic acid amide | 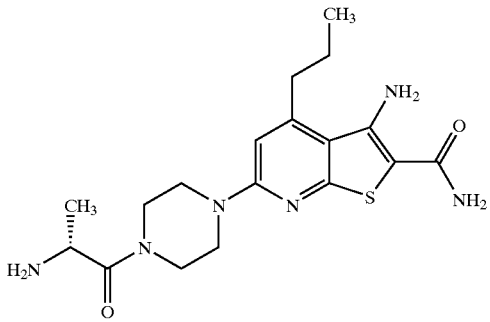 |
| 3-Amino-6-[4-((S)-2-amino-propanoyl)-piperazin-1-yl]-4-propyl-thieno[2,3-b]pyridine-2-carboxylic acid amide | 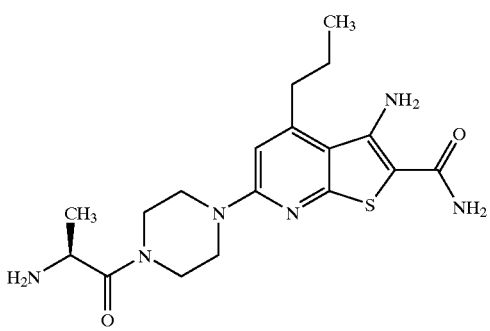 |
| 3-Amino-6-(4-hydroxy-4-methyl-piperidin-1-yl)-4-propyl-thieno[2,3-b]pyridine-2-carboxylic acid amide | 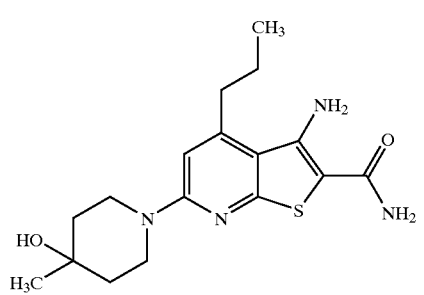 |
| 3-Amino-6-(4-methylamino-piperidin-1-yl)-4-propyl-thieno[2,3-b]pyridine-2-carboxylic acid amide | 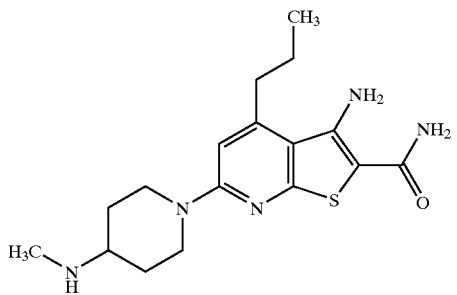 |

-continued

| Name | Structure |
|------|-----------|
| 3-Amino-6-(4-amino-piperidin-1-yl)-4-phenethyl-thieno[2,3-b]pyridine-2-carboxylic acid amide | 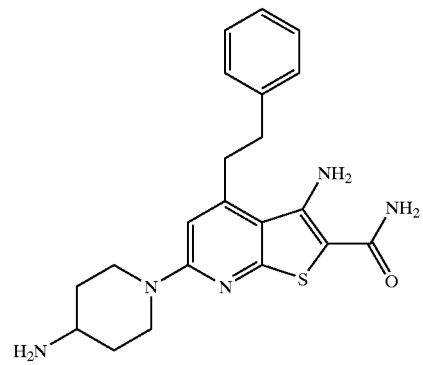 |
| 3-Amino-6-(4-aminomethyl-piperidin-1-yl)-4-propyl-thieno[2,3-b]pyridine-2-carboxylic acid amide | 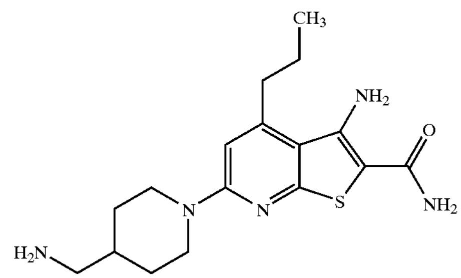 |
| 3-Amino-6-[1,4]diazepan-1-yl-4-propyl-thieno[2,3-b]pyridine-2-carboxylic acid amide | 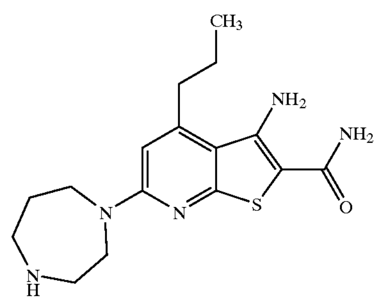 |
| 3-Amino-6-[4-(2,4-diamino-butanoyl)-piperazin-1-yl]-4-propyl-thieno[2,3-b]pyridine-2-carboxylic acid amide | 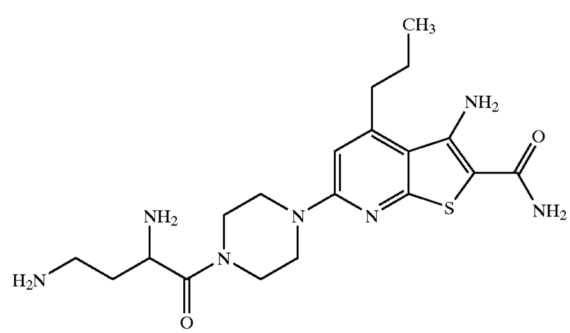 |

| Name | Structure |
|---|---|
| 3-Amino-6-[4-(1-piperidin-4-yl-methanoyl)-piperazin-1-yl]-4-propyl-thieno[2,3-b]pyridine-2-carboxylic acid amide | 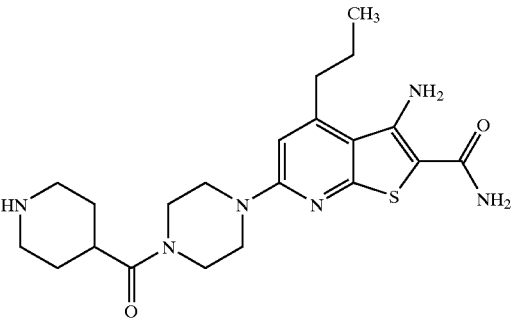 |
| 3-Amino-6-(4-methyl-[1,4]diazepan-1-yl)-4-propyl-thieno[2,3-b]pyridine-2-carboxylic acid amide | 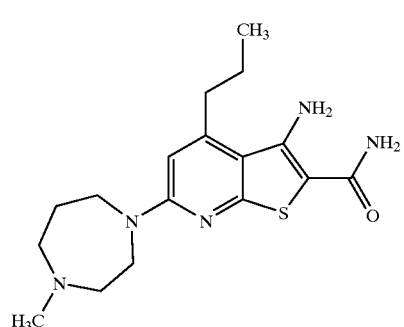 |
| 3-Amino-6-(3-amino-propylamino)-4-propyl-thieno[2,3-b]pyridine-2-carboxylic acid amide | 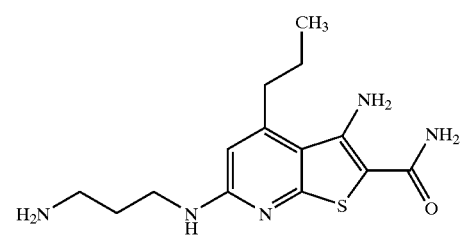 |
| 3-Amino-6-(3-carbamoyl-piperazin-1-yl)-4-propyl-thieno[2,3-b]pyridine-2-carboxylic acid amide | 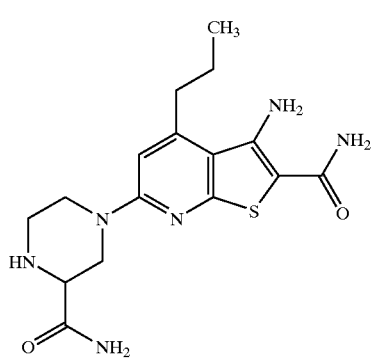 |

-continued
| Name | Structure |
|---|---|
| 6-(4-Acetyl-[1,4]diazepan-1-yl)-3-amino-4-propyl-thieno[2,3-b]pyridine-2-carboxylic acid amide | 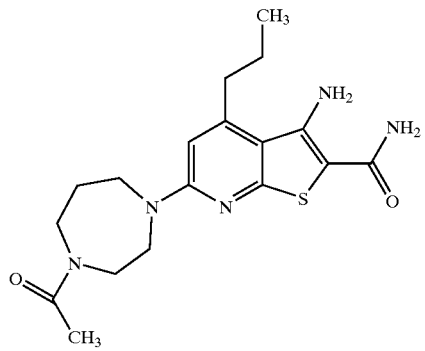 |
| 3-Amino-6-(3-carbamoyl-piperidin-1-yl)-4-propyl-thieno[2,3-b]pyridine-2-carboxylic acid amide | 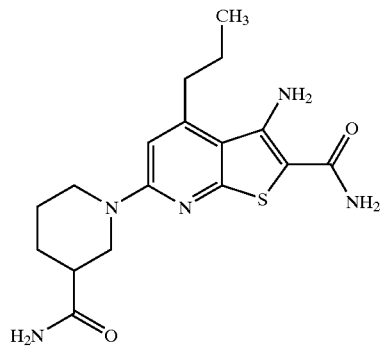 |
| 3-Amino-6-(3-amino-perhydro-azepin-1-yl)-4-propyl-thieno[2,3-b]pyridine-2-carboxylic acid amide | 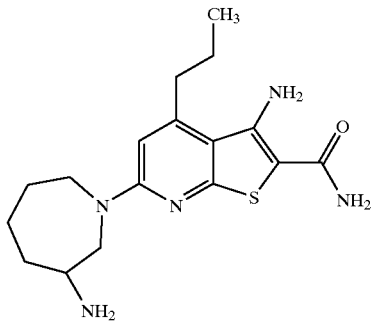 |
| 3-Amino-6-(3-aminomethyl-piperidin-1-yl)-4-propyl-thieno[2,3-b]pyridine-2-carboxylic acid amide | 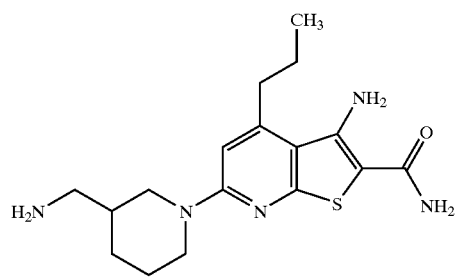 |

-continued

| Name | Structure |
|---|---|
| 3-Amino-6-(2-aminomethyl-piperidin-1-yl)-4-propyl-thieno[2,3-b]pyridine-2-carboxylic acid amide | 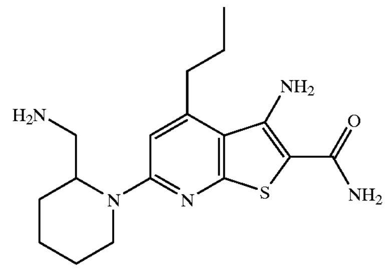 |
| 3-Amino-6-(2-hydroxymethyl-piperidin-1-yl)-4-propyl-thieno[2,3-b]pyridine-2-carboxylic acid amide | 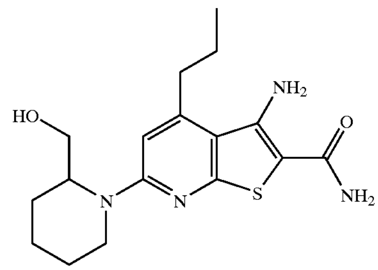 |
| 3-Amino-6-[4-((S)-2-amino-3-hydroxy-propionyl)-piperazin-1-yl]-4-propyl-thieno[2,3-b]pyridine-2-carboxylic acid amide | 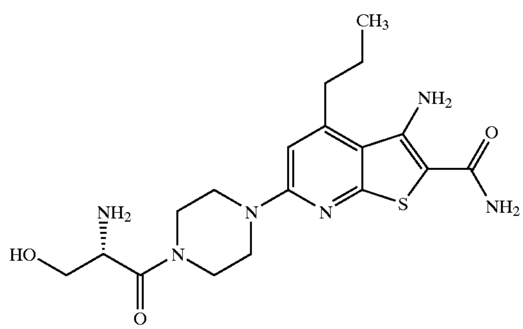 |
| 3-Amino-6-(4-carbamoyl-[1,4]diazepan-1-yl)-4-propyl-thieno[2,3-b]pyridine-2-carboxylic acid amide | 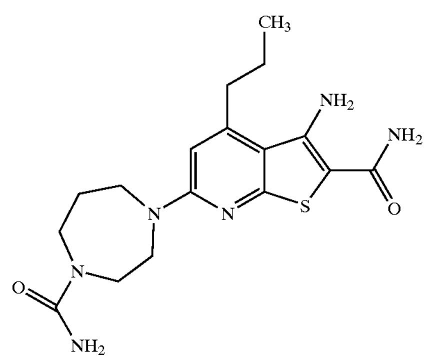 |
| 3-Amino-6-(5-oxo-[1,4]diazepan-1-yl)-4-propyl-thieno[2,3-b]pyridine-2-carboxylic acid amide | 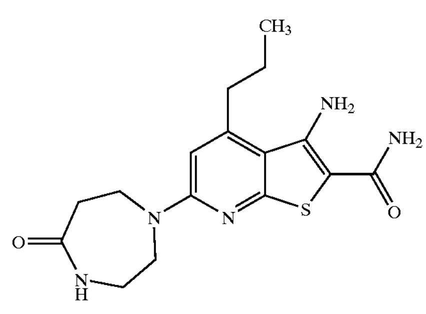 |

-continued

| Name | Structure |
|---|---|
| 3-Amino-6-[4-((S)-2-amino-4-hydroxy-butyryl)-piperazin-1-yl]-4-propyl-thieno[2,3-b]pyridine-2-carboxylic acid amide | 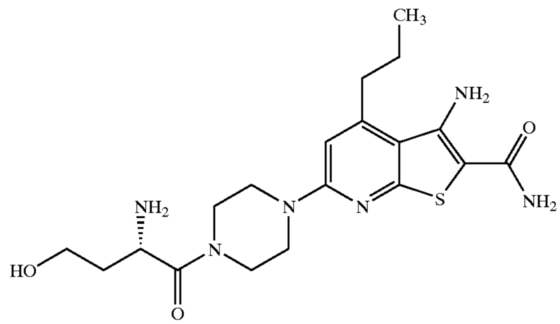 |
| 3-Amino-6-(4-ethylamino-piperidin-1-yl)-4-propyl-thieno[2,3-b]pyridine-2-carboxylic acid amide | 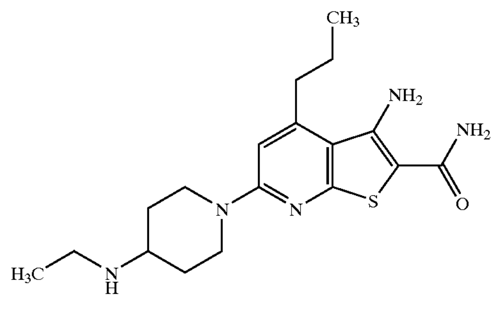 |
| 3-Amino-6-[4-(N-methylcarbamimidoyl)-piperazin-1-yl]-4-propyl-thieno[2,3-b]pyridine-2-carboxylic acid amide | 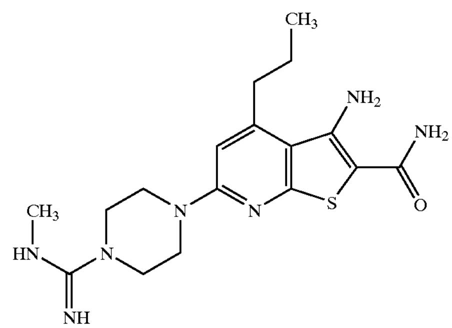 |
| 3-Amino-6-(4-hydroxyimino-piperidin-1-yl)-4-propyl-thieno[2,3-b]pyridine-2-carboxylic acid amide | 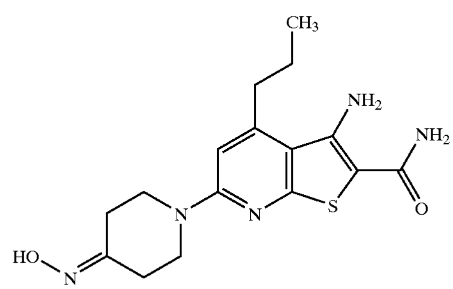 |
| 3-Amino-6-[4-(2,3-dihydroxy-propylamino)-piperidin-1-yl]-4-propyl-thieno[2,3-b]pyridine-2-carboxylic acid amide | 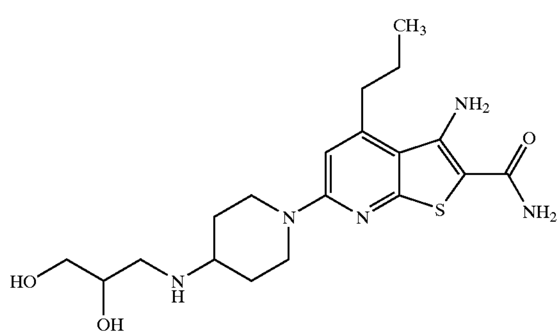 |

-continued

| Name | Structure |
|---|---|
| 3-Amino-6-(4-hydrazinocarbonyl-piperazin-1-yl)-4-propyl-thieno[2,3-b]pyridine-2-carboxylic acid amide | 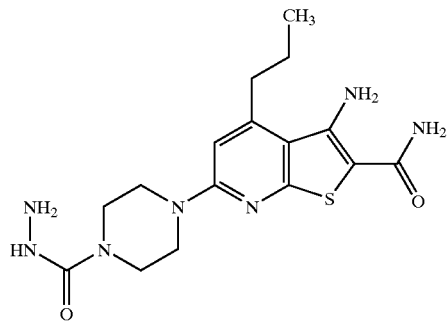 |
| 3-Amino-6-[4-(2-hydroxy-ethylamino)-piperidin-1-yl]-4-propyl-thieno[2,3-b]pyridine-2-carboxylic acid amide | 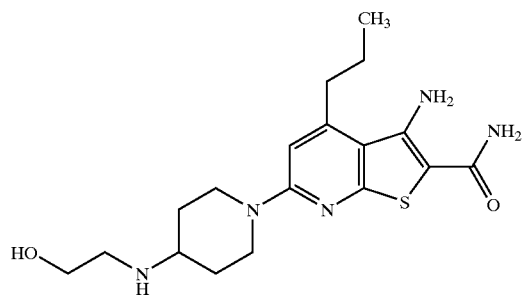 |
| 3-Amino-6-[4-((S)-2-hydroxy-1-methyl-ethylamino)-piperidin-1-yl]-4-propyl-thieno[2,3-b]pyridine-2-carboxylic acid amide | 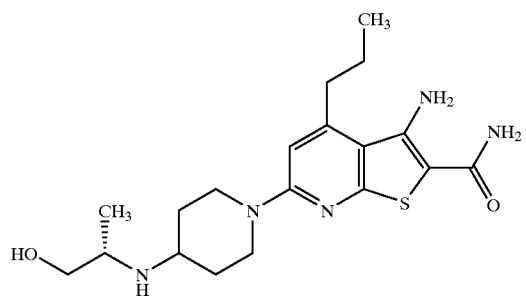 |
| 3-Amino-6-(4-methanesulfonylamino-piperidin-1-yl)-4-propyl-thieno[2,3-b]pyridine-2-carboxylic acid amide | 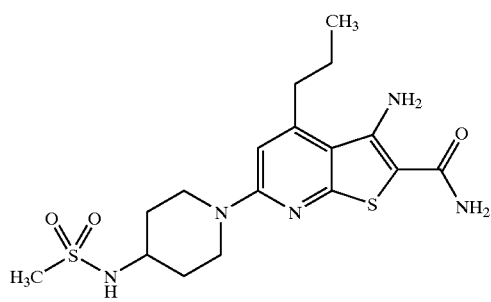 |
| 3-Amino-6-piperidin-4-yl-4-propyl-thieno[2,3-b]pyridine-2-carboxylic acid amide | 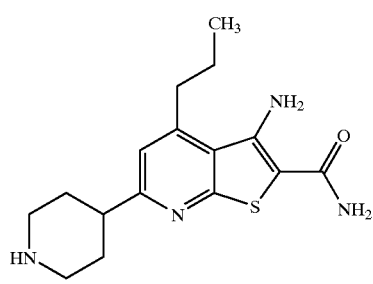 |

-continued

| Name | Structure |
|---|---|
| 3-Amino-6-[4-(N'-phenyl-hydrazinocarbonyl)-piperazin-1-yl]-4-propyl-thieno[2,3-b]pyridine-2-carboxylic acid amide | 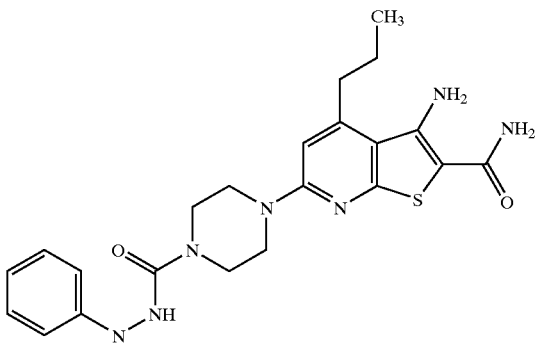 |
| 3-Amino-6-[4-((R)-2-hydroxy-propylamino)-piperidin-1-yl]-4-propyl-thieno[2,3-b]pyridine-2-carboxylic acid amide | 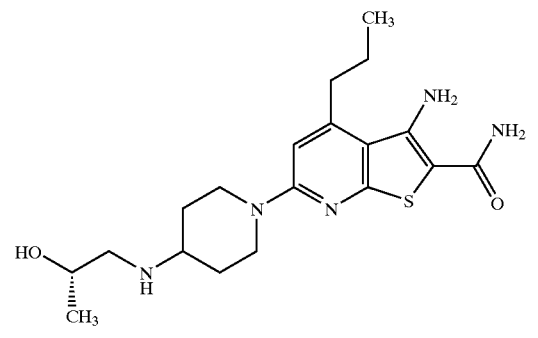 |
| 3-Amino-6-[4-((S)-2-hydroxy-propylamino)-piperidin-1-yl]-4-propyl-thieno[2,3-b]pyridine-2-carboxylic acid amide | 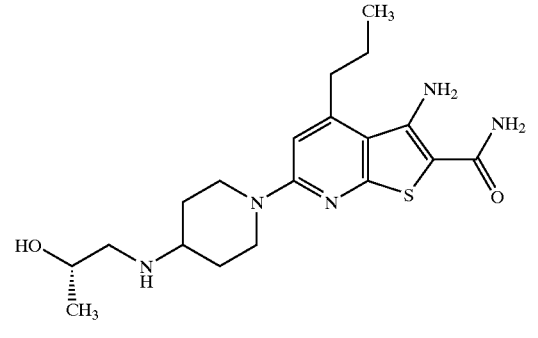 |
| 3-Amino-6-(4-hydroxy-azepan-1-yl)-4-propyl-thieno[2,3-b]pyridine-2-carboxylic acid amide | 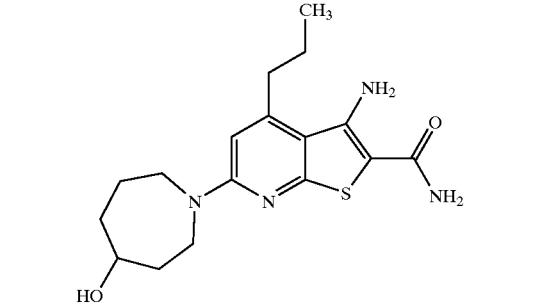 |

-continued

| Name | Structure |
|---|---|
| 3-Amino-6-(4-amino-azepan-1-yl)-4-propyl-thieno[2,3-b]pyridine-2-carboxylic acid amide | 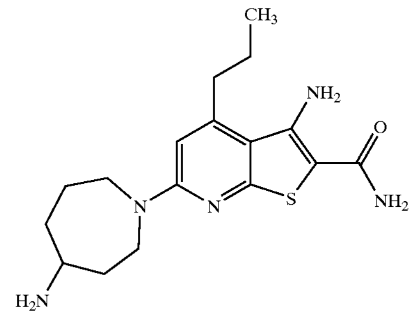 |
| 3-Amino-6-(4-amino-3-hydroxy-piperidin-1-yl)-4-propyl-thieno[2,3-b]pyridine-2-carboxylic acid amide | 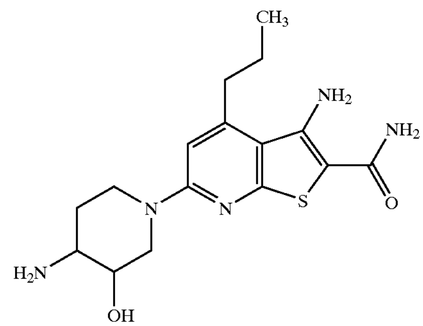 |
| 3-Amino-4-propyl-6-(4-sulfamoyl-piperazin-1-yl)-thieno[2,3-b]pyridine 2-carboxylic acid amide | 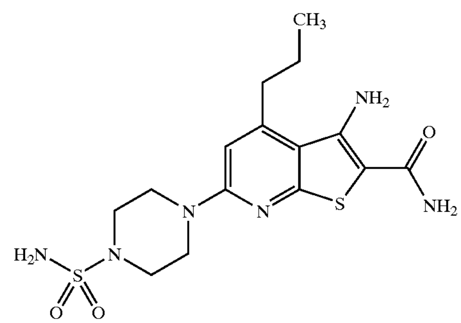 |
| 3-Amino-6-(1,1-dioxo-thiomorpholin-4-yl)-4-propyl-thieno[2,3-b]pyridine-2-carboxylic acid amide | 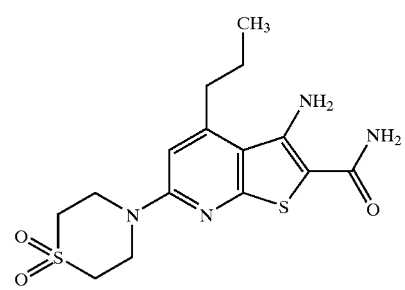 |
| 3-Amino-6-[(1H-indol-3-ylmethyl)-amino]-4-propyl-thieno[2,3-b]pyridine-2-carboxylic acid amide | 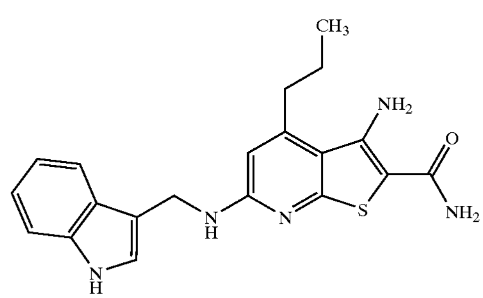 |

-continued

| Name | Structure |
|---|---|
| 3-Amino-6-{4-[2-(4-chloro-phenyl)-2-hydroxy-ethylamino]-piperidin-1-yl}-4-propyl-thieno[2,3-b]pyridine-2-carboxylic acid amide | 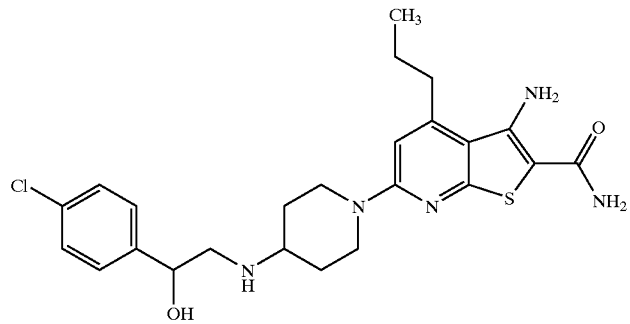 |
| 3-Amino-4-propyl-6-(4-ureido-piperidin-1-yl)-thieno[2,3-b]pyridine-2-carboxylic acid amide | 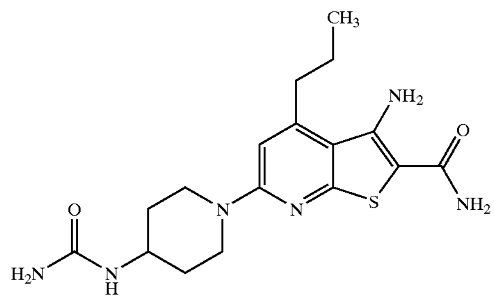 |
| 3-Amino-6-(4-hydroxymethyl-piperidin-1-yl)-4-propyl-thieno[2,3-b]pyridine-2-carboxylic acid amide | 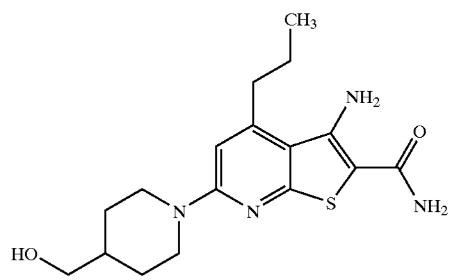 |
| 3-Amino-6-((S)-3,4-dihydroxy-piperidin-1-yl)-4-propyl-thieno[2,3-b]pyridine-2-carboxylic acid amide | 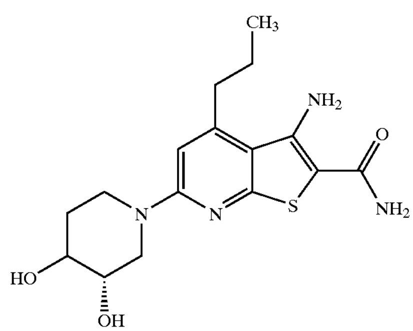 |
| 3-Amino-6-[3-hydroxy-4-(toluene-4-sulfonylamino)-piperidin-1-yl]-4-propyl-thieno[2,3-b]pyridine-2-carboxylic acid amide | 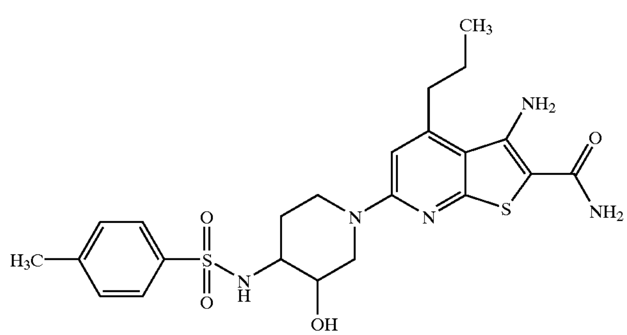 |

| Name | Structure |
|---|---|
| 3-Amino-6-[1,4]oxazepan-4-yl-4-propyl-thieno[2,3-b]pyridine-2-carboxylic acid amide | 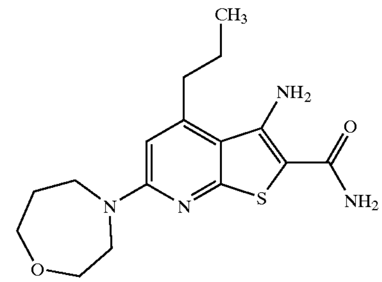 |
| 3-Amino-6-[4-(carbamoylmethyl-amino)-piperidin-1-yl]-4-propyl-thieno[2,3-b]pyridine-2-carboxylic acid amide | 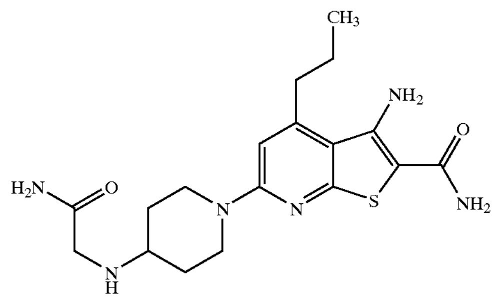 |
| 3-Amino-6-(4-amino-4-methyl-piperidin-1-yl)-4-propyl-thieno[2,3-b]pyridine-2-carboxylic acid amide | 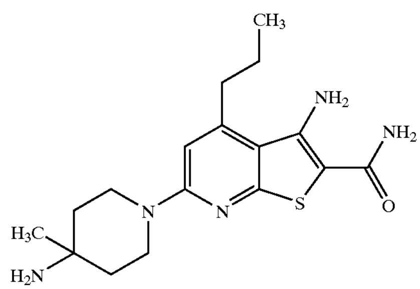 |
| 3-Amino-6-(4-hydroxy-piperidin-1-yl)-4-(3-hydroxy-propyl)-thieno[2,3-b]pyridine-2-carboxylic acid amide | 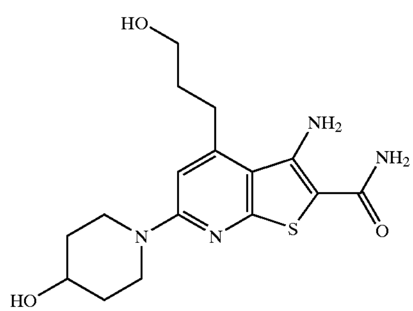 |
| 3-Amino-6-((S)-3-hydroxy-4-methanesulfonylamino-piperidin-1-yl)-4-propyl-thieno[2,3-b]pyridine-2-carboxylic acid amide | 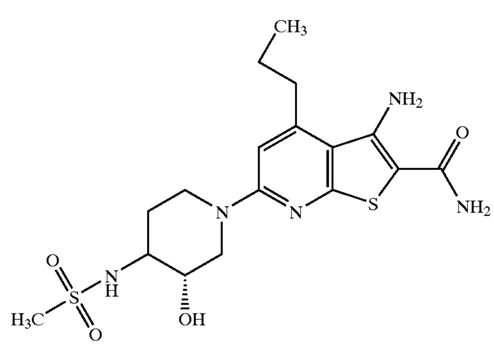 |

-continued

| Name | Structure |
|---|---|
| 3-Amino-6-[4-(N'-methylsulfonyl-hydrazino)-piperidin-1-yl]-4-propyl-thieno[2,3-b]pyridine-2-carboxylic acid amide | 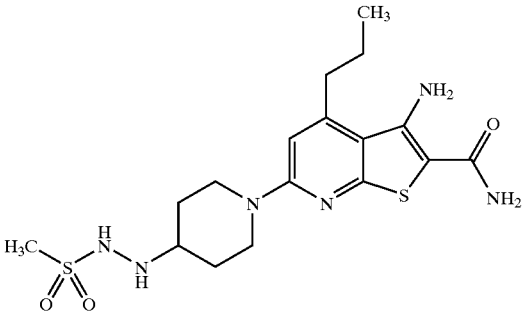 |
| 3-Amino-6-[4-(2-hydroxy-2-thiophen-2-yl-ethylamino)-piperidin-1-yl]-4-propyl-thieno[2,3-b]pyridine-2-carboxylic acid amide | 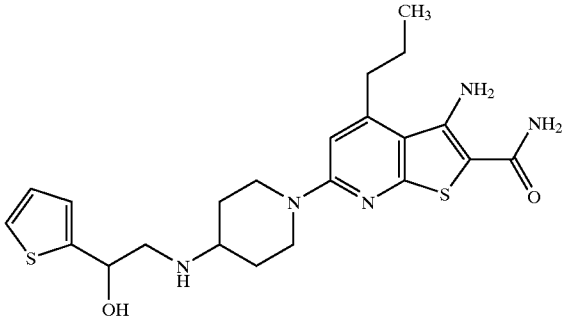 |
| 3-Amino-6-[4-(phenylcarbamoylmethyl-amino)-piperidin-1-yl]-4-propyl-thieno[2,3-b]pyridine-2-carboxylic acid amide | 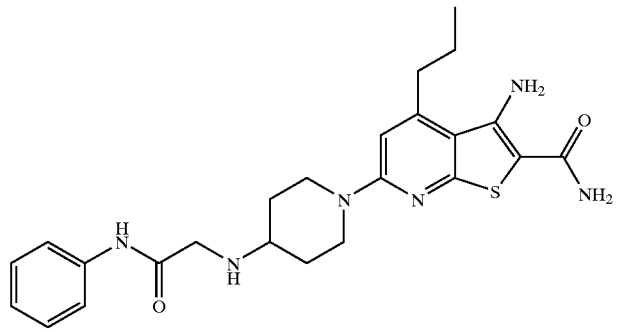 |
| 3-Amino-6-(4-{[(4-carbamoyl-phenylcarbamoyl)-methyl]-amino}-piperidin-1-yl)-4-propyl-thieno[2,3-b]pyridine-2-carboxylic acid amide | 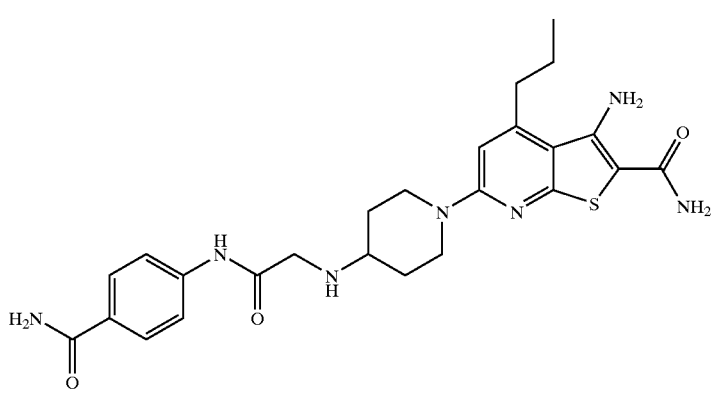 |

| Name | Structure |
|---|---|
| 3-Amino-6-[4-(2-hydroxy-3-phenoxy-propylamino)-piperidin-1-yl]-4-propyl-thieno[2,3-b]pyridine-2-carboxylic acid amide | 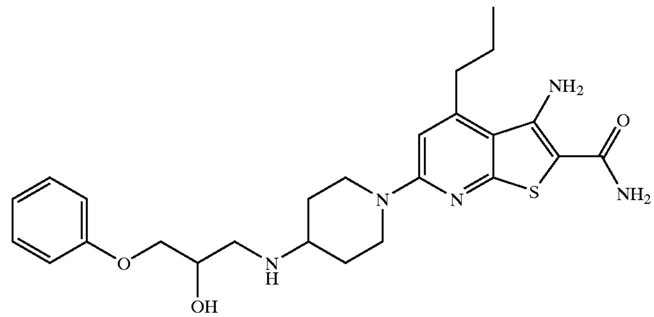 |
| 3-Amino-6-[4-(2-hydroxy-3-phenyl-propylamino)-piperidin-1-yl]-4-propyl-thieno[2,3-b]pyridine-2-carboxylic acid amide | 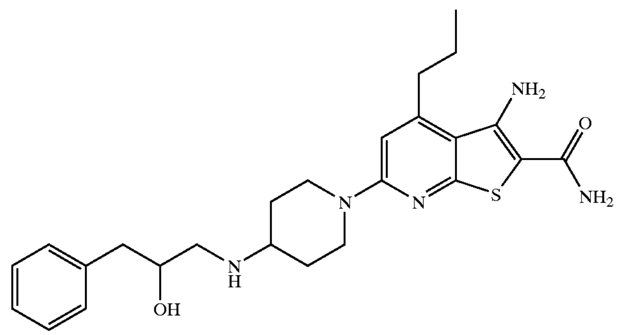 |
| 3-Amino-6-{4-[2-hydroxy-3-(4-methoxy-phenoxy)-propylamino]-piperidin-1-yl}-4-propyl-thieno[2,3-b]pyridine-2-carboxylic acid amide | 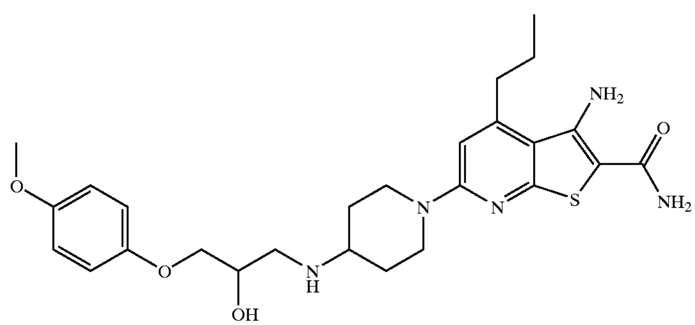 |
| 3-Amino-6-{4-[3-(4-carbamoyl-phenoxy)-2-hydroxy-propylamino]-piperidin-1-yl}-4-propyl-thieno[2,3-b]pyridine-2-carboxylic acid amide | 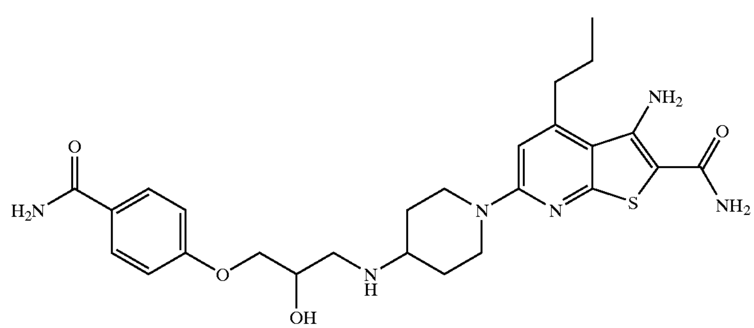 |

-continued

| Name | Structure |
|---|---|
| 3-Amino-6-[4-(1-imino-ethyl)-piperazin-1-yl]-4-propyl-thieno[2,3-b]pyridine-2-carboxylic acid amide | 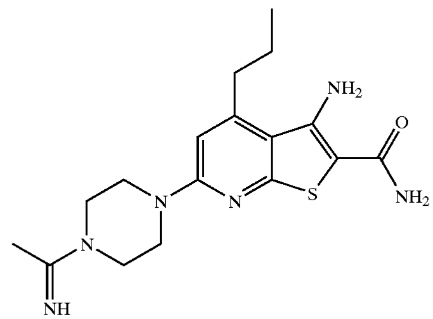 |
| 3-Amino-6-(4-amino-3,3-dimethyl-piperidin-1-yl)-4-propyl-thieno[2,3-b]pyridine-2-carboxylic acid amide | 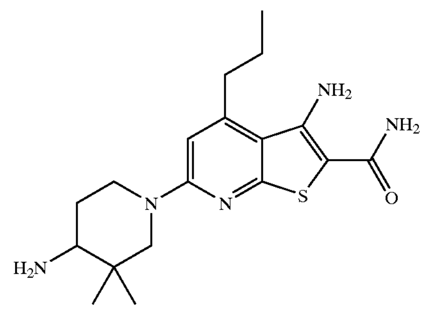 |
| 3-Amino-6-(4-hydroxy-3,3-dimethyl-piperidin-1-yl)-4-propyl-thieno[2,3-b]pyridine-2-carboxylic acid amide | 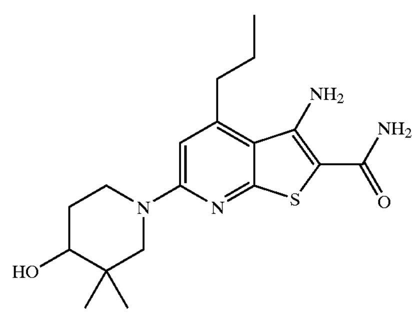 |
| 3-Amino-6-(4-amino-piperidin-1-yl)-4-cyclopropyl-thieno[2,3-b]pyridine-2-carboxylic acid amide | 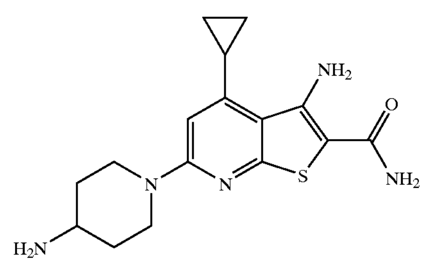 |
| 3-Amino-6-(4-amino-piperidin-1-yl)-4-tert-butyl-thieno[2,3-b]pyridine-2-carboxylic acid amide | 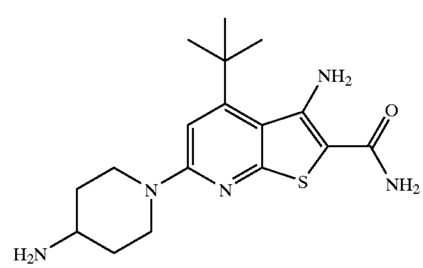 |

| Name | Structure |
|---|---|
| 3-Amino-6-(4-amino-piperidin-1-yl)-4-methyl-thieno[2,3-b]pyridine-2-carboxylic acid amide | 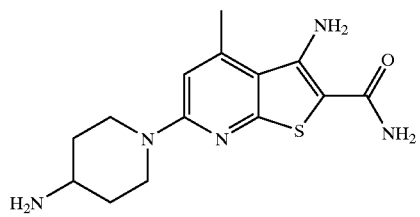 |
| 3-Amino-6-(4-amino-piperidin-1-yl)-4-ethyl-thieno[2,3-b]pyridine-2-carboxylic acid amide | 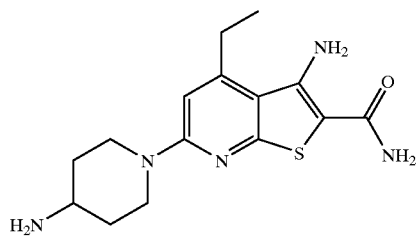 |
| 3-Amino-6-(4-amino-piperidin-1-yl)-4-isopropyl-thieno[2,3-b]pyridine-2-carboxylic acid amide | 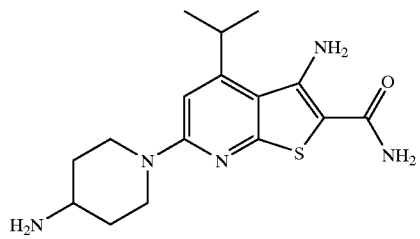 |
| 3-Amino-6-{4-[2-(4-carbamoyl-phenyl)-ethylamino]-piperidin-1-yl}-4-propyl-thieno[2,3-b]pyridine-2-carboxylic acid amide | 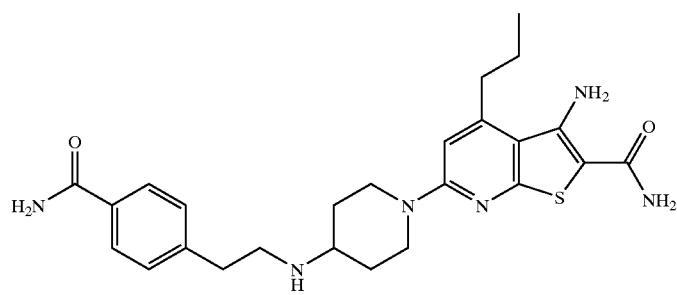 |
| 3-Amino-6-(4-cyclopropylamino-piperidin-1-yl)-4-propyl-thieno[2,3-b]pyridine-2-carboxylic acid amide | 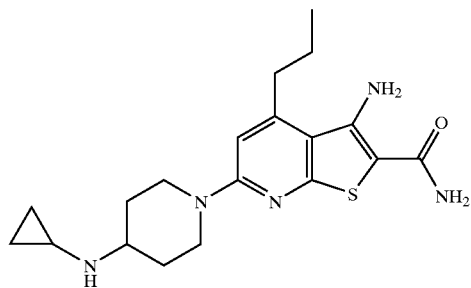 |

| Name | Structure |
|---|---|
| 3-Amino-4-propyl-6-{4-[(1H-tetrazol-5-ylmethyl)-amino]-piperidin-1-yl}-thieno[2,3-b]pyridine-2-carboxylic acid amide | 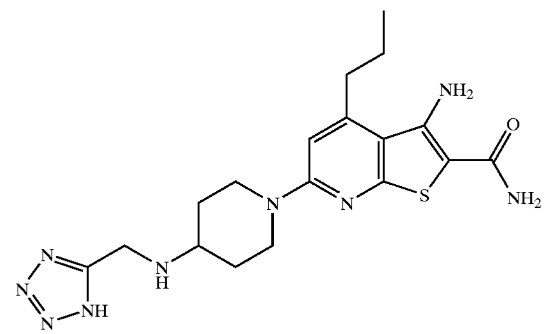 |
| [1-(3-Amino-2-carbamoyl-4-propyl-thieno[2,3-b]pyridin-6-yl)-piperidin-4-ylamino]-acetic acid | 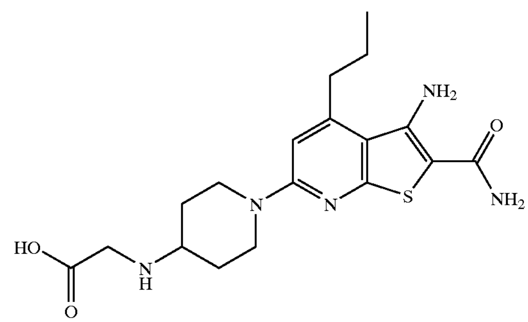 |
| 3-Amino-6-{4-[3-(3-cyano-phenoxy)-2-hydroxy-propylamino]-piperidin-1-yl}-4-propyl-thieno[2,3-b]pyridine-2-carboxylic acid amide | 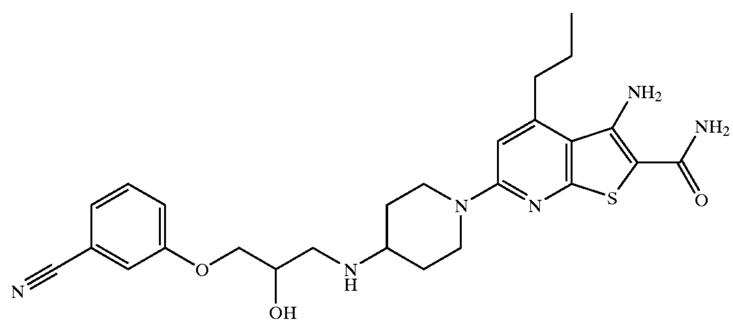 |
| 3-Amino-6-{4-[3-(4-cyano-phenoxy)-2-hydroxy-propylamino]-piperidin-1-yl}-4-propyl-thieno[2,3-b]pyridine-2-carboxylic acid amide | 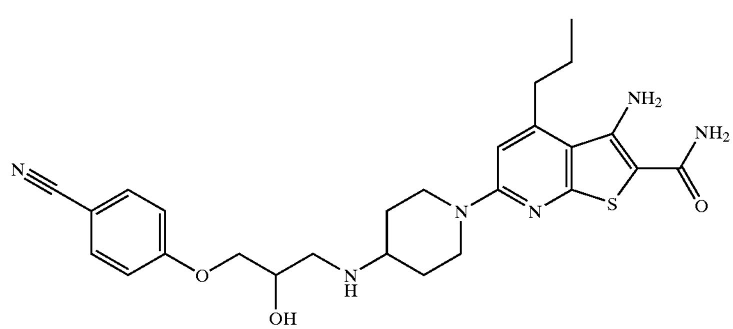 |

| Name | Structure |
|---|---|
| 3-Amino-6-[4-((R)-2-hydroxy-3-phenoxy-propylamino)-piperidin-1-yl]-4-propyl-thieno[2,3-b]pyridine-2-carboxylic acid amide | 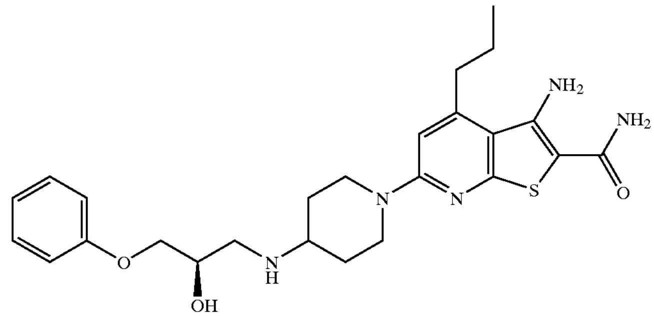 |
| 3-Amino-6-[4-((S)-2-hydroxy-3-phenoxy-propylamino)-piperidin-1-yl]-4-propyl-thieno[2,3-b]pyridine-2-carboxylic acid amide | 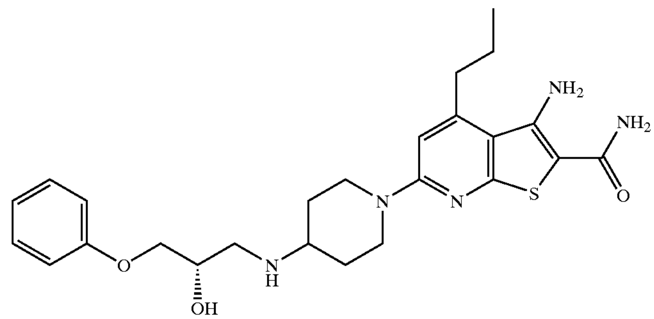 |
| 3-Amino-6-{4-[3-(4-fluoro-phenoxy)-2-hydroxy-propylamino]-piperidin-1-yl}-4-propyl-thieno[2,3-b]pyridine-2-carboxylic acid amide | 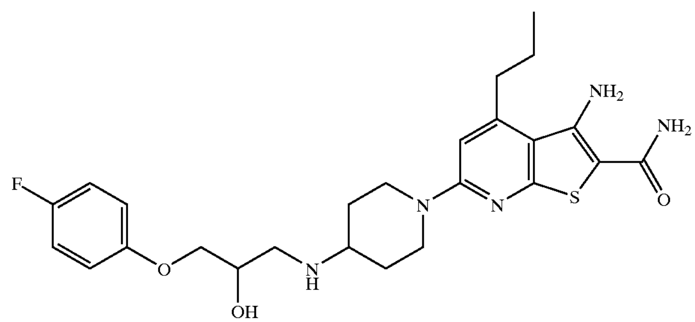 |
| 3-Amino-6-{4-[2-hydroxy-3-(3-methoxy-phenoxy)-propylamino]-piperidin-1-yl}-4-propyl-thieno[2,3-b]pyridine-2-carboxylic acid amide | 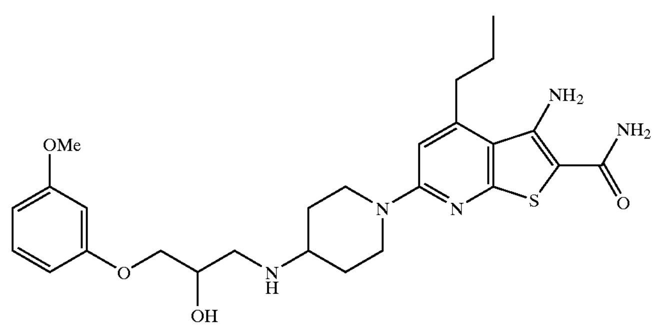 |

-continued

| Name | Structure |
|---|---|
| 3-Amino-6-{4-[2-hydroxy-3-(4-trifluoromethyl-phenoxy)-propylamino]-piperidin-1-yl}-4-propyl-thieno[2,3-b]pyridine-2-carboxylic acid amide | 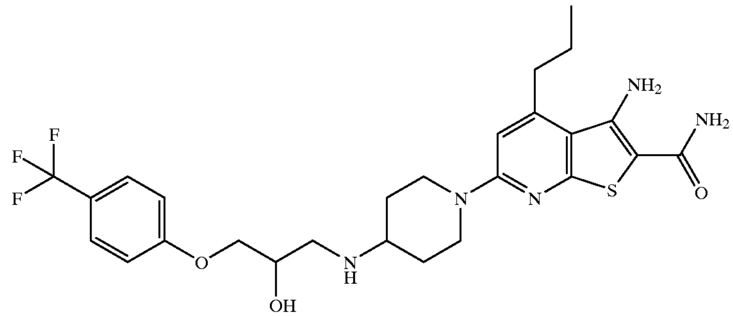 |
| 3-Amino-6-[4-(3-benzyloxy-2-hydroxy-propylamino)-piperidin-1-yl]-4-propyl-thieno[2,3-b]pyridine-2-carboxylic acid amide | 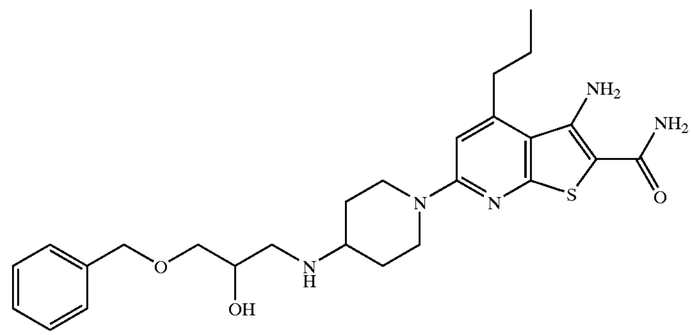 |
| 3-Amino-6-{4-[2-hydroxy-3-(naphthalen-1-yloxy)-propylamino]-piperidin-1-yl}-4-propyl-thieno[2,3-b]pyridine-2-carboxylic acid amide | 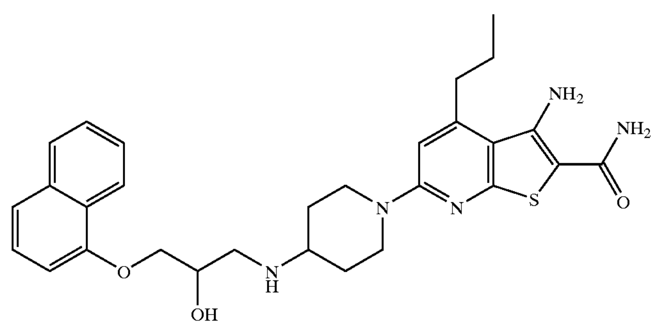 |
| 3-Amino-6-{4-[2-hydroxy-3-(naphthalen-2-yloxy)-propylamino]-piperidin-1-yl}-4-propyl-thieno[2,3-b]pyridine-2-carboxylic acid amide | 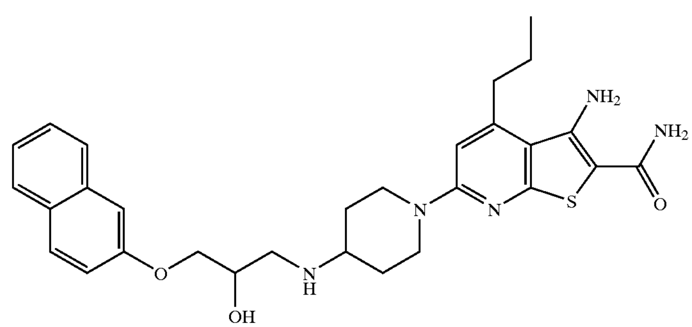 |

| Name | Structure |
|---|---|
| 3-Amino-6-{4-[3-(4-carbamoyl-phenyl)-2-hydroxy-propylamino]-piperidin-1-yl}-4-propyl-thieno[2,3-b]pyridine-2-carboxylic acid amide | 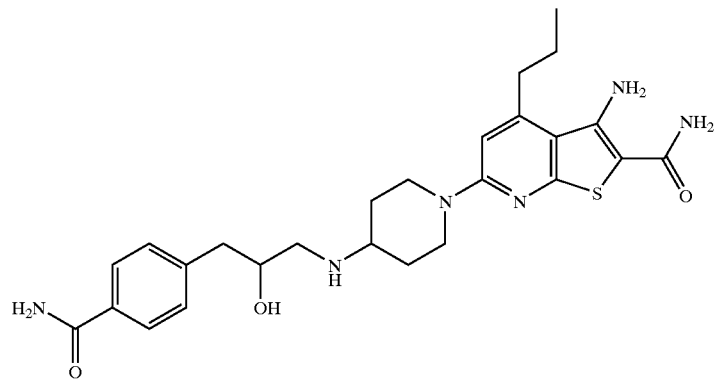 |
| 3-Amino-6-{4-[3-(3-carbamoyl-phenyl)-2-hydroxy-propylamino]-piperidin-1-yl}-4-propyl-thieno[2,3-b]pyridine-2-carboxylic acid amide | 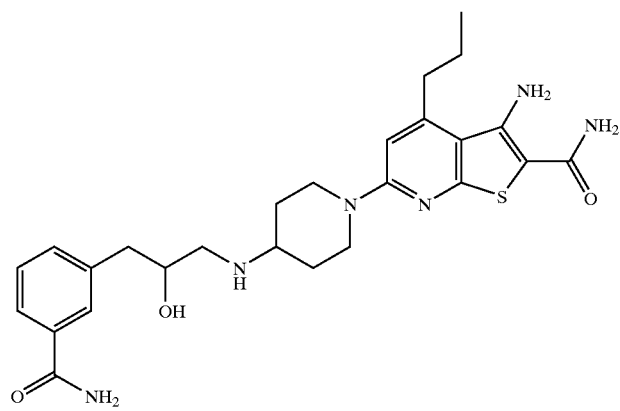 |
| 3-Amino-6-[4-(2-hydroxy-4-phenyl-butylamino)-piperidin-1-yl]-4-propyl-thieno[2,3-b]pyridine-2-carboxylic acid amide | 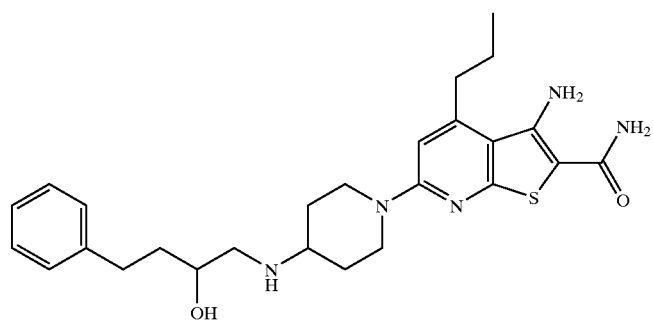 |
| 3-Amino-6-[4-(2-hydroxy-3-phenylamino-propylamino)-piperidin-1-yl]-4-propyl-thieno[2,3-b]pyridine-2-carboxylic acid amide | 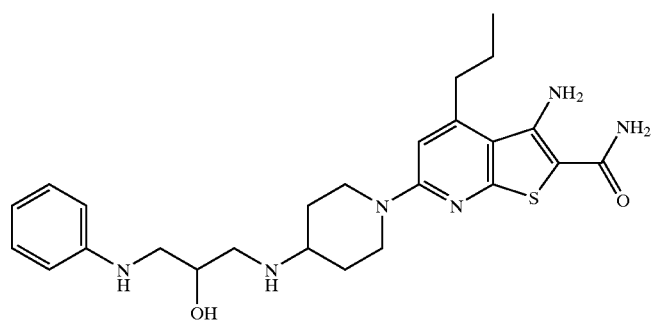 |

-continued

| Name | Structure |
|---|---|
| 3-Amino-6-{4-[3-(3-carbamoyl-phenylamino)-2-hydroxy-propylamino]-piperidin-1-yl}-4-propyl-thieno[2,3-b]pyridine-2-carboxylic acid amide | 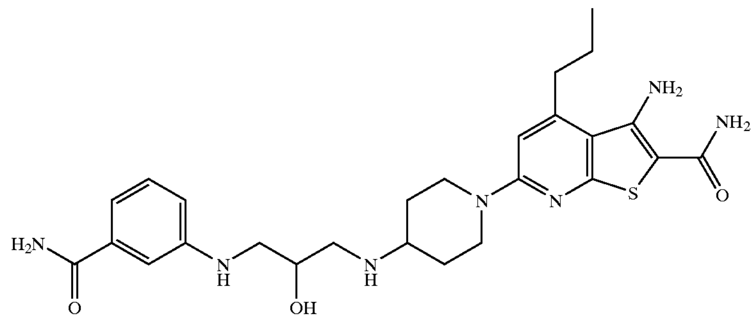 |
| 3-Amino-6-[4-(2-hydroxy-2-phenylcarbamoyl-ethylamino)-piperidin-1-yl]-4-propyl-thieno[2,3-b]pyridine-2-carboxylic acid amide | 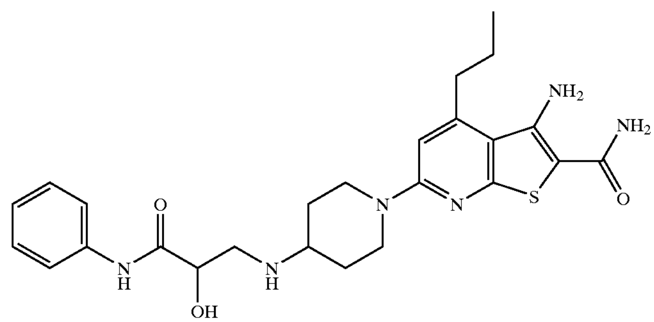 |
| 3-Amino-6-[4-(2-benzylcarbamoyl-2-hydroxy-ethylamino)-piperidin-1-yl]-4-propyl-thieno[2,3-b]pyridine-2-carboxylic acid amide | 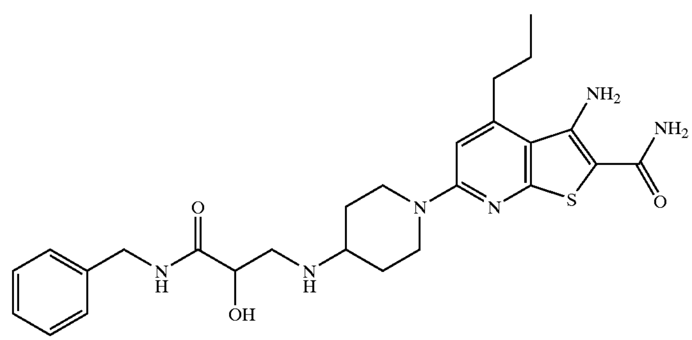 |
| 3-Amino-6-(4-{[(3-carbamoyl-phenylcarbamoyl)-methyl]-amino}-piperidin-1-yl)-4-propyl-thieno[2,3-b]pyridine-2-carboxylic acid amide | 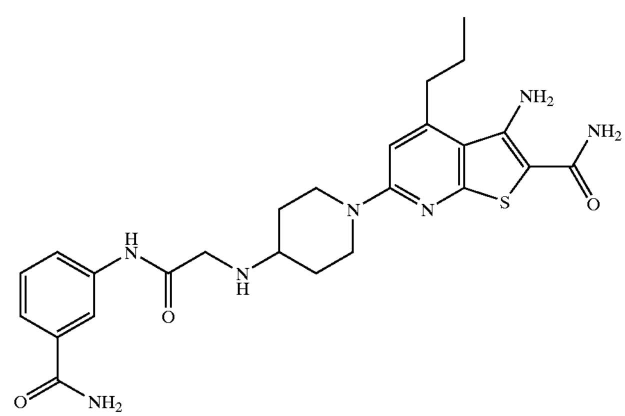 |

| Name | Structure |
|---|---|
| 3-Amino-6-(4-{[(2-carbamoyl-phenylcarbamoyl)-methyl]-amino}-piperidin-1-yl)-4-propyl-thieno[2,3-b]pyridine-2-carboxylic acid amide | 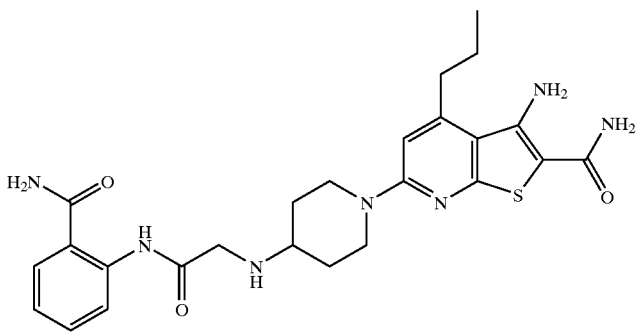 |
| 3-Amino-6-(4-{[(2-hydroxy-ethylcarbamoyl)-methyl]-amino}-piperidin-1-yl)-4-propyl-thieno[2,3-b]pyridine-2-carboxylic acid amide | 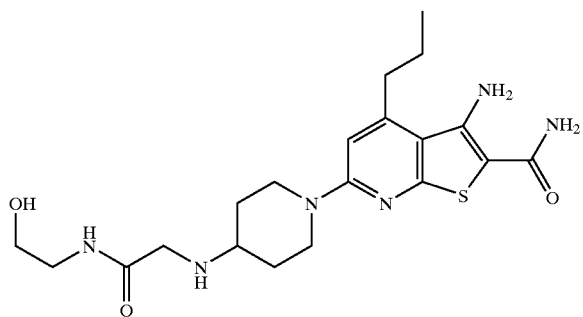 |
| 3-Amino-6-{4-[2-(4-hydroxy-piperidin-1-yl)-2-oxo-ethylamino]-piperidin-1-yl}-4-propyl-thieno[2,3-b]pyridine-2-carboxylic acid amide | 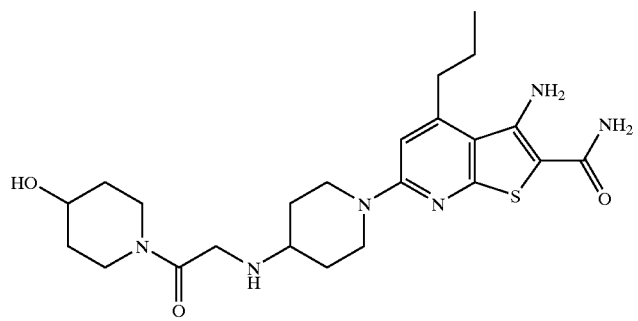 |
| 3-Amino-6-{4-[2-(4-hydroxy-piperidin-1-yl)-2-oxo-ethylamino]-piperidin-1-yl}-4-propyl-thieno[2,3-b]pyridine-2-carboxylic acid amide | 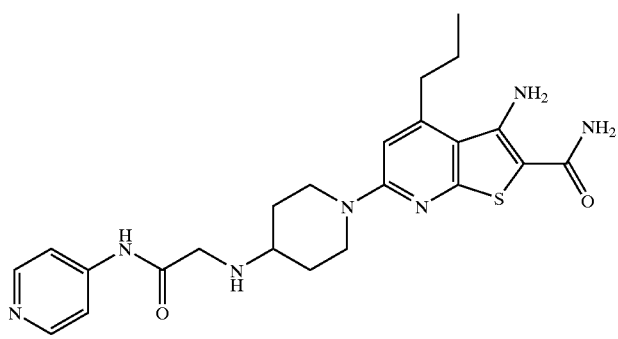 |

-continued

| Name | Structure |
|---|---|
| 3-Amino-4-propyl-6-{4-[(quinolin-3-ylcarbamoylmethyl)-amino]-piperidin-1-yl}-thieno[2,3-b]pyridine-2-carboxylic acid amide | 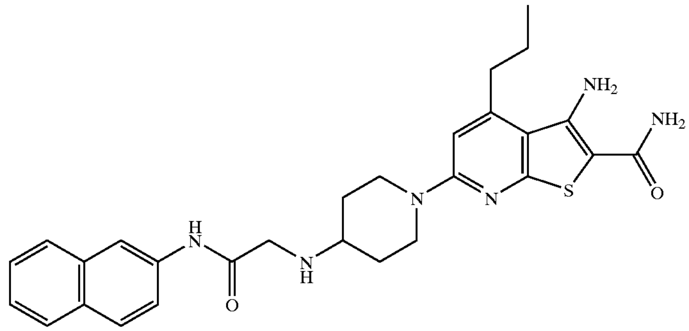 |
| 3-Amino-6-{4-[(naphthalen-1-ylcarbamoylmethyl)-amino]-piperidin-1-yl}-4-propyl-thieno[2,3-b]pyridine-2-carboxylic acid amide | 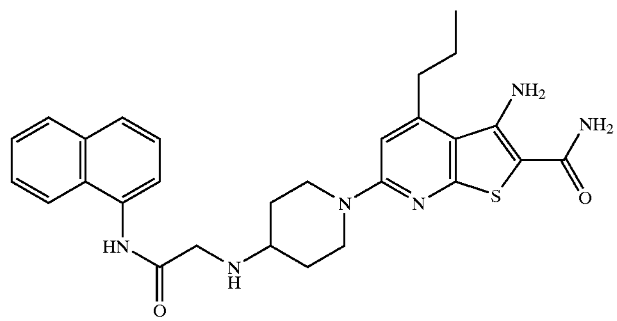 |
| 3-Amino-6-(4-{[(carbamoylmethyl-carbamoyl)-methyl]-amino}-piperidin-1-yl)-4-propyl-thieno[2,3-b]pyridine-2-carboxylic acid amide | 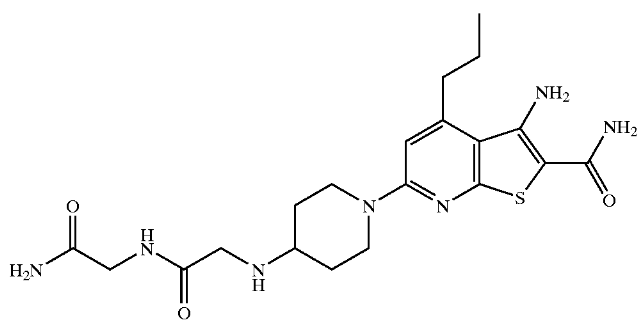 |
| 3-Amino-6-[4-(2-hydroxy-benzylamino)-piperidin-1-yl]-4-propyl-thieno[2,3-b]pyridine-2-carboxylic acid amide | | and pharmaceutically acceptable salts, esters, tautomers, individual isomers, and mixtures of isomers thereof.

Another embodiment of the invention provides the compounds of Table V:

3-Amino-6-(4-amino-piperidin-1-yl)-4-(4-methanesulfonyl-phenyl)-thieno[2,3-b]pyridine-2-carboxylic acid amide
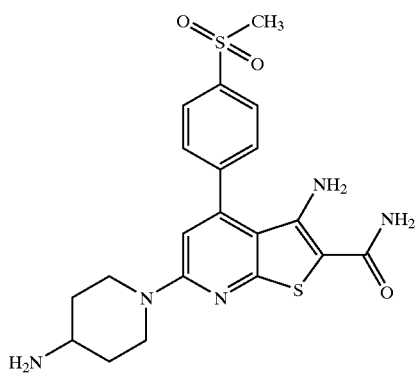
3-Amino-6-(4-amino-piperidin-1-yl)-4-(4-nitro-phenyl)-thieno[2,3-b]pyridine-2-carboxylic acid amide
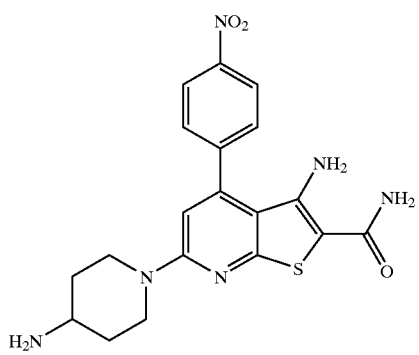
3-Amino-6-(4-amino-piperidin-1-yl)-4-phenyl-thieno[2,3-b]pyridine-2-carboxylic acid amide
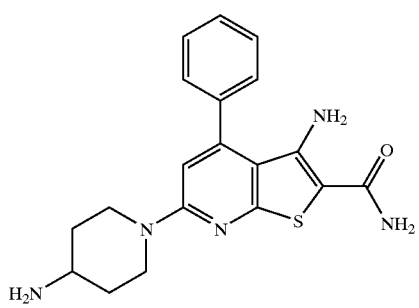
3-Amino-6-(4-amino-piperidin-1-yl)-4-(4-fluoro-phenyl)-thieno[2,3-b]pyridine-2-carboxylic acid amide
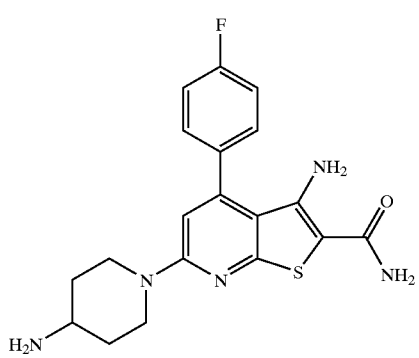

-continued
3-Amino-6-(4-amino-piperidin-1-yl)-4-(4-methoxy-phenyl)-thieno[2,3-b]pyridine-2-carboxylic acid amide
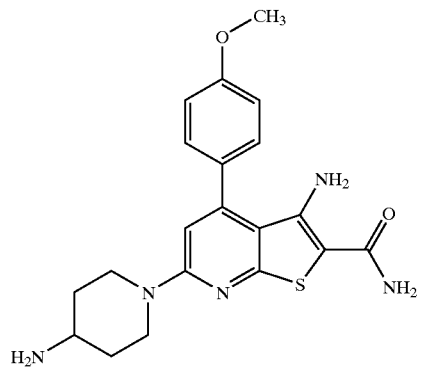
3-Amino-6-(4-amino-piperidin-1-yl)-4-(3-nitro-phenyl)-thieno[2,3-b]pyridine-2-carboxylic acid amide
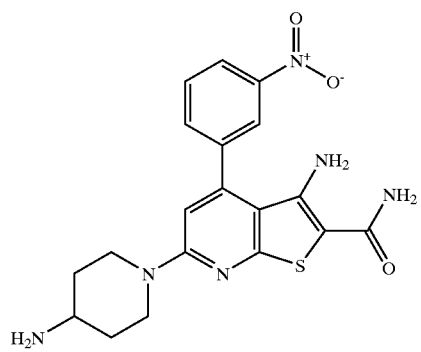
3-Amino-6-(4-amino-piperidin-1-yl)-4-(3-fluoro-phenyl)-thieno[2,3-b]pyridine-2-carboxylic acid amide
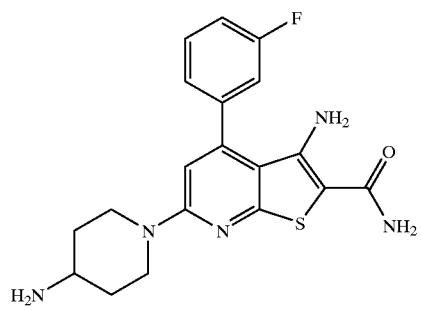
4-[3-Amino-6-(4-amino-piperidin-1-yl)-2-carbamoyl-thieno[2,3-b]pyridin-4-yl]-benzoic acid methyl ester
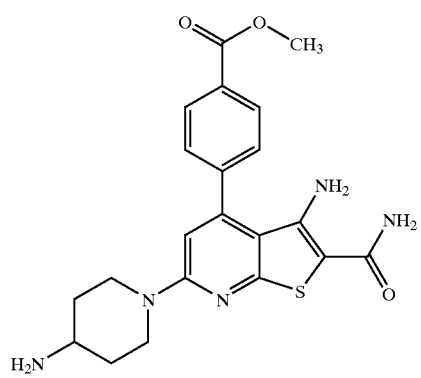

| | |
|---|---|
| 3-Amino-6-(4-amino-piperidin-1-yl)-4-(2,5-difluoro-phenyl)-thieno[2,3-b]pyridine-2-carboxylic acid amide | 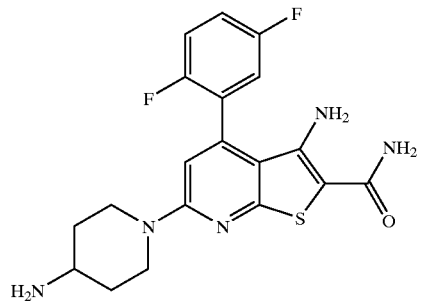 |
| 3-Amino-6-(4-amino-piperidin-1-yl)-4-(2,4-difluoro-phenyl)-thieno[2,3-b]pyridine-2-carboxylic acid amide | 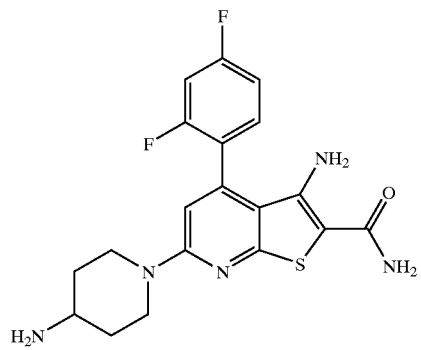 |
| 3-Amino-6-(4-amino-piperidin-1-yl)-4-(3,4-difluoro-phenyl)-thieno[2,3-b]pyridine-2-carboxylic acid amide | 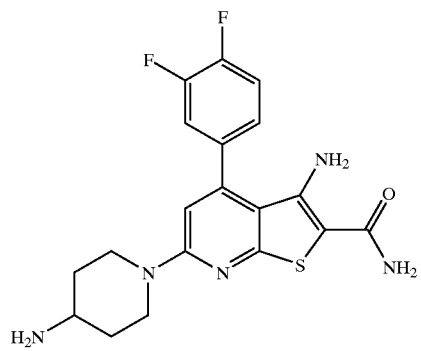 |
| 3-Amino-6-(4-amino-piperidin-1-yl)-4-(4-cyano-3-fluoro-phenyl)-thieno[2,3-b]pyridine-2-carboxylic acid amide | 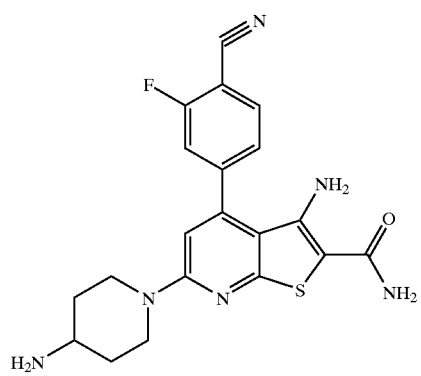 |

| | |
|---|---|
| 3-[3-Amino-6-(4-amino-piperidin-1-yl)-2-carbamoyl-thieno[2,3-b]pyridin-4-yl]-benzoic acid methyl ester | 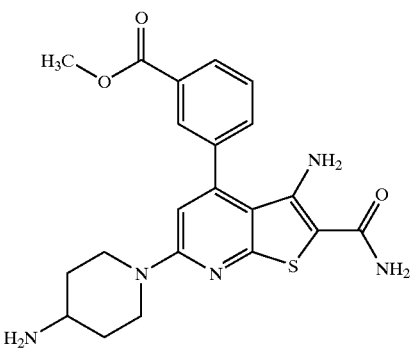 |
| 4-[3-Amino-6-(4-amino-piperidin-1-yl)-2-carbamoyl-thieno[2,3-b]pyridin-4-yl]-benzoic acid ethyl ester | 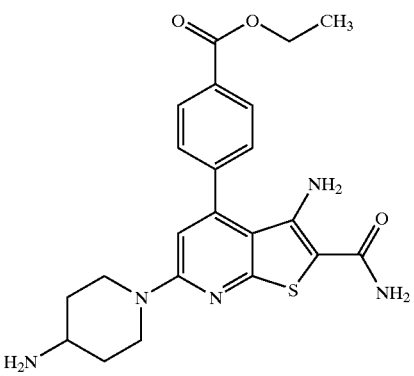 |
| 3-Amino-6-(4-hydroxy-piperidin-1-yl)-4-(4-methanesulfonyl-phenyl)-thieno[2,3-b]pyridine-2-carboxylic acid amide | 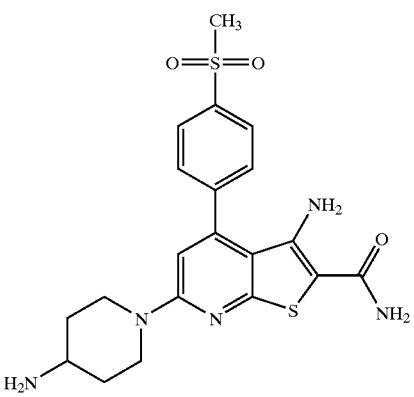 |
| 3-Amino-4-(4-cyano-3-fluoro-phenyl)-6-(4-hydroxy-piperidin-1-yl)-thieno[2,3-b]pyridine-2-carboxylic acid amide | 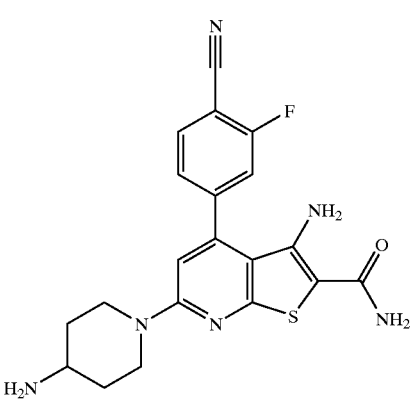 | and pharmaceutically acceptable salts, esters, tautomers, individual isomers, and mixtures of isomers thereof.

Another embodiment of the invention provides for Table VI:

| | |
|---|---|
| 3-Amino-6-(4-amino-piperidin-1-yl)-4-((E)-styryl)-thieno[2,3-b]pyridine-2-carboxylic acid amide | 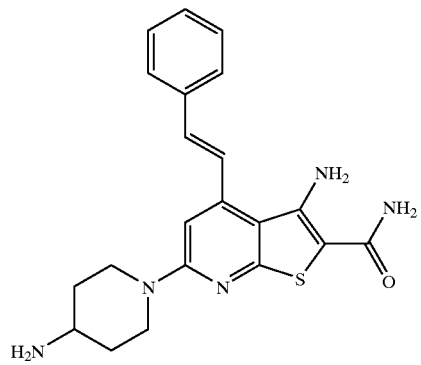 |
| 3-Amino-6-(4-amino-piperidin-1-yl)-4-[(E)-2-(4-chloro-phenyl)-vinyl]-thieno[2,3-b]pyridine-2-carboxylic acid amide | 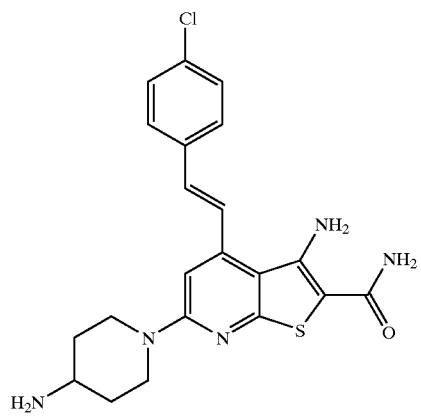 |
| 3-Amino-6-(4-amino-piperidin-1-yl)-4-[(E)-2-(2-chloro-phenyl)-vinyl]-thieno[2,3-b]pyridine-2-carboxylic acid amide | 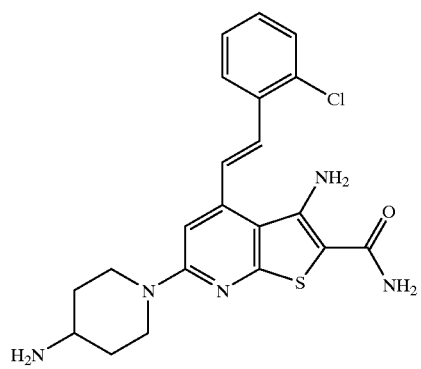 |
| 3-Amino-6-(4-amino-piperidin-1-yl)-4-[(E)-2-(4-methoxy-phenyl)-vinyl]-thieno[2,3-b]pyridine-2-carboxylic acid amide | 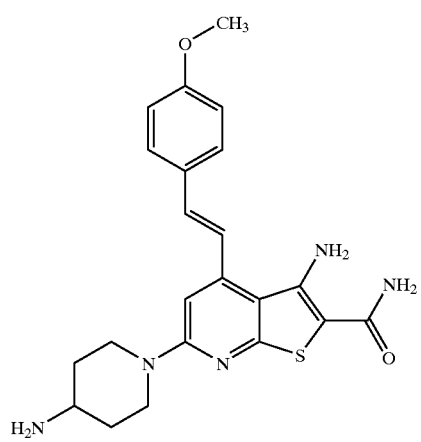 |

-continued

3-Amino-6-(4-amino-piperidin-1-yl)-4-[(E)-2-(4-fluoro-phenyl)-vinyl]-thieno[2,3-b]pyridine-2-carboxylic acid amide

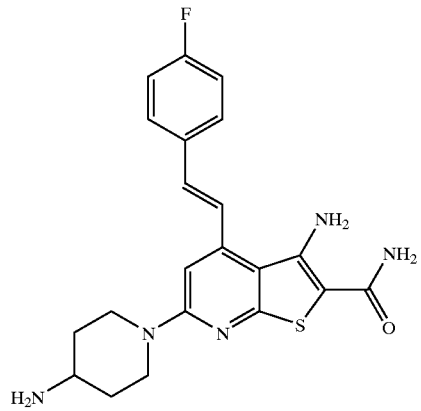

3-Amino-6-(4-amino-piperidin-1-yl)-4-[(E)-2-(4-trifluoromethyl-phenyl)-vinyl]-thieno[2,3-b]pyridine-2-carboxylic acid amide

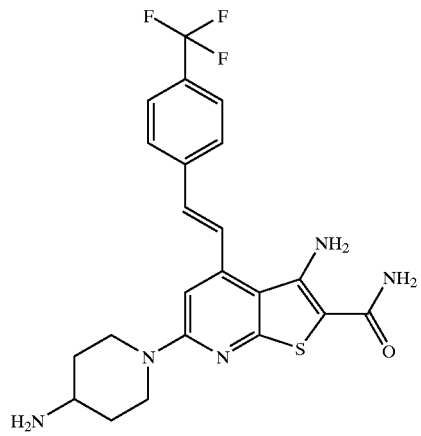

3-Amino-6-(4-amino-piperidin-1-yl)-4-((E)-2-p-tolyl-vinyl)-thieno[2,3-b]pyridine-2-carboxylic acid amide

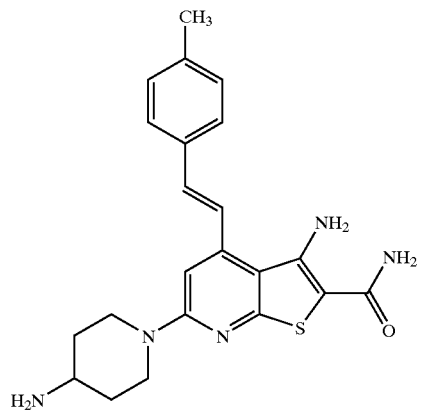

3-Amino-6-(4-amino-piperidin-1-yl)-4-[(E)-2-(2-fluoro-phenyl)-vinyl]-thieno[2,3-b]pyridine-2-carboxylic acid amide

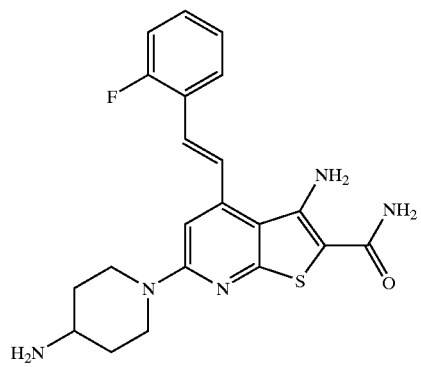

| | |
|---|---|
| 3-Amino-6-(4-amino-piperidin-1-yl)-4-((E)-2-m-tolyl-vinyl)-thieno[2,3-b]pyridine-2-carboxylic acid amide | 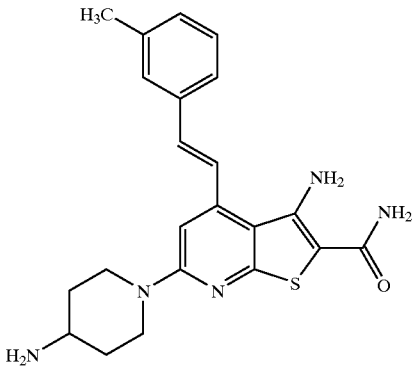 |
| 3-Amino-6-(4-amino-piperidin-1-yl)-4-[(E)-2-(3-chloro-phenyl)-vinyl]-thieno[2,3-b]pyridine-2-carboxylic acid amide | 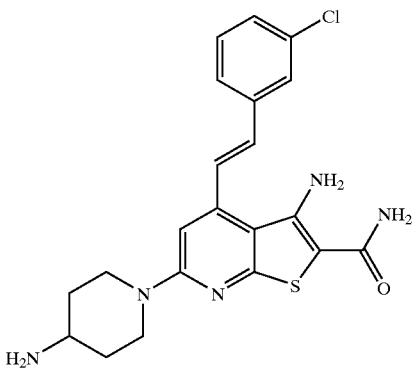 |
| 3-Amino-6-(4-amino-piperidin-1-yl)-4-[(E)-2-(3-methoxy-phenyl)-vinyl]-thieno[2,3-b]pyridine-2-carboxylic acid amide | 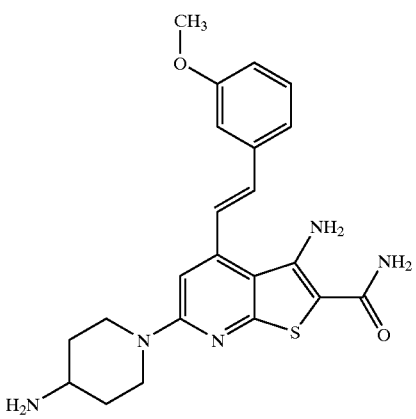 |
| 3-Amino-6-(4-amino-piperidin-1-yl)-4-((E)-2-pyridin-4-yl-vinyl)-thieno[2,3-b]pyridine-2-carboxylic acid amide | 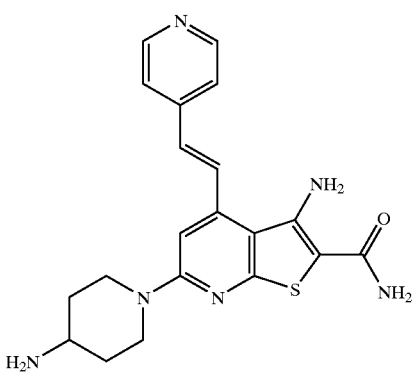 |

| | |
|---|---|
| 4-{(E)-2-[3-Amino-6-(4-amino-piperidin-1-yl)-2-carbamoyl-thieno[2,3-b]pyridin-4-yl]-vinyl}-benzoic acid methyl ester | 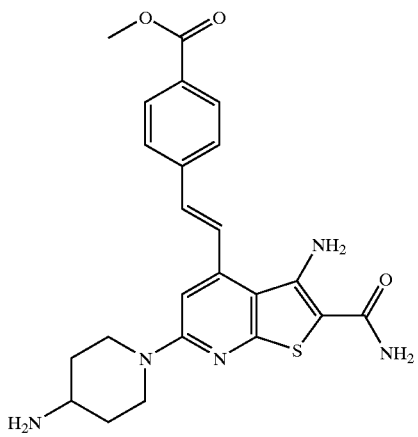 | and pharmaceutically acceptable salts, esters, tautomers, individual isomers, and mixtures of isomers thereof.

Another embodiment of the invention provides for Table VII:

| | |
|---|---|
| 3-Amino-6-(4-amino-piperidin-1-yl)-4-methylsulfanyl-thieno[2,3-b]pyridine-2-carboxylic acid amide | 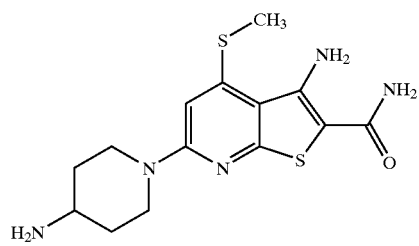 |
| 3-Amino-6-(4-hydroxy-piperidin-1-yl)-4-methylsulfanyl-thieno[2,3-b]pyridine-2-carboxylic acid amide | 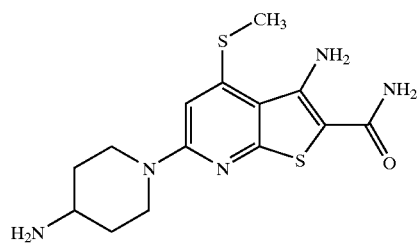 |
| 3-Amino-6-(4-methanesulfonylamino-piperidin-1-yl)-4-methylsulfanyl-thieno[2,3-b]pyridine-2-carboxylic acid amide | 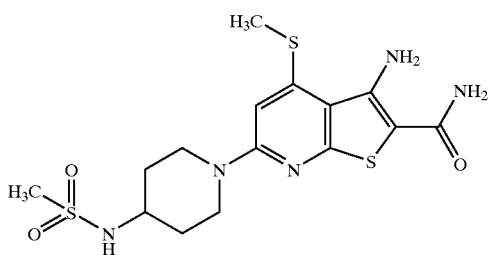 |

| | |
|---|---|
| 3-Amino-6-[4-(2-hydroxy-2-naphthalen-2-yl-ethylamino)-piperidin-1-yl]-4-methylsulfanyl-thieno[2,3-b]pyridine-2-carboxylic acid amide | 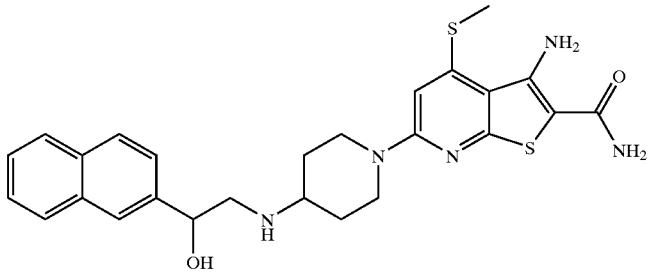 |
| 3-Amino-6-(4-methylamino-piperidin-1-yl)-4-methylsulfanyl-thieno[2,3-b]pyridine-2-carboxylic acid amide | 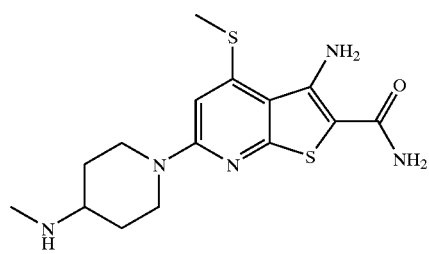 | and pharmaceutically acceptable salts, esters, tautomers, individual isomers, and mixtures of isomers thereof.

Another embodiment of the invention provides for the compounds of Table VIII

| | |
|---|---|
| 3-Amino-6-(4-amino-piperidin-1-yl)-4-ethoxy-thieno[2,3-b]pyridine-2-carboxylic acid amide | 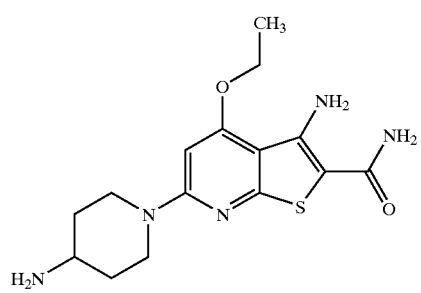 |
| 3-Amino-6-(4-amino-piperidin-1-yl)-4-isopropoxy-thieno[2,3-b]pyridine-2-carboxylic acid amide | 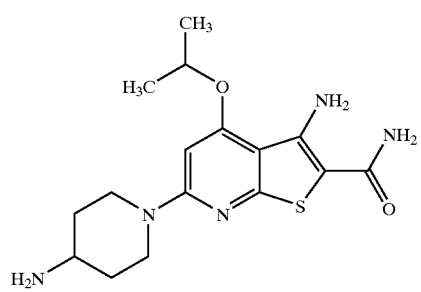 |
| 3-Amino-4-ethoxy-6-(4-hydroxy-piperidin-1-yl)-thieno[2,3-b]pyridine-2-carboxylic acid amide | 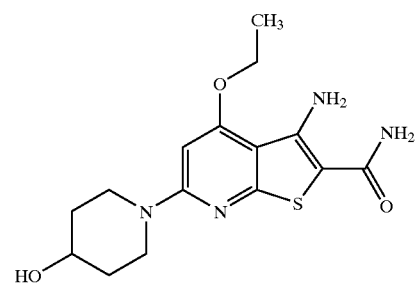 |

-continued

3-Amino-6-(4-hydroxy-piperidin-1-yl)-4-isopropoxy-thieno[2,3-b]pyridine-2-carboxylic acid amide

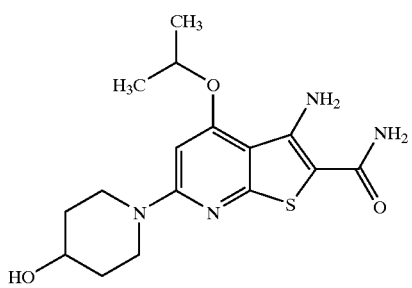

3-Amino-6-(1,1-dioxo-thiomorpholin-4-yl)-4-ethoxy-thieno[2,3-b]pyridine-2-carboxylic acid amide

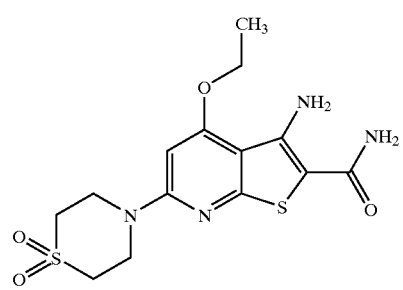

3-Amino-6-(4-amino-4-methyl-piperidin-1-yl)-4-ethoxy-thieno[2,3-b]pyridine-2-carboxylic acid amide

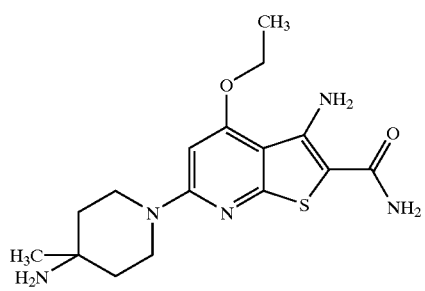

3-Amino-6-(4-methylamino-piperidin-1-yl)-4-(2,2,2-trifluoro-ethoxy)-thieno[2,3-b]pyridine-2-carboxylic acid amide

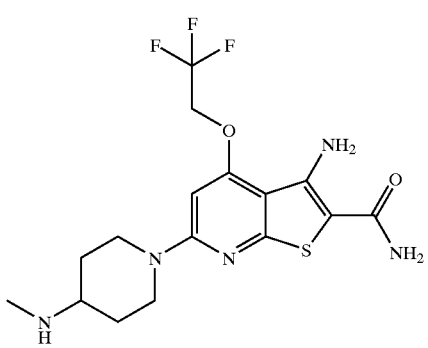

and pharmaceutically acceptable salts, esters, tautomers, individual isomers, and mixtures of isomers thereof.

Another embodiment of the invention provides for the compounds of Table IX:

3-Amino-6-(4-amino-piperidin-1-yl)-4-trifluoromethyl-thieno[2,3-b]pyridine-2-carboxylic acid amide

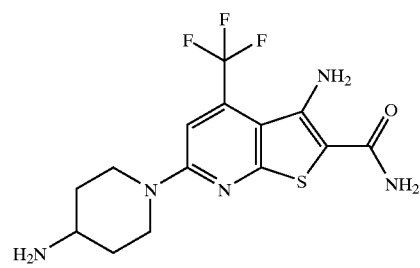

3-Amino-6-piperazin-1-yl-4-trifluoromethyl-thieno[2,3-b]pyridine-2-carboxylic acid amide

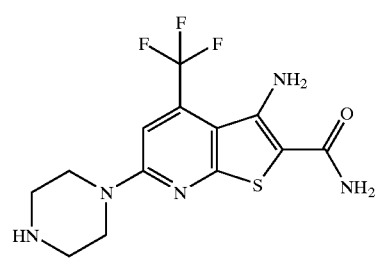

3-Amino-6-(4-hydroxy-piperidin-1-yl)-4-trifluoromethyl-thieno[2,3-b]pyridine-2-carboxylic acid amide

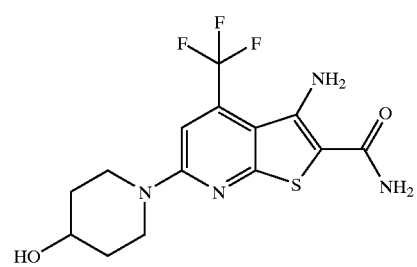

3-Amino-6-(4-methylamino-piperidin-1-yl)-4-trifluoromethyl-thieno[2,3-b]pyridine-2-carboxylic acid amide

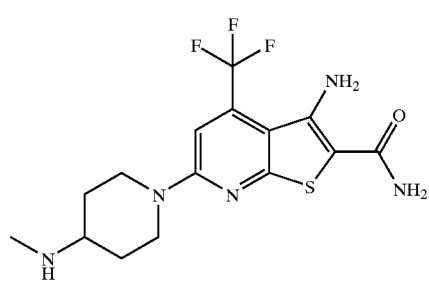

3-Amino-4-difluoromethyl-6-(4-methylamino-piperidin-1-yl)-thieno[2,3-b]pyridine-2-carboxylic acid amide

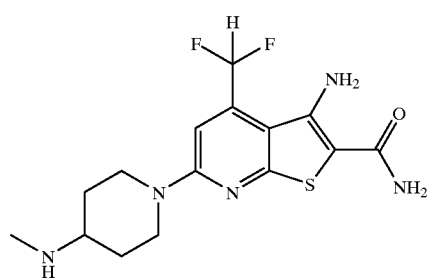

3-Amino-6-[4-(2-hydroxy-ethylamino)-piperidin-1-yl]-4-trifluoromethyl-thieno[2,3-b]pyridine-2-carboxylic acid amide

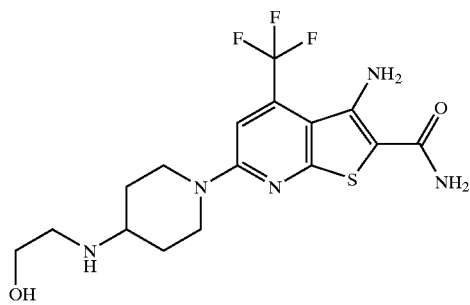

and pharmaceutically acceptable salts, esters, tautomers, individual isomers, and mixtures of isomers thereof.

Another embodiment of the invention provides for the compounds of Table X

3-Amino-6-{4-[2-(4-benzylcarbamoyl-phenyl)-2-hydroxy-ethylamino]-piperidin-1-yl}-4-trifluoromethyl-thieno[2,3-b]pyridine-2-carboxylic acid amide

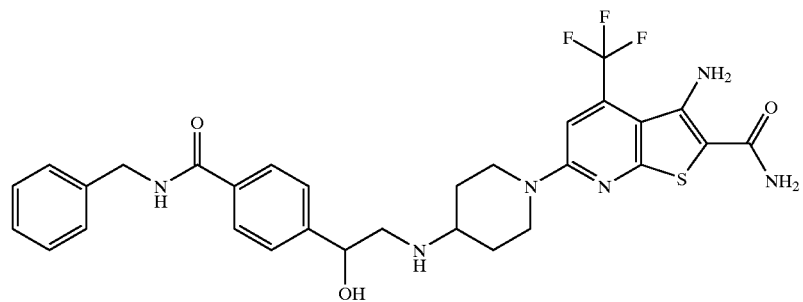

3-Amino-6-[4-(2-hydroxy-2-naphthalen-2-yl-ethylamino)-piperidin-1-yl]-4-trifluoromethyl-thieno[2,3-b]pyridine-2-carboxylic acid amide

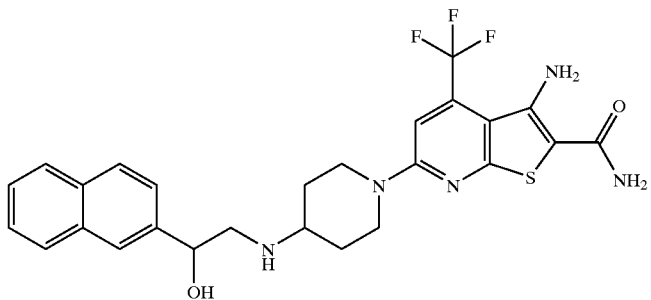

3-Amino-6-{4-[2-(4-cyano-phenyl)-2-hydroxy-ethylamino]-piperidin-1-yl}-4-trifluoromethyl-thieno[2,3-b]pyridine-2-carboxylic acid amide

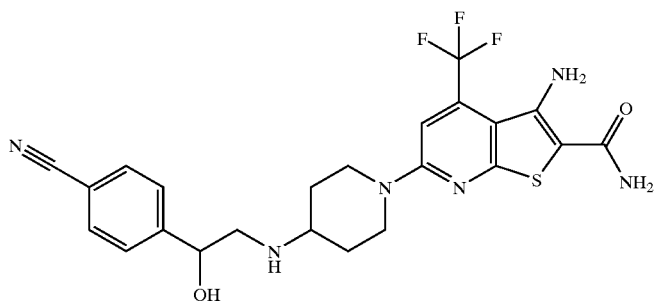

-continued

| | |
|---|---|
| 3-Amino-6-{4-[2-hydroxy-2-(4-methanesulfonyl-phenyl)-ethylamino]-piperidin-1-yl}-4-trifluoromethyl-thieno[2,3-b]pyridine-2-carboxylic acid amide | 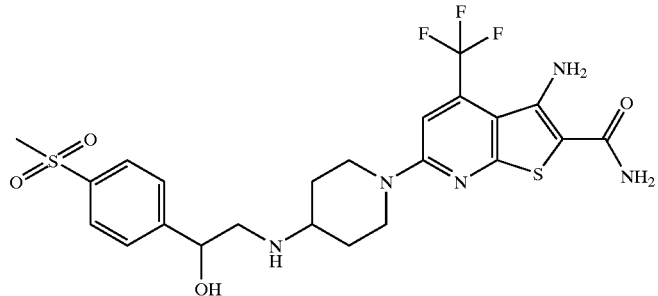 |
| 3-Amino-6-[4-((S)-2-hydroxy-2-phenyl-ethylamino)-piperidin-1-yl]-4-trifluoromethyl-thieno[2,3-b]pyridine-2-carboxylic acid amide | 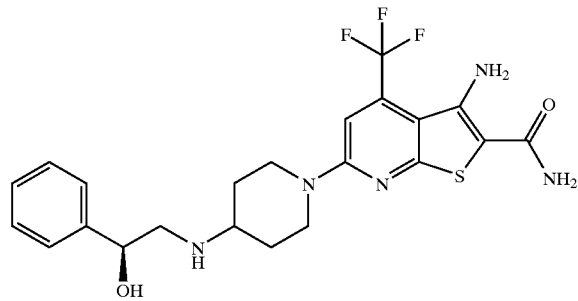 |
| 3-Amino-6-[4-((R)-2-hydroxy-2-phenyl-ethylamino)-piperidin-1-yl]-4-trifluoromethyl-thieno[2,3-b]pyridine-2-carboxylic acid amide | 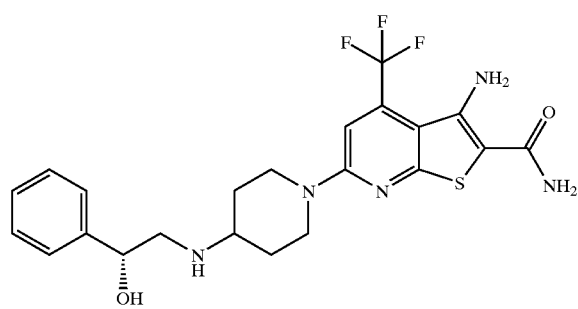 |
| 3-Amino-6-{4-[2-(4-fluoro-phenyl)-2-hydroxy-ethylamino]-piperidin-1-yl}-4-trifluoromethyl-thieno[2,3-b]pyridine-2-carboxylic acid amide | 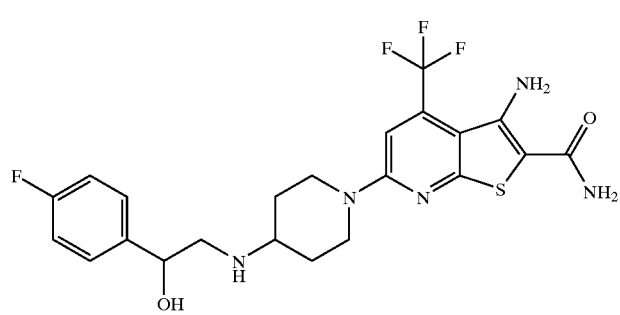 |
| 3-Amino-6-{4-[2-(2-fluoro-phenyl)-2-hydroxy-ethylamino]-piperidin-1-yl}-4-trifluoromethyl-thieno[2,3-b]pyridine-2-carboxylic acid amide | 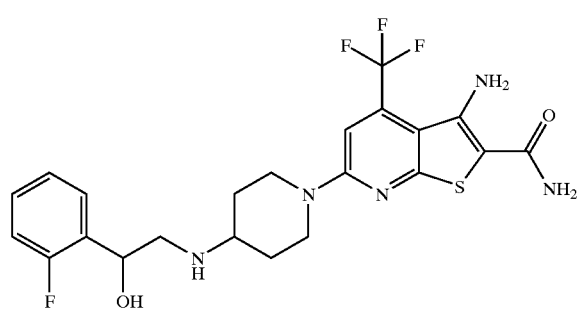 |

-continued

3-Amino-6-{4-[2-(3,4-difluoro-phenyl)-2-hydroxy-ethylamino]-piperidin-1-yl}-4-trifluoromethyl-thieno[2,3-b]pyridine-2-carboxylic acid amide

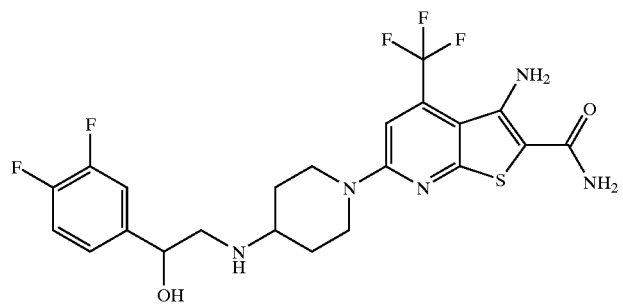

3-Amino-6-{4-[2-(4-difluoromethoxy-phenyl)-2-hydroxy-ethylamino]-piperidin-1-yl}-4-trifluoromethyl-thieno[2,3-b]pyridine-2-carboxylic acid amide

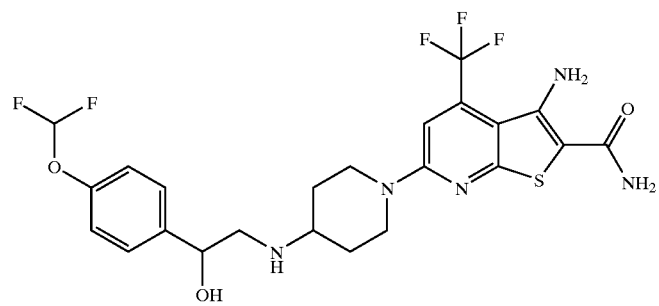

3-Amino-6-{4-[2-hydroxy-2-(4-trifluoromethoxy-phenyl)-ethylamino]-piperidin-1-yl}-4-trifluoromethyl-thieno[2,3-b]pyridine-2-carboxylic acid amide

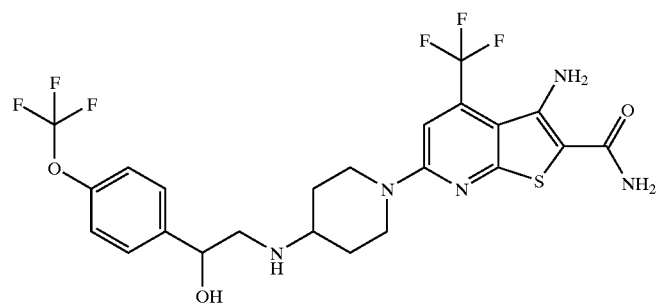

3-Amino-6-{4-[2-(3,5-difluoro-phenyl)-2-hydroxy-ethylamino]-piperidin-1-yl}-4-trifluoromethyl-thieno[2,3-b]pyridine-2-carboxylic acid amide

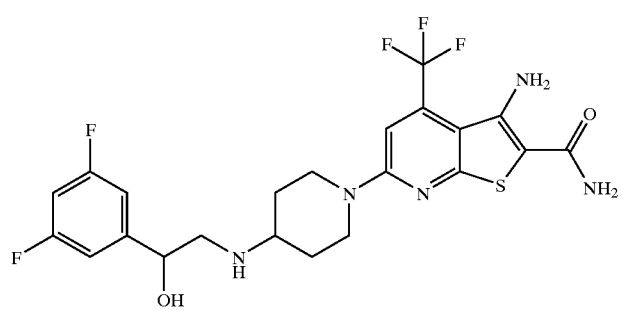

3-Amino-6-{4-[2-(3-fluoro-phenyl)-2-hydroxy-ethylamino]-piperidin-1-yl}-4-trifluoromethyl-thieno[2,3-b]pyridine-2-carboxylic acid amide

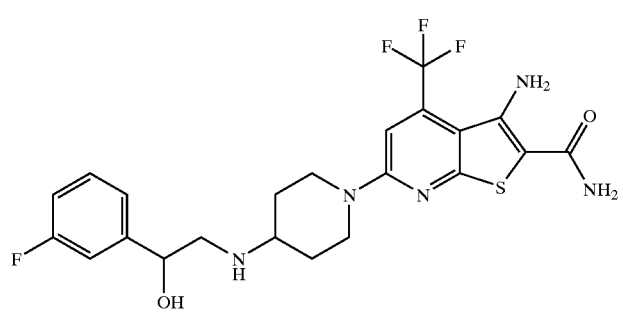

-continued

3-Amino-6-{4-[2-hydroxy-2-(3,4,5-trifluoro-phenyl)-ethylamino]-piperidrn-1-yl}-4-trifluoromethyl-thieno[2,3-b]pyridine-2-carboxylic acid amide

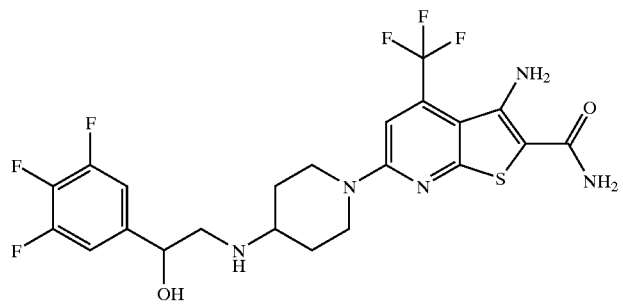

3-Amino-6-{4-[2-hydroxy-2-(4-hydroxy-phenyl)-ethylamino]-piperidin-1-yl}-4-trifluoromethyl-thieno[2,3-b]pyridine-2-carboxylic acid amide

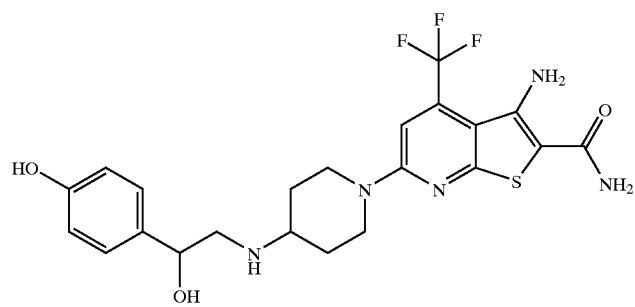

3-Amino-6-{4-[2-(3,4-dimethoxy-phenyl)-2-hydroxy-ethylamino]-piperidin-1-yl}-4-trifluoromethyl-thieno[2,3-b]pyridine-2-carboxylic acid amide

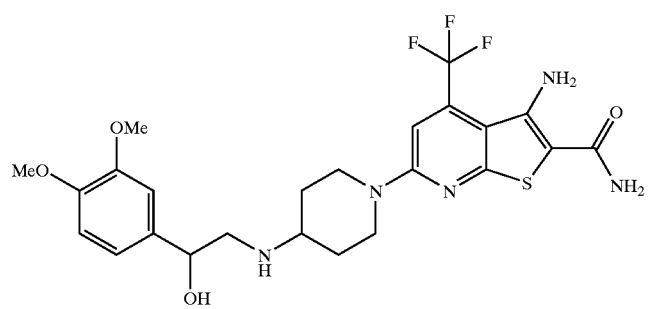

3-Amino-6-[4-(2-benzo[1,3]dioxol-5-yl-2-hydroxy-ethylamino)-piperidin-1-yl]-4-trifluoromethyl-thieno[2,3-b]pyridine-2-carboxylic acid amide

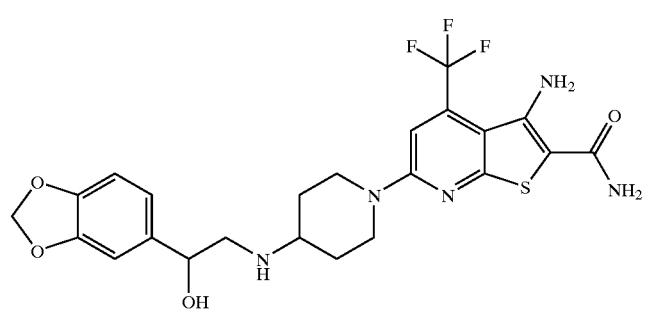

3-Amino-6-[4-(2-benzo[1,3]dioxol-4-yl-2-hydroxy-ethylamino)-piperidin-1-yl]-4-trifluoromethyl-thieno[2,3-b]pyridine-2-carboxylic acid amide

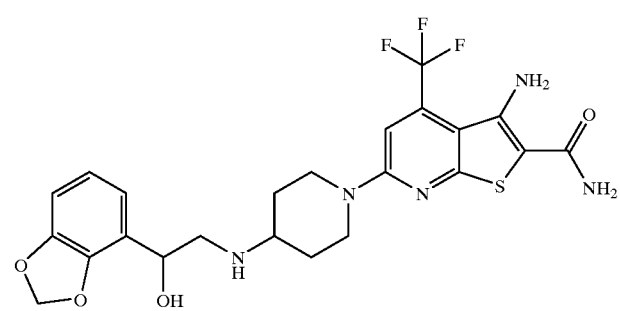

-continued

| | |
|---|---|
| 3-Amino-6-{4-[2-(2,2-difluoro-benzo[1,3]dioxol-5-yl)-2-hydroxy-ethylamino]-piperidin-1-yl}-4-trifluoromethyl-thieno[2,3-b]pyridine-2-carboxylic acid amide | 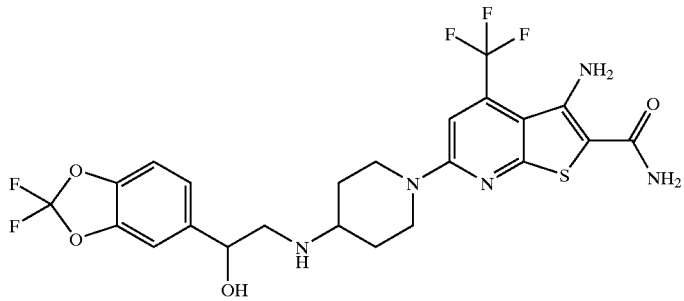 |
| 3-Amino-6-{4-[2-(4-benzyloxy-phenyl)-2-hydroxy-ethylamino]-piperidin-1-yl}-4-trifluoromethyl-thieno[2,3-b]pyridine-2-carboxylic acid amide | 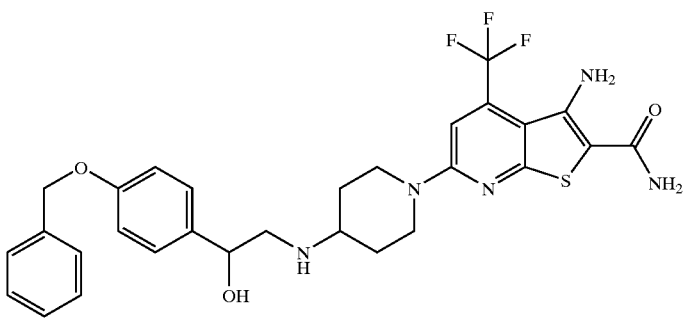 |
| 3-Amino-6-{4-[2-hydroxy-2-(4-morpholin-4-yl-phenyl)-ethylamino]-thieno[2,3-b]pyridine-2-carboxylic acid amide | 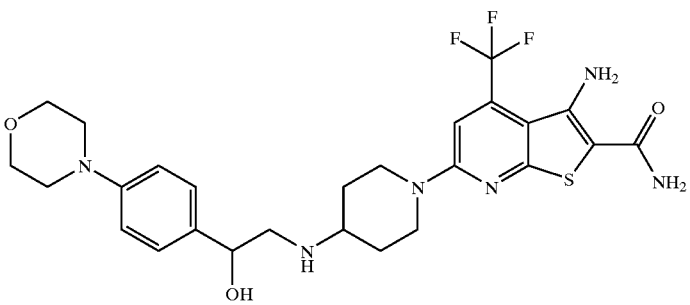 |
| 3-Amino-6-[4-(2-biphenyl-4-yl-2-hydroxy-ethylamino)-piperidin-1-yl]-4-trifluoromethyl-thieno[2,3-b]pyridine-2-carboxylic acid amide | 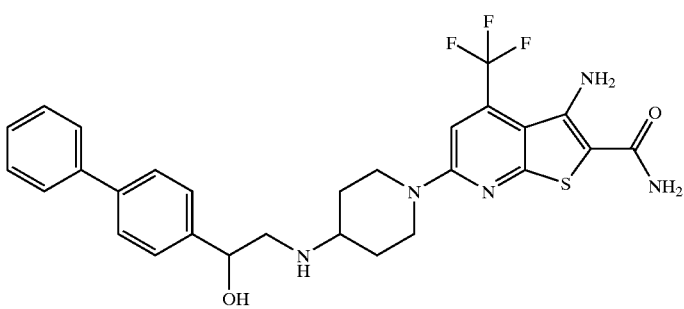 |
| 3-Amino-6-{4-[2-hydroxy-2-(4-pyridin-2-yl-phenyl)-ethylamino]-piperidin-1-yl}-4-trifluoromethyl-thieno[2,3-b]pyridine-2-carboxylic acid amide | 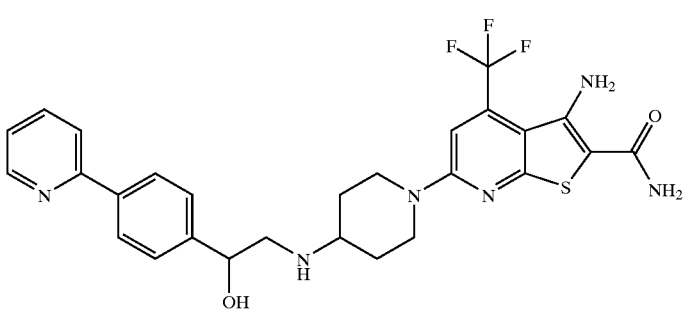 |

-continued

3-Amino-6-{4-[2-hydroxy-2-(4-pyridin-3-yl-phenyl)-ethylamino]-piperidin-1-yl}-4-trifluoromethyl-thieno[2,3-b]pyridine-2-carboxylic acid amide

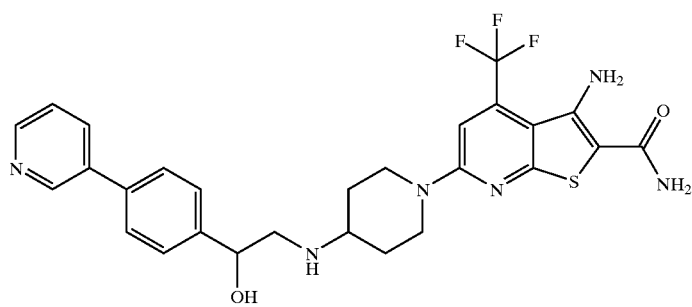

3-Amino-6-{4-[2-hydroxy-2-(4-pyridin-4-yl-phenyl)-ethylamino]-piperidin-1-yl}-4-trifluoromethyl-thieno[2,3-b]pyridine-2-carboxylic acid amide

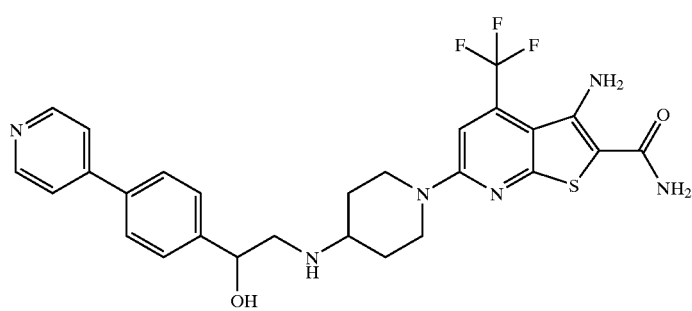

3-Amino-6-{4-[2-hydroxy-2-(4-pyrazin-2-yl-phenyl)-ethylamino]-piperidin-1-yl}-4-trifluoromethyl-thieno[2,3-b]pyridine-2-carboxylic acid amide

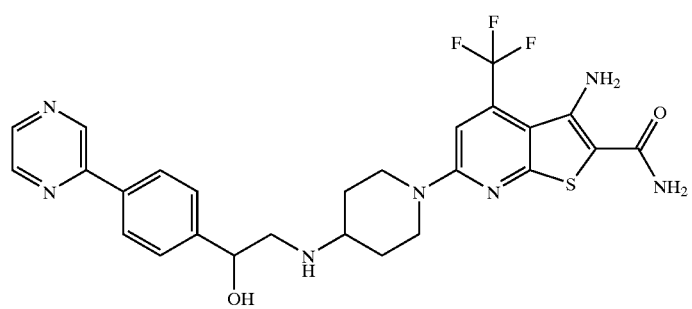

3-Amino-6-{4-[2-hydroxy-2-(4-thiazol-2-yl-phenyl)-ethylamino]-piperidin-1-yl}-4-trifluoromethyl-thieno[2,3-b]pyridine-2-carboxylic acid amide

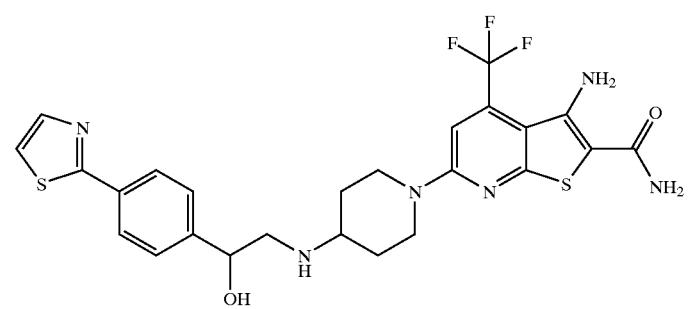

and pharmaceutically acceptable salts, esters, tautomers, individual isomers, and mixtures of isomers thereof.

Another embodiment of the invention provides for the compounds of Table XI:

3-Amino-6-(4-hydroxy-piperidin-1-yl)-
thieno[2,3-b]pyridine-2,4-dicarboxylic
acid 2-amide 4-pyridin-3-ylamide
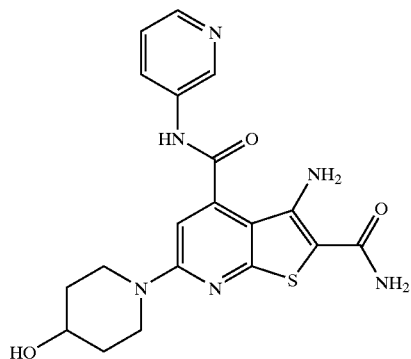
3-Amino-6-(4-hydroxy-piperidin-1-yl)-
thieno[2,3-b]pyridine-2,4-dicarboxylic
acid 2-amide 4-[(4-hydroxy-phenyl)-
amide]
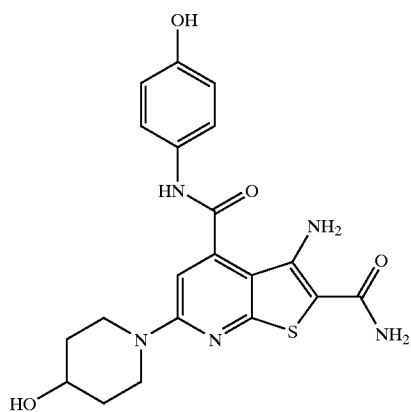
3-Amino-6-(4-hydroxy-piperidin-1-yl)-
thieno[2,3-b]pyridine-2,4-dicarboxylic
acid 2-amide 4-[(4-carbamoyl-phenyl)-
amide]
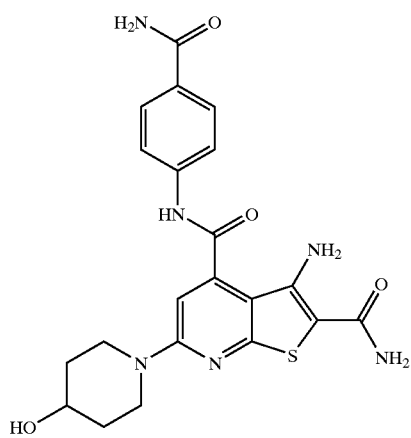

-continued

| | |
|---|---|
| 3-Amino-6-(4-hydroxy-piperidin-1-yl)-thieno[2,3-b]pyridine-2,4-dicarboxylic acid 2-amide 4-[(4-sulfamoyl-phenyl)-amide] | 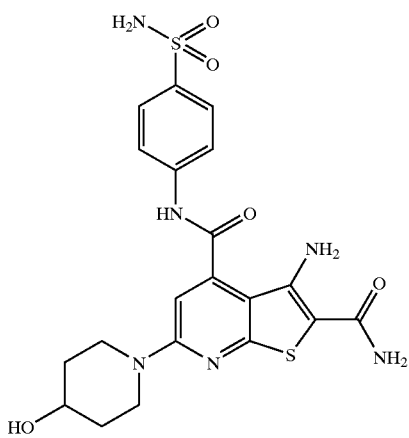 |
| 3-Amino-6-(4-hydroxy-piperidin-1-yl)-thieno[2,3-b]pyridine-2,4-dicarboxylic acid 2-amide 4-methylamide | 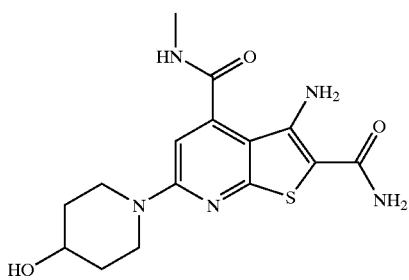 |
| 3-Amino-6-(4-hydroxy-piperidin-1-yl)-thieno[2,3-b]pyridine-2,4-dicarboxylic acid 2-amide 4-pyridin-4-ylamide | 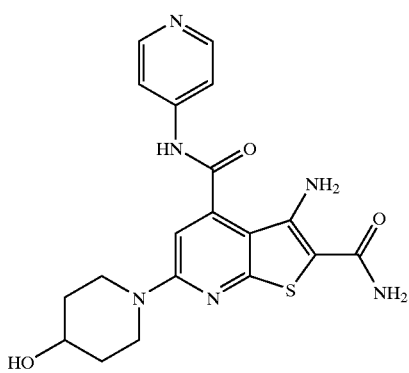 |
| 3-Amino-6-(4-amino-piperidin-1-yl)-thieno[2,3-b]pyridine-2,4-dicarboxylic acid diamide | 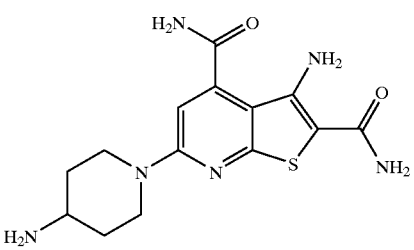 |
| 3-Amino-6-(4-amino-piperidin-1-yl)-thieno[2,3-b]pyridine-2,4-dicarboxylic acid 2-amide 4-methylamide | 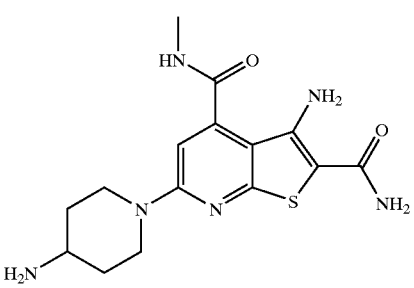 |

| | |
|---|---|
| 3-Amino-6-(4-amino-piperidin-1-yl)-thieno[2,3-b]pyridine-2,4-dicarboxylic acid 2-amide 4-phenylamide | 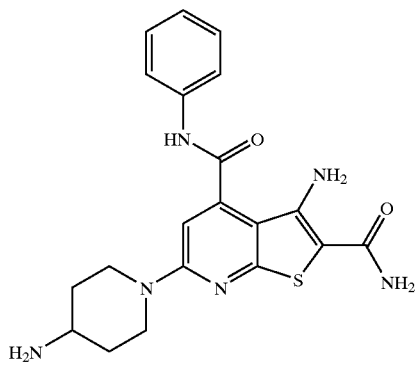 |
| 3-Amino-6-(4-amino-piperidin-1-yl)-thieno[2,3-b]pyridine-2,4-dicarboxylic acid 2-amide 4-pyridin-4-ylamide | 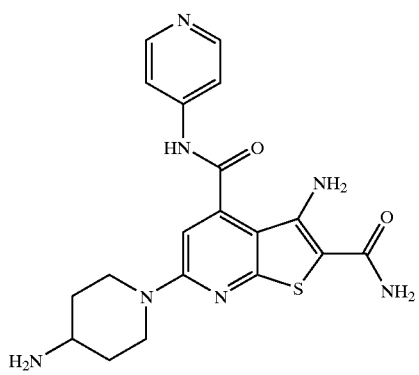 |
| 3-Amino-6-(4-amino-piperidin-1-yl)-thieno[2,3-b]pyridine-2,4-dicarboxylic acid 2-amide 4-pyridin-3-ylamide | 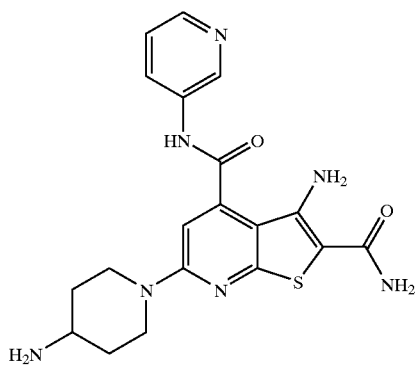 |
| 33-Amino-6-(4-amino-piperidin-1-yl)-thieno[2,3-b]pyridine-2,4-dicarboxylic acid 2-amide 4-[(3-morpholin-4-yl-propyl)-amide] | 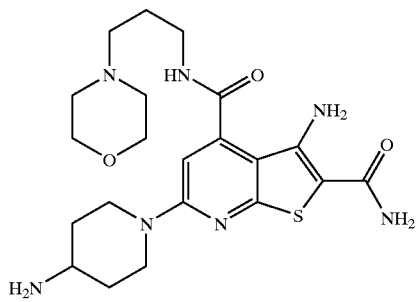 | and pharmaceutically acceptable salts, esters, tautomers, individual isomers, and mixtures of isomers thereof.

In another embodiment of the invention, there are provided the following compounds:

3-Amino-6-(4-amino-4-cyano-piperidin-1-yl)-4-propyl-thieno[2,3-b]pyridine-2-carboxylic acid amide;

3-Amino-6-(4-amino-piperidin-1-yl)-4-((E)-styryl)-thieno[2,3-b]pyridine-2-carboxylic acid amide;

3-Amino-6-(4-amino-piperidin-1-yl)-4-trifluoromethyl-thieno[2,3-b]pyridine-2-carboxylic acid amide;

3-Amino-6-piperazin-1-yl-4-trifluoromethyl-thieno[2,3-b]pyridine-2-carboxylic acid amide;

3-Amino-6-[4-(2-hydroxy-ethylamino)-piperidin-1-yl]-4-propyl-thieno[2,3-b]pyridine-2-carboxylic acid amide;
3-Amino-6-piperidin-4-yl-4-propyl-thieno[2,3-b]pyridine-2-carboxylic acid amide;
3-Amino-6-[4-((S)-2-hydroxy-2-phenyl-ethylamino)-piperidin-1-yl]-4-propyl-thieno[2,3-b]pyridine-2-carboxylic acid amide;
3-Amino-6-[4-((R)-2-hydroxy-2-phenyl-ethylamino)-piperidin-1-yl]-4-propyl-thieno[2,3-b]pyridine-2-carboxylic acid amide;
3-Amino-6-(4-amino-piperidin-1-yl)-4-ethoxy-thieno[2,3-b]pyridine-2-carboxylic acid amide;
3-Amino-6-{4-[2-hydroxy-2-(3-hydroxy-phenyl)-ethylamino]-piperidin-1-yl}-4-propyl-thieno[2,3-b]pyridine-2-carboxylic acid amide;
3-Amino-6-{4-[2-hydroxy-2-(4-hydroxy-phenyl)-ethylamino]-piperidin-1-yl)}4-propyl-thieno[2,3-b]pyridine-2-carboxylic acid amide;
3-Amino-6-(4-amino-azepan-1-yl)-4-propyl-thieno[2,3-b]pyridine-2-carboxylic acid amide;
3-Amino-6-(4-amino-3-hydroxy-piperidin-1-yl)-4-propyl-thieno[2,3-b]pyridine-2-carboxylic acid amide;
3-Amino-6-(4-amino-piperidin-1-yl)-4-(4-cyano-3-fluoro-phenyl)-thieno[2,3-b]pyridine-2-carboxylic acid amide;
3-Amino-6-(4-amino-piperidin-1-yl)-4-isopropoxy-thieno[2,3-b]pyridine-2-carboxylic acid amide;
3-Amino-6-(4-hydroxy-piperidin-1-yl)-4-trifluoromethyl-thieno[2,3-b]pyridine-2-carboxylic acid amide;
3-Amino-6-{4-[2-(4-amino-phenyl)-2-hydroxy-ethylamino]-piperidin-1-yl}-4-propyl-thieno[2,3-b]pyridine-2-carboxylic acid amide;
3-Amino-6-{4-[2-hydroxy-2-(4-methoxy-phenyl)-ethylamino]-piperidin-1-yl}-4-propyl-thieno[2,3-b]pyridine-2-carboxylic acid amide;
4-{2-[1-(3-Amino-2-carbamoyl-4-propyl-thieno[2,3-b]pyridin-6-yl)-piperidin-4-ylamino]-1-hydroxy-ethyl}-benzoic acid methyl ester;
3-Amino-4-ethoxy-6-(4-hydroxy-piperidin-1-yl)-thieno[2,3-b]pyridine-2-carboxylic acid amide;
3-Amino-6-((S)-3,4-dihydroxy-piperidin-1-yl)-4-propyl-thieno[2,3-b]pyridine-2-carboxylic acid amide;
3-Amino-6-{4-[2-(4-carbamoyl-phenyl)-2-hydroxy-ethylamino]-piperidin-1-yl}-4-propyl-thieno[2,3-b]pyridine-2-carboxylic acid amide;
3-Amino-6-((S)-3-hydroxy-4-methanesulfonylamino-piperidin-1-yl)-4-propyl-thieno[2,3-b]pyridine-2-carboxylic acid amide;
3-Amino-6-[4-(2-hydroxy-2-naphthalen-2-yl-ethylamino)-piperidin-1-yl]-4-propyl-thieno[2,3-b]pyridine-2-carboxylic acid amide;
3-Amino-6-[4-(2-hydroxy-2-naphthalen-1-yl-ethylamino)-piperidin-1-yl]-4-propyl-thieno[2,3-b]pyridine-2-carboxylic acid amide;
3-Amino-6-{4-[2-hydroxy-2-(4-methylcarbamoyl-phenyl)-ethylamino]-piperidin-1-yl}-4-propyl-thieno[2,3-b]pyridine-2-carboxylic acid amide;
3-Amino-6-{4-[2-(4-dimethylcarbamoyl-phenyl)-2-hydroxy-ethylamino]-piperidin-1-yl}-4-propyl-thieno[2,3-b]pyridine-2-carboxylic acid amide;
3-Amino-6-{4-[2-(4-benzylcarbamoyl-phenyl)-2-hydroxy-ethylamino]-piperidin-1-yl}-4-propyl-thieno[2,3-b]pyridine-2-carboxylic acid amide;
3-Amino-6-{4-[2-(3-carbamoyl-phenyl)-2-hydroxy-ethylamino]-piperidin-1-yl}-4-propyl-thieno[2,3-b]pyridine-2-carboxylic acid amide;
3-Amino-6-(4-hydroxy-piperidin-1-yl)-thieno[2,3-b]pyridine-2,4-dicarboxylic acid 2-amide 4-[(4-carbamoyl-phenyl)-amide];
3-Amino-6-(4-hydroxy-piperidin-1-yl)-thieno[2,3-b]pyridine-2,4-dicarboxylic acid 2-amide 4-[(4-sulfamoyl-phenyl)-amide];
3-Amino-6-(4-hydroxy-piperidin-1-yl)-thieno[2,3-b]pyridine-2,4-dicarboxylic acid 2-amide 4-pyridin-4-ylamide;
3-Amino-6-{4-[3-(4-carbamoyl-phenoxy)-2-hydroxy-propylamino]-piperidin-1-yl}-4-propyl-thieno[2,3-b]pyridine-2-carboxylic acid amide;
3-Amino-6-(4-{2-[4-(cyclopropylmethyl-carbamoyl)-phenyl]-2-hydroxy-ethylamino}-piperidin-1-yl)-4-propyl-thieno[2,3-b]pyridine-2-carboxylic acid amide
3-Amino-6-(4-{2-[4-(cyclohexylmethyl-carbamoyl)-phenyl]-2-hydroxy-ethylamino}-piperidin-1-yl)-4-propyl-thieno[2,3-b]pyridine-2-carboxylic acid amide
3-Amino-6-(4-{2-hydroxy-2-[4-(2-methyl-cyclohexylcarbamoyl)-phenyl]-ethylamino}-piperidin-1-yl)-4-propyl-thieno[2,3-b]pyridine-2-carboxylic acid amide
3-Amino-6-(4-{2-hydroxy-2-[4-(1-methyl-1-phenyl-ethylcarbamoyl)-phenyl]-ethylamino}-piperidin-1-yl)-4-propyl-thieno[2,3-b]pyridine-2-carboxylic acid amide
3-Amino-6-{4-[2-hydroxy-2-(4-phenethylcarbamoyl-phenyl)-ethylamino]-piperidin-1-yl}-4-propyl-thieno[2,3-b]pyridine-2-carboxylic acid amide
3-Amino-6-(4-{2-[4-(2-dimethylamino-ethylcarbamoyl)-phenyl]-2-hydroxy-ethylamino}-piperidin-1-yl)-4-propyl-thieno[2,3-b]pyridine-2-carboxylic acid amide
3-Amino-6-(4-{2-hydroxy-2-[4-(3-nitro-benzylcarbamoyl)-phenyl]-ethylamino}-piperidin-1-yl)-4-propyl-thieno[2,3-b]pyridine-2-carboxylic acid amide
3-Amino-6-(4-{2-hydroxy-2-[4-(3-methoxy-benzylcarbamoyl)-phenyl]-ethylamino}-piperidin-1-yl)-4-propyl-thieno[2,3-b]pyridine-2-carboxylic acid amide
3-Amino-6-(4-{2-[4-(3-chloro-benzylcarbamoyl)-phenyl]-2-hydroxy-ethylamino}-piperidin-1-yl)-4-propyl-thieno[2,3-b]pyridine-2-carboxylic acid amide
3-Amino-6-[4-(2-{4-[(benzo[b]thiophen-2-ylmethyl)-carbamoyl]-phenyl}-2-hydroxy-ethylamino)-piperidin-1-yl]-4-propyl-thieno[2,3-b]pyridine-2-carboxylic acid amide
3-Amino-6-(4-{2-hydroxy-2-[4-((S)-1-hydroxymethyl-2-phenyl-ethylcarbamoyl)-phenyl]-ethylamino}-piperidin-1-yl)-4-propyl-thieno[2,3-b]pyridine-2-carboxylic acid amide
3-Amino-6-(4-{2-hydroxy-2-[4-((R)-1-hydroxymethyl-2-phenyl-ethylcarbamoyl)-phenyl]-ethylamino}-piperidin-1-yl)-4-propyl-thieno[2,3-b]pyridine-2-carboxylic acid amide
3-Amino-6-(4-{2-hydroxy-2-[4-(3-hydroxy-propylcarbamoyl)-phenyl]-ethylamino}-piperidin-1-yl)-4-propyl-thieno[2,3-b]pyridine-2-carboxylic acid amide
(4-{2-[1-(3-Amino-2-carbamoyl-4-propyl-thieno[2,3-b]pyridin-6-yl)-piperidin-4-ylamino]-1-hydroxy-ethyl}-benzoylamino)-acetic acid methyl ester
3-Amino-6-(4-{2-[4-(3-carbamoyl-benzylcarbamoyl)-phenyl]-2-hydroxy-ethylamino}-piperidin-1-yl)-4-propyl-thieno[2,3-b]pyridine-2-carboxylic acid amide
3-Amino-6-[4-(2-{4-[(furan-2-ylmethyl)-carbamoyl]-phenyl}-2-hydroxy-ethylamino)-piperidin-1-yl]-4-propyl-thieno[2,3-b]pyridine-2-carboxylic acid amide
3-Amino-6-[4-(2-hydroxy-2-{4-[(pyridin-3-ylmethyl)-carbamoyl]-phenyl}-ethylamino)-piperidin-1-yl]-4-propyl-thieno[2,3-b]pyridine-2-carboxylic acid amide
3-Amino-6-{4-[2-(4-benzylcarbamoyl-phenyl)-2-hydroxy-ethylamino]-piperidin-1-yl}-4-trifluoromethyl-thieno[2,3-b]pyridine-2-carboxylic acid amide 4-{2-[1-(3-Amino-2-carbamoyl-4-propyl-thieno[2,3-b]pyridin-6-yl)-piperidin-4-ylamino]-1-hydroxy-ethyl}-benzoic acid 3-Amino-6-[4-(2-hydroxy-2-naphthalen-2-yl-ethylamino)-piperidin-1-yl]-4-methylsulfanyl-thieno[2,3-b]pyridine-2-carboxylic acid amide 3-Amino-6-[4-(2-hydroxy-2-naphthalen-2-yl-ethylamino)-piperidin-1-yl]-4-trifluoromethyl-thieno[2,3-b]pyridine-2-carboxylic acid amide 3-Amino-6-{4-[2-(4-cyano-phenyl)-2-hydroxy-ethylamino]-piperidin-1-yl}-4-propyl-thieno[2,3-b]pyridine-2-carboxylic acid amide 3-Amino-6-{4-[2-(4-cyano-phenyl)-2-hydroxy-ethylamino]-piperidin-1-yl}-4-trifluoromethyl-thieno[2,3-b]pyridine-2-carboxylic acid amide 3-Amino-6-{4-[2-hydroxy-2-(4-methanesulfonylamino-phenyl)-ethylamino]-piperidin-1-yl}-4-propyl-thieno[2,3-b]pyridine-2-carboxylic acid amide 3-Amino-6-{4-[2-hydroxy-2-(4-methanesulfonyl-phenyl)-ethylamino]-piperidin-1-yl}4-trifluoromethyl-thieno[2,3-b]pyridine-2-carboxylic acid amide 3-Amino-6-[4-((S)-2-hydroxy-2-phenyl-ethylamino)-piperidin-1-yl]-4-trifluoromethyl-thieno[2,3-b]pyridine-2-carboxylic acid amide 3-Amino-6-[4-((R)-2-hydroxy-2-phenyl-ethylamino)-piperidin-1-yl]-4-trifluoromethyl-thieno[2,3-b]pyridine-2-carboxylic acid amide 3-Amino-6-{4-[2-(4-fluoro-phenyl)-2-hydroxy-ethylamino]-piperidin-1-yl}-4-trifluoromethyl-thieno[2,3-b]pyridine-2-carboxylic acid amide 3-Amino-6-{4-[2-(3,4-difluoro-phenyl)-2-hydroxy-ethylamino]-piperidin-1-yl}-4-propyl-thieno[2,3-b]pyridine-2-carboxylic acid amide 3-Amino-6-{4-[2-(3,4-difluoro-phenyl)-2-hydroxy-ethylamino]-piperidin-1-yl}-4-trifluoromethyl-thieno[2,3-b]pyridine-2-carboxylic acid amide 3-Amino-6-{4-[2-(3-cyano-phenyl)-2-hydroxy-ethylamino]-piperidin-1-yl}-4-propyl-thieno[2,3-b]pyridine-2-carboxylic acid amide 3-Amino-6-{4-[2-(4-difluoromethoxy-phenyl)-2-hydroxy-ethylamino]-piperidin-1-yl}-4-propyl-thieno[2,3-b]pyridine-2-carboxylic acid amide 3-Amino-6-{4-[2-(4-difluoromethoxy-phenyl)-2-hydroxy-ethylamino]-piperidin-1-yl}-4-trifluoromethyl-thieno[2,3-b]pyridine-2-carboxylic acid amide 3-Amino-6-{4-[2-(3,5-difluoro-phenyl)-2-hydroxy-ethylamino]-piperidin-1-yl}-4-trifluoromethyl-thieno[2,3-b]pyridine-2-carboxylic acid amide 3-Amino-6-{4-[2-hydroxy-2-(4-hydroxy-phenyl)-ethylamino]-piperidin-1-yl}-4-trifluoromethyl-thieno[2,3-b]pyridine-2-carboxylic acid amide 3-Amino-6-{4-[2-(3,4-dimethoxy-phenyl)-2-hydroxy-ethylamino]-piperidin-1-yl}-4-trifluoromethyl-thieno[2,3-b]pyridine-2-carboxylic acid amide 3-Amino-6-[4-(2-benzo[1,3]dioxol-5-yl-2-hydroxy-ethylamino)-piperidin-1-yl]-4-propyl-thieno[2,3-b]pyridine-2-carboxylic acid amide 3-Amino-6-[4-(2-benzo[1,3]dioxol-5-yl-2-hydroxy-ethylamino)-piperidin-1-yl]-4-trifluoromethyl-thieno[2,3-b]pyridine-2-carboxylic acid amide 3-Amino-6-{4-[2-(2,2-difluoro-benzo[1,3]dioxol-5-yl)-2-hydroxy-ethylamino]-piperidin-1-yl}-4-trifluoromethyl-thieno[2,3-b]pyridine-2-carboxylic acid amide 3-Amino-6-{4-[2-hydroxy-2-(4-morpholin-4-yl-phenyl)-ethylamino]-piperidin-1-yl}-4-propyl-thieno[2,3-b]pyridine-2-carboxylic acid amide 3-Amino-6-{4-[2-hydroxy-2-(4-morpholin-4-yl-phenyl)-ethylamino]-piperidin-1-yl}-4-trifluoromethyl-thieno[2,3-b]pyridine-2-carboxylic acid amide 3-Amino-6-[4-(2-biphenyl-4-yl-2-hydroxy-ethylamino)-piperidin-1-yl]-4-trifluoromethyl-thieno[2,3-b]pyridine-2-carboxylic acid amide 3-Amino-6-{4-[2-hydroxy-2-(4-pyridin-2-yl-phenyl)-ethylamino]-piperidin-1-yl}-4-propyl-thieno[2,3-b]pyridine-2-carboxylic acid amide 3-Amino-6-{4-[2-hydroxy-2-(4-pyridin-2-yl-phenyl)-ethylamino]-piperidin-1-yl}-4-trifluoromethyl-thieno[2,3-b]pyridine-2-carboxylic acid amide 3-Amino-6-{4-[2-hydroxy-2-(4-pyridin-3-yl-phenyl)-ethylamino]-piperidin-1-yl}-4-propyl-thieno[2,3-b]pyridine-2-carboxylic acid amide 3-Amino-6-{4-[2-hydroxy-2-(4-pyridin-3-yl-phenyl)-ethylamino]-piperidin-1-yl}-4-trifluoromethyl-thieno[2,3-b]pyridine-2-carboxylic acid amide 3-Amino-6-{4-[2-hydroxy-2-(4-pyridin-4-yl-phenyl)-ethylamino]-piperidin-1-yl}-4-propyl-thieno[2,3-b]pyridine-2-carboxylic acid amide 3-Amino-6-{4-[2-hydroxy-2-(4-pyridin-4-yl-phenyl)-ethylamino]-piperidin-1-yl}-4-trifluoromethyl-thieno[2,3-b]pyridine-2-carboxylic acid amide 3-Amino-6-{4-[2-hydroxy-2-(4-pyrazin-2-yl-phenyl)-ethylamino]-piperidin-1-yl}-4-propyl-thieno[2,3-b]pyridine-2-carboxylic acid amide 3-Amino-6-{4-[2-hydroxy-2-(4-pyrazin-2-yl-phenyl)-ethylamino]-piperidin-1-yl}-4-trifluoromethyl-thieno[2,3-b]pyridine-2-carboxylic acid amide 3-Amino-6-{4-[2-hydroxy-2-(4-imidazol-1-yl-phenyl)-ethylamino]-piperidin-1-yl}-4-propyl-thieno[2,3-b]pyridine-2-carboxylic acid amide 3-Amino-6-{4-[2-hydroxy-2-(4-thiazol-2-yl-phenyl)-ethylamino]-piperidin-1-yl}-4-propyl-thieno[2,3-b]pyridine-2-carboxylic acid amide 3-Amino-6-{4-[2-hydroxy-2-(4-thiazol-2-yl-phenyl)-ethylamino]-piperidin-1-yl}-4-trifluoromethyl-thieno[2,3-b]pyridine-2-carboxylic acid amide 3-Amino-6-(4-{2-hydroxy-2-[4-(1-methyl-i H-imidazol-2-yl)-phenyl]-ethylamino}-piperidin-1-yl)-4-propyl-thieno[2,3-b]pyridine-2-carboxylic acid amide 3-Amino-6-(4-{2-[4-(1-benzyl-1H-imidazol-2-yl)-phenyl]-2-hydroxy-ethylamino}-piperidin-1-yl)-4-propyl-thieno[2,3-b]pyridine-2-carboxylic acid amide 3-Amino-6-(4-amino-piperidin-1-yl)-4-((E)-2-pyridin-4-yl-vinyl)-thieno[2,3-b]pyridine-2-carboxylic acid amide 3-Amino-6-(4-amino-piperidin-1-yl)-4-cyclopropyl-thieno[2,3-b]pyridine-2-carboxylic acid amide 3-Amino-6-(4-amino-piperidin-1-yl)-4-ethyl-thieno[2,3-b]pyridine-2-carboxylic acid amide 3-Amino-6-(4-amino-piperidin-1-yl)-4-isopropyl-thieno[2,3-b]pyridine-2-carboxylic acid amide 3-Amino-6-(4-methylamino-piperidin-1-yl)-4-trifluoromethyl-thieno[2,3-b]pyridine-2-carboxylic acid amide 3-Amino-6-(4-methylamino-piperidin-1-yl)-4-methylsulfanyl-thieno[2,3-b]pyridine-2-carboxylic acid amide 3-Amino-6-(4-methylamino-piperidin-1-yl)-4-(2,2,2-trifluoro-ethoxy)-thieno[2,3-b]pyridine-2-carboxylic acid amide 3-Amino-4-difluoromethyl-6-(4-methylamino-piperidin-1-yl)-thieno[2,3-b]pyridine-2-carboxylic acid amide 3-Amino-6-(4-amino-piperidin-1-yl)-thieno[2,3-b]pyridine-2,4-dicarboxylic acid diamide 3-Amino-6-(4-amino-piperidin-1-yl)-thieno[2,3-b]pyridine-2,4-dicarboxylic acid 2-amide 4-methylamide 3-Amino-6-(4-amino-piperidin-1-yl)-thieno[2,3-b]pyridine-2,4-dicarboxylic acid 2-amide 4-pyridin-4-ylamide 3-Amino-6-(4-amino-piperidin-1-yl)-thieno[2,3-b]pyridine-2,4-dicarboxylic acid 2-amide 4-pyridin-3-ylamide 3-Amino-6-(4-amino-piperidin-1-yl)-thieno[2,3-b]pyridine-2,4-dicarboxylic acid 2-amide 4-[(3-morpholin-4-yl-propyl)-amide]

3-Amino-6-[4-(2-hydroxy-ethylamino)-piperidin-1-yl]-4-trifluoromethyl-thieno[2,3-b]pyridine-2-carboxylic acid amide

[1-(3-Amino-2-carbamoyl-4-propyl-thieno[2,3-b]pyridin-6-yl)-piperidin-4-ylamino]-acetic acid 3-Amino-6-{4-[3-(3-cyano-phenoxy)-2-hydroxy-propylamino]-piperidin-1-yl}-4-propyl-thieno[2,3-b]pyridine-2-carboxylic acid amide 3-Amino-6-{4-[3-(4-cyano-phenoxy)-2-hydroxy-propylamino]-piperidin-1-yl}-4-propyl-thieno[2,3-b]pyridine-2-carboxylic acid amide 3-Amino-6-{4-[2-hydroxy-3-(naphthalen-2-yloxy)-propylamino]-piperidin-1-yl}-4-propyl-thieno[2,3-b]pyridine-2-carboxylic acid amide 3-Amino-6-{4-[3-(3-carbamoyl-phenylamino)-2-hydroxy-propylamino]-piperidin-1-yl}-4-propyl-thieno[2,3-b]pyridine-2-carboxylic acid amide 3-Amino-6-[4-(2-hydroxy-2-phenylcarbamoyl-ethylamino)-piperidin-1-yl]-4-propyl-thieno[2,3-b]pyridine-2-carboxylic acid amide 3-Amino-6-{4-[(naphthalen-1-ylcarbamoylmethyl)-amino]-piperidin-1-yl}-4-propyl-thieno[2,3-b]pyridine-2-carboxylic acid amide 3-Amino-6-(4-amino-3,3-dimethyl-cyclohexyl)-4-propyl-thieno[2,3-b]pyridine-2-carboxylic acid amide;

and pharmaceutically acceptable salts, esters, tautomers, individual isomers, and mixtures of isomers thereof.

The invention includes pharmaceutically acceptable derivatives of compounds of formula (I). A "pharmaceutically acceptable derivative" refers to any pharmaceutically acceptable acid, salt or ester of a compound of this invention, or any other compound which, upon administration to a patient, is capable of providing (directly or indirectly) a compound of this invention, a pharmacologically active metabolite or pharmacologically active residue thereof.

Pharmaceutically acceptable salts of the compounds of this invention include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, formic, benzoic, malonic, naphthalene-2-sulfonic and benzenesulfonic acids. Other acids, such as oxalic acid, while not themselves pharmaceutically acceptable, may be employed in the preparation of salts useful as intermediates in obtaining the compounds of this invention and their pharmaceutically acceptable acid addition salts. Salts derived from appropriate bases include alkali metal (e.g., sodium), alkaline earth metal (e.g., magnesium), ammonium and N—($C_1$–$C_4$ alkyl)$_4^+$ salts.

In addition, the compounds of this invention include prodrugs of compounds of the formula (I). Prodrugs include those compounds that, upon simple transformation, are modified to produce the compounds of the invention. Simple chemical transformations include hydrolysis, oxidation and reduction which occur enzymatically, metabolically or otherwise. Specifically, when a prodrug of this invention is administered to a patient, the prodrug may be transformed into a compound of formula (I), thereby imparting the desired pharmacological effect.

Any compounds of this invention containing one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations.

Some of the compounds of the invention can exist in more than one tautomeric form. The invention includes all such tautomers.

The compounds of the invention are only those which are contemplated to be 'chemically stable' as will be appreciated by those skilled in the art. For example, a compound which would have a 'dangling valency', or a 'carbanion' are not compounds contemplated by the invention.

As used herein, the following abbreviations are used:
DMF is dimethylformamide;
DMSO is dimethyl sulfoxide
EtOAc is ethyl acetate;
EtOH is ethanol;
HPLC is high-performance liquid chromatography
MeOH is methanol;
THF is tetrahydrofuran;
TLC is thin layer chromatography Terms not specifically defined herein should be given the meanings that would be given to them by one of skill in the art in light of the disclosure and the context. For example, "$C_{1-6}$alkoxy" is a $C_{1-6}$alkyl with a terminal oxygen, such as methoxy, ethoxy, propoxy, pentoxy and hexoxy. All alkyl, alkylene or alkynyl groups shall be understood as being branched, unbranched unless otherwise specified. Other more specific definitions are as follows:

The term "alkyl" refers to a saturated aliphatic radical containing from one to ten carbon atoms or a mono- or polyunsaturated aliphatic hydrocarbon radical containing from two to twelve carbon atoms unless otherwise stated. The mono- or polyunsaturated aliphatic hydrocarbon radical contains at least one double or triple bond, respectively. "Alkyl" refers to both branched and unbranched alkyl groups. Examples of "alkyl" include alkyl groups which are straight chain alkyl groups containing from one to eight carbon atoms and branched alkyl groups containing from three to ten carbon atoms. Other examples include lower alkyl groups which are straight chain alkyl groups containing from one to six carbon atoms and branched alkyl groups containing from three to six carbon atoms. It should be understood that any combination term using an "alk" or "alkyl" prefix refers to analogs according to the above definition of "alkyl". For example, terms such as "alkoxy", "alkythio" refer to alkyl groups linked to a second group via an oxygen or sulfur atom. "Alkanoyl" refers to an alkyl group linked to a carbonyl group (C=O). Each alkyl or alkyl analog described herein shall be understood to be optionally partially or fully halogenated.

The term "cycloalkyl" refers to the cyclic analog of an alkyl group, as defined above. Examples of cycloalkyl groups are saturated or unsaturated nonaromatic cycloalkyl groups containing from three to eight carbon atoms, and other examples include cycloalkyl groups having three to six carbon atoms.

The term "heterocycloalkyl" refers to a stable 4–8 membered (but preferably, 5 or 6 membered) monocyclic or 8–11 membered bicyclic heterocycle radical which may be either saturated or unsaturated, and is non-aromatic. Each heterocycle consists of carbon atoms and from 1 to 4 heteroatoms chosen from nitrogen, oxygen and sulfur. The heterocycle may be attached by any atom of the cycle, which results in the creation of a stable structure. Examples of "heterocycloalkyl" include radicals such as pyrrolinyl, pyrrolidinyl, pyrazolinyl, pyrazolidinyl, piperidinyl, morpholinyl, thiomorpholinyl, piperazinyl, indolinyl, azetidinyl, tetrahydropyranyl, tetrahydrothiopyranyl, tetrahydropyranyl, hexahydropyrimidinyl, tetrahydrofuranyl, hexahydropyrimidinyl, hexahydropyridazinyl, dihydro-oxazolyl, 1,2-thiazinanyl-1, 1-dioxide, 1,2,6-thiadiazinanyl-1,1-dioxide, isothiazolidinyl-1,1-dioxide and imidazolidinyl-2,4-dione.

The term "halogen" refers to bromine, chlorine, fluorine or iodine.

The term "aryl" shall be understood to mean a 6–12 membered aromatic carbocycle, which can be a single ring or can be multiple rings fused together or linked covalently. The term "aryl" includes, for example, phenyl and naphthyl; other terms comprising "aryl" will have the same definition for the aryl component, examples of these moieties include: arylalkyl, aryloxy or arylthio.

The term "heteroaryl" refers to a stable 5–8 membered (but preferably, 5 or 6 membered) monocyclic or 8–11 membered bicyclic aromatic heterocycle radical. Each heterocycle consists of carbon atoms and from 1 to 4 heteroatoms chosen from nitrogen, oxygen and sulfuir. The heteroaryl group may be attached by any atom of the ring which results in the creation of a stable structure. Examples of "heteroaryl" include radicals such as furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolizinyl, indolyl, isoindolyl, benzofuranyl, benzothienyl, indazolyl, benzimidazolyl, benzthiazolyl, benzoxazolyl, purinyl, quinolizinyl, quinolinyl, isoquinolinyl, cinnolinyl, phthalazinyl, quinazolinyl, quinoxalinyl, naphthyridinyl, pteridinyl, carbazolyl, acridinyl, phenazinyl, phenothiazinyl and phenoxazinyl.

The terms "optional" or "optionally" mean that the subsequently described event or circumstances may or may not occur, and that the description includes instances where the event or circumstance occurs and instances in which it does not. For example, "optionally substituted aryl" means that the aryl radical may or may not be substituted and that the description includes both substituted aryl radicals and aryl radicals having no substitution.

The term "substituted" means that any one or more hydrogens on an atom of a group or moiety, whether specifically designated or not, is replaced with a selection from the indicated group of substituents, provided that the atom's normal valency is not exceeded and that the substitution results in a stable compound. If a bond to a substituent is shown to cross the bond connecting two atoms in a ring, then such substituent may be bonded to any atom on the ring. When a substituent is listed without indicating the atom via which such substituent is bonded to the rest of the compound, then such substituent may be bonded via any atom in such substituent. For example, when the substituent is piperazinyl, piperidinyl, or tetrazolyl, unless specified otherwise, such piperazinyl, piperidinyl, or tetrazolyl group may be bonded to the rest of the compound of the invention via any atom in such piperazinyl, piperidinyl, or tetrazolyl group. Generally, when any substituent or group occurs more than one time in any constituent or compound, its definition on each occurrence is independent of its definition at every other occurrence. Thus, for example, if a group is shown to be substituted with 0 to 2 R, then such group is optionally substituted with up to two R groups and R at each occurrence is selected independently from the defined list of possible R. Such combinations of substituents and/or variables, however, are permissible only if such combinations result in stable compounds.

As used herein above and throughout this application, "nitrogen" and "sulfur" include any oxidized form of nitrogen and sulfur and the quaternized form of any basic nitrogen.

Methods of Therapeutic Use

In accordance with the invention, there are provided novel methods of using the compounds of the formula (I). The compounds of the invention are effective in inhibiting the activity of IKKβ and/or IKKα. In particular, these compounds are useful in blocking disease processes exacerbated by IKKβ-mediated NF-κB activation and IKKα activation of B cell activity or the cell cycle regulatory gene Cyclin D1. In blocking NF-κB activation, compounds of the invention effectively block transcription of genes encoding inflammatory cytokines including IL-1, IL-2, IL-6, IL-8, TNFα, chemokines including IL-8 and RANTES as well as other pro-inflammatory molecules including COX-2 and cell adhesion molecules such as ICAM-1, VCAM-1 and E-selectin. These mediators play a key role in the etiology of inflammatory, autoimmune and cardiovascular disorders and cancer. Preventing the production of these mediators is a desirable means for treating these disorders. Thus there are provided methods for treating these conditions using the compounds of the invention. Such inflammatory and autoimmune conditions include but are not limited to osteoarthritis, reperfusion injury, asthma, chronic obstructive pulmonary disease (COPD), multiple sclerosis, Guillain-Barre syndrome, Crohn's disease, ulcerative colitis, psoriasis, graft versus host disease, systemic lupus erythematosus, rheumatoid arthritis, Alzheimer's disease, toxic shock syndrome, insulin-dependent diabetes mellitis, acute and chronic pain, thermal injury, adult respiratory distress syndrome (ARDS), multiple organ injury secondary to trauma, acute glomerulonephritis, dermatoses with acute inflammatory components, acute purulent meningitis or other central nervous system disorders, Grave's disease, myasthenia gravis, scleroderma and atopic dermatitis. Such cardiovascular disorders include but are not limited to atherosclerosis, myocardial infarction and stroke. Such cancers include but are not limited to lymphoid—, myeloid- and epithelial-derived malignancies including leukemia, lymphomas and breast, gastric, colorectal, lung, and pancreatic cancers. The compounds of the invention can also be used to treat other disorders associated with IKK activation of NF-κB unrelated to those listed above or discussed in the Background of the Invention. For example, the compounds of the invention may also be useful in the treatment of cancer by enhancing the effectiveness of chemotherapeutic agents. Therefore, the invention also provides methods of treating inflammatory and autoimmune diseases, and other diseases including cancer, comprising administering to a patient in need of such treatment a pharmaceutically effect amount of a compound according to the invention.

For therapeutic use, the compounds of the invention may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous. Compositions comprising the compounds of the invention for each of the aforementioned routes of administration will be apparent to the skilled artisan. The invention also provides for pharmaceutical compositions including a therapeutically effective amount of the compounds according to the invention. Such pharmaceutical compositions will include pharmaceutically acceptable carriers and adjuvants as further described below.

The compounds of this invention may be administered alone or in combination with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 15%, but more preferably at least about 20%, of a compound of the invention (w/w) or a combination thereof. Alternatively, the compounds may be administered separately (either serially or in parallel). Separate dosing allows for greater flexibility in the dosing regime.

As mentioned above, dosage forms of the compounds of this invention include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed., Lea and Febiger (1990)). Dosage levels and requirements are well-recognized in the art and may be selected by those of ordinary skill in the art from available methods and techniques suitable for a particular patient. In some embodiments, dosage levels range from about 10–1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

Synthetic Methods

The invention additionally provides for methods for making the compounds of the formula (I). The compounds of the invention may be prepared by the general methods and examples presented below, and methods known to those of ordinary skill in the art. Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Reaction progress may be monitored by conventional methods such as thin layer chromatography (TLC). Intermediates and products may be purified by methods known in the art, including column chromatography, HPLC or recrystallization.

Compounds of the invention in which $R_2$ groups (as defined previously) are attached to the thienopyridine core through a heteroatom (Het) can be conveniently prepared through $SN_{AR}$ reactions upon aryl triflate or aryl halide intermediates. Variations of this approach allow access to a variety of $R_1$ substituents (as defined previously). As outlined in Scheme I, reaction of Ia with the desired nucleophile, such as an amine, in the presence of a suitable base such as triethylamine, optionally while heating at about 50° C. to 100° C. results in displacement of the sulfonyl ester by the nucleophile. Cyclization in situ may be achieved by adding a second suitable base such as aqueous sodium carbonate followed by continued heating to provide the desired compound of formula (I).

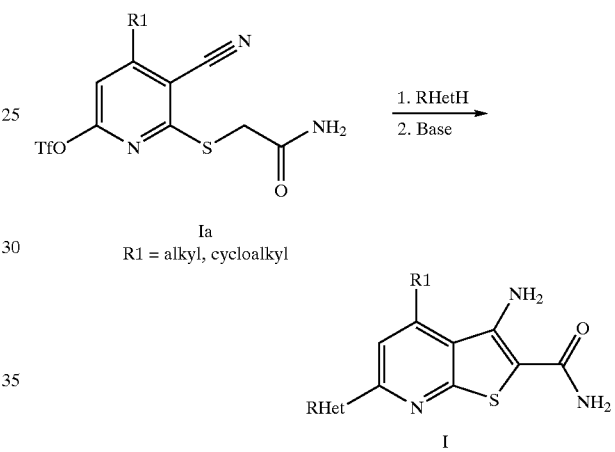

When $R_1$ is a attached via a sulfur atom, these $SN_{AR}$ reactions have been performed on the corresponding triflate intermediate in which the right hand side thiene ring is already cyclized. Alkoxy substituents can then be introduced as $R_1$ groups by base mediated displacement in cases where R1 is a sulfoxide or sulfonyl group as illustrated in Scheme II.

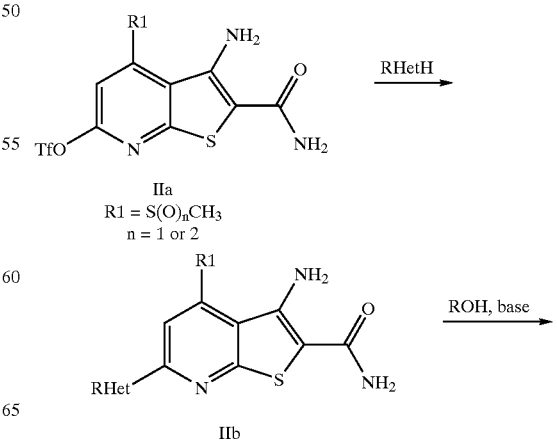

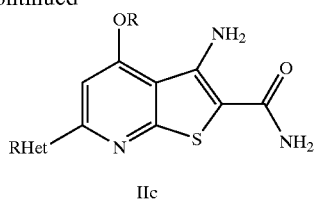

IIc

An alternative approach for assembling molecules of the invention has been developed in which sequential SN$_{AR}$ reactions are carried out on 2,6-dihalo-3-cyano pyridines (Scheme III). Introduction of a suitable R$_2$ substituent at the six position can be carried out at room temperature in the presence of a base such as triethylamine or Hunig's base in an appropriate solvent such as ethanol. A second addition is then carried out with 2-mercaptoacetamide on the resulting 2-chloro-3-cyano pyridine and cyclization to the bicylclic thienopyridine is accomplished with heating under basic conditions.

Scheme III

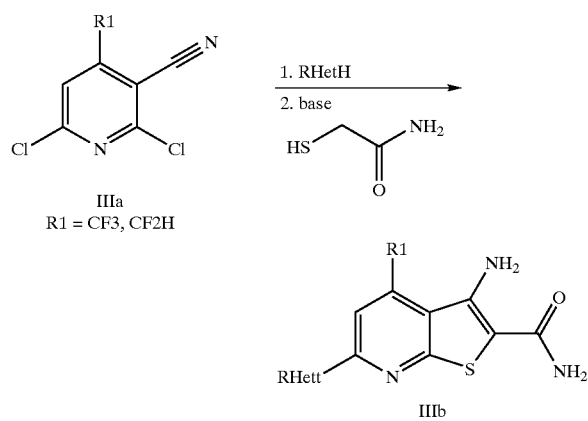

The requisite aryl triflate and aryl halide intermediates employed in Schemes I–III can be prepared in turn as described by the following general Schemes IV–VI:

Intermediates IVe which incorporate R$_1$ alkyl and cylcoalkyl groups are conveniently prepared as illustrated in Scheme IV. Either an alkynoate ester, or a □-keto ester, is reacted with 2-cyanothioacetamide in the presence of a suitable base such as morpholine in a suitable solvent such as ethanol to provide IVd. Sulfur alkylation of IVd is accomplished by treatment with a haloacetamide and the resulting pyridone intermediate (not shown) is converted to the desired pyridyl sulfonimide (trifluoromethane sulfonimide in this case) by reaction with a suitable sulfonating reagent such as N-phenyltrifluoromethane-sulfonimide or trifluoromethansulfonic acid anhydride in the presence of a suitable base such as diisopropylethylamine in a suitable solvent such as dioxane.

Scheme IV

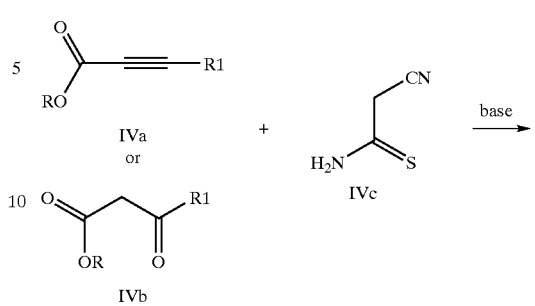

A synthetic method for incorporating thioalkyl substituents at R$_1$ is outlined in Scheme V. Meldrum's acid (Va) is treated with carbon disulfide, methyl iodide and a suitable base such as triethylamine, in a suitable solvent such as DMSO to provide the bis-methylsulfanylmethylene-dione intermediate Vb. Treatment of Vb with 2-cyanothioacetamide under suitable alkaline conditions such as sodium ethoxide in ethanol provides nitrile Vc. Reaction of Vc with 2-chloro or 2-bromoacetamide in the presence of a suitable base such as sodium hydride in a suitable solvent such as DMF provides Vd. Cyclization to the triflate intermediate Ve may be achieved by reacting Vd with N-phenyltrifluoromethane-sulfonimide in the presence of a suitable base such as sodium hydride in a suitable solvent such as DMF. As outlined in Sheme II this material may be taken on directly to compounds of the invention or first treated with an oxidizing agent such as meta-chloroperbenzoic acid or oxone to generate sulfoxide and/or sulfone derivatives which can be used to prepare derivatives with R1=alkoxy groups.

Scheme V

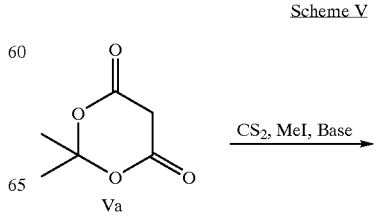

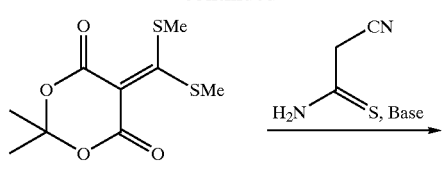
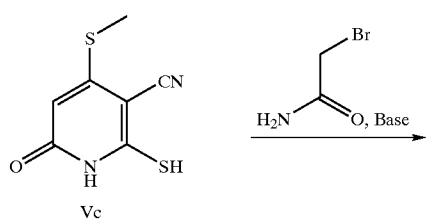
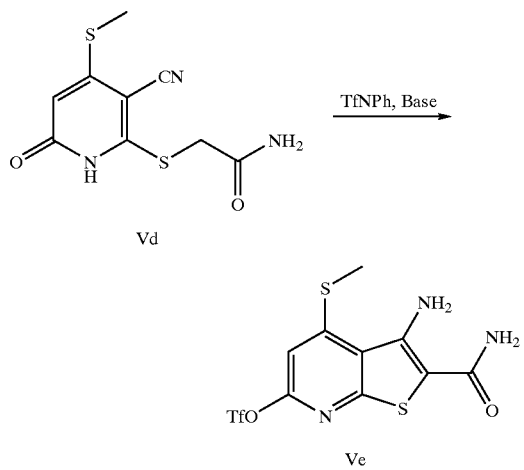
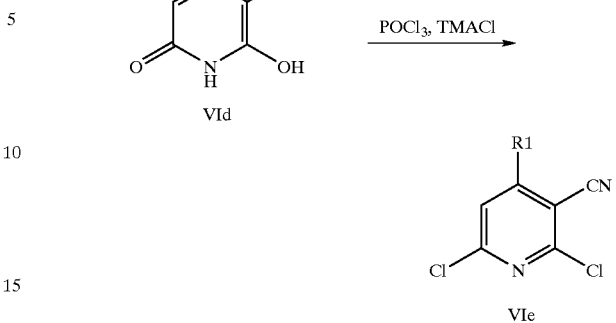

The synthetic methods described in Schemes I–III are most applicable when the left hand side RHetH groups are commercially available or easily preassembled. Synthesis of a representative class of RHetH groups is illustrated in Scheme VII. Aldehydes are reacted with trimethylsilylcyanide in the presence of a base such as triethylamine in a suitable solvent such as dichloromethane and the resulting cyanohydrins VIIb are treated with a reducing agent such as borane or lithium aluminum hydride to provide amino alcohols of type VIIc. Alternatively these amino alcohols can be prepared through the base mediated addition of ntiromethane to an aldehyde (Henry reaction) and subsequent reduction of the nitro alcohol intermediate VIId with Zn or hydrogen. Reductive amination of N-protected piperidones with these amino alcohols followed by N-deprotection provides VII f one class of $R_2$ groups of the invention.

An alternative approach for incorporating alkyl and halogenated alkyl $R_1$ groups is described in Scheme VI. In a similar fashion to Scheme IV alkynyl esters or □-ketoesters are reacted with cyano acetamide (instead of cyano thioacetamide) under basic conditions to provide the intermediate hydroxypyridones VId which are converted to the corresponding 2,6-dihalo-3-cyanopyridines VIe by subjecting to suitable halogenation conditions such as heating in phosphorous oxychloride with or without additives such as phosphorous pentachloride or tetramethyl ammonium chloride.

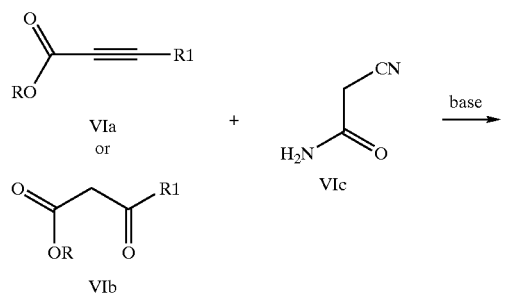
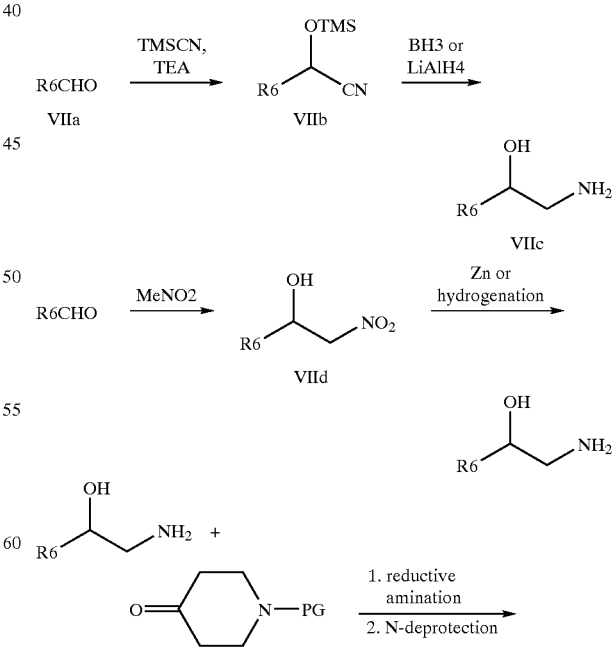

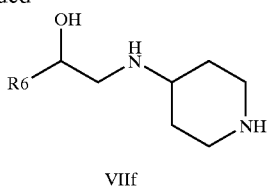

VIIf

This class of R$_2$ substituents may alternatively be accessed by nucleophilic addition of 4-amino piperidine derivatives to the corresponding epoxide starting materials as shown in scheme VIII.

Scheme VIII

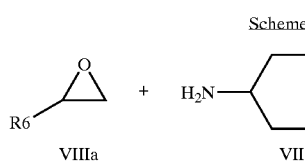

VIIIa        VIIIb

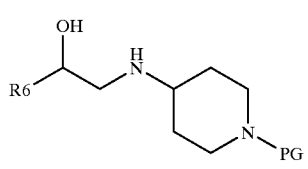

VIIIc

In instances where it may not be preferable to assemble the entire R$_2$ substituent at early stages of the synthesis, reductive amination reactions of the piperidone intermediate IXa as illustrated in Scheme IX have proven useful.

Scheme IX

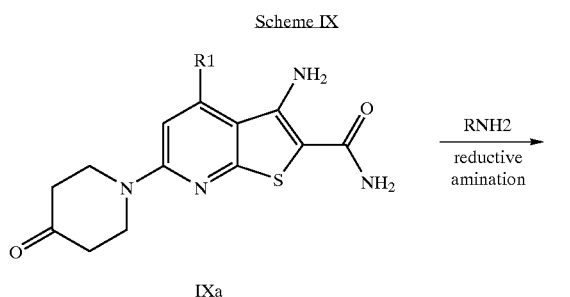

IXa

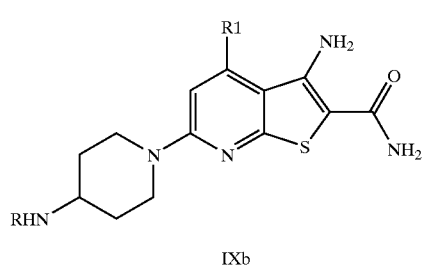

IXb

Compounds of formula (I) in which R$_2$ groups are not attached through heteroatom linkages may also be prepared starting with a 1,3-dione bearing substituents R$_1$ and R$_2$ (Xa) as illustrated in Scheme X. Reaction of Xa with cyanothioacetamide in a suitable solvent such as EtOH, in the presence of a suitable base such as triethylamine provides the substituted 2-mercaptonicotinonitrile Xb. Reaction of Xb with chloro- or bromoacetamide in a suitable solvent such as DMF, THF or EtOH, in the presence of a suitable base such as sodium carbonate, sodium hydroxide or sodium ethoxide, provides the desired compound of formula (I). Substituents R$_1$ and R$_2$ may be further modified by methods known in the art to produce additional compounds of the invention.

Scheme X

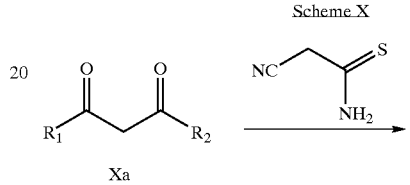

Xa

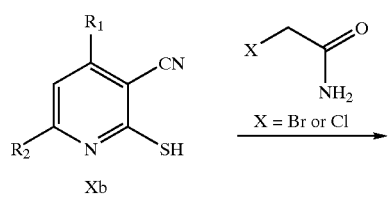

Xb

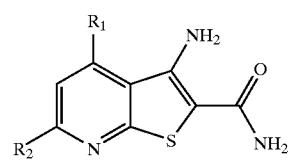

Xc

For example, as illustrated in Scheme XI, beginning with a diketo ester and using the procedure outlined above, one obtains ester XId (R$_1$=CO$_2$R', where R' is an alkyl group such as methyl or ethyl). By using methods known in the art, R$_1$ may be modified to make other desired R$_1$. For example, hydrolysis provides the carboxylic acid XIe (R$_1$=CO$_2$H) and reaction of the carboxylic acid with an amine R"NH$_2$ under standard coupling conditions provides the amide XIf (R$_1$=C(O)NHR"). Alternatively, reduction of the ester with a suitable reducing agent such as lithiun aluminum hydride provides an alcohol XIg (R$_1$=CH$_2$OH). Reaction of the alcohol with a phenol ArOH under Mitsunobu conditions provides the aryl ether XIh (R$_1$=CH$_2$OAr). These and other modifications are described in the Synthetic Examples section.

Scheme XI

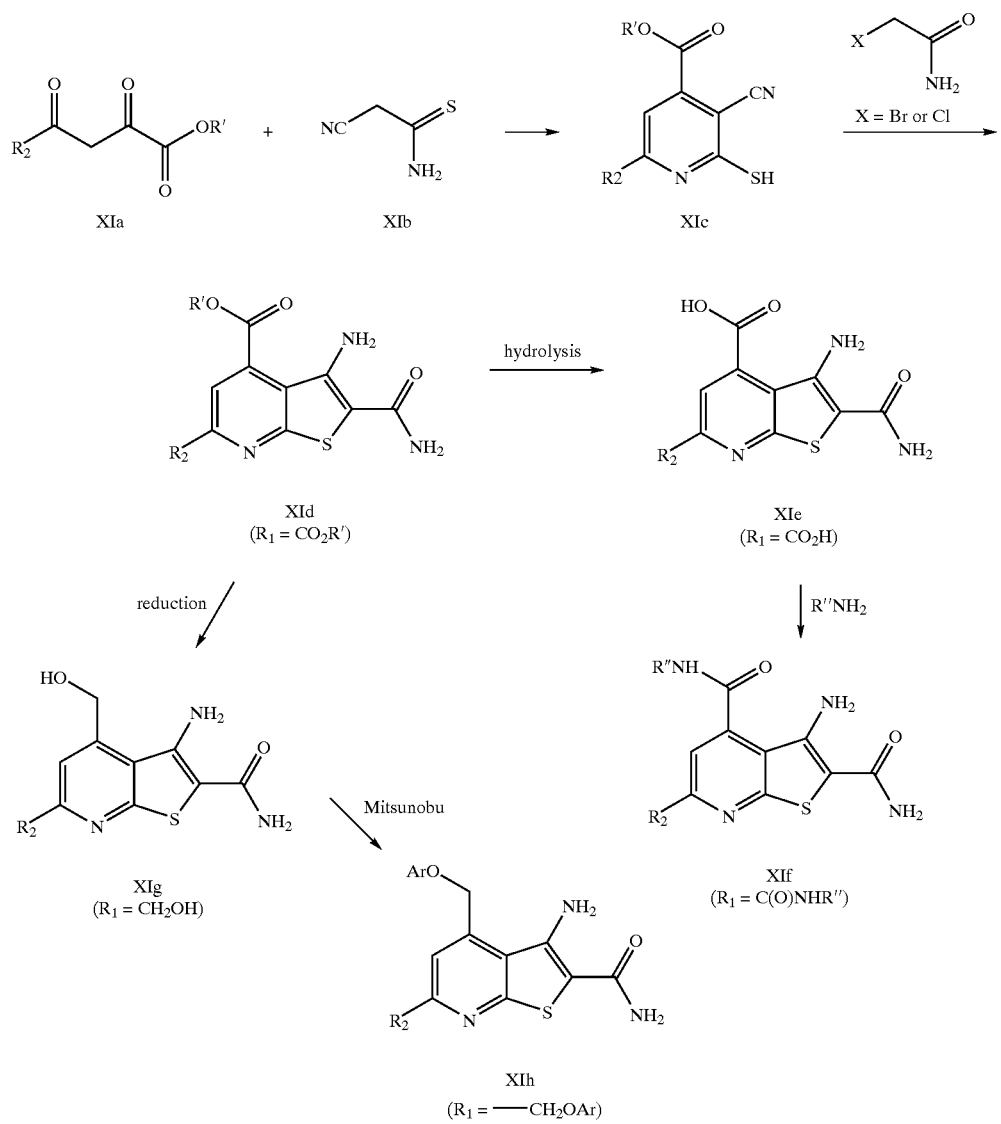

In a modification of the above procedure for preparing XIc, one may begin with a 2-chloro or 2-bromo-3-cyano-isonicotinic acid ester. The 2-halo group may then be converted to a 2-mercapto group by methods known in the art, for example by reaction with thiourea in a suitable solvent such as EtOH providing the ester intermediate VII.

Scheme XII

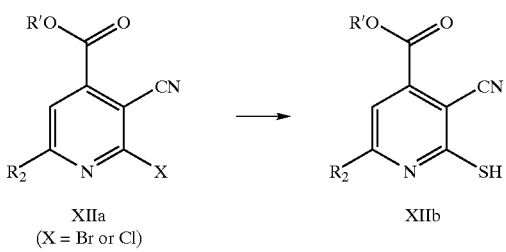

Scheme XIII illustrates a procedure by which one may obtain compounds of formula (I) having an amine at $R_1$. 2-Bromo-4-hydroxy-nicotinonitrile XIIIa is treated with 4-methoxybenzyl chloride in the presence of a suitable base such as sodium hydride in a suitable solvent such as DMF to provide the 4-methoxybenzyl ether XIIIb. This may then be converted to the 2-mercapto compound as described above in Scheme XII. The resulting mercapto compound may then be reacted with a haloacetamide to provide XIIIc ($R_1$=4-methoxybenzyl ether. Treatment of the ether with trifluoroacetic acid provides the salt XIIId. Reaction of XIIId with N-phenyltrifluoromethanesulfonimide in the presence of a suitable base such as diisopropylethylamine in a suitable solvent such as dioxane provides the trifluoromethane-sulfonate XIIIe. Reaction of XIIIe with an amine R'R"NH in a suitable solvent such as dioxane provides XIIIf ($R_1$= NR'R"). The reaction may optionally be heated for less reactive amines such as aryl amines.

Scheme XIII

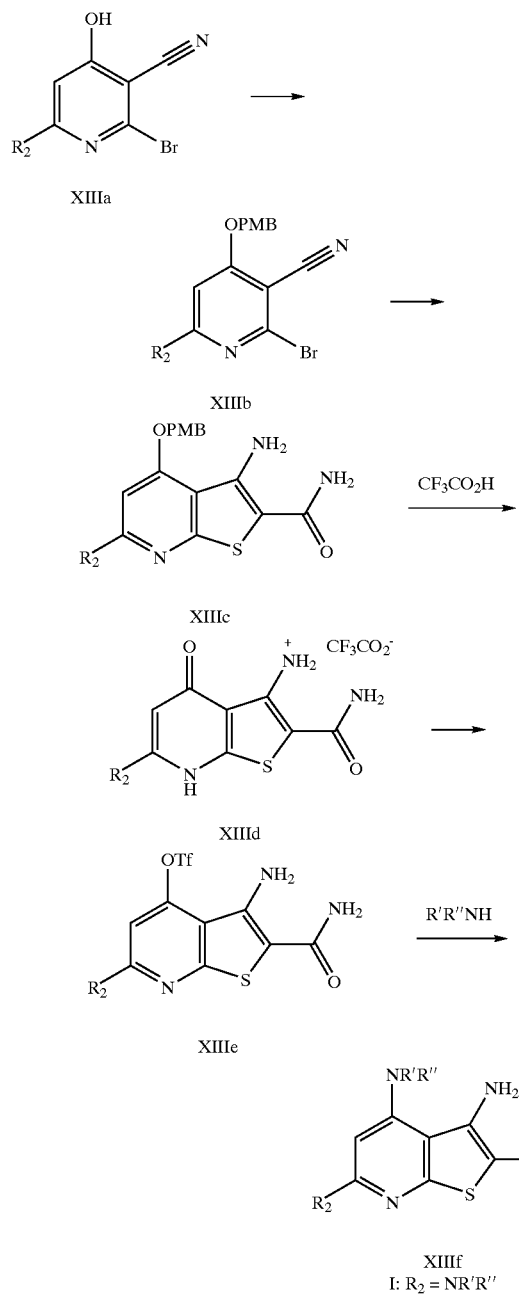

Scheme XIV

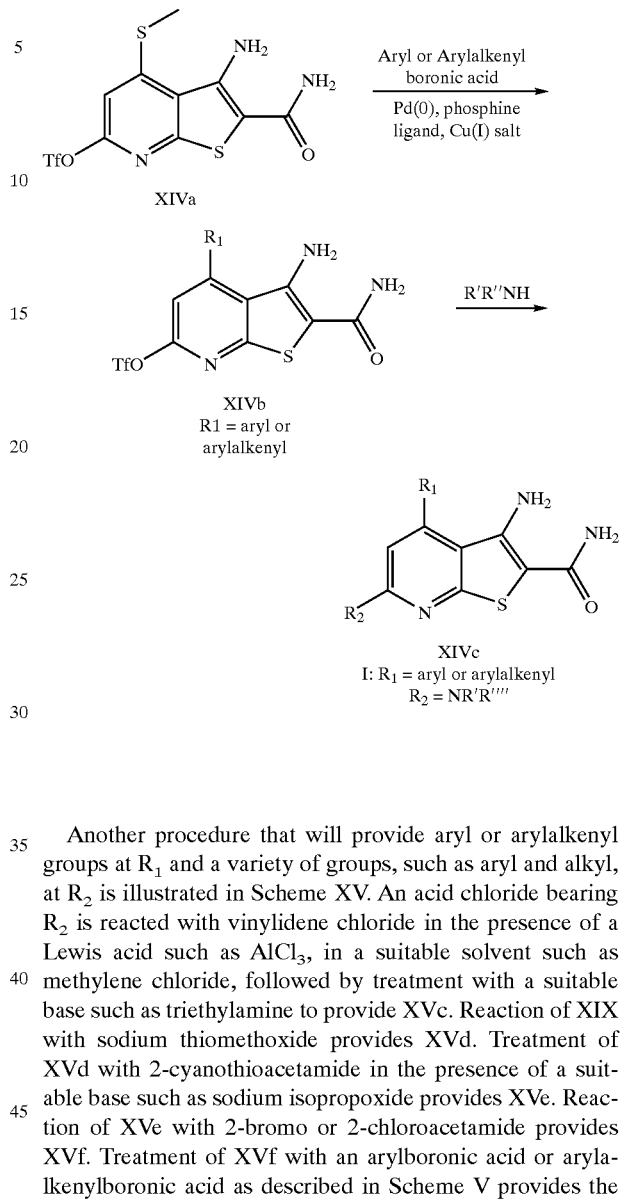

Scheme XIV describes one method for preparing compounds of the invention in which R2 is an aryl or arylalkenyl group. Reacting a triflate intermediate such as XIva with the desired aryl boronic acid or arylalkenyl boronic acid in the presence of a suitable palladium catalyst, preferably tris(dibenzylideneacetone)dipalladium(0)-chloroform adduct, a phosphine ligand, preferably tri-2-furylphosphine and a copper salt, preferably copper(I)thiophene-2-carboxylate, in a suitable solvent such as THF, provides the desired aryl or arylalkenyl intermediate XIVb. Reaction of XIVb with the desired nucleophile such as an amine R'R"NH as shown, in a suitable solvent such as dioxane, provides the desired compound of formula (I). Alcohols (R'OH) or thiols (R'SH) in the presence of a suitable base could be used in place of an amine to obtain ethers or thioethers respectively at $R_2$.

Another procedure that will provide aryl or arylalkenyl groups at $R_1$ and a variety of groups, such as aryl and alkyl, at $R_2$ is illustrated in Scheme XV. An acid chloride bearing $R_2$ is reacted with vinylidene chloride in the presence of a Lewis acid such as $AlCl_3$, in a suitable solvent such as methylene chloride, followed by treatment with a suitable base such as triethylamine to provide XVc. Reaction of XIX with sodium thiomethoxide provides XVd. Treatment of XVd with 2-cyanothioacetamide in the presence of a suitable base such as sodium isopropoxide provides XVe. Reaction of XVe with 2-bromo or 2-chloroacetamide provides XVf. Treatment of XVf with an arylboronic acid or arylalkenylboronic acid as described in Scheme V provides the desired compound of formula (I).

Scheme XV

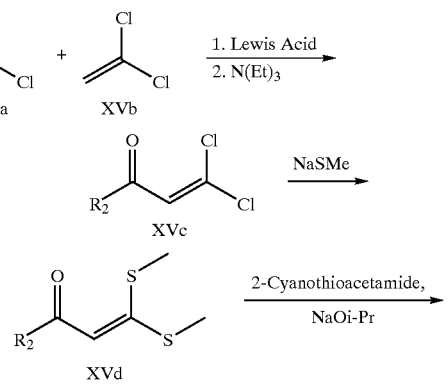

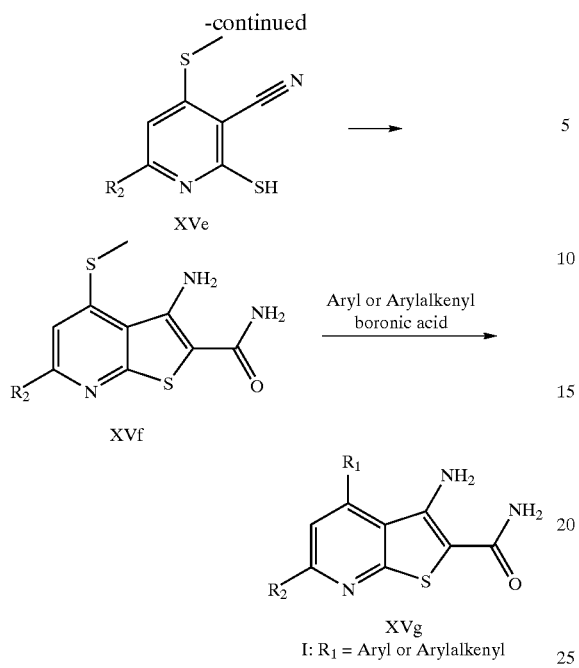

An additional procedure that may be used to prepare compounds of formula (I) is illustrated in Scheme XVI. An aldehyde bearing $R_1$ is reacted with a triphenylphosphoranylidene bearing $R_2$ (XVIa) in the presence of a suitable acid such as acetic acid, in a suitable solvent such as toluene, to provide the alpha, beta-unsaturated ketone XVIc. Treatment of XVIc with 2-cyanothioacetamide in the presence of a suitable base such as soduim t-butoxide provides XVId. This is converted to I as described previously

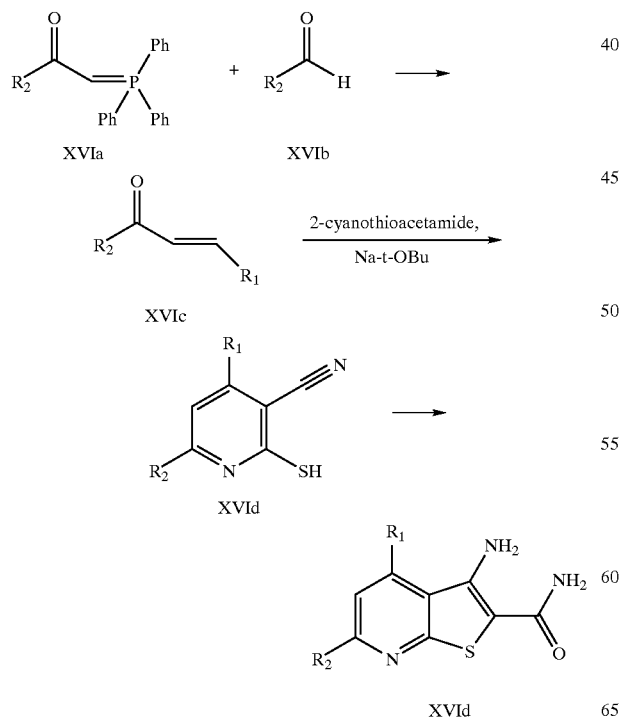

SYNTHETIC EXAMPLES

Example 1

Synthesis of 3-amino-6-piperazin-1-yl-4-propyl-thieno[2,3-b]pyridine-2-carboxylic acid amide

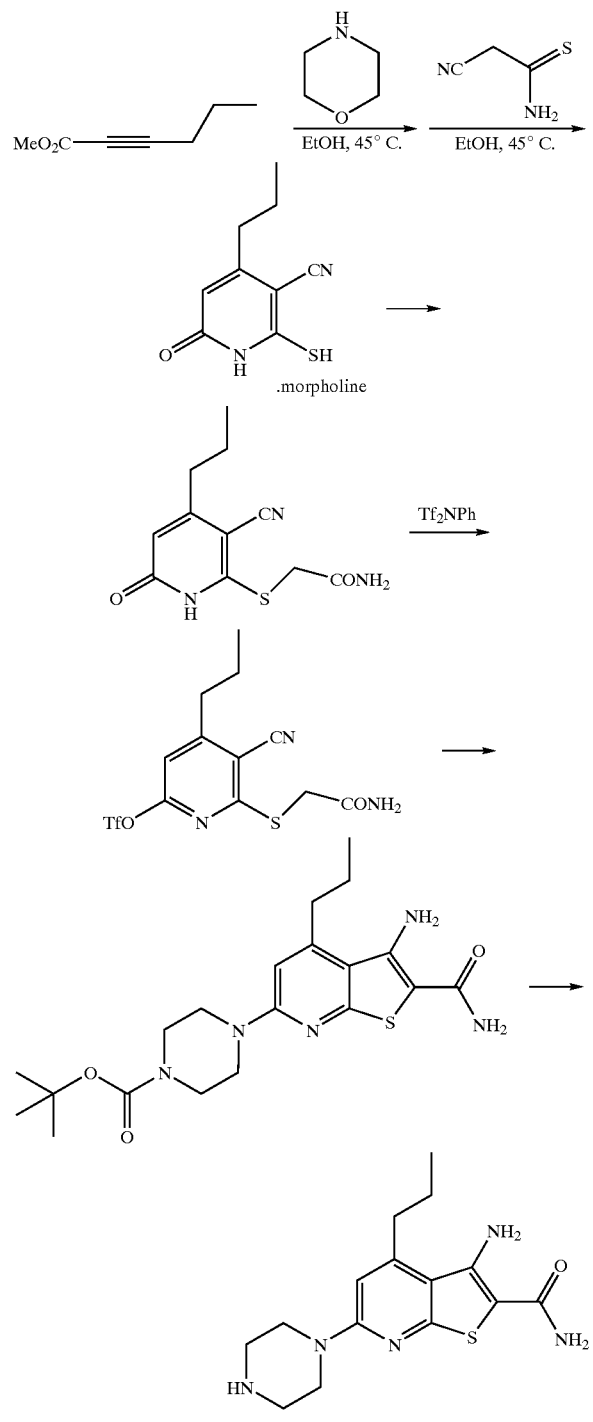

To a solution of hex-2-ynoic acid methyl ester (15 g, 0.119 mol) in EtOH (40 mL) was added morpholine (10.5 g, 0.120 mol) dropwise at room temperature. The solution was then warmed to 45° C. for 4 h under nitrogen. Solid NCCH$_2$C (S)NH₂ (12.1 g, 0.120 mol) was then added in small portions. After stirring at 45° C. for 30 min, the mixture was stirred at room temperature overnight. The yellow precipitate was collected by filtration, giving 10.9 g of the desired mercaptopyridone as a complex with 1 molecule of morpholine.

A mixture of the above mercaptopyridone (5.25 g, 18.68 mmol), 2-bromoacetamide (2.58 g, 18.68 mmol) and K₂CO₃ (2.58 g, 18.68 mmol) in dry DMF (50 mL) was heated under Ar at 70° C. for 4 h. The mixture was then cooled to 0° C., and acidified to pH~2 with 6 N HCl (~3 mL). The mixture was kept at 0° C. for 2 h, and the resulting white precipitate was collected by filtration. The product was washed with cold water to give 5.5 g of the desired mercaptoacetamide To a mixture of the above mercaptoacetamide (4.15 g, 16.54 mmol)) and iPr₂NEt (4.6 mL, 32.82 mmol) in dry dioxane (40 mL) was added in small portions N-phenyltrifluoromethane-sulfonimide (5.91 g, 16.54 mmol). The mixture was stirred under nitrogen for 16 h, concentrated and purified by silica gel column chromatography eluting with 50–80% EtOAc-hexane (gradient) to give 4.7 g of the desired 2-(3-cyano-4-n-propyl-6-trifluoromethanesulfonylpyridin-2-ylmercapto)acetamide.

To a solution of 600 mg (1.57 mmol) of the above acetamide was added 542.4 mg (2.86 mmol) of 1-Boc-piperazine and 379.8 microL (2.72 mmol) of triethylamine. The resulting mixture was stirred for 2 h at 100° C. A 2 M solution (4 mL) of sodium carbonate was then added. The stirring was continued overnight at 100° C. The reaction mixture was then diluted with EtOAc, dried with sodium sulfate and concentrated. The crude product was chromatographed (preparative TLC on silica gel eluting with 10% MeOH/dichloromethane, rf=0.75) to afford 408.4 mg (62.2%) of the desired N-Boc-piperazine intermediate.

To a suspension of 408.4 mg (0.97 mmole) of the above N-Boc intermediate in 9 mL of EtOAc was added 6 mL of a 6 M solution of HCl in MeOH. The resulting mixture was stirred for 4 h at room temperature. The solvent was then removed in vacuo, the residue was suspended in dichloromethane, stirred for 10 min and filtered. The product was washed with methylene chloride twice. The solid was dried in vacuo to afford 295 mg of the title compound.

Example 2

Synthesis of 3-Amino-6-dimethylamino-4-methyl-thieno[2,3-b]pyridine-2-carboxylic acid amide

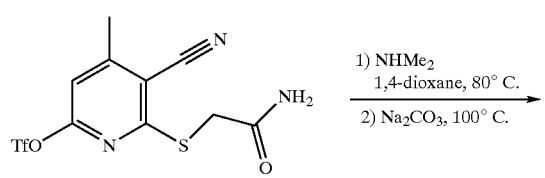

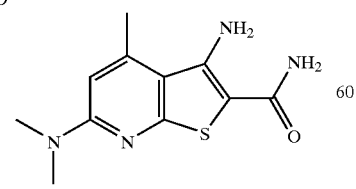

2-(3-Cyano-4-methyl-6-trifluoromethanesulfonylpyridin-2-ylmercapto)acetamide (30.0 mg, 0.08 mmol) (prepared as described in Example 1 for the n-propyl analog but using methyl 2-butynoate) and dimethylamine (170.0 microL, 0.34 mmol) were mixed in 1,4-dioxane (0.5 mL) in a pressure tube and heated at 80° C. for 1 h. 2.0 M Aqueous sodium carbonate (520 □L, 1.04 mmol) was added, and the reaction heated at 100° C. for 6 h, then cooled to room temperature overnight. The mixture was poured into saturated aqueous ammonium chloride, and extracted with EtOAc. The organic extract was washed with brine, dried (Na₂SO₄), filtered, and concentrated in vacuo to afford 23.0 mg of the crude product. This was purified via automated flash silica chromatography (4 g silica gel column, 30–100% EtOAc/hexanes) to afford 9.0 mg (0.02 mmol, 45% yield) of the title compound.

The following compounds were also made using the procedure described in Example 2 and the appropriate amine:

3-Amino-4-methyl-6-morpholin-4-yl-thieno[2,3-b]pyridine-2-carboxylic acid amide

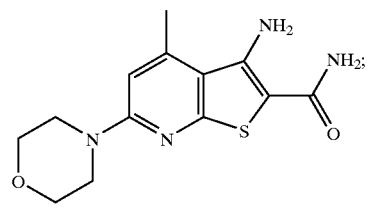

3-Amino-6-(2-hydroxy-ethylamino)-4-methyl-thieno[2,3-b]pyridine-2-carboxylic acid amide

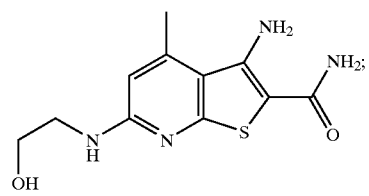

3-Amino-4-methyl-6-piperidin-1-yl-thieno[2,3-b]pyridine-2-carboxylic acid amide

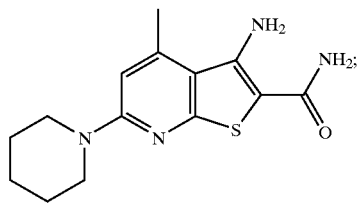

3-Amino-6-(4-hydroxy-piperidin-1-yl)-4-methyl-
thieno[2,3-b]pyridine-2-carboxylic acid amide

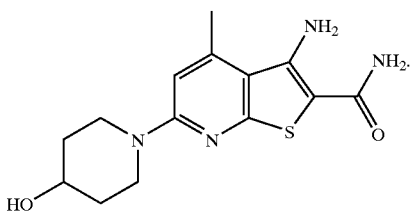

Example 3

Synthesis of 3-Amino-6-(4-amino-piperidin-1-yl)-4-
propyl-thieno[2,3-b]pyridine-2-carboxylic acid
amide

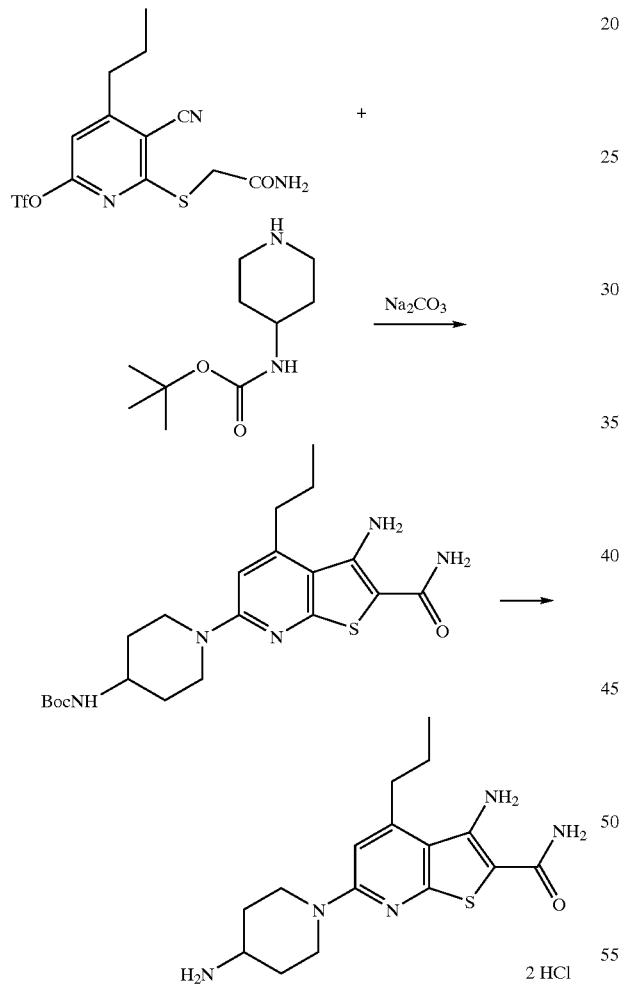

400 mg (1.04 mmol) of pyridine-triflate intermediate (see Example 1) was dissolved in 1,4-dioxane (10 mL), and placed in a dry pressure tube equipped with a magnetic stir bar and under Ar atmosphere. 4-N-Boc-aminopiperidine (640 mg, 3.13 mmol) was added, and the tube was sealed up. The reaction was stirred while heating at 80° C. for 35 min. TLC indicated the complete disappearance of starting tri-flate. The reaction was cooled to room temperature, and a 2.0 M aqueous solution of sodium carbonate (4.0 mL, 8.00 mmol) was added. The reaction was heated to 100° C., where it stirred for 20 h, after which it was cooled to room temperature.

The reaction mixture was concentrated in vacuo, and the residue was taken up in acetone/MeOH (about 50:50). The resulting mixture was filtered and the filtrate was concentrated in vacuo. The material was pre-adsorbed onto diatomaceous earth and purified first via automated flash silica gel chromatography (10 g silica gel column, 30–70% EtOAc/hexanes gradient with EtOAc flush) to afford 274 mg of slightly crude product. This was further purified via regular flash chromatography on silica gel (30 mm diameter column by 4" height) eluting with 33%–50% EtOAc/hexanes step gradient, then an EtOAc flush, to afford 249.3 mg (55% yield) of [1-(3-Amino-2-carbamoyl-4-propyl-thieno[2,3-b]pyridin-6-yl)-piperidin-4-yl]-carbamic acid tert-butyl ester.

249.3 mg (0.57 mmol) of the above compound was suspended in 10.0 mL of EtOAc. The material was completely dissolved by the addition of methanol (2.0 mL) and dichloromethane (2.0 mL). To this was added 5.0 mL (30.0 mmol) of a 6 M solution of hydrochloric acid in methanol. This reaction mixture stirred for 4 h at rt while a yellow solid slowly precipitated out of solution. TLC showed the complete disappearance of starting material, so the reaction was concentrated in vacuo. The residue was washed off the flask walls with a small amount of methanol, and then triturated with ethyl acetate. The yellow solid was collected via suction filtration, and washed successively with ethyl acetate, dichloromethane, and acetone. The solid was dried in vacuo to afford 191.3 mg of the title compound (83% yield).

3-Amino-6-(-4-amino-piperidin-1-yl)-4-cyclopropyl-
thieno[2,3-b]pyridine-2-carboxylic acid amide

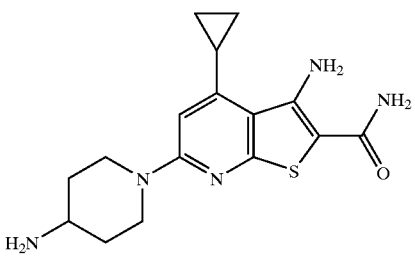

This compound was prepared as described in Example 3 for the n-propyl analog but the corresponding cyclopropyl pyridine triflate intermediate was used. This intermediate was prepared in an analogous fashion to the the n-propyl intermediate except Cyclopropyl-propynoic acid methyl ester was used as a starting material instead of hex-2-ynoic acid methyl ester 3-Amino-6-(-4-amino-piperidin-1-yl)-4-tert-butyl-thieno[2,3-b]pyridine-2-carboxylic acid amide

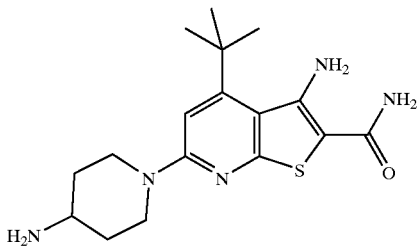

This compound was prepared as described in Example 3 for the n-propyl analog but the corresponding tert-butyl pyridine triflate intermediate was used. This intermediate was prepared in an analogous fashion to the the n-propyl intermediate except the b-keto ester 4,4-dimethyl-3-oxo-pentanoic acid methyl ester was used as a starting material instead of hex-2-ynoic acid methyl ester 3-Amino-6-(4-amino-piperidin-1-yl)-4-methyl-thieno[2,3-b]pyridine-2-carboxylic acid amide

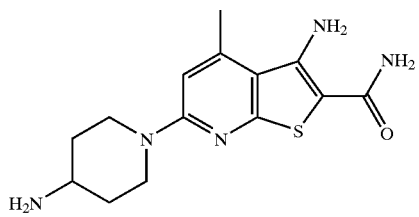

This compound was prepared as described in Example 3 for the n-propyl analog but corresponding methyl pyridine triflate intermediate was used. This intermediate was prepared in an analogous fashion to the the n-propyl derivative except but-2-ynoic acid methyl ester was used as a starting material instead of hex-2-ynoic acid methyl ester.

3-Amino-6-(-4-amino-piperidin-1-yl)-4-ethyl-thieno[2,3-b]pyridine-2-carboxylic acid amide

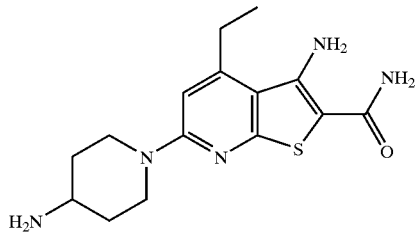

This compound was prepared as described in Example 3 for the n-propyl analog but corresponding methyl pyridine triflate intermediate was used. This intermediate was prepared in an analogous fashion to the the n-propyl derivative except pent-2-ynoic acid methyl ester was used as a starting material instead of hex-2-ynoic acid methyl ester.

3-Amino-6-(-4-amino-piperidin-1-yl)-4-isopropyl-thieno[2,3-b]pyridine-2-carboxylic acid amide

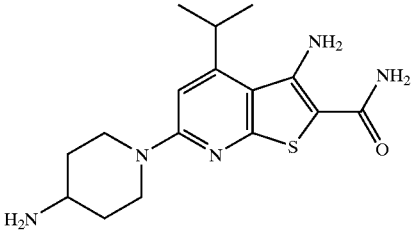

This compound was prepared as described in Example 3 for the n-propyl analog but corresponding ethyl pyridine triflate intermediate was used. This intermediate was prepared in an analogous fashion to the the n-propyl intermediate except 4-methyl-3-oxo-pentanoic acid methyl ester was used as a starting material instead of hex-2-ynoic acid methyl ester.

Example 4

Synthesis of 3-Amino-6-(4-amino-piperidin-1-yl)-4-trifluoromethyl-thieno[2,3-b]pyridine-2-carboxylic acid amide

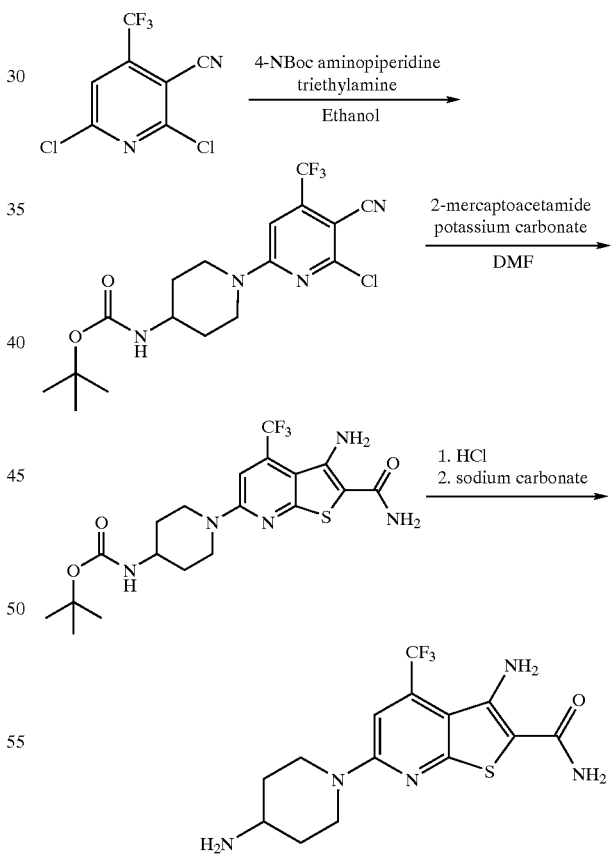

4-N-Boc aminopiperidine (3.08 g, 15.4 mmol) was added to a suspension of 2,6-dichloro-3-cyano-4-trifluoromethylpyridine (3.60 g, 14.9 mmol) and triethylamine (2.20 mL, 15.6 mmol) in ethanol (100 mL) cooled in an ice/water bath. The reaction was stirred and allowed to warm to room temperature overnight. The product was collected by filtration and air dried to provide 4.36 g (72%) of a white solid.

A suspension of this chloropyridine intermediate (4.36 g, 10.8 mmol), 2-mercaptoacetamide (35 mL of 1 g/10 mL solution in methanolic ammonia), and potassium carbonate (13.5 g, 97.7 mmol) in DMF (30 mL) was heated at 80° C. with vigorous stirring for 62 h. The reaction mixture was cooled to room temperature and filtered. The yellow precipitate was collected, suspended in water (500 mL), stirred for 30 min then refiltered. The resulting bright yellow solid was washed with water (2×200 mL) and air dried to provide 4.76 g (96%) of a bright yellow powder.

4 N HCl in dioxane (16.0 mL, 64.0 mmol) was added to a suspension of the above material (4.70 g, 10.2 mmol) in dichloromethane (100 mL). The reaction was stirred overnight then filtered. The precipitate was washed with ether (3×25 mL) then dried on a rotary evaporator to provide 4.4 g (99%) of a crunchy yellow solid.

2.30 g (5.3 mmol) of the above hydrochloride salt was stirred vigorously in 0.5 N aqueous sodium carbonate solution (250 mL) for 30 min. The suspension was filtered and the precipitate was washed with water (3×200 mL) then diethyl ether (3×25 mL). The resulting yellow solid was dried to provide 1.76 g (92%) of the title compound as a fluffy yellow powder, m/z calculated for $C_{14}H_{16}F_3N_5OS$ 359.4. observed 360.3 MH+.

3-Amino-6-piperazin-1-yl-4-trifluoromethyl-thieno[2,3-b]pyridine-2-carboxylic acid amide

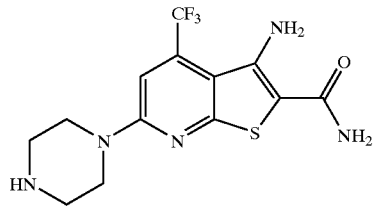

This compound was prepared as described in Example 4 using mono N-Boc piperazine as a starting material instead of 4-NBoc aminopiperidine, m/z calculated for $C_{13}H_{14}F_3N_5OS$ 345.3. observed 346.2 MH+.

3-Amino-6-(4-methylamino-piperidin-1-yl)-4-trifluoromethyl-thieno[2,3-b]pyridine-2-carboxylic acid amide

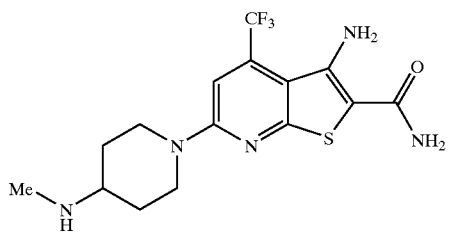

This compound was prepared as described in Example 4 using 4-N-Boc-4-N-methyl aminopiperidine as a starting material instead of 4-NBoc aminopiperidine, m/z calculated for $C_{15}H_{18}F_3N_5OS$ 373.4. observed 374.4 MH+.

3-Amino-4-difluoromethyl-6-(4-methylamino-piperidin-1-yl)-thieno[2,3-b]pyridine-2-carboxylic acid amide

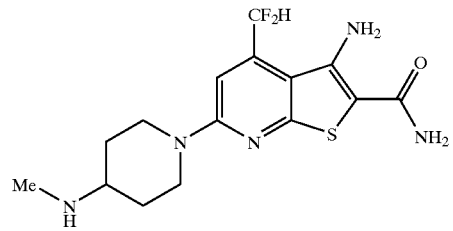

This compound was prepared as described in Example 4 using 4-N-Boc-4-Nmethyl aminopiperidine and 2,6-dichloro-3-cyano-4-difluoromethylpiperidine as starting materials instead of 4-N-Boc aminopiperidine and 2,6-dichloro-3-cyano-4-trifluoromethylpiperidine, m/z calculated for $C_{15}H_{19}F_2N_5OS$ 355.4. observed 356.3 MH+.

Example 5

Synthesis of 3-Amino-6-[4-((S)-2-hydroxy-2-phenylethylamino)-piperidin-1-yl]-4-trifluoromethyl-thieno[2,3-b]pyridine-2-carboxylic acid amide

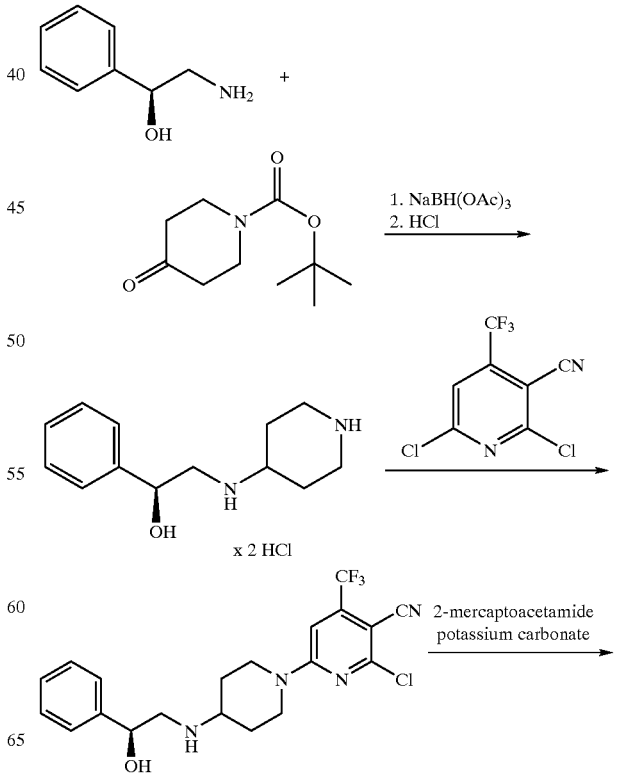

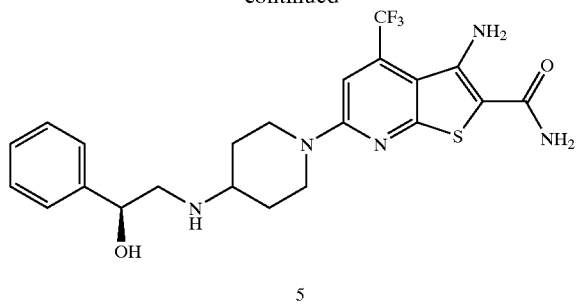

A mixture of 4-N-Boc piperidone (1.12 g, 5.6 mmol), (S)-(+)-2-amino-1-phenylethanol (0.77 g, 5.6 mmol) and sodium triacetoxyborohydride (2.97 g, 14.0 mmol) were stirred in 3% HOAc/THF (21 mL) overnight at room temperature. The reaction mixture was then basified with an aqueous saturated solution of sodium bicarbonate and extracted with ethyl acetate (2×50 mL). The combined organic phases were dried (sodium sulfate) and concentrated to provide 1.66 g (92%) of a yellow foam The above material was dissolved in dichloromethane (20 mL) and N-deprotected by treatment with 4N HCl in dioxane (5.2 mL). The reaction mixture was filtered and dried to provide 1.21 g (91%) of a yellow solid A solution of the above piperidine hydrochloride intermediate (1.08 g, 3.68 mmol), 2,6-dichloro-3-cyano-4-trifluoromethylpyridine (0.85 g, 3.53 mmol) and N,N-diisopropylethylamine (1.85 mL, 10.6 mmol) in ethanol (50 mL) was stirred at 0° C. for 3 h. The reaction mixture was then concentrated and the resulting residue was purified by chromatography over silica gel using a gradient of methanol in dichloromethane as the eluant to provide 550 mg (37%) of a colorless solid.

A suspension of the above chloropyridine (0.55 g, 1.30 mmol), 2-mercaptoacetamide (5.9 mL of 1 g /10 mL solution in methanolic ammonia), and potassium carbonate (1.79 g, 13.0 mmol) and ethanol (20 mL) was heated in a sealed tube at 100° C. with vigorous stirring for 18 h. The reaction mixture was cooled to room temperature and filtered. The filtrate was concentrated and the resulting residue was purified by chromatography over silica gel using a gradient of ammonium hydroxide and methanol in dichloromethane to provide 153 mg (25%) of the title compound as a bright yellow powder, m/z calculated for $C_{22}H_{24}F_3N_5O_2S$ 479.5. observed 480.7 MH+.

3-Amino-6-[4-((R)-2-hydroxy-2-phenylethylamino)-piperidin-1-yl]-4-trifluoromethyl-thieno[2,3-b]pyridine-2-carboxylic acid amide

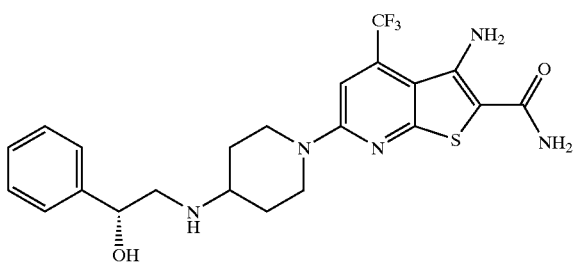

This compound was prepared in an analogous fashion to Example 5 using the opposite enantiomer (R)-(−)-2-amino-1-phenylethanol as a starting material instead of (S)-(+)-2-amino-1-phenylethanol, m/z calculated for $C_{22}H_{24}F_3N_5O_2S$ 479.5. observed 480.7 MH+.

3-Amino-6-[4-(2-hydroxy-ethylamino)-piperidin-1-yl)-4-trifluoromethyl-thieno[2,3-b]pyridine-2-carboxylic acid amide

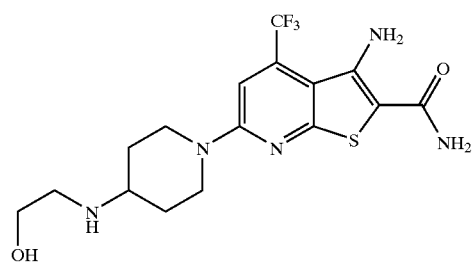

This compound was prepared in an analogous fashion to Example 5 using 2-amino ethanol instead of, (S)-(+)-2-amino-1-phenylethanol as a starting material, m/z calculated for $C_{16}H_{20}F_3N_5O_2S$ 403. observed MH+404.

3-Amino-6-[4-(2-hydroxy-2-napthylene-2yl-ethylamino)-piperidin-1-yl)-4-trifluoromethyl-thieno[2,3-b]pyridine-2-carboxylic acid amide

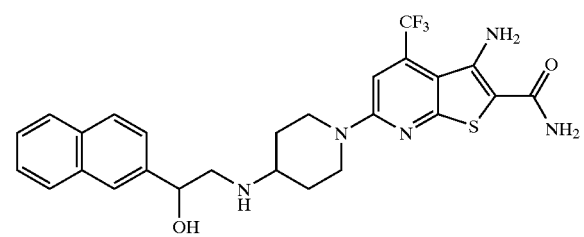

This compound was prepared in an analogous fashion to Example 5 using 2-amino-1-naphthalen-2-yl-ethanol instead of, (S)-(+)-2-amino-1-phenylethanol as a starting material, m/z calculated for $C_{26}H_{26}F_3N_5O_2S$ 529.6. observed MH+530.

Example 6

Synthesis of 3-Amino-6-{4-[-2-(4-benzylcarbamoylphenyl)-2-hydroxy-ethylamino)-piperidin-1-yl]-4-trifluoromethyl-thieno[2,3-b]pyridine-2-carboxylic acid amide

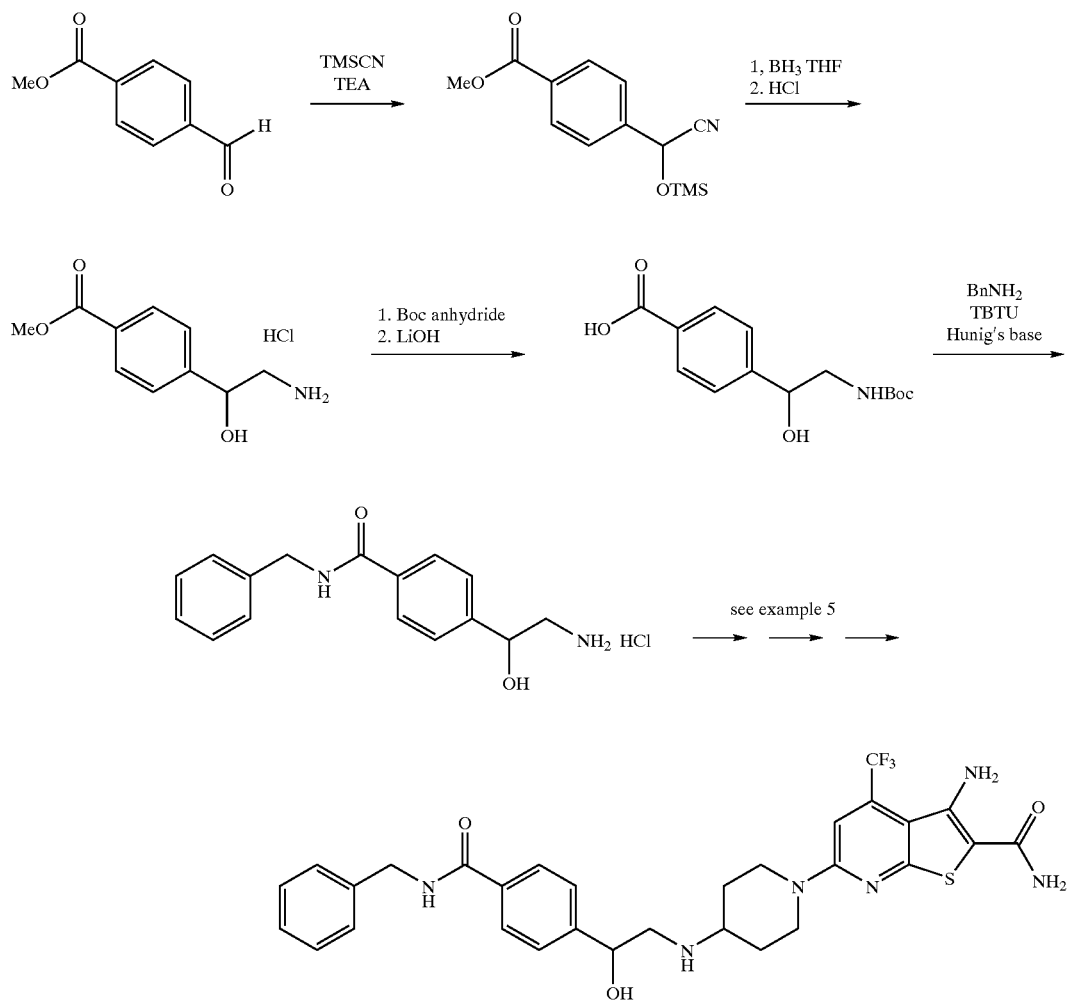

6

A solution of methyl-4-formyl benzoate (15.0 g, 90 nmrol), trimethylsilyl cyanide (25 mL, 184 mmol), and triethylamine (2.5 mL, 18 mmol) in dichloromethane (200 mL) was stirred at 0° C. under an argon atmosphere for 2 h. The reaction mixture was concentrated to provide 24.1 g (100%) of the crude cyanohydrin which was used without further purification.

The cyanohydrin (24.0 g, 91 mmol) in dry THF (250 mL) was added to an ice-cold solution of 1 M borane THF complex (100 mL, 100 mmol). The reaction was stirred under an argon atmosphere overnight and allowed to slowly warm to room temperature. The reaction was then cooled in an ice bath and quenched with methanol and concentrated. The resulting residue was taken up in a minimal amount of ethyl acetate, cooled in an ice bath and treated with 4 N HCl in dioxane (100 mL, 400 mmol) and stirred at room temperature for 15 min. The reaction was diluted with 200 mL of diethyl ether, filtered, and dried to provide 18.9 g (90%) of amine hydrochloride intermediate.

A solution of 13.6 g (59 mmol) of the above material, Boc anhydride (13.0 g, 59 mmol), and Hunig's base (10.4 mL, 59 mmol) in dichloromethane (200 mL) was stirred for 3 h. The reaction mixture was washed with 1 M sodium hydrogen sulfate, brine, dried over sodium sulfate, and concentrated. The resulting residue was purified via chromatography over silica gel using a gradient of ethyl acetate in hexanes to provide 9.51 g (55%) of the Boc protected amino alcohol.

A suspension of 9.5 g (32 mmol) of the above material and lithium hydroxide monohydrate (10.0 g, 234 mmol) in THF/water (80 mL/80 mL) was heated to 70° C. for 1 h then quenched with 2 N HCl, extracted with ethyl acetate, washed with brine, dried over sodium sulfate and concentrated to afford 7.90 g (87%) of the benzoic acid intermediate.

Subjecting the above acid to standard peptide coupling conditions with TBTU tetrafluoroborate, Hunig's base and benzylamine and subsequent N-deprotected by treatment with 4N HCl in dioxane as described previously to provided 1.64 (100%) of the amino alcohol hydrochloride salt. Using the procedures provided in Example 5 this material was carried on to the title compound, m/z calculated for $C_{30}H_{31}F_3N_6O_3S$ 612.7. observed MH+613.2.

3-Amino-6-{4-[2-(4-cyano-phenyl)-2-hydroxy-ethylamino]-piperidin-1-yl}-4-trifluoromethyl-thieno[2,3-b]pyridine-2-carboxylic acid amide

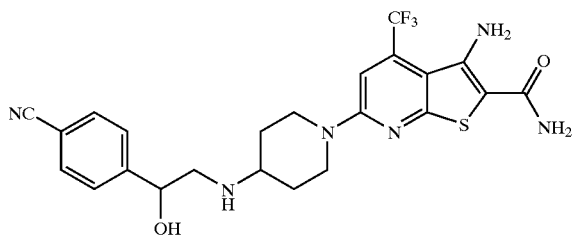

This compound was prepared in an analogous fashion to Example 6 with the exceptions that ammonia was used instead of benzylamine and ethylchloroformate instead of TBTU in the coupling reaction and the resulting primary amide was dehydrated with cyanuric chloride to install the the 4-cyano group, m/z calculated for $C_{25}H_{23}F_3N_6O_2S$ 478. observed MH+479.

3-Amino-6-{4-[2-hydroxy-2-(4-hydroxy-phenyl)-ethylamino]-piperidin-1-yl}-4-trifluoromethyl-thieno[2,3-b]pyridine-2-carboxylic acid amide

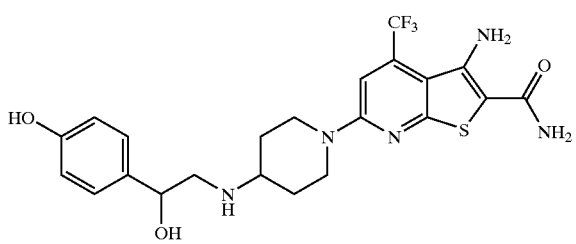

This compound was prepared in an analogous fashion to Example 6 with the exception that 4-hydroxybenzaldehyde was used as a starting material for the cyanohydrin formation m/z calculated for $C_{22}H_{24}F_3N_5O_3S$ 495. observed MH+496.

3-Amino-6-{4-[2-hydroxy-2-(4-morpholin-4-yl-phenyl)-ethylamino]-piperidin-1-yl)}-4-trifluoromethyl-thieno[2,3-b]pyridine-2-carboxylic acid amide

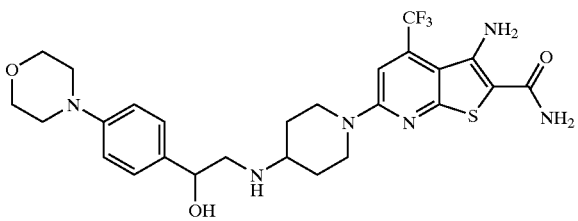

This compound was prepared in an analogous fashion to Example 6 with the exception that 4-morpholin-4-yl benzaldehyde was used as a starting material for the cyanohydrin formation m/z calculated for $C_{26}H_{31}F_3N_6O_3S$ 564. observed MH+565.

3-Amino-6-[4-(2-biphenyl-4-yl-2-hydroxy-ethylamino)-piperidin-1-yl]-4-trifluoromethyl-thieno[2,3-b]pyridine-2-carboxylic acid amide

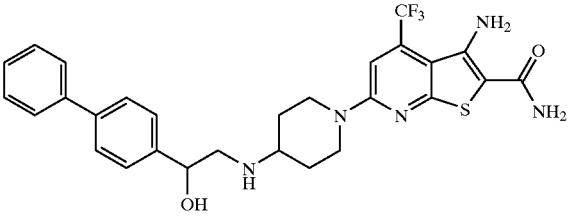

This compound was prepared in an analogous fashion to Example 6 with the exception that biphenyl-4-carbaldehyde was used as a starting material for the cyanohydrin formation m/z calculated for $C_{28}H_{28}F_3N_5O_2S$ 555. observed MH+556.

3-Amino-6-{4-[2-hydroxy-2-(4-pyridin-2-yl-phenyl)-ethylamino]-piperidin-1-yl}-4-trifluoromethyl-thieno[2,3-b]pyridine-2-carboxylic acid amide

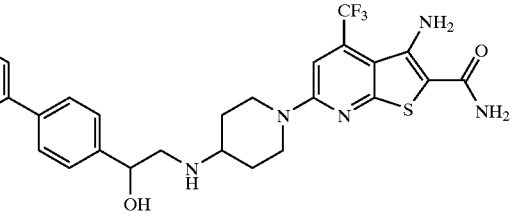

This compound was prepared in an analogous fashion to Example 6 with the exception that 4-pyridin-2-yl-benzaldehyde was used as a starting material for the cyanohydrin formation m/z calculated for $C_{27}H_{27}F_3N_6O_2S$ 556. observed MH+557.

3-Amino-6-{4-[2-hydroxy-2-(4-pyridin-3-yl-phenyl)-ethylamino]-piperidin-1-yl}-4-trifluoromethyl-thieno[2,3-b]pyridine-2-carboxylic acid amide This compound was prepared in an analogous fashion to Example 6 with the exception that 4-pyridin-3-yl-benzaldehyde was used as a starting material for the cyanohydrin formation m/z calculated for $C_{27}H_{27}F_3N_6O_2S$ 556. observed MH+557.

3-Amino-6-{4-[2-hydroxy-2-(4-pyridin-4-yl-phenyl)-ethylamino]-piperidin-1-yl}-4-trifluoromethyl-thieno[2,3-b]pyridine-2-carboxylic acid amide

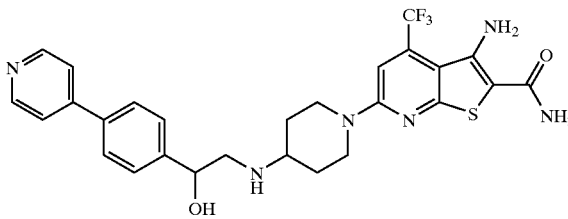

This compound was prepared in an analogous fashion to Example 6 with the exception that 4-pyridin-4-yl-benzaldehyde was used as a starting material for the cyanohydrin formation m/z calculated for $C_{27}H_{27}F_3N_6O_2S$ 556. observed MH+557.

Example 7

Synthesis of 3-Amino-6-{4-[2-hydroxy-2-(4-thiazol-2-yl-phenyl)-ethylamino]-piperidin-1-yl}-4-trifluoromethyl-thieno[2,3-b]pyridine-2-carboxylic acid amide

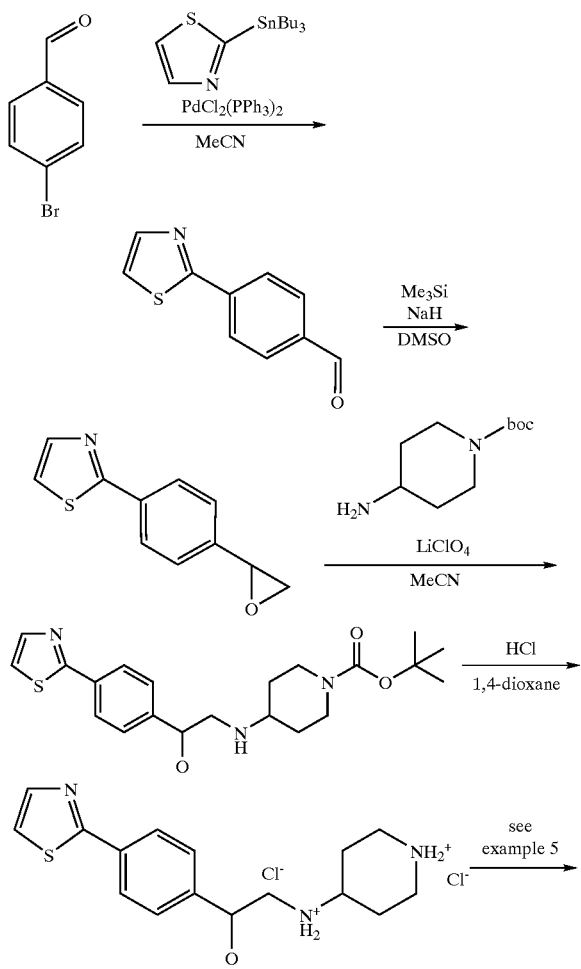

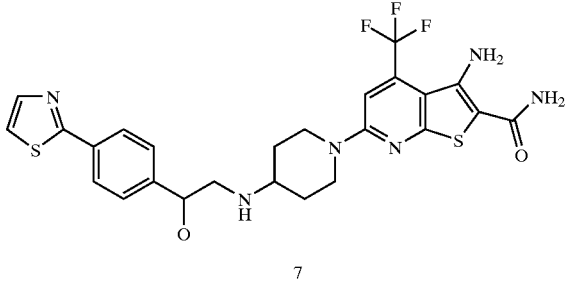

To a solution of 0.500 g (2.70 mmol) of 4-bromobenzaldehyde and 1.00 g (2.67 mmol) of 2-tributylstannylthiazole in MeCN (25 mL), degassed by bubbling $N_2$ through for 10 min, was added 0.100 g (0.140 mmol) of palladium dichloride bis(triphenylphosphine). The mixture was heated to 60° C. for 15 h. The mixture was cooled to room temperature and filtered through diatomaceous earth. The mixture was diluted with $H_2O$ and washed with EtOAc. The combined organic phase was dried over anhydrous $Na_2SO_4$ and concentrated under reduced pressure. The residue was purified by flash silica gel chromatography to provide 0.400 g (79.1%) of 4-thiazol-2-yl-benzaldehyde as a yellow solid.

To a suspension of 0.063 g (1.5 mmol) of sodium hydride in DMSO (10 mL) was added 0.300 g (1.47 mmol) of trimethylsulfonium iodide as a solution in DMSO (5 mL). After stirring at room temperature for 5 min 0.130 g (0.687 mmol) of the above aldehyde was added as a solution in DMSO (5 mL). The mixture was allowed to stir at room temperature for 2 h. The mixture was poured into $H_2O$ and washed with EtOAc. The combined organic phase was washed with $H_2O$, dried over anhydrous $MgSO_4$ and concentrated under reduced pressure. The residue was purified by flash silica gel chromatography to provide 0.129 g (92.3%) of 2-(4-oxiranyl-phenyl)-thiazole as a clear oil.

A mixture of 0.200 g (0.984 mmol) of N-tertbutoxycarbonyl-4-aminopiperidine, 0.100 g (0.499 mmol) of the above epoxide and 0.110 g (1.03 mmol) of lithium perchlorate in MeCN (5 mL) was heated to 60° C. for 15 h. The mixture was cooled to room temperature and loaded directly onto silica gel. The residue was purified by flash silica gel chromatography to provide 0.196 g (97.3%) of 4-[2-hydroxy-2-(4-thiazol-2-yl-phenyl)-ethylamino]-piperidine-1-carboxylic acid tert-butyl ester as a white foam.

To a solution of 0.196 g (0.491 mmol) of the above boc-protected amine in $CH_2Cl_2$ (5 mL) was added 0.50 mL (2.0 mmol) of hydrogen chloride as a 4.0 M solution in 1,4-dioxane. The mixture was stirred at room temperature for 15 h during which time a solid precipitated from solution. The solid was collected by filtration, washed with $CH_2Cl_2$, and dried under reduced pressure to provide 0.122 g (66.0%) of [2-hydroxy-2-(4-thiazol-2-yl-phenyl)-ethyl]-piperidinium-4-yl-ammonium dichloride as a white solid.

The above dichloride salt was reacted under the conditions described in Example 5 to provide the title compound as a yellow solid, m/z calculated for. $C_{25}H_{26}F_3N_6O_2S_2$ 562.7. observed MH+563.34.

3-Amino-6-{4-[2-(4-fluoro-phenyl)-2-hydroxy-ethylamino]-piperidin-1-yl}-4-trifluoromethyl-thieno[2,3-b]pyridine-2-carboxylic acid amide

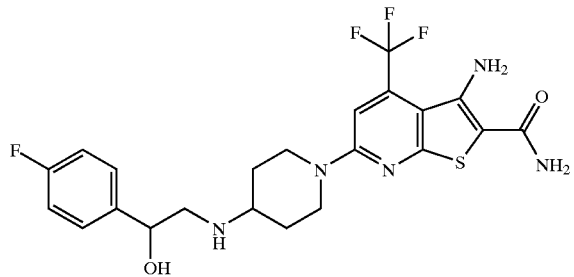

This compound was prepared in an analogous fashion to Example 7 starting with 4-fluoro-benzaldehyde, mp: 236–238° C. (dec.), m/z calculated for $C_{22}H_{23}F_4N_5O_2S$ 497. observed. 498 m/z (MH$^+$).

3-Amino-6-{4-[2-(2-fluoro-phenyl)-2-hydroxy-ethylamino]-piperidin-1-yl}-4-trifluoromethyl-thieno[2,3-b]pyridine-2-carboxylic acid amide

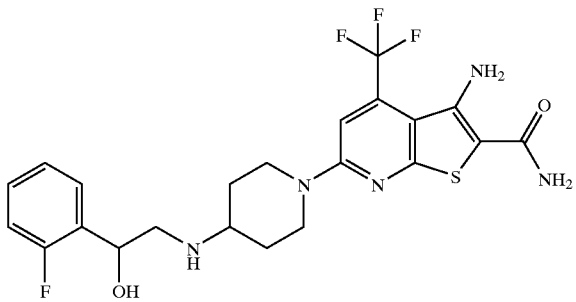

This compound was synthesized in an analogous fashion to Example 7 described above starting from 2-fluoro-benzaldehyde. mp: 192–194° C., m/z calculated for $C_{22}H_{23}F_4N_5O_2S$ 497. observed. 498 m/z (MH$^+$).

3-Amino-6-{4-[2-(3-fluoro-phenyl)-2-hydroxy-ethylamino]-piperidin-1-yl}-4-trifluoromethyl-thieno[2,3-b]pyridine-2-carboxylic acid amide

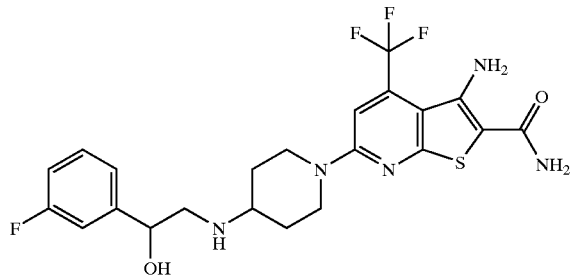

This compound was synthesized in an analogous fashion to Example 7 described above starting from 3-fluoro-benzaldehyde. mp: 215° C., m/z calculated for $C_{22}H_{23}F_4N_5O_2S$ 497. observed. 498 m/z (MH$^+$).

3Amino-6-{4-[2-(2,4-difluoro-phenyl)-2-hydroxy-ethylamino]-piperidin-1yl}-4-trifluoromethyl-thieno[2,3-b]pyridine-2-carboxytic acid amide

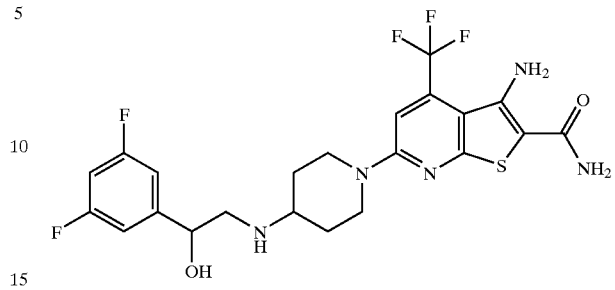

This compound was synthesized in an analogous fashion to Example 7 described above starting from 2,4-difluoro-benzaldehyde. mp: 221–222° C., m/z calculated for $C_{22}H_{22}F_5N_5O_2S$ 515. observed. 516 m/z (MH$^+$).

3-Amino-6-[4-(2-benzo[1,3]dioxol-5-yl-2-hydroxy-ethylamino)-piperidin-1-yl]-4-trifluoromethyl-thieno[2,3-b]pyridine-2-carboxylic acid amide

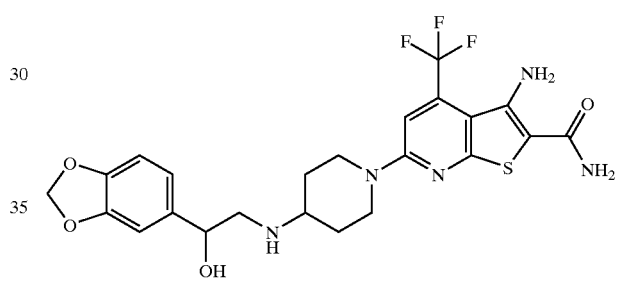

This compound was synthesized in an analogous fashion to Example 7 starting from piperonal. mp: 232–234° C., m/z calculated for $C_{23}H_{24}F_3N_5O_4S$ 523. observed. 524 m/z (MH$^+$).

3-Amino-6-[4-(2-benzo[1,3]dioxol-4-yl-2-hydroxy-ethylamino)-piperidin-1-yl]-4-trifluoromethyl-thieno[2,3-b]pyridine-2-carboxylic acid amide

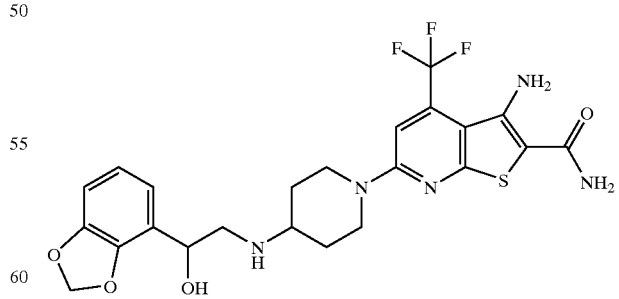

This compound was synthesized in an analogous fashion to Example 7, starting from 1,3-benzodioxole-4-carboxaldehyde. mp: 221–223° C., m/z calculated for $C_{23}H_{24}F_3N_5O_4S$ 523. observed. 524 m/z (MH$^+$).

3-Amino-6-{4-[2-(2,2-difluoro-benzo[1,3]dioxol-5-yl)-2-hydroxy-ethylamino]-piperidin-1-yl}-4-trifluoromethyl-thieno[2,3-b]pyridine-2-carboxylic acid amide

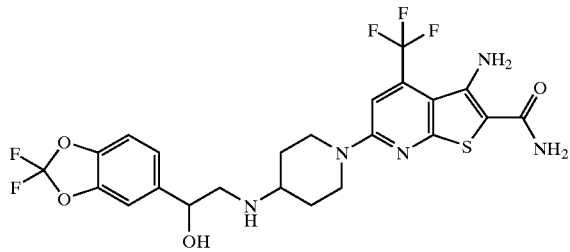

This compound was synthesized in an analogous fashion to the methods described in Example 7 starting from 2,2-difluoro-1,3-benzodioxole-4-carboxaldehyde. mp: 214–216° C., m/z calculated for $C_{23}H_{22}F_5N_5O_4S$ 559. observed. 560 m/z (MH$^+$).

Example 8

Synthesis of 3-Amino-6-{4-[2-(4-difluoromethoxy-phenyl)-2-hydroxy-ethylamino]-piperidin-1-yl}-4-trifluoromethyl-thieno[2,3-b]pyridine-2-carboxylic acid amide

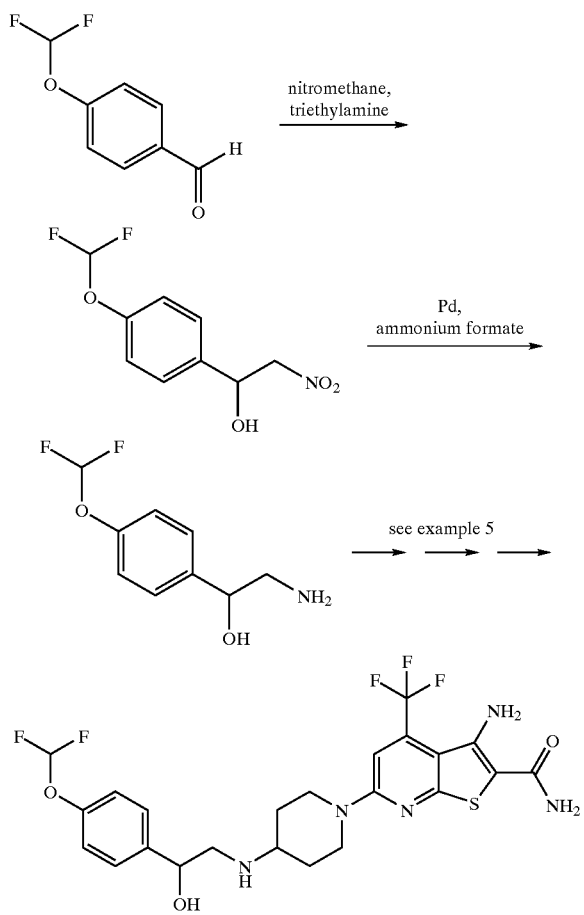

To a round bottom flask was added 4-(difluoromethoxy)benzaldehyde (600 mg, 3.49 mmol) in 8 mL of nitromethane, followed by the addition of triethylamine (352 mg, 3.49 mmol). The reaction mixture was stirred at room temperature for 3 h. The reaction mixture was concentrated in vacuo. The residue was loaded to a flash column. The column was eluted with 5–20% EtOAc/hexane. The product fractions were collected and concentrated to afford 560 mg (68.9%) of the desired nitro alcohol intermediate. (TLC: Rf=0.3, 25% EtOAc/hexane).

To a round bottom flask was added 1-(4-Difluoromethoxy-phenyl)-2-nitro-ethanol (560 mg, 2.40 mmol), ammonium formate (757 mg, 12 mmol) and palladium 10% on activated carbon (100 mg) in 20 mL of methanol and 20 mL of THF. The reaction mixture was stirred at room temperature for 18 h. The reaction mixture was filtered through diatomaceous earth and concentrated in vacuo to afford 488 mg (100%) of the desired amino alcohol intermediate MH$^+$=204.35

Following the procedures described in Example 5, this amino alcohol intermediate was carried on to the title compound, m/z calculated for $C_{23}H_{24}F_5N_5O_3S$ 545. observed. 546 m/z (MH$^+$).

3-Amino-6-{4-[2-hydroxy-2-(4-trifluoromethoxy-phenyl)-ethylamino]-piperidin-1-yl}-4-trifluoromethyl-thieno[2,3-b]pyridine-2-carboxylic acid amide

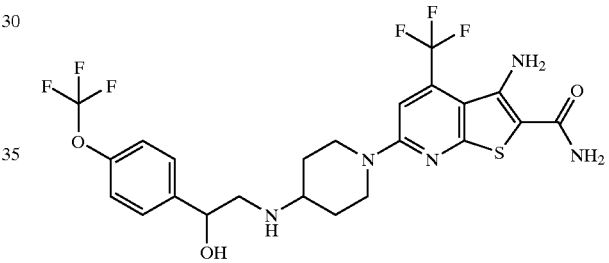

This compound was synthesized in an analogous fashion to Example 8 described above starting from 4-trifluoromethoxy-benzaldehyde, m/z calculated for $C_{23}H_{23}F_6N_5O_3S$ 563. observed. 564 m/z (MH$^+$).

3-Amino-6-{4-[2-(3,4,5-trifluoro-phenyl)-2-hydroxy-ethylamino]-piperidin-1-yl}-4-trifluoromethyl-thieno[2,3-b]pyridine-2-carboxylic acid amide

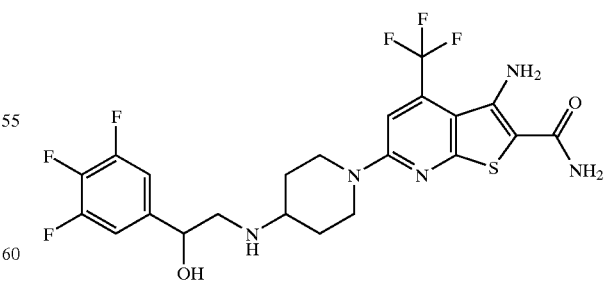

This compound was synthesized in an analogous fashion to Example 8 described above starting from 3,4,5-trifluoro-benzaldehyde, m/z calculated for $C_{22}H_{21}F_6N_5O_2S$ 533. observed. m/z 534 (MH$^+$).

3-Amino-6-{4-[2-(3,4-dimethoxy-phenyl)-2-hydroxy-ethylamino]-piperidin-1-yl}-4-trifluoromethyl-thieno[2,3-b]pyridine-2-carboxylic acid amide

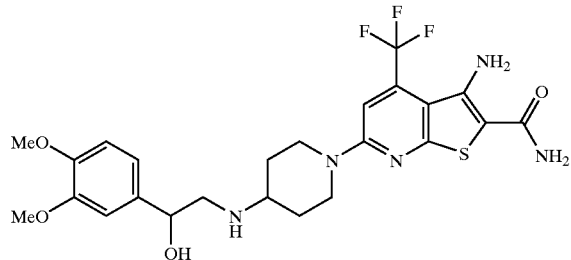

This compound was synthesized in an analogous fashion to Example 8 described above starting from 3,4-dimethoxy-benzaldehyde, m/z calculated for $C_{24}H_{28}F_3N_5O_2S$ 539. observed. 540 m/z (MH$^+$).

3-Amino-6-{4-[2-hydroxy-2-(4-methanesulfonyl-phenyl)-ethylamino3-piperidin-1-yl]-4-trifluoromethyl-thieno[2,3-b]pyridine-2-carboxylic acid amide

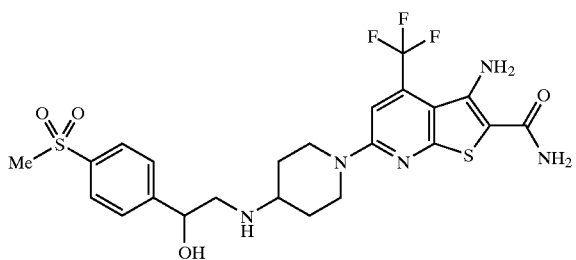

This compound was synthesized in an analogous fashion to Example 8 described above starting from 4-methanesulfonyl benzaldehyde, m/z calculated for $C_{23}H_{26}F_3N_5O_4S_2$ 557. observed. 558 m/z (MH$^+$).

3-Amino-6-{4-[2-hydroxy-2-(4-pyrazin-2-yl-phenyl)-ethylamino]-piperidin-1-yl}-4-trifluoromethyl-thieno[2,3-b]pyridine-2-carboxylic acid amide

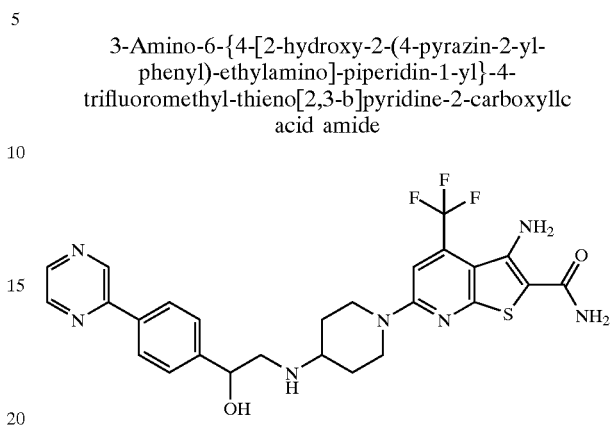

This compound was synthesized in an analogous fashion to Example 8 described above starting from 4-(2-pyrazinyl)-benzaldehyde, m/z calculated for $C_{26}H_{26}F_3N_7O_2S$ 557 observed. 558 m/z (MH$^+$).

Example 9

Synthesis of 3-Amino-6-(4-{-2-[4-(cylopropylmethyl-carbamoyl)-phenyl]-2-hydroxy-ethylamino}-piperidin-1-yl}-4-propyl-thieno[2,3-b]pyridine-2-carboxylic acid amide

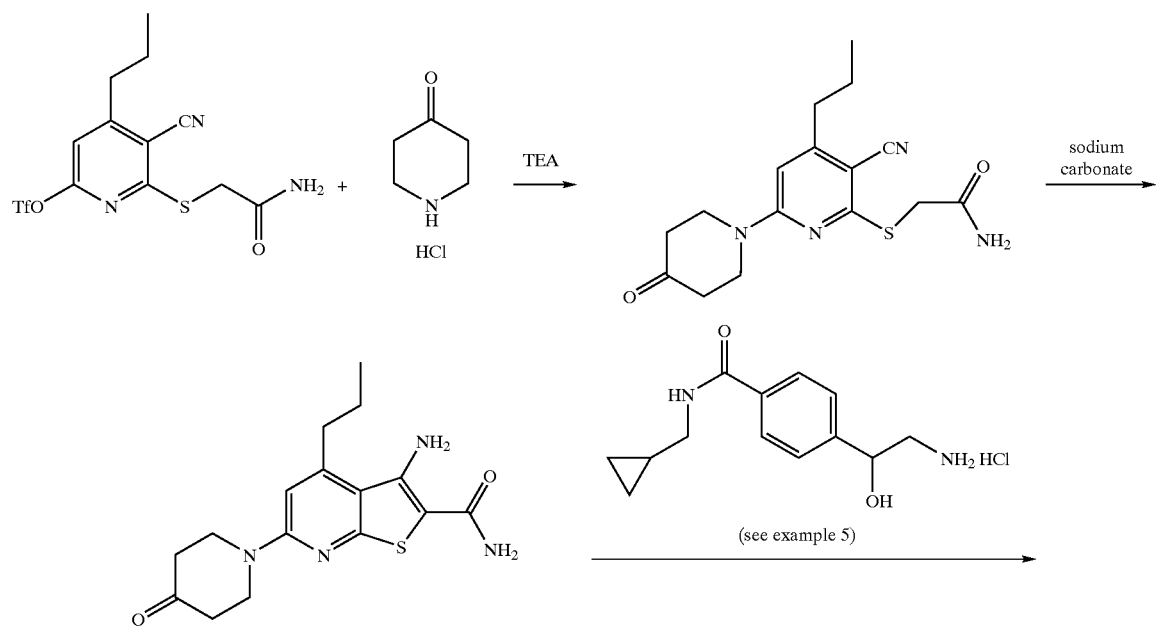

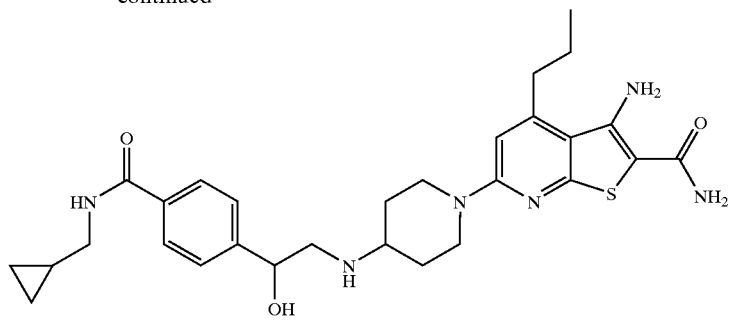

9

4-Piperidone hydrochloride (710 mg, 5.2 mmol) was added to a solution of trifluoro-methanesulfonic acid 6-carbamoylmethylsulfanyl-5-cyano-4-propyl-pyridin-2-yl ester (2.0 g, 5.2 mmol) and triethylamine (2.2 mL, 16.2 mmol) in dioxane (20 mL) preheated to 80° C. The reaction mixture was stirred for 1 h then cooled to room temperature, concentrated, and the resulting residue was purified by column chromatography over silica gel using a gradient of methanol in dichloromethane as the eluant to provide 1.42 g of the piperidone adduct.

6.23 g (18.7 mmol) of the above material was dissolved in dioxane (30 mL) and treated with an aqueous solution of sodium carbonate (2N, 40 mL). The reaction mixture was heated to 100° C. in a sealed tube for 4.5 h, then cooled to room temperature and the organic phase was decanted. The aqueous phase was extracted with ethyl acetate and the combined organic phases were then dried over sodium sulfate and concentrated to provide 6.02 g (97%) of the desired thienopyridine intermediate A mixture of the above material (100 mg, 0.3 mmol), 4-(2-amino-1-hydroxy-ethyl)-N-cyclopropylmethyl-benzamide (139 mg, 0.51 mmol) (prepared in analogous fashion to Example 5 using cyclopropyl methylamine instead of benzylamine), polymer supported cyanoborohydride (188 mg, 1.7 mmol) and triethylamine (150 uL, 1 mmol) in THF (3 mL) were mixed in a 2-dram vial at room temperature overnight. The reaction was then filtered, and the borohydride resin was rinsed with MeOH, and then filtered again. The combined filtrates were quenched with 5 M $NH_3$/MeOH and concentrated in vacuo and the resulting residue was preadsorbed onto diatomaceous earth and purified via chromatography over silica gel using a gradient of ammonia and methanol in dichloromethane to afford 74 mg (45%) of the title compound, m/z calculated for $C_{29}H_{38}N_6O_3S$ 550.7. observed m/z 551.2 (MH+).

3-Amino-6-(4-{2-[4-(cyclohexylmethyl-carbamoyl)-phenyl]-2-hydroxy-ethylamino}-piperidin-1-yl)-4-propyl-thieno[2,3-b]pyridine-2-carboxylic acid amide

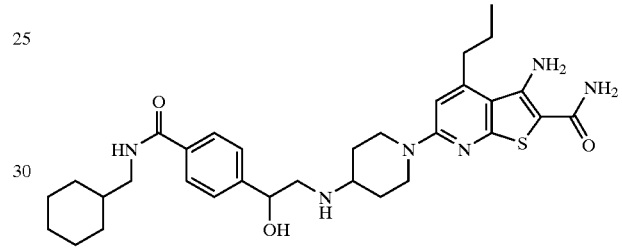

This compound was prepared in an analogous fashion to Example 9 using cyclohexylmethylamine instead of cyclopropylmethylamine, m/z calculated for $C_{32}H_{44}N_6O_3S$ 592. observed m/z 593 (MH+).

3-Amino-6-(4-{2-hydroxy-2-[4-(2-methyl-cyclohexylcarbamoyl)-phenyl]-ethylamino}-piperidin-1-yl)-4-propyl-thieno[2,3-b]pyridine-2-carboxylic acid amide

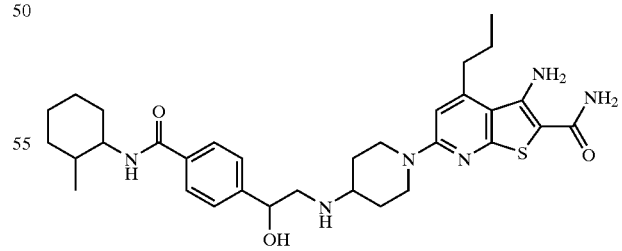

This compound was prepared in an analogous fashion to Example 9 using 2-methylcyclohexylamine instead of cyclopropylmethylamine, m/z calculated for $C_{32}H_{44}N_6O_3S$ 592. observed m/z 593 (MH+).

3-Amino-6-(4-{2-hydroxy-2-[4-(1-methyl-1-phenyl-ethylcarbamoyl)-phenyl]-ethylamino}-piperidin-1-yl)-4-propyl-thieno[2,3-b]pyridine-2-carboxylic acid amide

3-Amino-6-(4-{2-hydroxy-2-[4-(3-nitro-benzylcarbamoyl)-phenyl]-ethylamino}-piperidin-1-yl)-4-propyl-thieno[2,3-b]pyridine-2-carboxylic acid amide

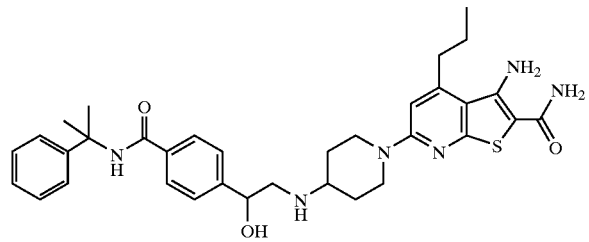

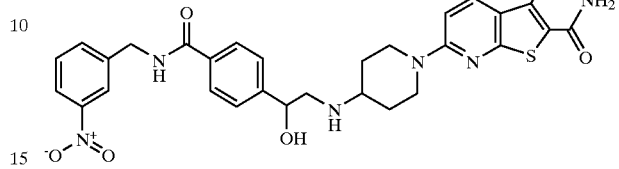

This compound was prepared in an analogous fashion to Example 9 using 1,1-dimethylbenzylamine instead of cyclopropylmethylamine, m/z calculated for $C_{34}H_{42}N_6O_3S$ 614. observed m/z 615 (MH+).

This compound was prepared in an analogous fashion to Example 9 using 3-nitrobenzylamine instead of cyclopropylmethylamine, m/z calculated for $C_{32}H_{37}N_7O_5S$ 631. observed m/z 632 (MH+).

3-Amino-6-{4-[2-hydroxy-2-(4-phenethylcarbamoyl-phenyl)-ethylamino]-piperidin-1-yl}-4-propyl-thieno[2,3-b]pyridine-2-carboxylic acid amide

3-Amino-6-(4-{2-hydroxy-2-[4-(3-methoxy-benzylcarbamoyl)-phenyl]-ethylamino}-piperidin-1-yl)-4-propyl-thieno[2,3-b]pyridine-2-carboxylic acid amide

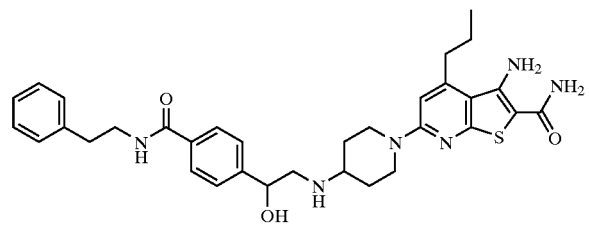

This compound was prepared in an analogous fashion to Example 9 using phenylethylamine instead of cyclopropylmethylamine, m/z calculated for $C_{34}H_{40}N_6O_3S$ 600. observed m/z 601 (MH+).

This compound was prepared in an analogous fashion to Example 9 using 3-methoxybenzylamine instead of cyclopropylmethylamine, m/z calculated for $C_{33}H_{40}N_6O_4S$ 616. observed m/z 617 (MH+).

3-Amino-6-(4-{2-[4-(2-dimethylamino-ethylcarbamoyl)-phenyl]-2-hydroxy-ethylamino}-piperidin-1-yl)-4-propyl-thieno[2,3-b]pyridine-2-carboxylic acid amide

3-Amino-6-(4-{2-[4-(3-chloro-benzylcarbamoyl)-phenyl]-2-hydroxy-ethylamino}-piperidin-1-yl)-4-propyl-thieno[2,3-b]pyridine-2-carboxylic acid amide

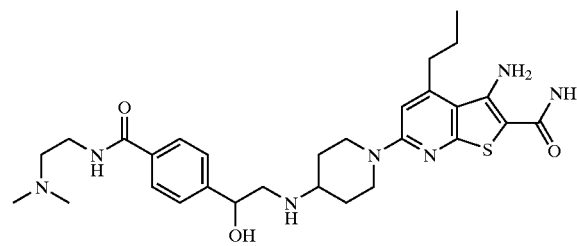

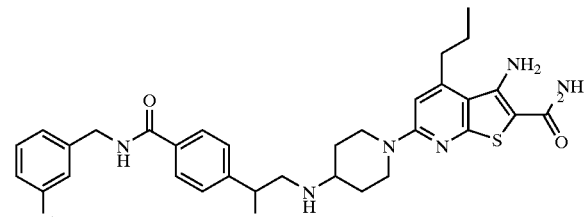

This compound was prepared in an analogous fashion to Example 9 using N,N-dimethyldiaminoethane instead of cyclopropylmethylamine, m/z calculated for $C_{29}H_{41}N_6O_3S$ 567. observed m/z 568 (MH+).

This compound was prepared in an analogous fashion to Example 9 using 3-chlorobenzylamine instead of cyclopropylmethylamine, m/z calculated for $C_{32}H_{37}ClN_6O_3S$ 621. observed m/z 622 (MH+).

181

3-Amino-6-(4-{2-hydroxy-2-[4-(4-hydroxy-piperidine-1-carbonyl)-phenyl]-ethylamino}-piperidin-1-yl)-4-propyl-thieno[2,3-b]pyridine-2-carboxylic acid amide

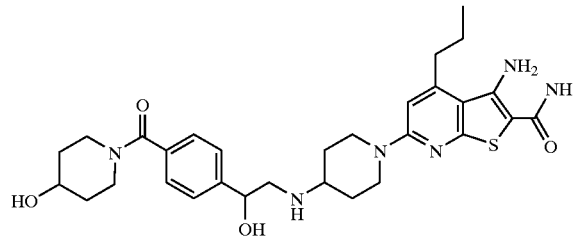

This compound was prepared in an analogous fashion to Example 9 using 4-hydroxypiperidine instead of cyclopropylmethylamine, m/z calculated for $C_{30}H_{40}N_6O_4S$ 580. observed m/z 581 (MH+).

3-Amino-6-{4-[2-hydroxy-2-(4-isobutylcarbamoyl-phenyl)-ethylamino]-piperidin-1-yl}-4-propyl-thieno[2,3-b]pyridine-2-carboxylic acid amide

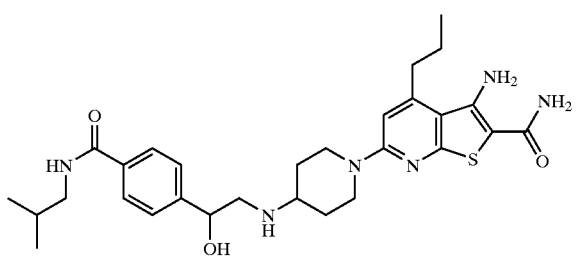

This compound was prepared in an analogous fashion to Example 9 using iso-butylamine instead of cyclopropylmethylamine, m/z calculated for $C_{29}H_{40}N_6O_3S$ 552. observed m/z 553 (MH+).

3-Amino-6-[4-(2-{4-[(benzo[b]thiophen-2-ylmethyl)-carbamoyl]-phenyl}-2-hydroxy-ethylamino)-piperidin-1-yl]-4-propyl-thieno[2,3-b]pyridine-2-carboxylic acid amide

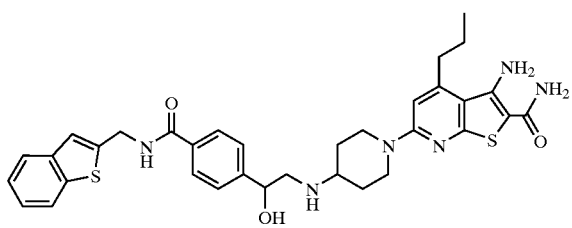

This compound was prepared in an analogous fashion to Example 9 using 2-methylamino benzothiophene instead of cyclopropylmethylamine, m/z calculated for $C_{34}H_{38}N_6O_3S_2$ 642. observed m/z 643 (MH+).

182

3-Amino-6-(4-{2-hydroxy-2-[4-((S)-1-hydroxymethyl-2-phenyl-ethylcarbamoyl)-phenyl]-ethylamino}-piperidin-1-yl)-4-propyl-thieno[2,3-b]pyridine-2-carboxylic acid amide

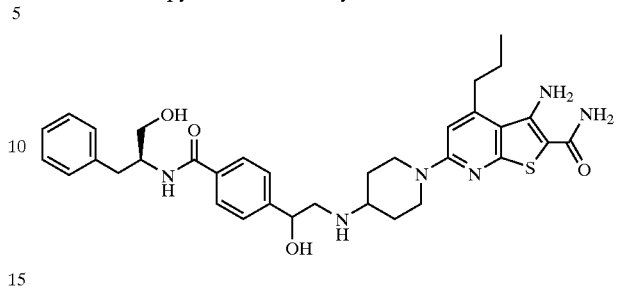

This compound was prepared in an analogous fashion to Example 9 using (S)-1-hydroxymethylphenylethylamine instead of cyclopropylmethylamine, m/z calculated for $C_{34}H_{42}N_6O_4S$ 630. observed m/z 631 (MH+).

3-Amino-6-(4-{2-hydroxy-2-[4-((R)-1-hydroxymethyl-2-phenyl-ethylcarbamoyl)-phenyl]-ethylamino}-piperidin-1-yl)-4-propyl-thieno[2,3-b]pyridine-2-carboxylic acid amide

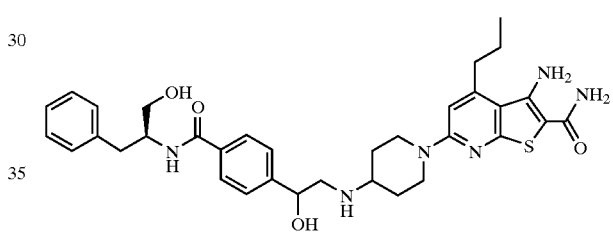

This compound was prepared in an analogous fashion to Example 9 using (R)-1-hydroxymethylphenylethylamine instead of cyclopropylmethylamine, m/z calculated for $C_{34}H_{42}N_6O_4S$ 630. observed m/z 631 (MH+).

3-Amino-6-(4-{2-hydroxy-2-[4-(3-hydroxy-propylcarbamoyl)-phenyl]-ethylamino}-piperidin-1-yl)-4-propyl-thieno[2,3-b]pyridine-2-carboxylic acid amide

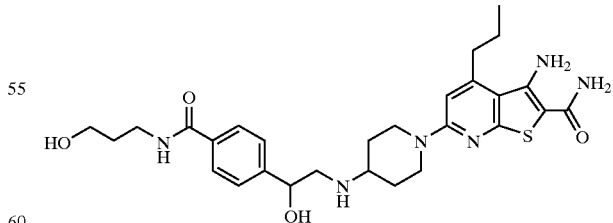

This compound was prepared in an analogous fashion to Example 9 using 3-hydroxypropylamine instead of cyclopropylmethylamine, m/z calculated for $C_{28}H_{38}N_6O_4S$ 554. observed m/z 555 (MH+).

(4-{2-[1-(3-Amino-2-carbamoyl-4-propyl-thieno[2,3-b]pyridin-6-yl)-piperidin-4-ylamino]-1-hydroxy-ethyl}-benzoylamino)-acetic acid methyl ester

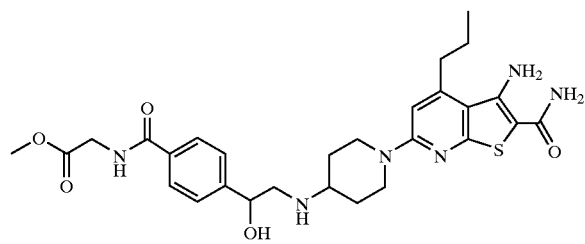

This compound was prepared in an analogous fashion to Example 9 using glycine methyl ester instead of cyclopropylmethylamine, m/z calculated for C$_{28}$H$_{36}$N$_6$O$_5$S 568. observed m/z 569 (MH+).

3-Amino-6-(4-{2-hydroxy-2-[4-(morpholine-4-carbonyl)-phenyl]-ethylamino}-piperidin-1-yl)-4-propyl-thieno[2,3-b]pyridine-2-carboxylic acid amide

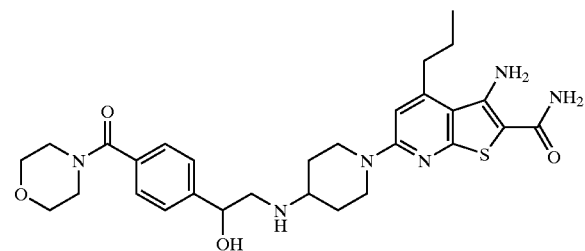

This compound was prepared in an analogous fashion to Example 9 using morpholine instead of cyclopropylmethylamine, m/z calculated for C$_{29}$H$_{38}$N$_6$O$_4$S 566. observed m/z 567 (MH+).

3-Amino-6-(4-{2-hydroxy-2-[4-(3-trifluoromethyl-benzylcarbamoyl)-phenyl]-ethylamino}-piperidin-1-yl)-4-propyl-thieno[2,3-b]pyridine-2-carboxylic acid amide

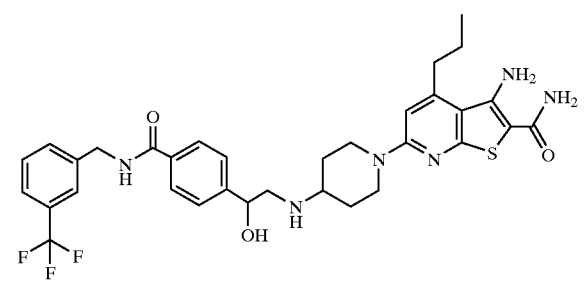

This compound was prepared in an analogous fashion to Example 9 using 3-trifluoromethylbenzylamine instead of cyclopropylmethylamine, m/z calculated for C$_{33}$H$_{37}$N$_6$O$_3$S 654. observed m/z 655 (MH+).

3-Amino-6-(4-{2-[4-(3-carbamoyl-benzylcarbamoyl)-phenyl]-2-hydroxy-ethylamino}-piperidin-1-yl)-4-propyl-thieno[2,3-b]pyridine-2-carboxylic acid amide

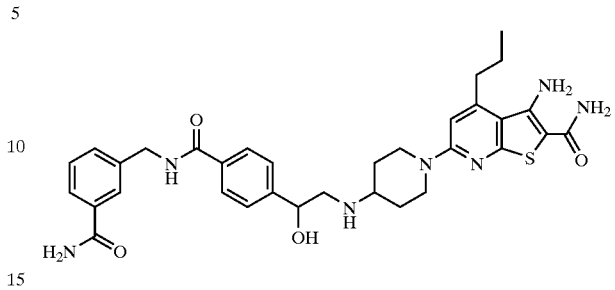

This compound was prepared in an analogous fashion to Example 9 using 3-carboxamidebenzylamine instead of cyclopropylmethylamine, m/z calculated for C$_{33}$H$_{39}$N$_7$O$_4$S 629. observed m/z 630 (MH+).

3-Amino-6-[4-(2-{4-[(furan-2-ylmethyl)-carbamoyl]-phenyl}-2-hydroxy-ethylamino)-piperidin-1-yl]-4-propyl-thieno[2,3-b]pyridine-2-carboxylic acid amide

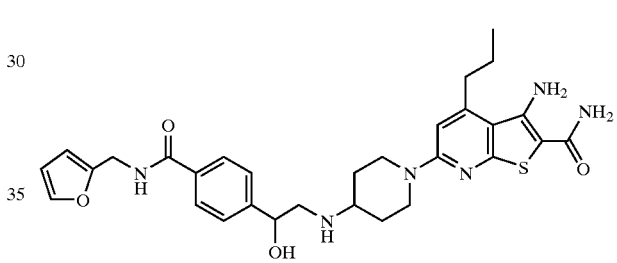

This compound was prepared in an analogous fashion to Example 9 using 2-methylaminofuran instead of cyclopropylmethylamine, m/z calculated for C$_{30}$H$_{36}$N$_6$O$_4$S 576. observed m/z 577 (MH+).

3-Amino-6-[4-(2-hydroxy-2-{4-[(pyridin-3-ylmethyl)-carbamoyl]-phenyl}-ethylamino)-piperidin-1-yl]-4-propyl-thieno[2,3-b]pyridine-2-carboxylic acid amide

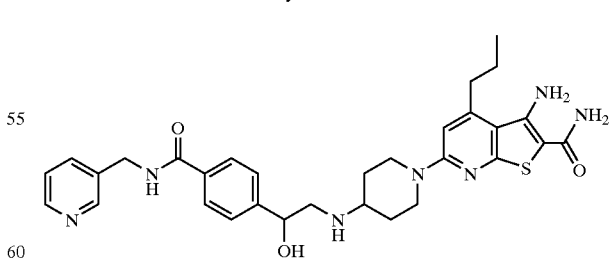

This compound was prepared in an analogous fashion to Example 9 using 3-methylaminopyridine instead of cyclopropylmethylamine, m/z calculated for C$_{31}$H$_{37}$N$_7$O$_3$S 587. observed m/z 588 (MH+).

4-{2-[1-(3-Amino-2-carbamoyl-4-propyl-thieno[2,3-b]pyridin-6-yl)-piperidin-4-ylamino]-1-hydroxy-ethyl}-benzoic acid

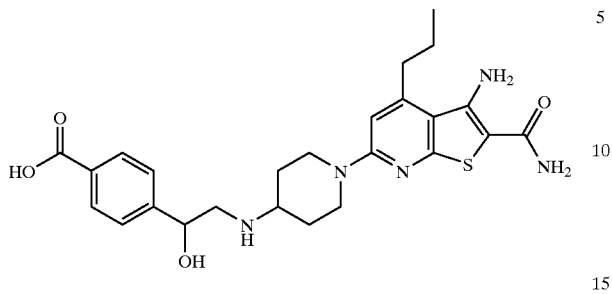

This compound was prepared via a variation of Example 9 in which no amide coupling was performed and the carboxylic acid functionality was carried through the synthesis, m/z calculated for $C_{25}H_{31}N_5O_4S$ 497. observed m/z 498 (MH+).

3-Amino-6-{4-[2-(4-cyano-phenyl)-2-hydroxy-ethylamino]-piperidin-1-yl}-4-propyl-thieno[2,3-b]pyridine-2-carboxylic acid amide

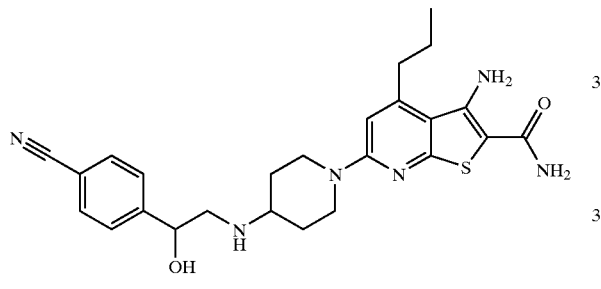

This compound was prepared via a variation of Example 9 in which an amide coupling was carried out with ammonia and the resulting primary amide was dehydrated to a nitrile group with cyanuric chloride, m/z calculated for $C_{25}H_{30}N_6O_4S$ 478. observed m/z 479 (MH+).

3-Amino-6-{4-[2-(4-carbamoyl-phenyl)-ethylamino]-piperidin-1-yl}-4-propyl-thieno[2,3-b]pyridine-2-carboxylic acid amide

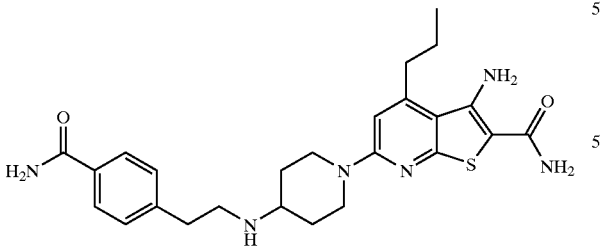

This compound was prepared via a similar reductive amination as shown in Example 9 using sodium triacetoxyborohydride as the reducing agent and 4-(2-amino-ethyl) benzamide (prepared from 4-(2-amino-ethyl) benzoic acid) as the amine, m/z calculated for $C_{25}H_{32}N_6O_2S$ 480. observed m/z 481 (MH+).

3-Amino-6-(4-cyclopropylamino-piperidin-1-yl)-4-propyl-thieno[2,3-b]pyridine-2-carboxylic acid amide

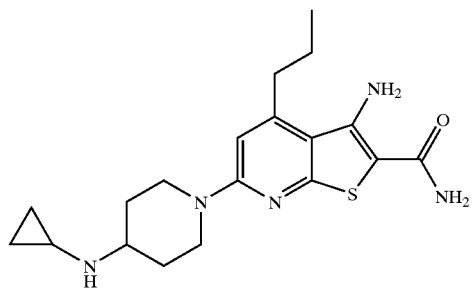

This compound was prepared via a similar reductive amination as shown in Example 9 using sodium triacetoxyborohydride as the reducing agent and cyclopropylamine as the amine, m/z calculated for $C_{19}H_{27}N_5OS$ 373. observed m/z 374 (MH+).

3-Amino-4-propyl-6-{4-[(1H-tetrazol-5-ylmethyl)-amino]-piperidinyl-1-yl}-thieno[2,3-b]pyridine-2-carboxylic acid amide

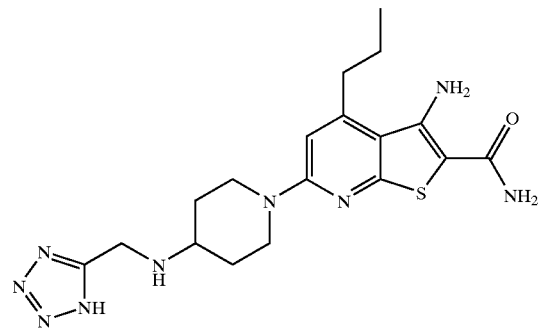

This compound was prepared via a similar reductive amination as shown in Example 9 using sodium triacetoxyborohydride as the reducing agent and 5-aminomethyl tetrazole as the amine, m/z calculated for $C_{18}H_{25}N_9OS$ 415. observed m/z 416 (MH+).

3-Amino-6-[4-(2-hydroxy-benzylamino)-piperidin-1-yl]-4-propyl-thieno[2,3-b]pyridine-2-carboxylic acid amide

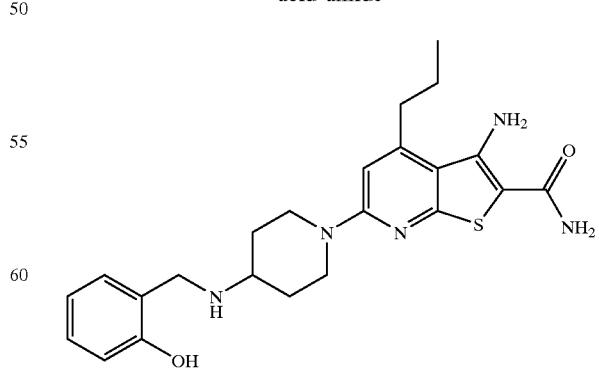

This compound was prepared via a similar reductive amination as shown in Example 9 using sodium triacetoxyborohydride as the reducing agent and 2-hydroxy benzylamine as the amine, m/z calculated for $C_{23}H_{29}N_5O_2S$ 439. observed m/z 440 (MH+).

Example 10

Synthesis of 3-Amino-6-{4-[2-(4-difluoromethoxy-phenyl)-2-hydroxy-ethylamino]-piperidin-1-yl}-4-propyl-thien[2,3b]pyridine-2-carboxylic acid amide

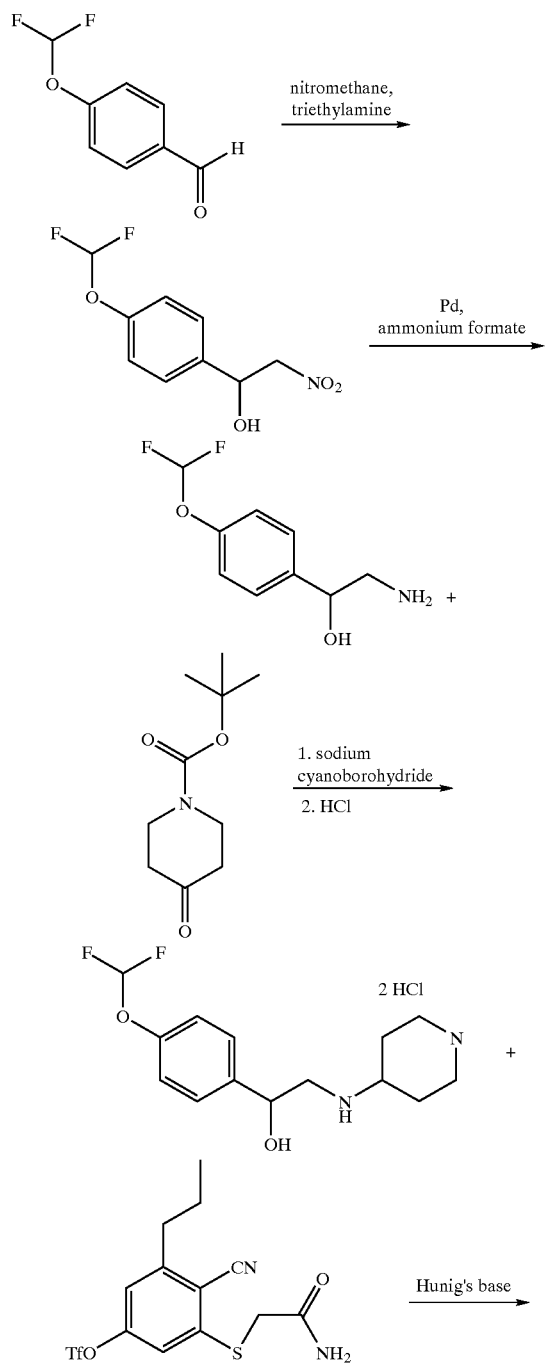

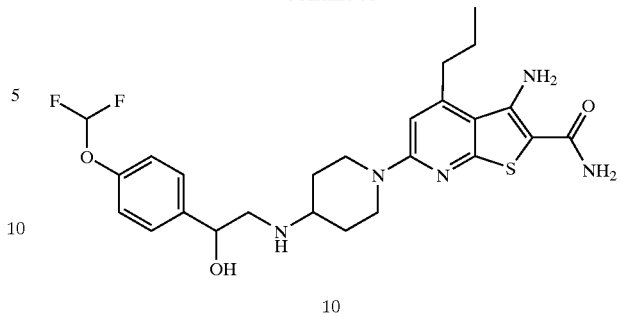

To a round bottom flask was added 4-(difluoromethoxy) benzaldehyde (600 mg, 3.49 mmol) in 8 mL of nitromethane, followed by the addition of triethylamine (352 mg, 3.49 mmol). The reaction mixture was stirred at room temperature for 3 h. The reaction mixture was concentrated in vacuo. The residue was loaded to a flash colurnn. The column was eluted with 5–20% EtOAc/hexane. The product fractions were collected and concentrated to afford 560 mg (68.9%) of the nitro alcohol intermediate.

To a round bottom flask was added 1-(4-difluoromethoxy-phenyl)-2-nitro-ethanol (560 mg, 2.40 mmol), ammonium formate (757 mg, 12 mmol) and palladium 10% on activated carbon (100 mg) in 20 mL of methanol and 20 mL of THF. The reaction mixture was stirred at room temperature for 18 h. The reaction mixture was filtered through diatomaceous earth and concentrated in vacuo to afford 488 mg (100%) of the amino alcohol intermediate. $MH^+=204.35$ To a round bottom flask was added 2-amino-1-(4-difluoromethoxy-phenyl)-ethanol (488 mg, 2.40 mmol) in 40 mL of $CH_2Cl_2$, followed by the addition of tert-butyl-4-oxo-1-piperidinecarboxylate (526 mg, 2.64 mmol), sodium cyanoborohydride (151 mg, 2.40 mmol) and 10 drops of acetic acid. The reaction mixture was stirred at room temperature for 1 h. The reaction mixture was concentrated in vacuo. The residue was loaded to a flash column. The column was eluted with 0–5% 2M $NH_3$ in $MeOH/CH_2Cl_2$. The product fractions were collected and concentrated to afford 507 mg (54.6%) of light brown oil, $MH^+=387.40$ To a round bottom flask was added 4-[2-(4-difluoromethoxy-phenyl)-2-hydroxy-ethylamino]-piperidine-1-carboxylic acid tert-butyl ester (507 mg, 1.31 mmol) in 10 mL of hydrogen chloride (4.0M in 1,4-dioxane) and 5 mL of methanol. The reaction mixture was stirred at room temperature for 1 h. The reaction mixture was concentrated by high vacuum pump to afford 470 mg (99.7%) of product of the bis hydrochloride adduct. $MH^+=287.31$ To a sealed tube was added trifluoro-methanesulfonic acid 6-carbamoylmethylsulfanyl-5-cyano-4-propyl-pyridin-2-yl ester (228 mg, 0.595 mmol) in 15 mL of dry DMF, followed by the addition of 1-(4-difluoromethoxy-phenyl)-2-(piperidin-4-ylamino)-ethanol di-hydrogen chloride salt (235 mg, 0.654 mmol) and N-N-diisopropylethylamine (615 mg, 4.76 mmol). The reaction mixture was stirred at 80° C. for 2 h. The reaction mixture was concentrated on a rotary evaporator. The resulting residue was dissolved in 10 mL of methanol, and treated with sodium methoxide, 0.5 M solution in methanol (6 mL, 3 mmol). The reaction mixture was stirred at 70° C. for 2 h. The reaction was cooled to room temperature and filtered. The precipitate was washed with cold methanol and dried to afford 213 mg (68.9%) of the title compound as a white solid, m/z calculated for $C_{25}H_{31}F_2N_5O_3S$ 519.6. observed m/z. 520.3 (MH+).

3-Amino-6-{4-[2-(3-cyano-phenyl)-2-hydroxy-ethylamino]-piperidin-1-yl}-4-propyl-thieno[2,3-b]pyridine-2-carboxylic acid amide

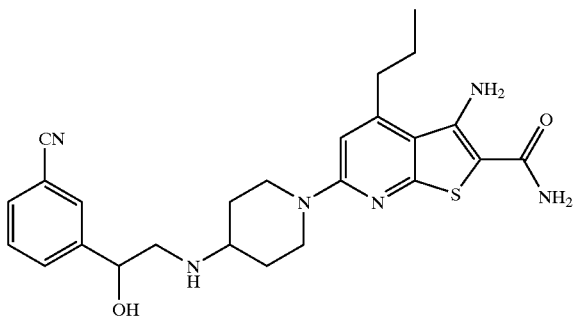

This compound was synthesized using procedures from Examples 9 and 10 using 3-cyano benzaldehyde as a starting material (amino alcolohol was prepared via nitro aldol reaction but reductive amination was carried out on piperidone intermediate synthesized in Example 9), m/z calculated for $C_{25}H_{30}N_6O_2S$ 478. observed m/z 479 (MH+).

3-Amino-6-{4-[2-hydroxy-2-(4-trifluoroethoxy-phenyl)-ethylamino]-piperidin-1-yl}-4-propyl-thieno[2,3-b]pyridine-2-carboxylic acid amide

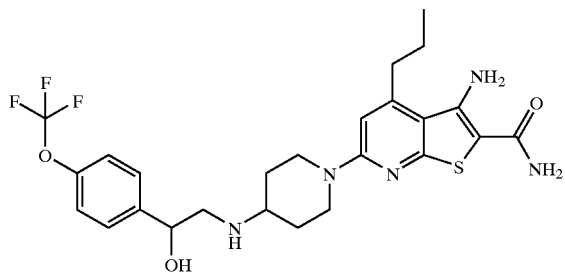

This compound was prepared in an analogous fashion to Example 10 using 4-trifluoromethoxy benzaldehyde as a starting material instead of 4-difluorethoxybenzaldehyde, m/z calculated for $C_{25}H_{30}F_3N_5O_3S$ 537. observed m/z 538 (MH+).

3-Amino-6-{4-[2-hydroxy-2-(3-pyridin-2-yl-phenyl)-ethylamino]-piperidin-1-yl}-4-propyl-thieno[2,3-b]pyridine-2-carboxylic acid amide

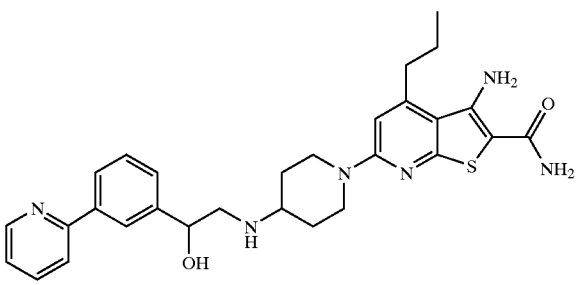

This compound was synthesized using procedures from Examples 9 and 10 using 3-(2-pyridyl)-benzaldehyde as a starting material (amino alcolohol was prepared via nitro aldol reaction but reductive amination was carried out on piperidone intermediate synthesized in Example 9), m/z calculated for $C_{29}H_{34}F_3N_6O_2S$ 530. observed m/z 531 (MH+).

3-Amino-6-{4-[2-hydroxy-2-(4-pyrazin-2-yl-phenyl)-ethylamino]-piperidin-1-yl}-4-propyl-thieno[2,3-b]pyridine-2-carboxylic acid amide

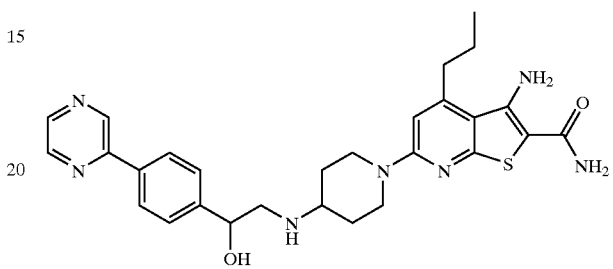

This compound was synthesized using procedures from Examples 9 and 10 using 4-(2-pyrazinyl)-benzaldehyde as a starting material (amino alcolohol was prepared via nitro aldol reaction but reductive amination was carried out on piperidone intermediate synthesized in Example 9), m/z calculated for $C_{25}H_{33}F_3N_7O_2S$ 531. observed m/z 532 (MH+).

3-Amino-6-{4-[2-hydroxy-2-(4-pyrimidin-5-yl-phenyl)-ethylamino]-piperidin-1-yl}-4-propyl-thieno[2,3-b]pyridine-2-carboxylic acid amide

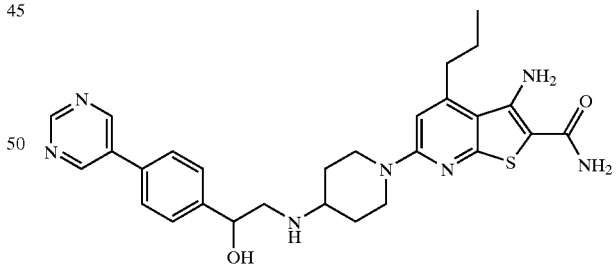

This compound was synthesized using procedures from Examples 9 and 10 using 4-(5-pyrimidinyl)-benzaldehyde as a starting material (amino alcolohol was prepared via nitro aldol reaction but reductive amination was carried out on piperidone intermediate synthesized in Example 9), m/z calculated for $C_{28}H_{33}F_3N_7O_2S$ 531. observed m/z 532 (MH+).

Example 11

3-Amino-6-(4-{2-hydroxy-2-[4-(1-methyl-1H-imidazol-2-yl)-phenyl]-ethylamino}-piperidin-1-yl)-4-propyl-thieno[2,3-b]pyridine-2-carboxylic acid amide

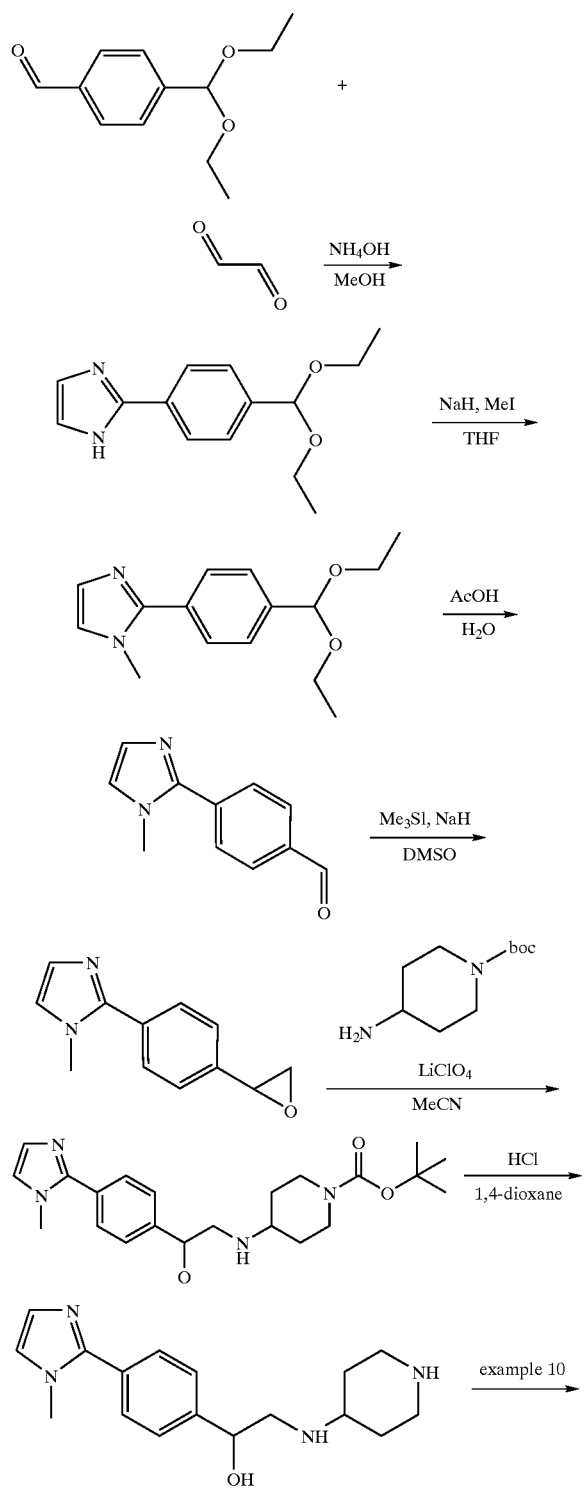

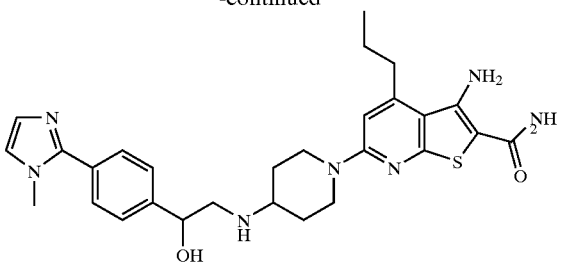

11

To a solution of 4.00 g (19.2 mmol) of 4-diethoxymethyl-benzaldehyde in MeOH (40 mL) was added 12 mL (110 mmol) of ammonium hydroxide followed by 10 mL (69 mmol) of glyoxal as a 40% wt. solution in $H_2O$. The solution was stirred at room temperature for 4 h during which time the mixture became very cloudy and dark. The mixture was poured into $H_2O$ and allowed to stand for 15 h during which time a solid precipitated from solution. The tan solid was collected by filtration, washed with $H_2O$ and dried under vacuum to provide 2.50 g (52.8%) of 2-(4-diethoxymethyl-phenyl)-1H-imidazole.

To a solution of 1.00 g (4.06 mmol) of the above imidzole in DMF (40 ML), cooled to 0° C., was added 0.175 g (4.37 mmol) of sodium hydride as a 60% dispersion in oil. The mixture was stirred at 0° C. for 1 h then 0.52 mL (4.4 mmol) of benzyl bromide was added dropwise. The mixture was allowed to slowly warm to room temperature and stirred for 2 h. The reaction was diluted with $H_2O$ and washed with EtOAc. The combined organic phase was dried over anhydrous $Na_2SO_4$ and concentrated under reduced pressure to provide 0.777 g (73.5%) of 2-(4-diethoxymethyl-phenyl)-1-methyl-1H-imidazole as a black oil.

A solution of 0.200 g (0.768 mmol) of the above imidazole in a 4:1 mixture of acetic acid:$H_2O$ (5 mL) was stirred at room temperature for 4 h. The mixture was neutralized by pouring into a saturated aqueous solution of $NaHCO_3$. The mixture was washed with $CH_2Cl_2$ and the combined organic phase was dried over anhydrous $Na_2SO_4$ and concentrated under reduced pressure to provide 0.100 g (69.9%) of 4-(1-methyl-1H-imidazol-2-yl)-benzaldehyde as a brown oil.

To a suspension of 0.045 g (1.1 mmol) of sodium hydride in DMSO (2 mL) was added a 0.225 g (1.10 mmol) of trimethylsulfonium iodide as a solution in DMSO (2 mL). The mixture was allowed to stir at room temperature for 10 min then a solution of 0.100 g (0.537 mmol) of the above aldehyde in DMSO (1 mL) was added dropwise. The mixture was stirred at room temperature for 4 h then diluted with $H_2O$ and washed with EtOAc. The combined organic phase was washed with $H_2O$, dried over anhydrous $Na_2SO_4$ and concentrated under reduced pressure. The residue was purified by flash silica gel chromatography to provide 0.056 g (52.1%) of 1-methyl-2-(4-oxiranyl-phenyl)-1H-imidazole as a yellow oil.

To a solution of 0.056 g (0.280 mmol) of the above epoxide in MeCN (6 mL) was added 0.140 g (0.699 mmol) of 1-N-boc-4-aminopiperidine followed by 0.150 g (1.41 mmol) of lithium perchlorate. The mixture was heated to 60° C. for 15 h then cooled to room temperature and filtered through diatomaceous earth. The filtrate was concentrated under reduced pressure and the residue purified by flash silica gel chromatography to provide 0.056 g (21%) of 4-{2-hydroxy-2-[4-(1-methyl-1H-imidazol-2-yl)-phenyl]-ethylamino}-piperidine-1-carboxylic acid tert-butyl ester as a white solid.

To a solution of 0.056 g (0.14 mmol) of the above boc-protected amine in CH$_2$Cl$_2$ (2 mL) was added 0.15 mL (0.6 mmol) of hydrogen chloride as a 4.0 M solution in 1,4-dioxane.

The mixture was stirred at room temperature for 15 h then made basic by pouring into a saturated aqueous solution of Na$_2$CO$_3$. The mixture was washed with CH$_2$Cl$_2$ and the combined organic phase was dried over anhydrous Na$_2$SO$_4$ and concentrated under reduced pressure to provide 0.040 g (99%) of 1-[4-(1-methyl-1H-imidazol-2-yl)-phenyl]-2-(piperidin-4-ylamino)-ethanol as a yellow oil.

The above amino alcohol was reacted under the conditions described in Example 10 to provide the title compound as a yellow solid, m/z calculated for C$_{28}$H$_{36}$N$_7$O$_2$S 533.7 observed m/z 534.4 (MH+).

3-Amino-6-(4-{2-[4-(1-benzyl-1H-imidazol-2-yl)-phenyl]-2-hydroxy-ethylamino}-piperidin-1-yl)-4-propyl-thieno[2,3-b]pyridine-2-carboxylic acid amide

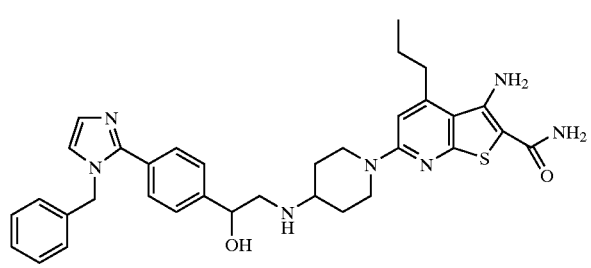

This compound was prepared in a similar fashion to Example 11 except the intermediate imidazole was alkylated with benzyl bromide instead of iodomethane and the resulting aldehyde was carried onto the aminoalcohol through the Henry nitroaldol reaction instead of the epoxide route. m/z calculated for C$_{34}$H$_{39}$N$_7$O$_2$S 609. observed 610 m/z (MH+).

3-Amino-6-{4-[2-hydroxy-2-(4-thiazol-2-yl-phenyl)-ethylamino]-piperidin-1-yl}-4-propyl-thieno[2,3-b]pyridine-2-carboxylic acid amide

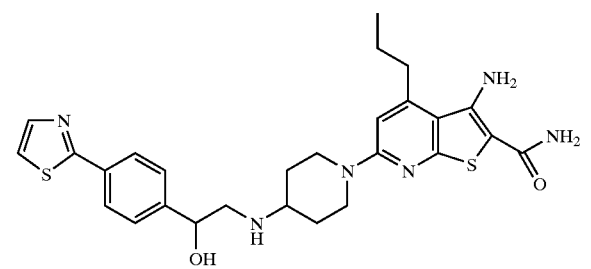

This compound was prepared in a similar fashion to Example 11. The left hand side piperidine salt was prepared as described previously for the 4-CF$_3$ analog, m/z calculated for C$_{27}$H$_{33}$N$_6$O$_2$S$_2$ 536.73. observed m/z: 537.6 (MH+).

3-Amino-6-{4-[2-(4-fluoro-phenyl)-2-hydroxy-ethylamino]-piperidin-1-yl}-4-propyl-thieno[2,3-b]pyridine-2-carboxylic acid amide

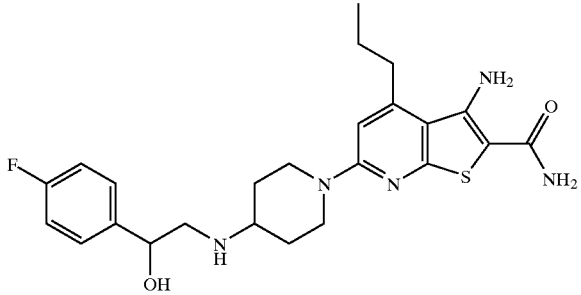

This compound was synthesized according to the procedure for Example 11 starting with 4-fluoro-benzaldehyde mp210–212° C. (dec), m/z calculated for C$_{24}$H$_{30}$FN$_5$O$_2$S 471 observed m/z 472 (MH$^+$).

3-Amino-6-{4-[2-(2-fluoro-phenyl)-2-hydroxy-ethylamino]-piperidin-1-yl}-4-propyl-thieno[2,3-b]pyridine-2-carboxylic acid amide

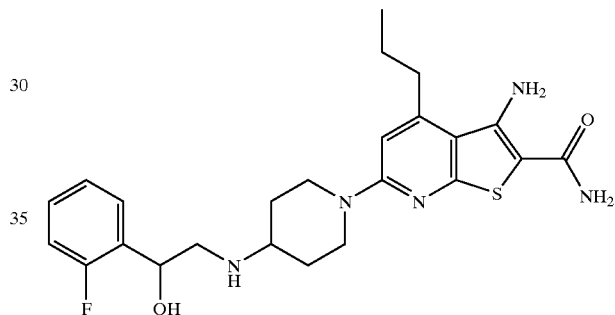

This compound was synthesized according to the procedure for Example 11 starting with 2-fluoro-benzaldehyde mp 169–171° C. (dec), m/z calculated for C$_{24}$H$_{30}$FN$_5$O$_2$S 471 observed m/z 472 (MH$^+$).

3-Amino-6-{4-[2-(3,5-difluoro-phenyl)-2-hydroxy-ethylamino]-piperdin-1-yl}-4-propyl-thieno[2,3-b]pyridine-2-carboxylic acid amide

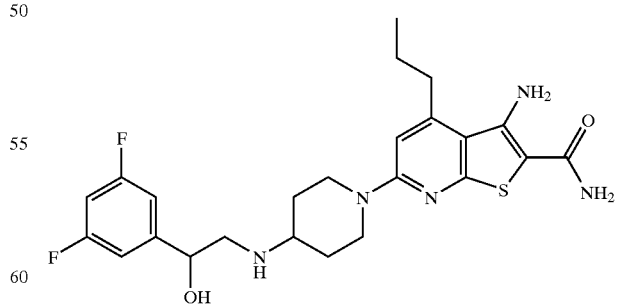

This compound was synthesized according to the procedure for Example 11 starting with 3,5-difluoro-benzaldehyde mp201–202° C., m/z calculated for C$_{24}$H$_{29}$F$_2$N$_5$O$_2$S 489. observed m/z 490 (MH$^+$).

3-Amino-6-[4-(2-benzo[1,3]dioxol-5-yl-2-hydroxy-ethylamino)-piperidin-1-yl]-4-propyl-thieno[2,3-b]pyridine-2-carboxylic acid amide

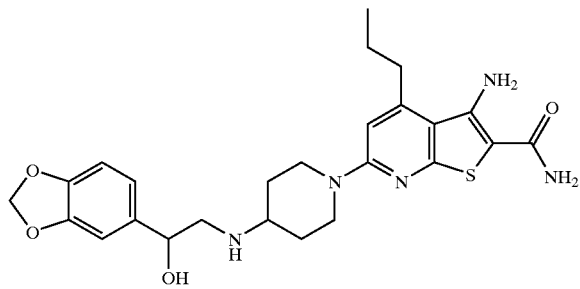

This compound was synthesized according to the procedure for Example 11 starting with piperonal mp204–206° C. (dec), m/z calculated for $C_{25}H_{31}FN_5O_4S$ 497. observed m/z 498 (MH$^+$).

3-Amino-6-[4-(2-benzoylsulfamoyl-phenyl)-2-hydroxy-ethylamino)-piperidin-1-yl]-4-propyl-thieno[2,3-b]pyridine-2-carboxylic acid amide

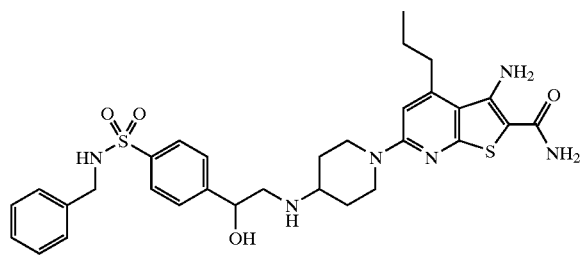

This compound was synthesized using procedures from Examples 6 and 10 (amino alcohol was prepared via cyanohydrin route and reductive amination was carried out on piperidone intermediate from Example 10) using 4-(benzoylsulfamoyl)-benzaldehyde, m/z calculated for $C_{31}H_{38}N_6O_4S_2$ 622. observed m/z 623 (MH$^+$).

3-Amino-6-{4-[2-hydroxy-2-(4-morpholin-4-yl-phenyl)-ethylamino]-piperidin-1-yl}-4-propyl-thieno[2,3-b]pyridine-2-carboxylic acid amide

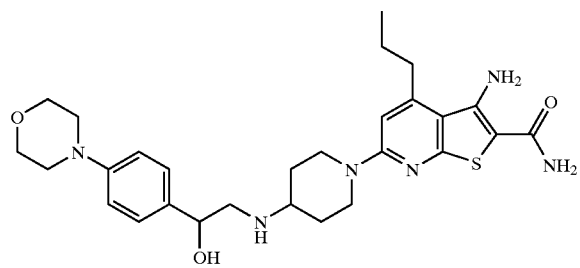

This compound was synthesized using procedures from Examples 6 and 10 (amino alcohol was prepared via cyanohydrin route and reductive amination was carried out on piperidone intermediate from Example 10) using 4-(4-morpholinyl)benzaldehyde, m/z calculated for $C_{28}H_{38}N_6O_3S$ 538. observed m/z 539 (MH$^+$).

3-Amino-6-[4-(2-biphenyl-4-yl-2-hydroxy)-ethylamino)-piperidin-1-yl}-4-propyl-thieno[2,3-b]pyridine-2-carboxylic acid amide

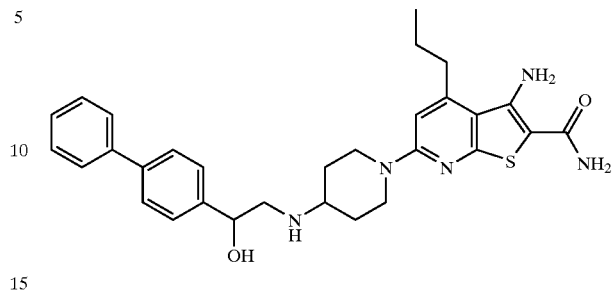

This compound was synthesized using procedures from Examples 6 and 10 (amino alcohol was prepared via cyanohydrin route and reductive amination was carried out on piperidone intermediate from Example 10) using biphenyl-4-carbaldehyde, m/z calculated for $C_{30}H_{35}N_5O_2S$ 529. observed m/z 530 (MH$^+$).

3-Amino-6-{4-[2-hydroxy-2-(4-pyridin-2-yl-phenyl)-ethylamino]-piperidin-1-yl}-4-propyl-thieno[2,3-b]pyridine-2-carboxylic acid amide

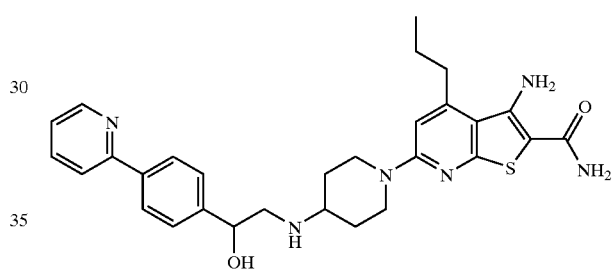

This compound was synthesized using procedures from Examples 6 and 10 (amino alcohol was prepared via cyanohydrin route and reductive amination was carried out on piperidone intermediate from Example 10) using 4-(2-pyridyl)benzaldehyde, m/z calculated for $C_{29}H_{34}N_6O_2S$ 530. observed m/z 531 (MH$^+$).

3-Amino-6-{4-[2-hydroxy-2-(4-pyridin-3-yl-phenyl)-ethylamino]-piperidin-1-yl}-4-propyl-thieno[2,3-b]pyridine-2-carboxylic acid amide

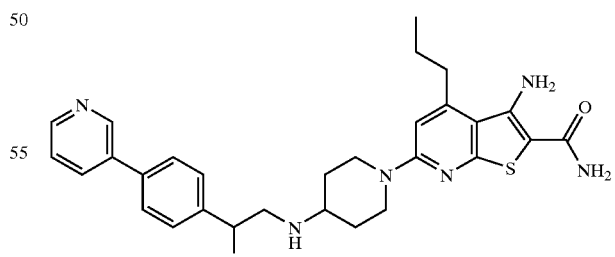

This compound was synthesized using procedures from Examples 6 and 10 (amino alcohol was prepared via cyanohydrin route and reductive amination was carried out on piperidone intermediate from Example 10) using 4-(3-pyridyl)benzaldehyde, m/z calculated for $C_{29}H_{34}N_6O_2S$ 530. observed m/z 531 (MH$^+$).

197
3-Amino-6-{4-[2-hydroxy-2-(4-pyridin-4-yl-phenyl)-ethylamino]-piperidin-1-yl}-4-propyl-thieno[2,3-b]pyridine-2-carboxylic acid amide

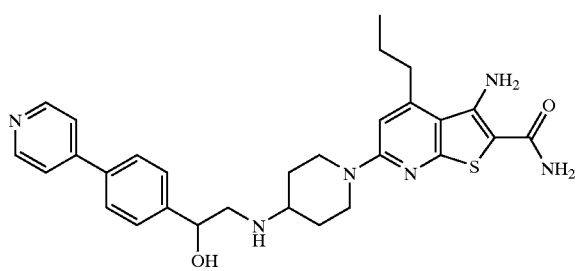

This compound was synthesized using procedures from Examples 6 and 10 (amino alcohol was prepared via cyanohydrin route and reductive amination was carried out on piperidone intermediate from Example 10) using 4-(4-pyridyl)benzaldehyde, m/z calculated for $C_{29}H_{34}N_6O_2S$ 530. observed m/z 531 (MH$^+$).

198
3-Amino-6-{4-[2-hydroxy-2-(4-imidazol-1-yl-phenyl)-ethylamino]-piperidin-1-yl}-4-propyl-thieno[2,3-b]pyridine-2-carboxylic acid amide

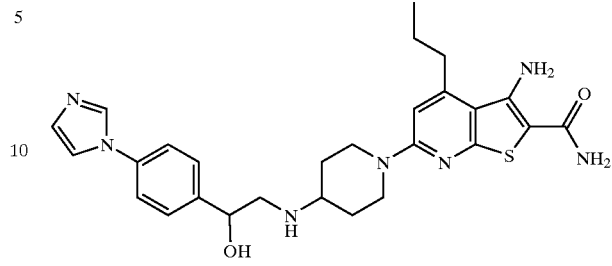

This compound was synthesized using procedures from Examples 6 and 10 (amino alcohol was prepared via cyanohydrin route and reductive amination was carried out on piperidone intermediate from Example 10) using 4-(1-imidazolyl)benzaldehyde, m/z calculated for $C_{29}H_{34}N_6O_2S$ 530. observed m/z 531 (MH$^+$).

Example 12
3-Amino-6-{4-[2-hydroxy-2-(4-methanesulfonylamino-phenyl)-ethylamino)-piperidin-1-yl]-4-propyl-thieno[2,3-b]pyridine-2-carboxylic acid amide

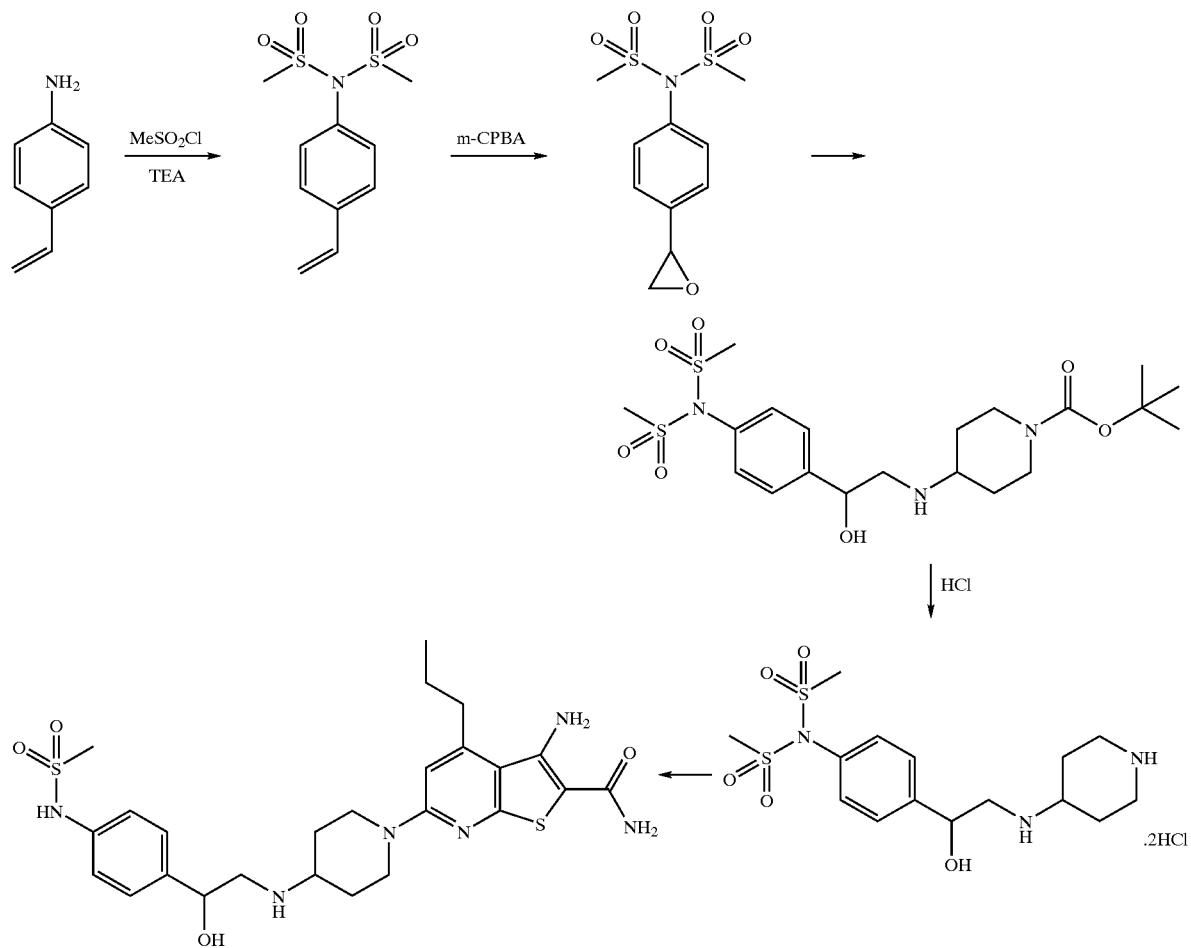

4-Amino-styrene (0.767 g, 6.44 mmol) was suspended in 20 mL CH$_2$Cl$_2$, cooled to 0° C., and treated with methane sulfonyl chloride (1.2 mL, 13.2 mmol), triethylamine (2.1 mL, 15.0 mmol) and a catalytic amount of DMAP. The reaction mixture was left stirring for 6 h at room temperature, then was quenched with water and extracted with CH$_2$Cl$_2$. Combined organics were dried (Na$_2$SO$_4$), filtered and the solvent was removed in vacuo. Yield: 1.75 g of a yellow solid (99% of theory). Used as is in the next step.

4-Bis-sulfonamido-styrene from above (854 mg, 3.1 mmol) was dissolved in 15 mL CH$_2$Cl$_2$ and cooled to 0° C. A solution of m-CPBA (60%, 1.43 g, 5.2 mmol) in 45 mL CH$_2$Cl$_2$ was added and the resulting mixture was stirred for 1.5 h at room temperature. The reaction mixture was transferred to a separatory funnel and washed with dilute aqueous NaHCO$_3$ solution three times. The organic layer was dried (Na$_2$SO$_4$), filtered, and the solvent was removed in vacuo. The resulting white solid was purified by flash column chromatography on SiO$_2$ using EtOAc and hexanes mixtures as eluent. The desired epoxide was obtained as a white solid, 511 mg (57% of theory).

The bis-sulfonamide-epoxide from above (500 mg, 1.72 mmol) was dissolved in 5 mL acetonitrile, and treated with 4-amino-1-Boc-piperidine (369 mg, 1.84 mmol) and LiClO$_4$ (196 mg, 1.84 mmol). The resulting mixture was diluted with another 5 mL acetonitrile and left stirring at room temperature overnight. The flask was then placed in a 60° C. oil bath and heated overnight. The solvent was removed in vacuo and the residue was partitioned between EtOAc and water. The aqueous layer was extracted with another portion of EtOAc. The combined organics were washed with brine, dried (Na$_2$SO$_4$), filtered, and the solvent was removed in vacuo. The crude product was purified by flash column chromatography on SiO$_2$ using MeOH in CH$_2$Cl$_2$ mixtures as eluent. The purified product was isolated as a white foam, 507 mg (60% of theory).

The Boc-protected piperidine (507 mg, 1.03 mmol) was dissolved in 5 mL MeOH and treated with 4 mL 4 N HCl in 1,4-dioxane. The mixture was stirred at room temperature for 2 h, then the solvent was removed in vacuo, affording 488 mg of the dihydrochloride salt as a colorless foam.

The piperidine dihydrochloride salt from above (488 mg, 1.05 mmol) was dispersed in 10 mL anhydrous 1,4-dioxane. Triethylamine (1.62 mL, 11.6 mmol) was added via syringe and the mixture was stirred for 2 mins. The pyridyl triflate intermediate (322 mg, 0.84 mmol) was added and the flask was placed in a 70° C. oil bath and stirred for 3 h. The mixture was then treated with 14 mL 2 N Na$_2$CO$_3$ aqueous solution, transferred to a sealed tube, purged with Argon, and heated to 100° C. while stirring overnight. After cooling, the mixture was diluted with water and extracted with EtOAc three times. Combined organic extracts were washed with brine, dried (Na$_2$SO$_4$), filtered, and the solvent was removed in vacuo. The resulting greenish foam was triturated in hot MeOH, and the resulting yellow solid was collected by filtration. This product is the mono-sulfonamide, 203 mg (44% of theory). mp: 199–200° C., m/z calculated for C$_{25}$H$_{34}$N$_6$O$_4$S$_2$ 546. observed m/z 547(MH$^+$).

Example 13

Synthesis of 3-amino-6-{4-[2-hydroxy-2-(4-methylaminomethyl-phenyl)-ethylamino]-piperidin-1-yl}-4-propyl-thieno[2,3-b]pyridine-2-carboxylic acid amide

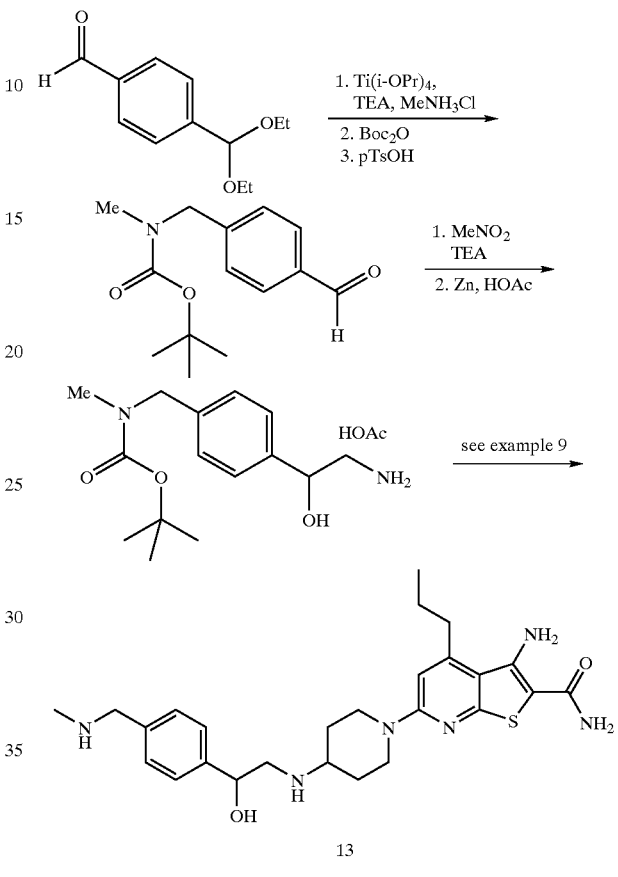

A solution of terephthaldehyde mono-diethyl acetal (5.00 g, 24 mmol), methylamine hydrochloride (3.24 g, 32 mmol), and triethylamine in ethanol (50 mL) was stirred under a nitrogen atmosphere for 5 h. Titanium tetraisopropoxide (14.2 mL, (48 mmol) was then added and stirred for 18 h. The mixture was diluted with water and filtered. The filtrate was concentrated and purified via chromatography over silica gel using a gradient of methanol in dichloromethane to provide a colorless liquid (2.59 g, 48%).

This material was taken up in THF (30 mL) and Boc anhydride (2.53 g, 11.6 mmol) was added. The reaction mixture was stirred for 4 h and concentrated to provide the Boc methyl amine intermediate which was used without further purification (3.17 g, 85%).

A solution of the above diethyl acetal (2.96 g, 9.14 mmol) and p-toluene sulfonic acid monohydrate (300 mg, 1.58 mmol) in dioxane (50 mL) and water (25 mmL) was heated to 95° C. for 18 h. The reaction mixture was cooled to room temperature and concentrated. The resulting residue was partitioned between ethyl acetate and water, the organic phase was dried over sodium sulfate and concentrated. The crude material was further purified via chromatography over silica gel using a gradient of ethyl acetate in hexanes to provide 1.0 g, (44%) of the desired aldehyde intermediate.

(4-Formyl-benzyl)-methyl-carbamic acid tert-butyl ester was carried on to the desired amino alcohol via the Henry nitroaldol/reduction protocol described in Example 10, using modified reduction conditions to avoid N-debenzylation (Zn and acetic acid instead of Pd ammonium formate). The resulting amino alcohol was taken on to the title compound by a similar reductive amination as described in Example 9, followed by N-boc deprotection with HCl in dioxane, m/z calculated for $C_{26}H_{36}N_6O_2S$ 496. observed m/z 511 (MH⁺).

3-Amino-6-{4-[2-(4-dimethylaminomethyl-phenyl)-2-hydroxy-ethylamino]-piperidin-1-yl}-4-propyl-thieno[2,3-b]pyridine-2-carboxylic acid amide

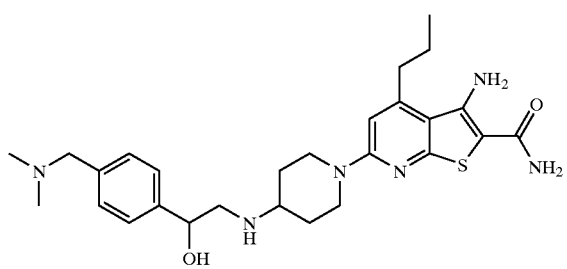

This compound was prepared as described in Example 13 with the exception that dimethyl amine hydrochloride was used in place of methylamine hydrochloride and as such no N-Boc protection deprotection sequence wa required, m/z calculated for $C_{27}H_{38}N_6O_2S$ 510 observed m/z 511 (MH⁺).

Example 14

3-Amino-6-{4-[2-(4-hydroxy-piperidin-1-yl)-2-oxo-ethylamino]-piperidin-1-yl}-4-propylthieno[2,3-b]pyridine-2-carboxylic acid amide

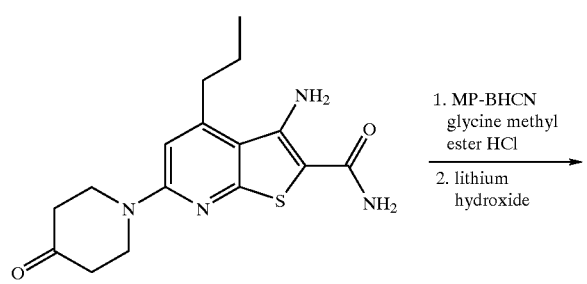

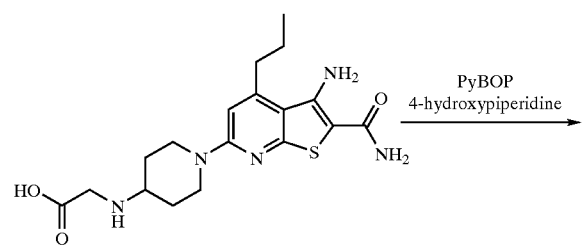

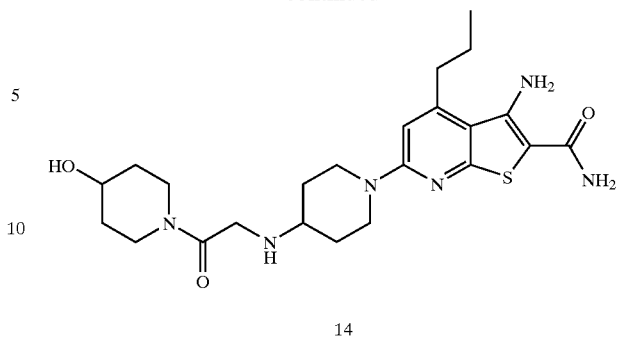

14

A mixture of 3-Amino-6-(4-oxo-piperidin-1-yl)-4-propyl-thieno[2,3-b]pyridine-2-carboxylic acid amide (0.6 g, 1.8 mmol), glycine methyl ester hydrochloride (0.226 g, 1.8 mmol), MP-cyanoborohydride(1.0 g, 9.0 mmol) and acetic acid (catalytic amount) in THF (15 mL) was stirred at room temperature overnight. The resin was filtered and washed with MeOH (5 mL). Next a solution of ammonia in MeOH (2.0 M, 10 mL) was added and the mixture was extracted with ethyl acetate. The organic phase was washed with brine, dried with sodium sulfate, concentrated and purified by chromatography on silica gel using a gradiant of methanol in dichloromethane to give the reductive amination product (0.13 g, 17.8%).

To a stirred solution of the above material (100 mg, 0.247 mmol) in 1,4-dioxane was added a solution of 1 N lithium hydroxide (10 mL, 10 mmol). The reaction was stirred at room temperature overnight then solvent was removed to provide the carboxylic acid intermediate (92 mg, 95.1%). MS m/z calculated for $C_{18}H_{25}N_5O_3S$: 391. observed m/z: 392 (MH+).

To a solution of the above carboxylic acid (100 mg, 0.25 mmol) in DMF (10 mL) was added 4-hydroxypiperidine (26 mg, 0.25 mmol), PyBOP (133 mg, 0.25 mmol) and NN-diisopropylethyl amine (90 mg, 0.78 mmol). The reaction was stirred at room temperature overnight. The solvent was concentrated and the resulting residue was washed with MeOH to provide the title compound as a solid(40 mg, 33%), MS m/z calculated for $C_{23}H_{34}N_6O_3S$ 474. observed m/z: 475 (MH+).

The following compounds were made using the procedure described in Example 14 or by a subtle modification in which the amine was first coupled to N-Bocglycine, N-Boc deprotected and then attached via reductive amination to the piperidone intermediate

203

3-Amino-4-propyl-6-{4-[(pyridin4-ylcarbamoylmethyl)-amino]-piperidin-1-yl}-thieno[2,3-b]pyridine-2-carboxylic acid amide

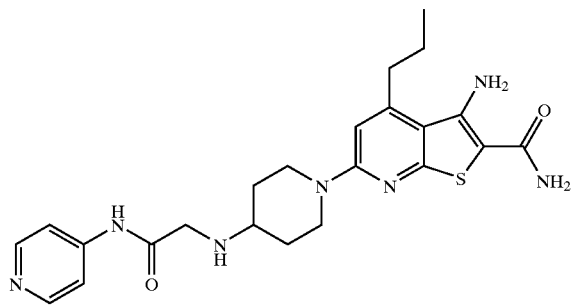

MS m/z calculated for $C_{23}H_{29}N_7O_2S$ 467. observed: 468 (MH+).

3-Amino-4-propyl-6-{4-[(quinolin-3-ylcarbamoylmethyl)-amino]-piperidin-1-yl}-thieno[2,3-b]pyridine-2-carboxylic acid amide

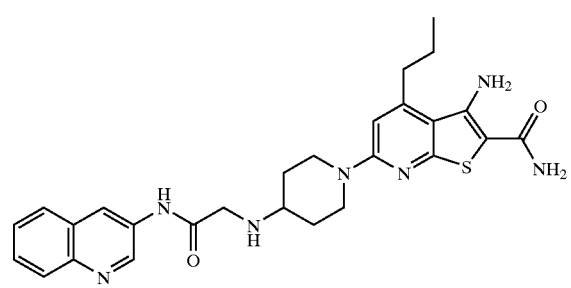

MS m/z calculated for $C_{27}H_{31}N_7O_2S$ 517. observed: 518 (MH+).

3-Amino-6-{4-[(naphthalen-1-ylcarbamoylmethyl)-amino]-piperidin-1-yl}-4-propyl-thieno[2,3-b]pyridine-2-carboxylic acid amide

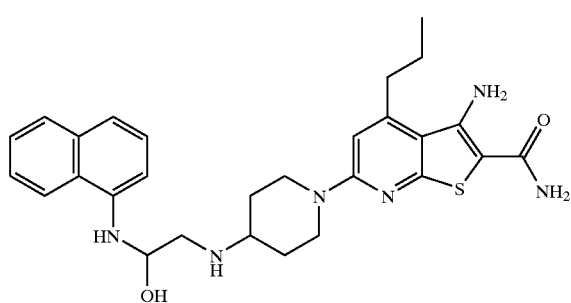

MS m/z calculated for $C_{28}H_{32}N_6O_2S$ 517. observed: 518 (MH+).

204

3-Amino-6-(4-{[(carbamoylmethyl-carbamoyl)-methyl]-amino}-piperidin-1-yl)-4-propyl-thieno[2,3-b]pyridine-2-carboxylic acid amide

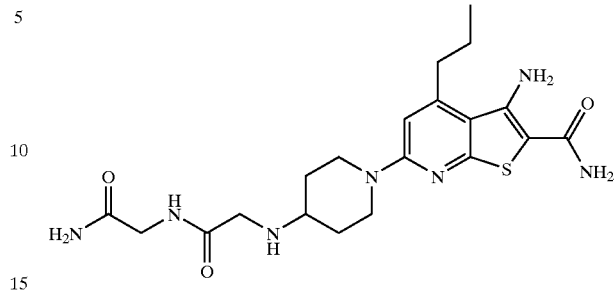

MS m/z calculated for $C_{20}H_{29}N_7O_3S$ 447. observed: 448 (MH+).

Example 15

Synthesis of 3-Amino-6-[4-(2-benzylcarbamoyl-2-hydroxy-ethylamino)-piperidin-1-yl]-4-propyl-thieno[2,3-b]pyridine-2-carboxylic acid amide

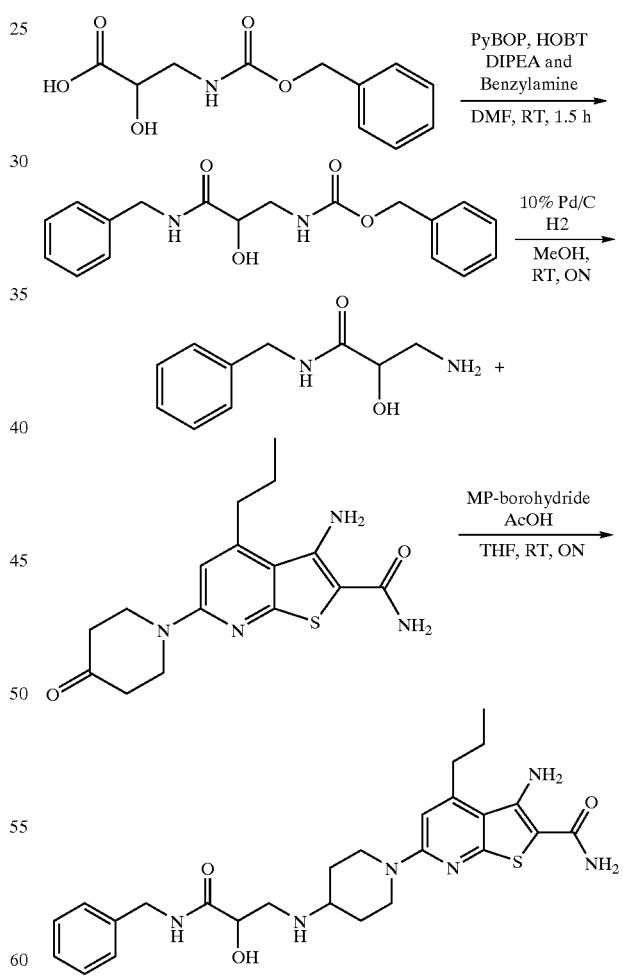

3-Benzyloxycarbonylamino-2-hydroxy-propionic acid was prepared via the method outlined in *Synthesis* 1991, 5, 409.

The (2-hydroxy-2-phenylcarbamoyl-ethyl)-carbamic acid benzyl ester (250 mg, 1.045 mmol) was dissolved into 2 mL of dry DMF. To this was added PyBOP (652.3 mg, 1.254 mmol), HOBT (169.4 mg, 1.254 mmol), benzylamine (0.228 mL, 2.090 mmol) and DIPEA (0.728 mL, 4.18 mmol). The reaction stirred for 1.5 h. LC-MS analysis of the crude indicated complete consumption of the S.M. and the presence of the product. 40 mL of EtOAc was added and the organic mixture washed with 2×20 mL NH4Cl, 2×20 mL of H$_2$O and 1×20 mL of brine. Dried organic phase with MgSO$_4$, filtered and concentrated to a yellow film. Dissolved in CH$_2$Cl$_2$, applied to a SiO$_2$ Column and purified (10–30% EtOAc/hexanes) to give a quantitative yield of (2-benzylcarbamoyl-2-hydroxy-ethyl)-carbamic acid benzyl ester.

(2-Benzylcarbamoyl-2-hydroxy-ethyl)-carbamic acid benzyl ester (372.4 mg, 1.134 mmol) was dissolved into 3 mL of MeOH and added 10% Pd/C (100 mg) and placed under balloon pressure H$_2$ overnight. Filtered the reaction mixture through diatomaceous earth and concentrated on a rotary evaporator to give 169 mg, 76.7% of 3-amino-N-benzyl-2-hydroxy-propionamide.

The title compound was prepared using the reductive amination procedure described in Example 14 ES$^+$ 511.2 m/z (MH$^+$).

3-Amino-6-[4-(2-hydroxy-2-phenylcarbamoyl-ethylamino)-piperidin-1-yl]-4-propyl-thieno[2,3-b]pyridine-2-carboxylic acid amide

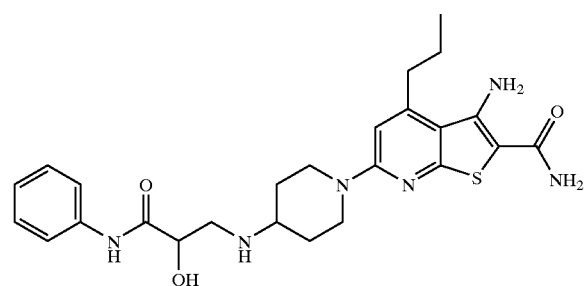

This compound was prepared in an analogous fashion to Example 15 using 3-amino-2-hydroxy-N-phenyl-propionamide as the amino alcohol substrate for reductive amination, ES$^+$ 497.2 m/z (MH$^+$).

Example 16

Synthesis of 3-amino-6-(4-methylamino-piperidin-1-yl)-4-methylsulfanyl-thieno[2,3-b]pyridine-2-carboxylic acid amide

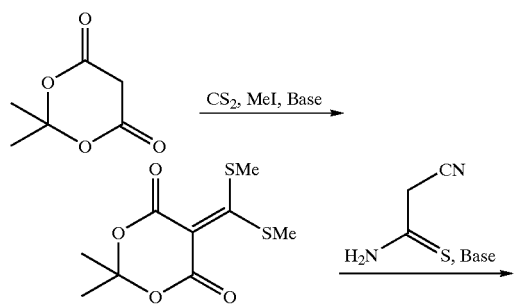

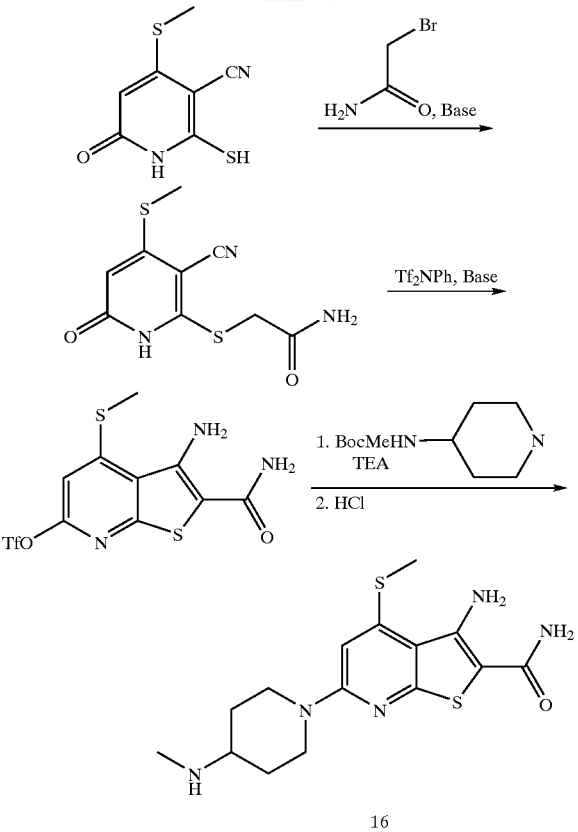

16

To a solution of 2,2-dimethyl-1,3-dioxane-4,6-dione (60.0 g, 416 rnmol) in DMSO (150 mL) was added carbon disulfide (25 mL, 420 mmol) and triethylamine (116 mL, 832 mmol). This mixture was stirred at room temperature for 1 h, the cooled to 0° C. and iodomethane was added (52 mL, 830 mmol). The reaction mixture was then slowly warmend to room temperature and stirred for 15 h then poured into ice water. The resulting precipitate was collected by filtration, washed with a 1:1 mixture of petroleum ether and diethyl ether, and dried to provide 30 g (29%) of an orange solid.

A solution of the above material (30 g, 121 mmol) in ethanol (100 mL)was added to a stirred solution of sodium ethoxide (123 mmol) and cyanothioacetamide (12.5 g, 122 mmol) in ethanol (150 mL). The reaction mixture was heated to reflux for 15 h, then cooled to room temperature and filtered. The precipitate was washed with ethanol and dried to provide 12.5 g (52%) of the pyridone intermediate as a yellow solid.

NaH (2.60 g, 65.0 mmol) was added to a solution of 2-mercapto-4-methylsulfanyl-6-oxo-1,6-dihydro-pyridine-3-carbonitrile (12.5 g, 63 mmol) in DMF (300 mL) cooled in an ice water bath. The mixture was stirred for 30 min then 2-bromoacetamide was added (8.80 g, 64 mmol) as a solid in one portion. The mixture was slowly warmed to room temperature and stirred for 15 h then poured onto ice water. The mixture was acidified with 2N HCl, filtered, and the resulting precipitate was washed with diethyl ether then hexanes to provide 11.3 g (70%) of 2-(3-cyano-4-methylsulfanyl-6-oxo-1,6-dihydro-pyridin-2-ylsulfanyl)-acetamide as a tan solid.

To a solution of 11.26 g (44.1 mmol) of the material from above in DMF (300 mL) cooled in an ice water bath, was added sodium hydride (3.60 g, 90 mmol). After stirring for 30 min, a solution of N-phenyltrifluoromethanesulfonamide (15.8 g, 44.2 mmol) in DMF (100 mL) was added. The mixture was slowly warmed to room temperature and stirred for 15 h then poured into water. The resulting precipitate was collected by filtration, washed with water, and dried under reduced pressure to provide the key trifluoromethane-sulfonic acid 3-amino-2-carbamoyl-4-methylsulfanyl-thieno[2,3-b]pyridin-6-yl ester intermediate as a yellow powder (8.95 g, 52%).

A mixture of the above triflate (225 mg, 0.58 mmol), methyl-piperidin-4-yl-carbamic acid tert-butyl ester (249 mg, 1.16 mmol), and Hunig's base (150 mg, 1.16 mmol) in DMF (1 mL) was heated in a pressure tube at 80° C. for 4 h. The reaction mixture was then concentrated and the resulting residue was purified by chromatography over silica gel using a gradient of methanol in dichloromethane as the eluant to provide 246 mg (94%) of a yellow solid.

A solution of the above N-protected intermediate (240 mg, 0.53 mmol) in dichloromethane (5 mL) was treated with 4N HCl in dioxane (0.8 mL, 3.2 mmol) and stirred at room temperature for 6 h. The reaction mixture was treated with saturated potassium carbonate solution, stirred for 1 h, and filtered. The resulting solid was washed with water and dried to provide 128 mg (69%) of the title compound as a pale yellow powder, m/z calculated for $C_{15}H_{21}N_5OS_2$ 351. observed m/z 352 (MH+).

3-Amino-6-[4-(2-hydroxy-2-naphthalen-2-yl-ethylamino)-piperidin-1-yl-]-4-methylsulfanyl-thieno[2,3-b]pyridine-2-carboxylic acid amide

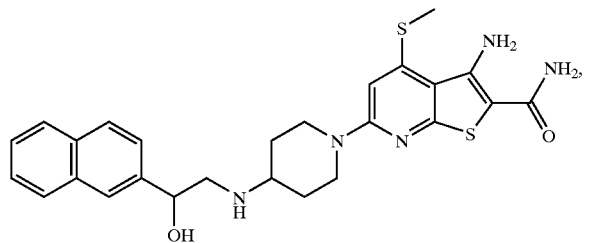

This compound was prepared using procedures from Examples 5 and 16 (left hand side was prepared by reductive amination of amino alcohol and N-Boc piperidone, this piece was deprotected and added into triflate intermediate from Example 13), calculated for $C_{26}H_{29}N_5O_2S_2$ 507. observed m/z 508 (MH+).

Example 17

Synthesis of 3-amino-6-(4-hydroxy-piperidin-1-yl)-4-ethoxy-thieno[2,3-b]pyridine-2-carboxylic acid amide

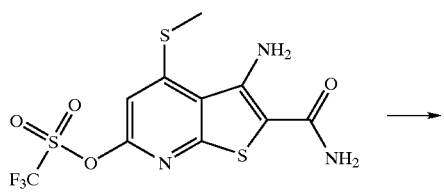

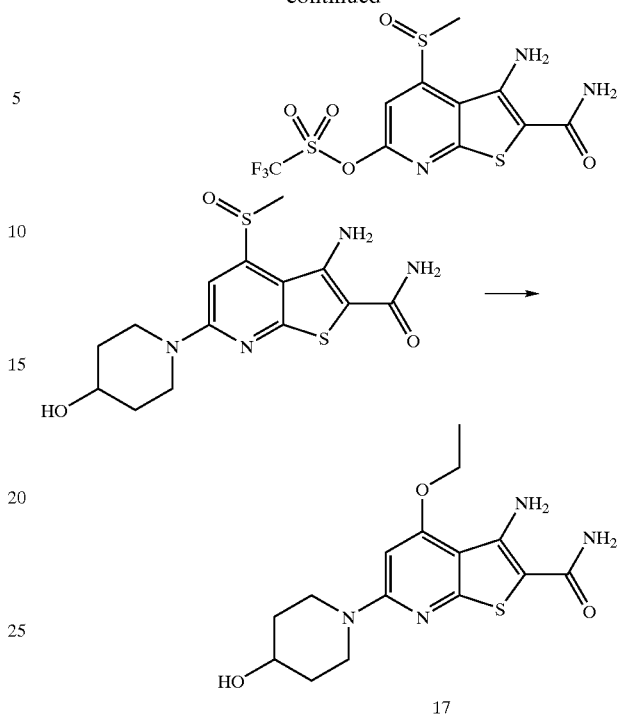

Trifluoromethanesulfonic acid 3-amino-2-carbamoyl-4-methylsulfanyl-thieno[2,3-b]pyridin-6-yl ester (500 mg, 1.29 mmol) was dissolved in MeOH (10 mL), chilled to 0° C., and potassium peroxymonosulfate (950 mg, 1.55 mmol) dissolved in water (15 mL) was added. The mixture was stirred for 18 h after which it was filtered to give the desired trifluoromethanesulfonic acid 3-amino-2-carbamoyl-4-methanesulfinyl-thieno[2,3-b]pyridin-6-yl ester in 86% yield.

The above ester (100 mg, 0.25 mmol) was dissolved in dioxane (5 mL), 4-hydroxypiperidine (100 mg, 1.0 mmol) was added and the mixture was stirred overnight at room temperature. The mixture was diluted with saturated ammonium chloride solution and the aqueous phase was extracted with dichloromethane several times. The combined organic phases were dried over $MgSO_4$ and evaporated. The product was finally purified by column chromatography to yield 43 mg of 3-amino-6-(4-hydroxy-piperidin-1-yl)-4-methanesulfinyl-thieno[2,3-b]pyridine-2-carboxylic acid amide (49%).

The above product was dissolved in EtOH and 235 microL of a 2.7 M solution of sodium ethoxide in EtOH was added. The solution was heated at 80° C. for 6 h. The mixture was poured into aqueous $NH_4Cl$ solution and the aqueous phase was extracted three times with dichloromethane. The combined phases were dried over $MgSO_4$, filtered, and evaporated. The product was purified by column chromatography to yield 23 mg of the title compound (54%).

The following compounds were prepared in the manner described above:

209

3-Amino-6-(4-amino-piperidin-1-yl)-4-ethoxy-thieno[2,3-b]pyridine-2-carboxylic acid amide:

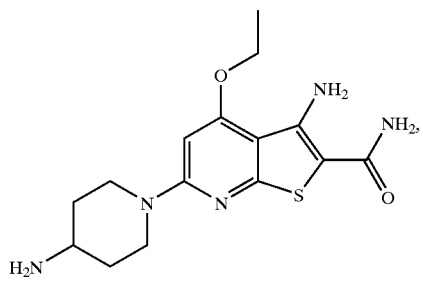

3-Amino-6-(4-amino-4-methyl-piperidin-1-yl)-4-ethoxy-thieno[2,3-b]pyridine-2-carboxylic acid amide

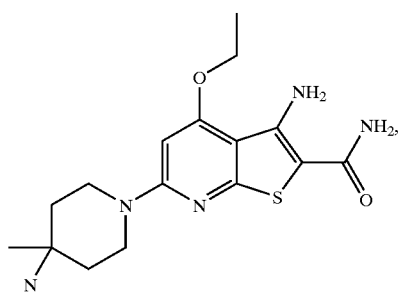

3-Amino-6-(4-hydroxy-piperidin-1-yl)-4-isopropoxy-thieno[2,3-b]pyridine-2-carboxylic acid amide

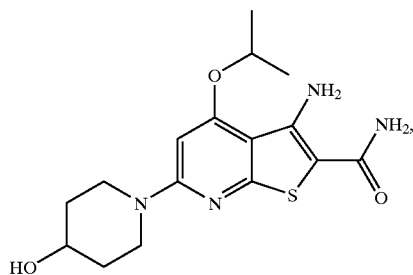

3-Amino-6-(4-amino-piperidin-1-yl)-4-isopropoxy-thieno[2,3-b]pyridine-2-carboxylic acid amide

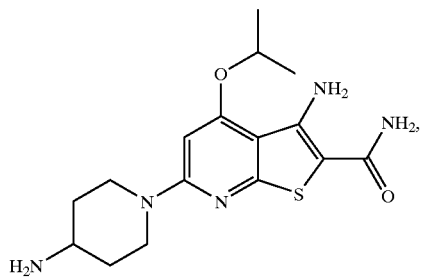

210

3-Amino-6-(1,1-dioxo-1-thiomorpholin-4-yl)-4-ethoxy-thieno[2,3-b]pyridine-2-carboxylic acid amide

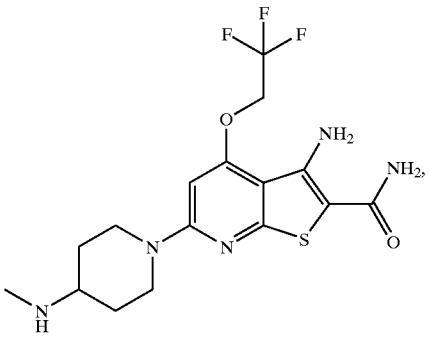

3-Amino-6-(4-methylamino-piperidin-1-yl)-4-(2,2,2-trifluoro-ethoxy-thieno[2,3-b]pyridine-2-carboxylic acid amide

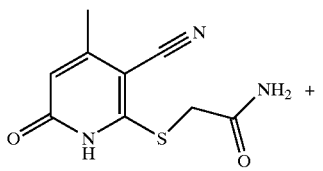

This compound was prepared in an analogous fashion to Example 17 using trifluoroethanol as a reactant.

Example 18

Synthesis of 3-Amino-4-methyl-6-(pyridin-4-ylmethoxy)-thieno[2,3-b]pyridine-2-carboxylic acid amide

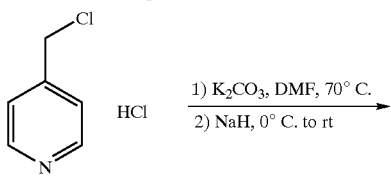

211

-continued

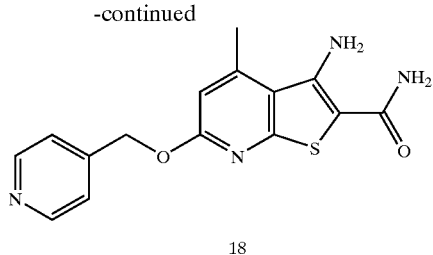

18

4-chloromethylpyridine hydrochloride (57.0 mg, 0.34 mmol) was combined with 50 mg of 4-methyl-mercaptopyridone intermediate (0.22 mmol), and potassium carbonate (95.0 mg, 0.68 mmol) in DMF (1.0 mL) in a flame-dried pressure tube, under Ar. The tube was sealed and heated at 70° C. for 45 min. TLC showed complete disappearance of starting material and a new spot formed. The reaction was cooled to 0° C., and sodium hydride (9.0 mg, 0.23 mmol) was added. The reaction was warmed to room temperature and stirred for 30 min, after which it was cooled in an ice bath and quenched with aqueous sodium bicarbonate (saturated). The resulting mixture was extracted twice with EtOAc. The organic layers were combined, washed with brine, dried ($Na_2SO_4$), filtered, and concentrated in vacuo to afford 65.8 mg of the crude product which was purified via automated flash silica to afford 41.8 mg (0.13 mmol, 59% yield) of the title compound.

Example 19

Synthesis of (3-Amino-2-carbamoyl-4-methyl-thieno[2,3-b]pyridin-6-yloxy)-acetic acid methyl ester

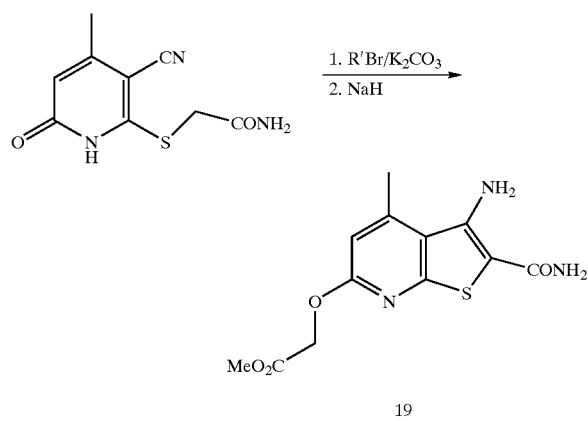

19

To a mixture of the 4-methyl-mercaptopyridone intermediate (prepared analogous to Example 1) (62 mg) and $K_2CO_3$ (70 mg) in DMF (1 mL) was added methyl bromoacetate (50 mg). The mixture was heated under Ar at 70° C. for 2 h. After cooling to 0° C., the mixture was treated with NaH (60%, 10 mg) and stirred at room temperature for 30 min. The mixture was then poured into ice—$NH_4Cl$ mixture, extracted with EtOAc, dried with $Na_2SO_4$ and concentrated. The residue was purified by preparative TLC, providing 5 mg of the title compound (white solid).

212

Example 20

Synthesis of 3-Amino-6-(1-methyl-pyrrolidin-2-ylmethoxy)-4-propyl-thieno[2,3-b]pyridine-2-carboxylic acid amide

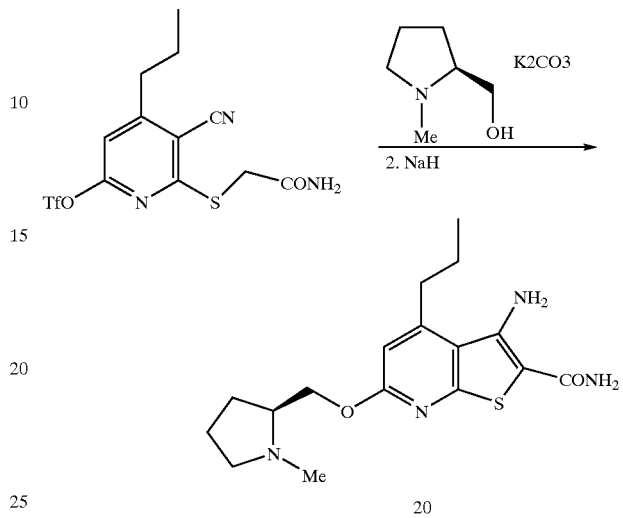

20

A mixture pyridine-triflate intermediate (see Example 1) (10 mg) and N-methyl-L-prolinol (40 mg) in dioxane was heated under Ar at 90° C. for 3 h. The mixture was cooled to room temperature, and $Na_2CO_3$ (2 M, 0.2 mL) was added. The mixture was heated at 100° C. under Ar for 10 h, cooled to room temperature and diluted with water (1 mL). The mixture was extracted with EtOAc, dried with $Na_2SO_4$ and concentrated. The residue was purified by preparative silica gel chromatography to give 6 mg of the title compound as a white solid.

Example 21

Synthesis of 3-Amino-6-imidazol-1-yl-4-methyl-thieno[2,3-b]pyridine-2-carboxylic acid amide

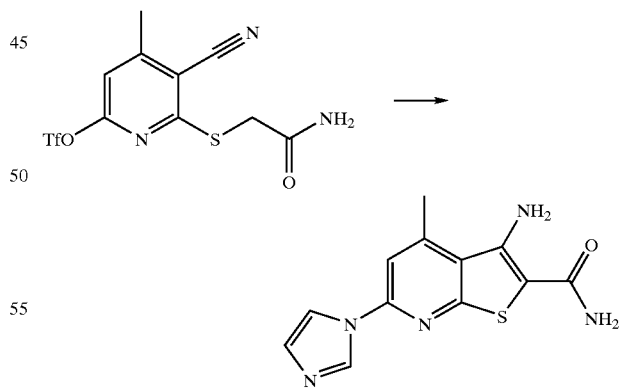

21

To a solution of 20 mg (0.067 mmol) of starting 4-methylpyridine triflate intermediate (see Example 2) in 1.2 mL of 1,4-dioxane was added 9.2 mg of imidazole. The resulting mixture was stirred for 2 h at 80° C. After that time 0.5 mL of 2M solution of sodium carbonate was added. The stirring was continued overnight at 100° C. The reaction mixture was then cooled to room temperature, diluted with EtOAc, dried with sodium sulfate and concentrated. The crude product was chromatographed (preparative TLC on silica gel eluting with 10% MeOH/methylene chloride, Rf=0.56) to afford 3.7 mg of product, which was further purified by HPLC (reverse phase—solvent system: isocratic 60% water/acetonitrile providing 2.7 mg (14.7%) of the title compound.

Example 22

Synthesis of 3-amino-6-isobutyl-4-methyl-thieno[2,3-b]pyridine-2-carboxylic acid amide

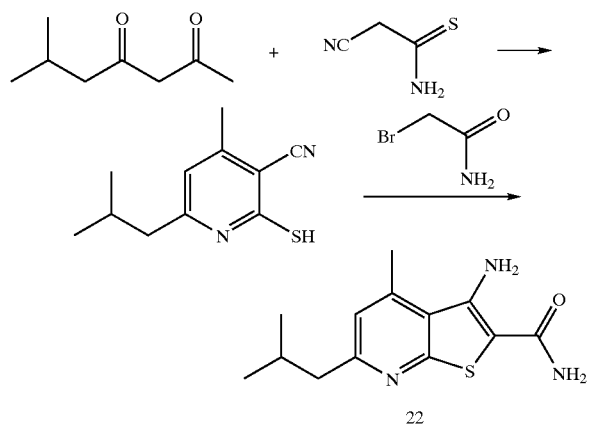

To a stirred solution of cyanothioacetamide (2.20 g, 22 mmol) and 6-methyl-2,4-heptanedione (3.12 g, 22 mmol) in anhydrous EtOH (40 ML) was added triethylamine (0.4 mL) and the reaction was heated at 50° C. for 1 h before it was allowed to cool to room temperature. Filtration and washing of the precipitates with EtOH gave 6-isobutyl-2-mercapto-4-methylnicotinonitrile as a yellow solid (2.8 g, 61%).

A mixture of the above nitrile (1.00 g, 4.85 mmol), bromoacetamide (0.67 g, 4.85 mmol), and sodium ethoxide (0.68 g, 10 mmol) in DMF (20 mL) was heated at 70° C. for 1 h before it was allowed to cool to room temperature. The resulting mixture was diluted with water, filtrated and the precipitates washed with ETOH providing the title compound (0.5 g, 39%).

Example 23

Synthesis of 3-amino-4-methyl-6-pentyl-thieno[2,3-b]pyridine-2-carboxylic acid amide

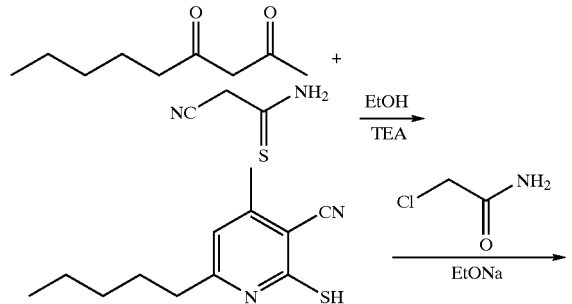

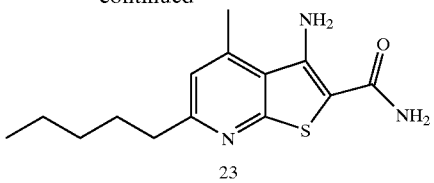

To a stirred solution of 2-cyanothioacetamide (1.4 g, 14 mmol) and 2,4-nonanedione (2.0 g, 13 mmol) in anhydrous EtOH (40 mL) was added triethylamine (0.5 mL) and the reaction was heated at 50° C. for 1 h and then was allowed to cool to room temperature. Filtration and washing of the precipitates with EtOH gave 6-pentyl-2-mercapto4-methyl-nicotinonitrile as a yellow solid (1.84 g, 62.1%).

A mixture of the above nonitrile (1.84 g, 6.7 mmol), 2-chloroacetamide (0.63 g, 6.7 mmol) and sodium ethoxide (0.91 g, 13.4 mmol) in MeOH (35 mL) was heated at 75° C. for 2 h and then it was allowed to cool to room temperature. Filtration and washing of the precipitates with EtOH provided the title compound as a solid (1.31 g, 71.2%).

Example 24

Synthesis of 3-amino-6-methyl-thieno[2,3-b]pyridine-2,4-dicarboxylic acid 2-amide 4-phenylamide

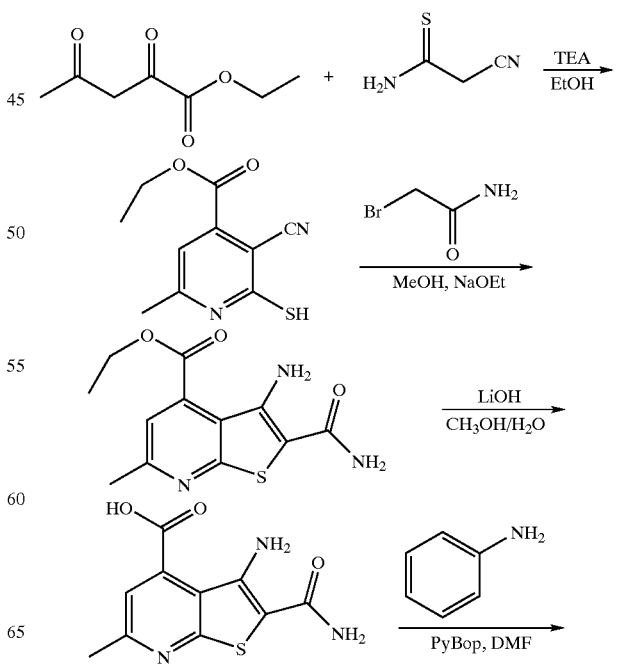

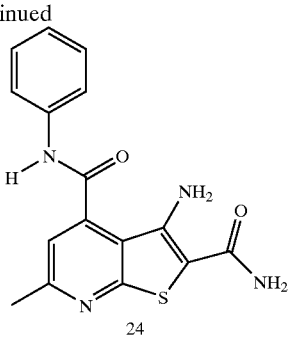

24

To a stirred solution of 2-cyanothioacetamide (3.52 g, 35 mmol) and ethyl 2,4-dioxovalerate (5.0 g, 32 mmol) in anhydrous EtOH (75 mL) at room temperature was added triethylamine (0.5 mL) and the reaction was stirred overnight. Filtration and washing of the precipitates with EtOH gave 3-cyano-2-mercapto-6-methyl-isonicotinic acid ethyl ester as a yellow solid (4.54 g, 64.5%). A mixture of this ester (3.54 g, 16 mmol), bromoacetamide (2.15 g, 16 mmol) and sodium ethoxide (2.18 g, 32 mmol) in MeOH was heated at reflux overnight. It was then allowed to cool to room temperature. Filtration and washing of the precipitates with EtOH provided 3-amino-2-carbamoyl-6-methyl-thieno[2,3-b]pyridine-4-carboxylic acid ethyl ester as a solid (0.94 g, 21.1%).

A mixture of the above ester (0.94 g. 3.4 mmol) and lithium hydroxide (0.11 g, 4.7 mmol) in MeOH/H$_2$O (100 mL, MeOH: H$_2$O=3:1) was stirred for 2 h at room temperature. The reaction was neutralized with 2 M HCl and concentrated in vacuo to afford 3-amino-2-carbamoyl-6-methyl-thieno[2,3-b]pyridine-4-carboxylic acid as an orange solid (0.78 g, 63.2%). A mixture of this acid (0.3 g, 1.2 mmol), aniline (0.56 g, 6.0 mmol) and PyBop (0.63 g, 1.4 mmol) in DMF (10 mL) was stirred at room temperature overnight. The reaction was then diluted with water, filtered and the resulting solid washed with EtOH providing the title compound as a solid (0.27 g, 73.6%).

Example 25

3-Amino-6-methyl-4-(morpholine-4-carbonyl)-thieno[2,3-b]pyridine-2-carboxylic acid amide

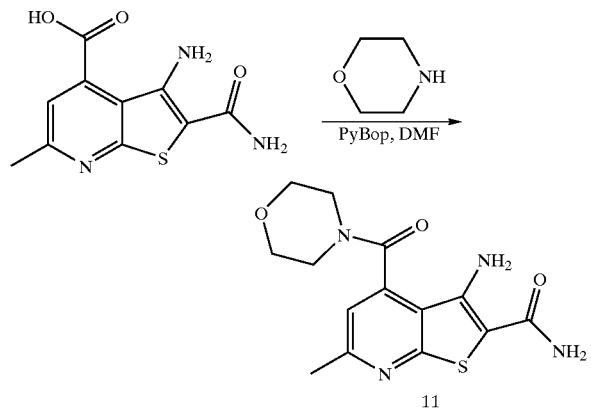

11

A mixture of 3-amino-2-carbamoyl-6-methyl-thieno[2,3-b]pyridine-4-carboxylic acid (see Example 10) (0.5 g, 2.0 mmol), morpholine (0.87 g, 10 mmol) and PyBop (0.88 g, 2.0 mmol) in DMF (10 mL) was stirred at room temperature overnight. It was diluted with water and extracted with methylene chloride (50 mL). Concentration of the organic phase the title compound as an orange solid (0.45 g, 70.3%).

Example 26

Synthesis of 3-Amino-6-methyl-4-phenoxymethyl-thieno[2,3-b]pyridine-2-carboxylic acid amide

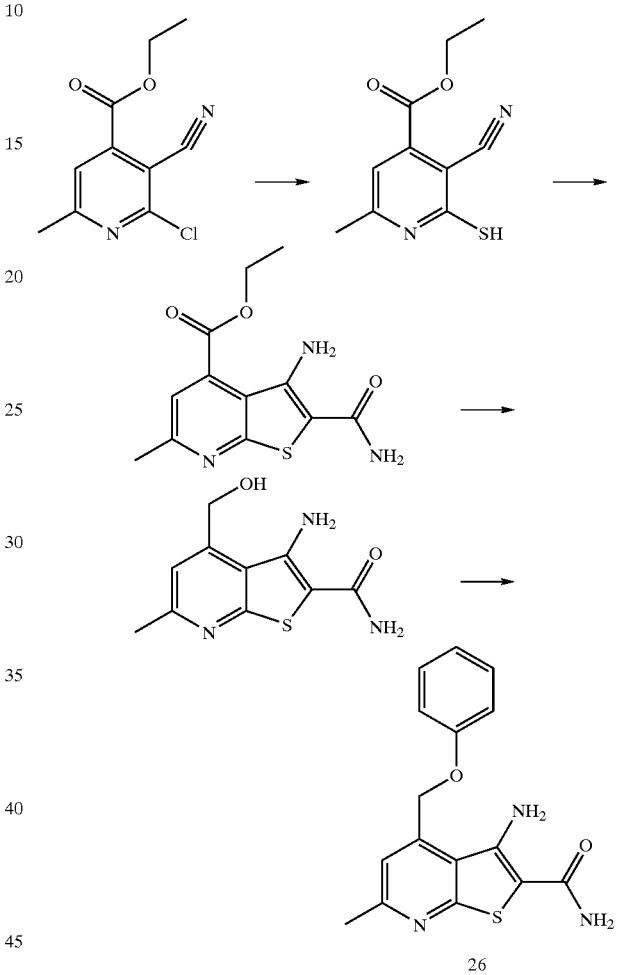

26

Thiourea (339 mg, 4.46 mmol) was added to a solution of 2-chloro-3-cyano-6-methyl-isonicotinic acid ethyl ester (500 mg, 2.23 mmol) in EtOH (25 mL) at room temperature. The mixture was heated to reflux for 24 h. The mixture was cooled (crystallization began upon cooling) to room temperature. The solid was collected by vacuum filtration giving 3-cyano-2-mercapto-6-methyl-isonicotinic acid ethyl ester (250 mg, 50%) as a yellow orange solid.

NaH (39 mg, 0.95 mmol) was added to a solution of the above ester (210 mg, 0.95 mmol) in THF (15 mL) at room temperature. After stirring for 5 min, α-bromoacetamide (134 mg, 0.97 mmol) and n-Bu$_4$NI (10 mg) were added. The mixture was stirred at room temperature for 1 h, then NaH (39 mg, 0.95 mmol) was added, and the mixture was stirred for an additional 0.5 h. The reaction was quenched by addition of saturated aqueous NH$_4$Cl, diluted with EtOAc, washed with brine, dried over Na$_2$SO$_4$, and concentrated giving an orange solid. The crude residue was recrystallized from MeOH giving 3-amino-2-carbamoyl-6-methyl-thieno

[2,3-b]pyridine-4-carboxylic acid ethyl ester (160 mg, 60%), m.p. 205–208° C.

LiBH$_4$ (62 mg, 2.04 mmol) was added to a solution of 3-Amino-2-carbamoyl-6-methyl-thieno[2,3-b]pyridine-4-carboxylic acid ethyl ester (205 mg, 0.73 mmol) in 10:1 THF:MeOH (15 mL) at room temperature. After stirring for 2 h, the reaction was quenched by addition of 1M HCl. The mixture was buffered to a pH ≈7, diluted with EtOAc, washed sequentially with H$_2$O, brine, dried over Na$_2$SO$_4$, concentrated, and triturated with 50% EtOAc/hexane giving 3-amino-4-hydroxymethyl-6-methyl-thieno[2,3-b]pyridine-2-carboxylic acid amide (123 mg, 71%) as a yellow solid, m.p. >210° C.

Diisopropyl azodicarboxylate (DIAD) (14 mg, 0.069 mmol) was added to a solution of 3-amino-4-hydroxymethyl-6-methyl-thieno[2,3-b]pyridine-2-carboxylic acid amide (15 mg, 0.063 mmol), phenol (6 mg, 0.069 mmol), and Ph$_3$P (18 mg, 0.069 mmol) in THF (1.5 mL) at 0° C. The mixture was warmed to room temperature and stirred for 24 h. The reaction mixture was concentrated and fractionated by preparative TLC (10% MeOH/CH$_2$Cl$_2$) providing the title compound (12 mg, 61%) as an orange solid, m.p. 194–196° C.

Example 27

Synthesis of amino-4-(4-carbamoyl-phenoxymethyl)-6-methyl-thieno[2,3-b]pyridine-2-carboxylic acid amide

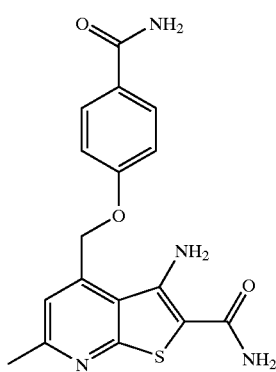

27

DIAD (23 mg, 0.116 mmol) was added to a solution of 3-amino-4-hydroxymethyl-6-methyl-thieno[2,3-b]pyridine-2-carboxylic acid amide (see Example 12) (25 mg, 0.105 mmol), 4-hydroxy-benzamide (15 mg, 0.116 mmol), and Ph$_3$P (30 mg, 0.116 mmol) in THF (2.5 mL) at 0° C. The mixture was warmed to room temperature and stirred for 24 h. The reaction mixture was concentrated and triturated with 2:1 EtOAc:MeOH giving the title compound (7 mg, 19%) as an orange solid, m.p.>250° C.

Example 28

Synthesis of 3-Amino-4,6-dimethyl-thieno[2,3-b]pyridine-2-carboxylic acid amide

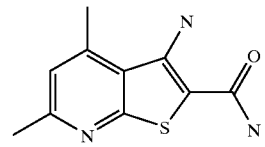

α-Bromoacetamide (388 mg, 2.81 mmol) was added to a solution of 2-mercapto-4,6-dimethyl-nicotinonitrile (420 mg, 2.56 mmol) in MeOH (25 mL) at room temperature. This was followed by addition of sodium methoxide (1.76 mL, 25% NaOMe in MeOH, 7.7 mmol). The reaction mixture was heated to reflux. Heating at reflux was continued overnight, after which time the reaction mixture was cooled and filtered. The product was dried overnight providing 450 mg (80%) of the title compound, m.p. 238–40° C.

Example 29

Synthesis of 3-amino-4-(1-hydroxy-ethyl)-6-methyl-thieno[2,3-b]pyridine-2-carboxylic acid amide

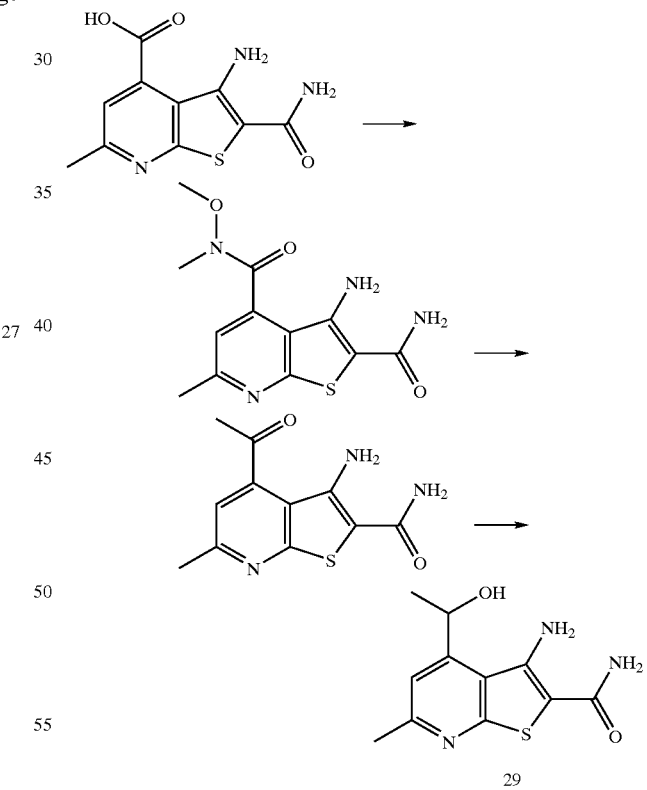

29

To a solution of 0.80 g 3-amino-2-carbamoyl-6-methyl-thieno[2,3-b]pyridine-4-carboxylic acid and 0.37 g N,O-dimethylhydroxylamine hydrochloride in DMF was added 1.8 mL diisopropylethylamine and 1.23 g O-benzotriazol-1-yl-N,N,N',N'-tetramethyluronium tetrafluoroborate. The solution was stirred at room temperature overnight. The reaction was poured into aqueous NH$_4$Cl, extracted 4 times with EtOAc, washed 4 times with water and aqueous Na₂CO₃, dried and concentrated in vacuo to 0.74 g. The aqueous phase was re-extracted 4 times with n-butanol, washed with aqueous Na₂CO₃, concentrated in vacuo, and azeotroped 3 times with toluene to get 0.71 g more product. The aqueous phase was made basic with Na₂CO₃, re-extracted 4 times with n-butanol, washed with water, concentrated in vacuo, and azeotroped 3 times with toluene to get a third crop of 0.52 g. The three crops were combined and flash-chromatographed on silica gel eluting with 5% MeOH—CH₂Cl₂ to provide 0.62 g 3-amino-6-methyl-thieno[2,3-b]pyridine-2,4-dicarboxylic acid 2-amide 4-(methoxy-methyl-amide) as a yellow solid.

To 100 mg 3-amino-6-methyl-thieno[2,3-b]pyridine-2,4-dicarboxylic acid 2-amide 4-(methoxy-methyl-amide) in 3 mL dry THF in an ice bath was added 0.68 mL 3 M methylmagnesium bromide and the reaction was stirred 1 h in the cold and at room temperature overnight under argon. Aqueous NH₄Cl was added and the product was extracted 4 times into EtOAc, dried, and concentrated in vacuo. Purification on a 2 mm silica gel prep plate in 5% MeOH—CH2Cl2 afforded 12.2 mg of 4-acetyl-3-amino-6-methyl-thieno[2,3-b]pyridine-2-carboxylic acid amide.

A spatula tip full of NaBH₄ was added to a solution of 9.9 mg 4-acetyl-3-amino-6-methyl-thieno[2,3-b]pyridine-2-carboxylic acid amide in 1 mL MeOH. After 0.5 h, the reaction was concentrated in vacuo, quenched with aqueous NH₄Cl, extracted 4 times into EtOAc, concentrated in vacuo, dissolved in MeOH—CH₂Cl₂, filtered, concentrated and dried in vacuo at 60° C. to provide 8.1 mg of the title compound as a beige solid.

Example 30

Synthesis of 3-amino-4-(hydroxy-phenyl-methyl)-6-methyl-thieno[2,3-b]pyridine-2-carboxylic acid amide

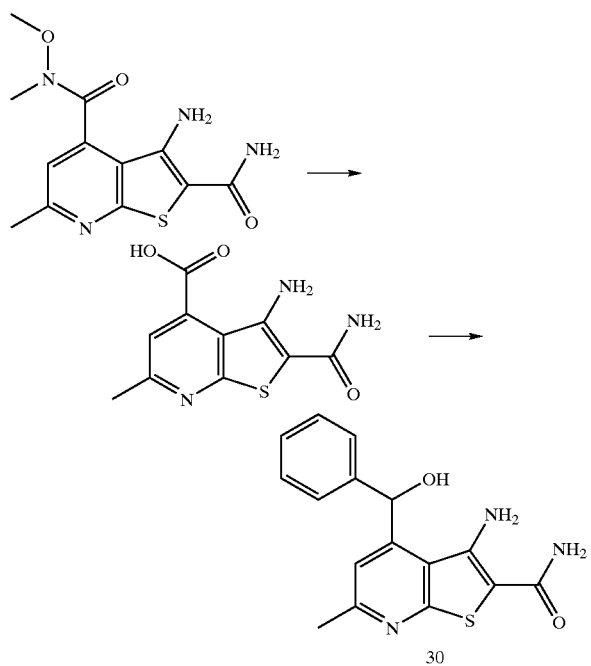

LiAlH₄ (0.31 g) was added to a suspension of 0.60 g of 3-amino-6-methyl-thieno[2,3-b]pyridine-2,4-dicarboxylic acid 2-amide 4-(methoxy-methyl-amide) (see Example 15) in 15 mL dry THF at −10° C. and stirred 1 h under Ar. Aqueous NH₄Cl was added slowly and the mixture was filtered through diatomaceous earth, washing with H₂O and EtOAc. The aqueous phase was separated and extracted 3 times with more with EtOAc and the combined organics were and concentrated in vacuo to a resin that was flashed chromatographed eluting with 30% acetone-petroleum ether to afford 163 mg 3-amino-4-fonnyl-6-methyl-thieno[2,3-b] pyridine-2-carboxylic acid amide as a dark resin.

To a suspension of 314 mg CeCl₃ in 3 mL dry THF at −78° C. was added 0.425 mL 3M phenylmagnesium bromide and the reaction was stirred 1.5 h under Ar. Then, 50 mg of 3-amino-4-formyl-6-methyl-thieno[2,3-b]pyridine-2-carboxylic acid amide was added and the reaction was stirred 5 h in the cold and then allowed to warm to room temperature over 0.5 h. Aqueous NH₄Cl was added and the reaction was filtered through diatomaceous earth, washing with EtOAc, and the aqueous phase was separated and extracted 3 times with more with EtOAc. The combined organics were dried, and concentrated in vacuo, and the product was purified on a prep plate developed with 5% MeOH—CH₂Cl₂. Starting material impurity was removed by dissolving the product in EtOAc with a trace MeOH and washing 3 times with aqueous NaHSO₃. The organics were dried, concentrated in vacuo, re-dissolved in MeOH—CH₂Cl₂, filtered, concentrated and dried in vacuo at 60° C. to provide 8.2 mg of the title compound as a yellow solid.

Example 31

Synthesis of 3-amino-4-(1-hydroxy-2-phenyl-ethyl)-6-methyl-thieno[2,3-b]pyridine-2-carboxylic acid amide

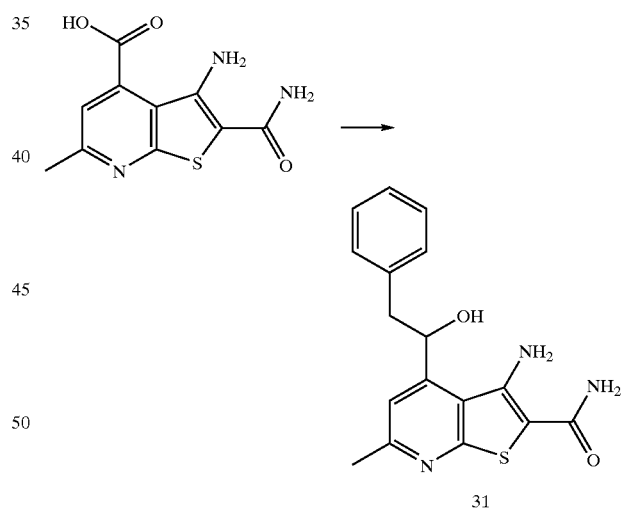

To a suspension of 344 mg CeCl₃ in 3 mL dry THF at −78° was added 0.70 mL 2 M benzylmagnesium chloride and the reaction was stirred 1.5 h under Ar. Then, 41 mg of 3-amino-4-formyl-6-methyl-thieno[2,3-b]pyridine-2-carboxylic acid amide (see Example 16) was added and the reaction was stirred 3.5 h in the cold and then allowed to warm to room temperature over 0.5 h. Aqueous NH₄Cl was added and the reaction was filtered through diatomaceous earth, washing with EtOAc, and the aqueous phase was separated and extracted 3 times more with EtOAc. The combined organics were dried, concentrated in vacuo, and re-dissolved in EtOAc with a trace MeOH and washed 3

Example 32

Synthesis of 3-amino-4-(4-methoxy-benzyloxy)-thieno[2,3-b]pyridine-2-carboxylic acid amide

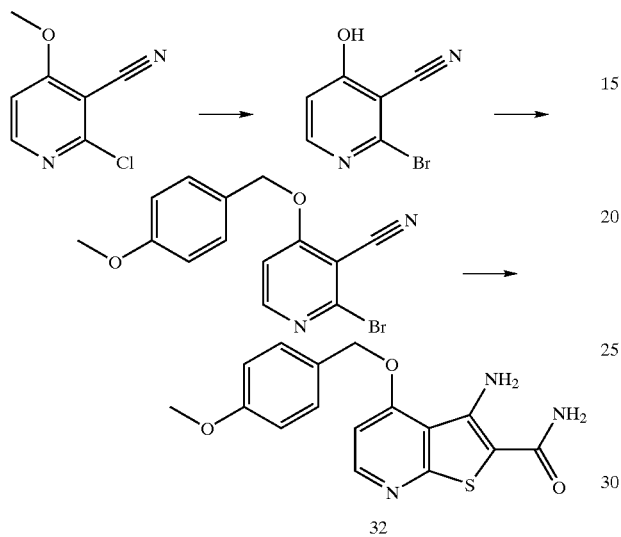

2-Chloro-4-methoxy-nicotinonitrile (M. Mittelbach et al., Arch. Pharm. (Weinheim Ger.), 1985, GE, 318, 6, 481–486) (6.92 g) was suspended in 70 mL of 30% HBr in acetic acid in a pressure vessel and heated with stirring at 100° C. for 2 h. The reaction was cooled to room temperature and filtered, washing well with $H_2O$, and dried in vacuo overnight at 50° C. providing 4.85 g 2-bromo-4-hydroxy-nicotinonitrile as a white solid. Proton NMR(DMSO) indicated the product was a mixture of 69% bromo compound with 31% starting chloro analog.

To a solution of 5.85 g of the above mixture in 30 mL of dry DMF was added 1.52 g 60% NaH in mineral oil in portions and the brown reaction was stirred 15 min at room temperature under Ar. 4-Methoxybenzyl chloride (5.16 mL) was added and the reaction was heated at 60° C. for 2.5 h and then quenched with aqueous $NH_4Cl$. Extraction into EtOAc, followed by washing with $H_2O$ gave precipitation of a white solid side-product in the separatory funnel that was filtered off. The filtrate was dried and stripped to 9.4 g of a semisolid that was triturated in $CH_2Cl_2$ and filtered to afford 730 mg more side-product. The filtrate was concentrated and flash-chromatographed on silica gel eluting with $CH_2Cl_2$ providing 4.80 g of a white waxy solid. Proton NMR(DMSO) indicated the product was a 2:1 mixture of 2-bromo-4-(4-methoxy-benzyloxy)-nicotinonitrile with its 2-chloro analog.

A mercaptoacetamide solution in MeOH (6.80 mL) was concentrated in vacuo providing 928 mg. 2.75 g of the above 2:1 mixture was added and dissolved in 14 mnL dry DMF under a $N_2$ purge. A 60% NaH suspension in mineral oil (723 mg) was added and stirred at 60° C. overnight under Ar. Aqueous $NH_4Cl$ was added and the product was filtered, washed with $H_2O$, and dried in vacuo at 50° C. providing 1.97 g crude product that was recrystallized from MeOH to afford 1.25 g of the title compound as a yellow solid.

The following compounds were prepared in the manner described above from 2-bromo-4-hydroxy-nicotinonitrile and the appropriate alkyl halide. In the case of alkyl ethers, the alkyl bromide or iodide was used. In the case of benzyl ethers, the benzyl chloride or bromide was used.:

3-Amino-4-methoxy-thieno[2,3-b]pyridine-2-carboxylic acid amide

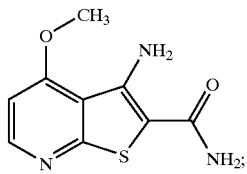

3-Amino-4-ethoxy-thieno[2,3-b]pyridine-2-carboxylic acid amide

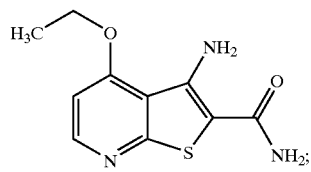

3-Amino-4-propoxy-thieno[2,3-b]pyridine-2-carboxylic acid amide;

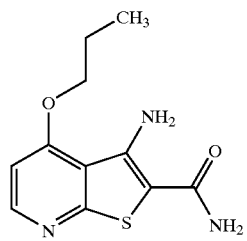

3-Amino-4-isopropoxy-thieno[2,3-b]pyridine-2-carboxylic acid amide

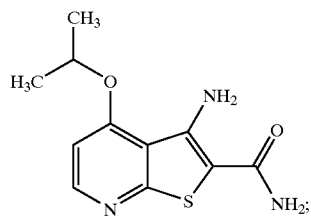

223

3-Amino-4-benzyloxy-thieno[2,3-b]pyridine-2-carboxylic acid amide

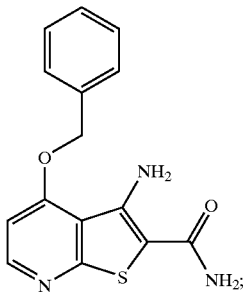

3-Amino-4-(3-methoxybenzyloxy)-thieno[2,3-b]pyridine-2-carboxylic acid amide

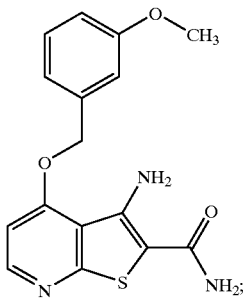

3-Amino-4-(cyclohexylmethoxy)-thieno[2,3-b]pyridine-2-carboxylic acid amide

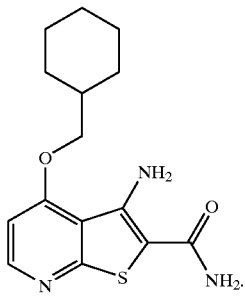

Example 33

Synthesis of 3-amino-4-phenylamino-thieno[2,3-b]pyridine-2-carboxylic acid amide

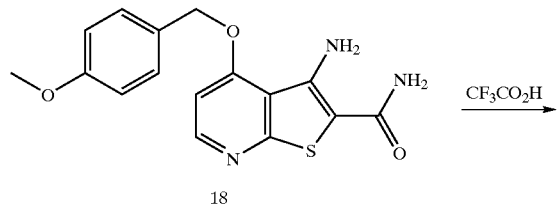

224

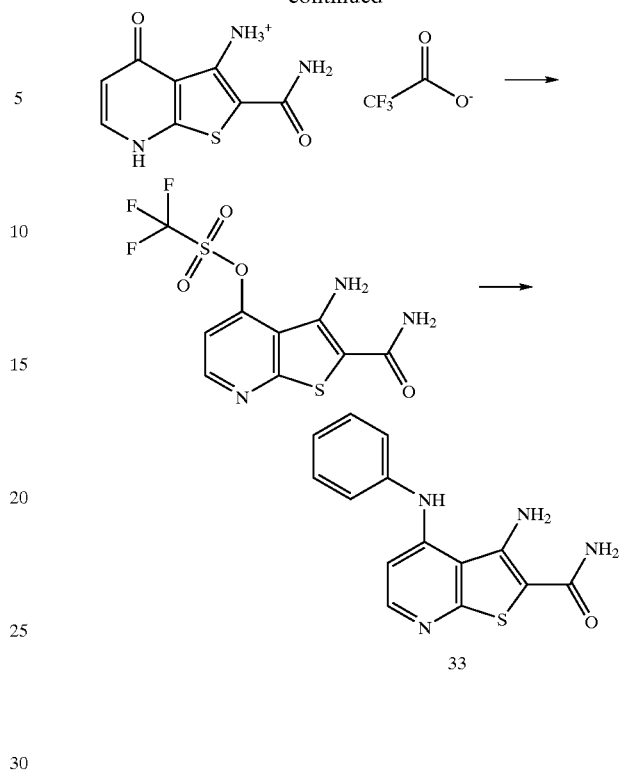

A solution of 2.43 g 3-amino-4-(4-methoxy-benzyloxy)-thieno[2,3-b]pyridine-2-carboxylic acid amide (Example 18) was stirred 6 h in 20 mL trifluoroacetic acid with a drying tube. The reaction was concentrated in vacuo and then co-evaporated 3 times with toluene and 2 times with $CH_2Cl_2$ to give a yellow resin. This was triturated in EtOAc and filtered to give 1.88 g 3-amino-4-oxo-4,7-dihydro-thieno[2,3-b]pyridine-2-carboxylic acid amide trifluoroacetic acid salt as a yellow solid.

A mixture of 1.0 g 3-amino-4-oxo-4,7-dihydro-thieno[2,3-b]pyridine-2-carboxylic acid amide trifluoroacetic acid salt and 2.76 g N-phenyltrifluoromethanesulfomimide and 1.35 mL diisopropylethylamine was stirred in 10 mL dioxane at room temperature under Ar overnight. EtOAc was added and the mixture was washed with $H_2O$, two times with aqueous $NH_4Cl$, and once with aqueous $Na_2CO_3$. The EtOAc solution was dried and concentrated in vacuo to 3.63 g yellow solid. Flash-chromatography, eluting with acetone-petroleum ether, afforded 1.05 g of trifluoromethanesulfonic acid 3-amino-2-carbamoyl-thieno[2,3-b]pyridin-4-yl ester as a yellow solid.

A solution of 20 mg trifluoromethanesulfonic acid 3-amino-2-carbamoyl-thieno[2,3-b]pyridin-4-yl ester and 27 microL aniline in 1 mL of THF was heated at 55° C. overnight under Ar. The reaction was applied to a 2 mm silica gel prep plate that was developed twice in 5% MeOH—$CH_2Cl_2$. The band was eluted with 50% MeOH—$CH_2Cl_2$ to get 18 mg. This was dissolved in 5% MeOH—$CH_2Cl_2$, filtered, concentrated, and dried in vacuo at 60° C. overnight to provide 10.5 mg of the title compound as a yellow-green solid.

Example 34

Synthesis of 3-amino-4-(4-nitro-phenylamino)-thieno[2,3-b]pyridine-2-carboxylic acid amide

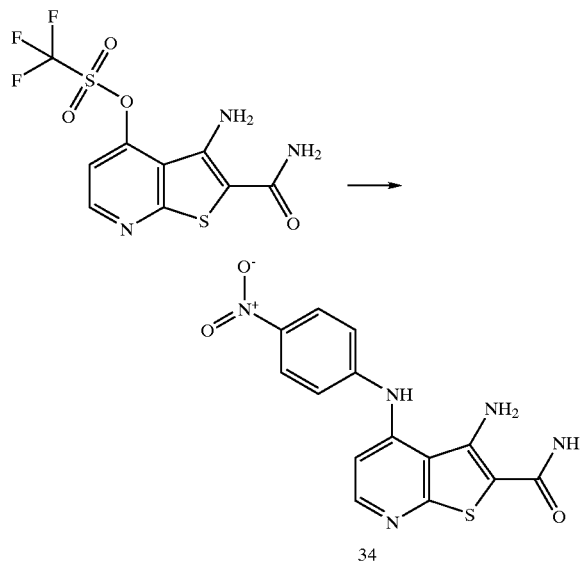

34

A solution of 20 mg trifluoromethanesulfonic acid 3-amino-2-carbamoyl-thieno[2,3-b]pyridin-4-yl ester (see Example 19) and 40.5 mg 4-nitroaniline in 1 mL of dry dioxane was heated at 95° C. overnight under $N_2$. The reaction was concentrated and applied to a 2 mm silica gel prep plate that was developed twice in 7.5% MeOH—$CH_2Cl_2$. The band was eluted with 20% MeOH—$CH_2Cl_2$, concentrated in vacuo, re-dissolved in 5% MeOH—$CH_2Cl_2$, filtered, concentrated, and dried in vacuo at 60° overnight to get 2.2 mg of the title compound as an orange solid.

Example 35

Synthesis of 3-amino-4-(4-benzyl-piperazin-1-yl)-thieno[2,3-b]pyridine-2-carboxylic acid amide

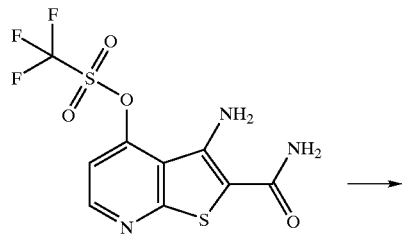

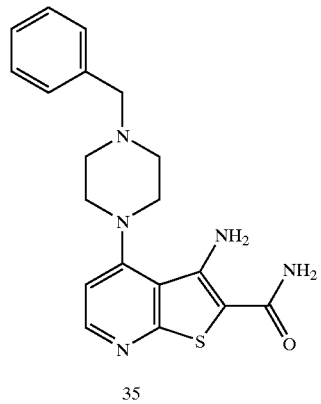

35

A mixture of 20 mg trifluoromethanesulfonic acid 3-amino-2-carbamoyl-thieno[2,3-b]pyridin-4-yl ester and 50 microl of N-benzylpiperazine in 1 mL of dry dioxane was purged with $N_2$ and capped and left at room temperature overnight. The reaction was diluted with EtOAc, washed four times with water, dried and concentrated to dryness in vacuo. The product was purified on a 2 mm silica gel prep plate, developing and eluting the band with MeOH—$CH_2Cl_2$ mixtures and then concentrating to dryness. The product was re-dissolved in 5–10% MeOH—$CH_2Cl_2$, filtered to remove silica gel, concentrated, and dried in vacuo at 60° C. overnight to provide 7.9 mg of the title compound as a beige solid.

The following compounds were prepared using the same procedure described in the above Example. If the intermediate secondary amine was a solid, 50 molar equivalents were used rather than 50 microL. In some cases, if the product was thought to have appreciable solubility in water, the reaction mixture was concentrated without extraction and the residue purified by prep TLC as above. Other slight modifications are noted for particular compounds.

3-Amino-4-(4-methyl-piperazin-1-yl)-thieno[2,3-b]pyridine-2-carboxylic acid amide

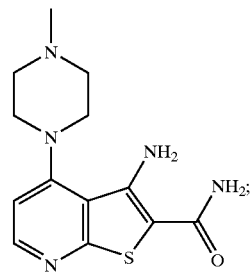

227

3-Amino-4-piperidin-1-yl-thieno[2,3-b]pyridine-2-carboxylic acid amide

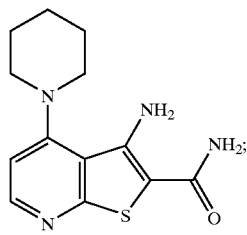

3-Amino-4-morpholin-4-yl-thieno[2,3-b]pyridine-2-carboxylic acid amide

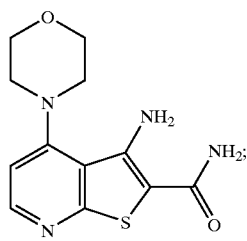

3-Amino-4-[methyl-(2-pyridin-2-yl-ethyl)-amino]-thieno[2,3-b]pyridine-2-carboxylic acid amide

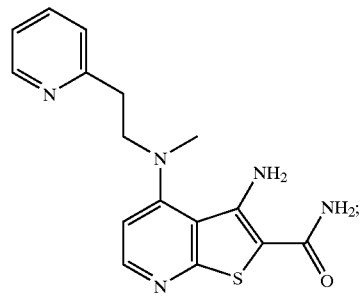

3-Amino-4-[4-(isopropylcarbamoyl-methyl)-piperazin-1-yl]-thieno[2,3-b]pyridine-2-carboxylic acid amide

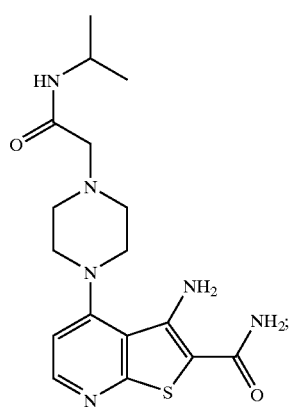

228

3-Amino-4-(4-phenyl-piperidin-1-yl)-thieno[2,3-b]pyridine-2-carboxylic acid amide

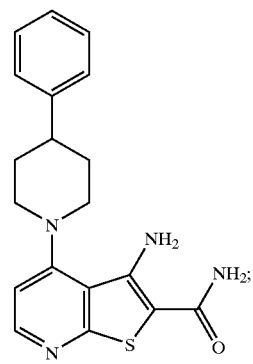

3-Amino-4-(4-hydroxy-4-phenyl-piperidin-1-yl)-thieno[2,3-b]pyridine-2-carboxylic acid amide

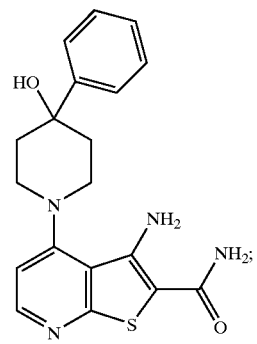

3-Amino-4-(4-phenyl-piperazin-1-yl)-thieno[2,3-b]pyridine-2-carboxylic acid amide

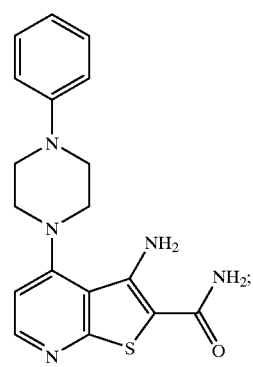

229

3-Amino-4-(4-oxo-1-phenyl-1,3,8-triaza-spiro[4.5]dec-8-yl)-thieno[2,3-b]pyridine-2-carboxylic acid amide

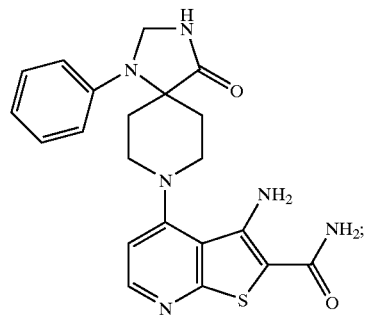

3-Amino-4-[1,4']bipiperidinyl-1'-yl-thieno[2,3-b]pyridine-2-carboxylic acid amide

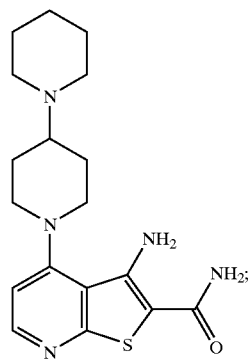

3-Amino-4-(benzyl-methyl-amino)-thieno[2,3-b]pyridine-2-carboxylic acid amide

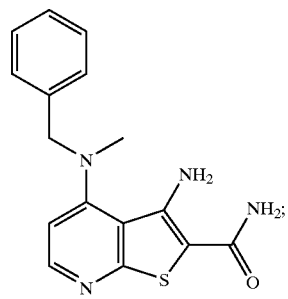

230

3-Amino-4-(methyl-phenethyl-amino)-thieno[2,3-b]pyridine-2-carboxylic acid amide

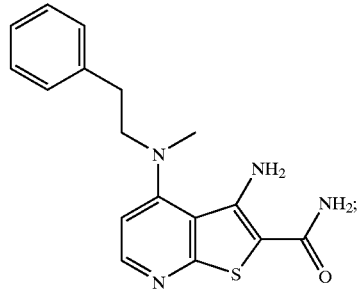

3-Amino-4-(4-benzyl-piperidin-1-yl)-thieno[2,3-b]pyridine-2-carboxylic acid amide

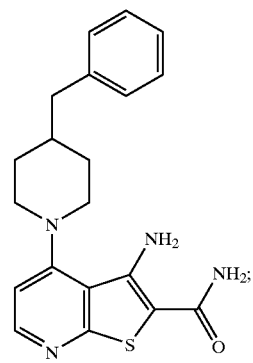

3-Amino-4-[(2-hydroxy-2-phenyl-ethyl)-methyl-amino]-thieno[2,3-b]pyridine-2-carboxylic acid amide

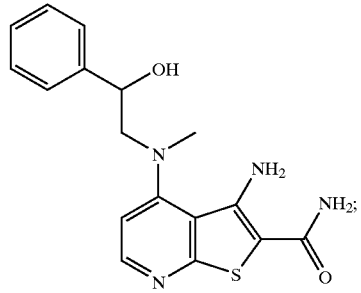

231

4-(3-Amino-2-carbamoyl-thieno[2,3-b]pyridin-4-yl)-piperazine-1-carboxylic acid benzyl ester

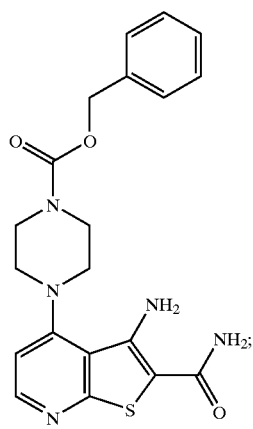

4-(3-Amino-2-carbamoyl-thieno[2,3-b]pyridin-4-yl)-piperazine-1-carboxylic acid tert-butyl ester

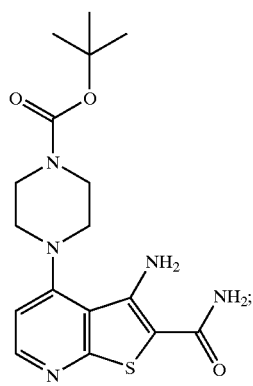

3-Amino-4-[4-(2-oxo-2,3-dihydro-benzoimidazol-1-yl)-piperidin-1-yl]-thieno[2,3-b]pyridine-2-carboxylic acid amide

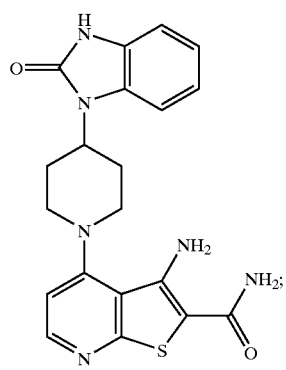

232

3-Amino-4-[4-(furan-2-carbonyl)-piperazin-1-yl]-thieno[2,3-b]pyridine-2-carboxylic acid amide

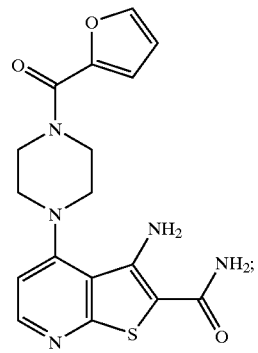

3-Amino-4-(4-benzenesulfonyl-piperazin-1-yl)-thieno[2,3-b]pyridine-2-carboxylic acid amide

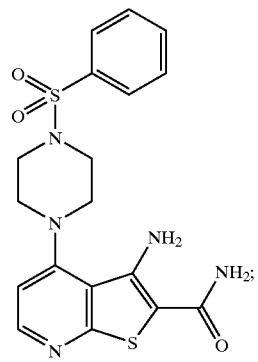

3-Amino-4-(ethyl-methyl-amino)-thieno[2,3-b]pyridine-2-carboxylic acid amide

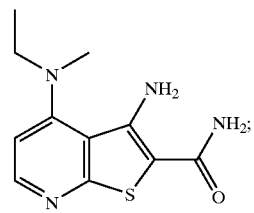

3-Amino-4-(methyl-propyl-amino)-thieno[2,3-b]pyridine-2-carboxylic acid amide

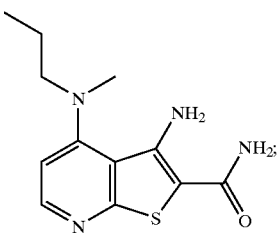

233

3-Amino-4-(butyl-methyl-amino)-thieno[2,3-b]pyridine-2-carboxylic acid amide

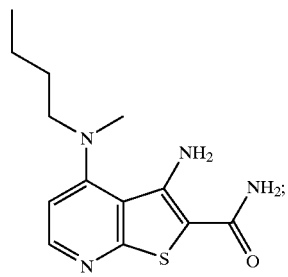

3-Amino-4-pyrrolidin-1-yl-thieno[2,3-b]pyridine-2-carboxylic acid amide

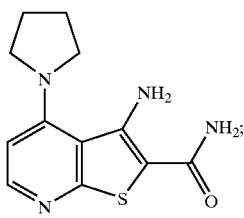

3-Amino-4-(4-hydroxy-piperidin-1-yl)-thieno[2,3-b]pyridine-2-carboxylic acid amide This product was purified after the prep plate by HPLC on a C8 column eluting with 75% H$_2$O-25% acetonitrile

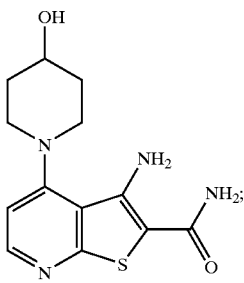

3-Amino-4-(3-hydroxy-piperidin-1-yl)-thieno[2,3-b]pyridine-2-carboxylic acid amide This product was purified after the prep plate by HPLC on a C8 column eluting with 65% H$_2$O-35% acetonitrile

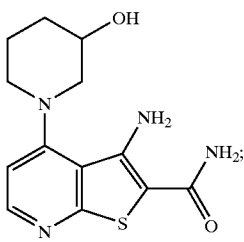

234

3-Amino-4-piperazin-1-yl-thieno[2,3-b]pyridine-2-carboxylic acid amide

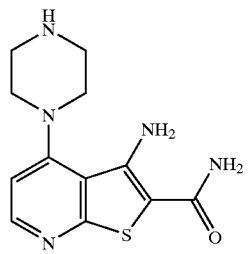

A solution of 18 mg 4-(3-amino-2-carbamoyl-thieno[2,3-b]pyridin-4-yl)-piperazine-1-carboxylic acid tert-butyl ester in 1 mL CH$_2$Cl$_2$+1 mL trifluoroacetic acid was stirred with a drying tube for 4 h at room temperature. The reaction was concentrated in vacuo and developed prep plate in 25% MeOH—CH$_2$Cl$_2$–2% NH$_4$OH and the band was eluted with 50% MeOH—CH$_2$Cl$_2$ to get an oil that was re-dissolved 10% MeOH—CH$_2$Cl$_2$, filtered, concentrated, and dried in vacuo at 60° C. to provide 4.6 mg of the product as a yellow solid.

Example 36

Synthesis of 3-amino-6-(4-amino-piperidin-1-yl)-4-((E)-styryl)-thieno[2,3-b]pyridine-2-carboxylic acid amide

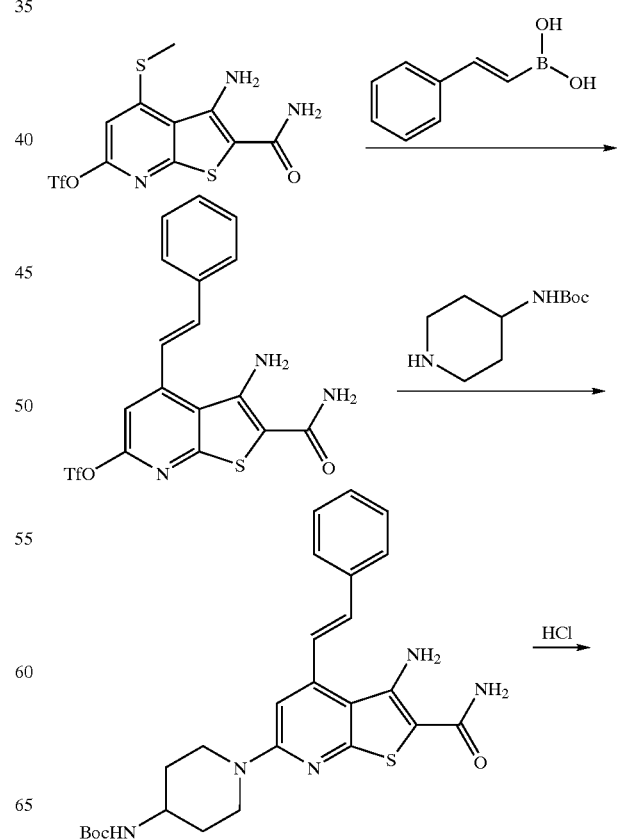

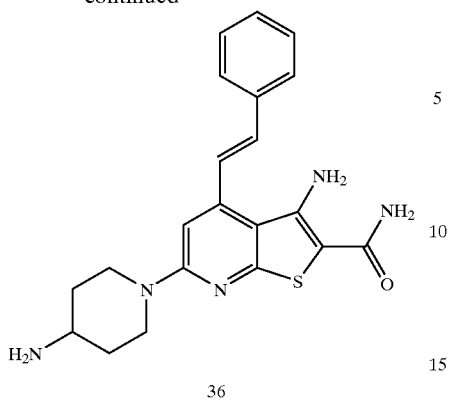

36

30 mL of dry THF was added into a sealable flask and a stream of Ar was bubbled through the solvent for 5 min. Tris(dibenzylideneacetone)dipalladium(0)-chloroform adduct (76.1 mg, 73.5 μmol), tris-2-furylphosphine (121.9 mg, 0.5 mmol), copper(I) thiophene-2-carboxylate (541.2 mg, 2.7 mmol), trans-2-phenylvinylboronic acid (621.4 mg, 4.2 mmol), and 3-amino-4-methylthio-6-trifluoromethylsuflonyl-thieno[2,3-b]pyridine-2-carboxylic acid amide (800.0 mg, 2.1 mmol) were added and the sealed flask was heated at 40° C. for 20 h. The solution was diluted with CH$_2$Cl$_2$ and the organic phase was extracted with saturated NaHCO$_3$-solution. The aqueous phase was extracted twice with CH$_2$Cl$_2$ and the combined organic phases were washed with brine. The solution was dried over MgSO$_4$, filtered, and evaporated. The residue was chromatographed on silica gel using a gradient (0–2.5% MeOH/ CH$_2$Cl$_2$ over 50 min). The fractions containing product were combined, evaporated and purified by preparative TLC (10% acetone/Ether) to yield 415 mg (45%) of the 4-(E)-styryl intermediate.

The above intermediate was dissolved in dioxane (20 mL), 4-N-Boc-aminopiperidine (382.6 mg, 1.9 mmol) was added and the mixture was stirred for 8 h at 100° C. The solution was cooled to room temperature and saturated NH$_4$Cl solution was added. The aqueous phase was extracted with ethyl acetate and the combined organic phases were dried over MgSO$_4$. The compound was further purified by preparative TLC (5% MeOH/CH$_2$Cl$_2$) to yield 220 mg (48%) of product.

The above carbamate was dissolved in dioxane (10 mL) and a 4 N solution of HCl dioxane (5 nmL) was added. The suspension was stirred for 3 h after which the solvent was evaporated. The residue was purified by preparative TLC (10% 4N NH$_3$ in MeOH/90% CH$_2$Cl$_2$) to yield 115 mg (65%) of the title compound.

Example 37

Synthesis of 3-amino-4-(4-methanesulfonyl-phenyl)-6-methyl-thieno[2,3-b]pyridine-2-carboxylic acid amide

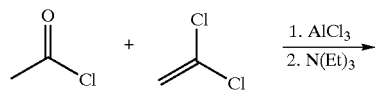

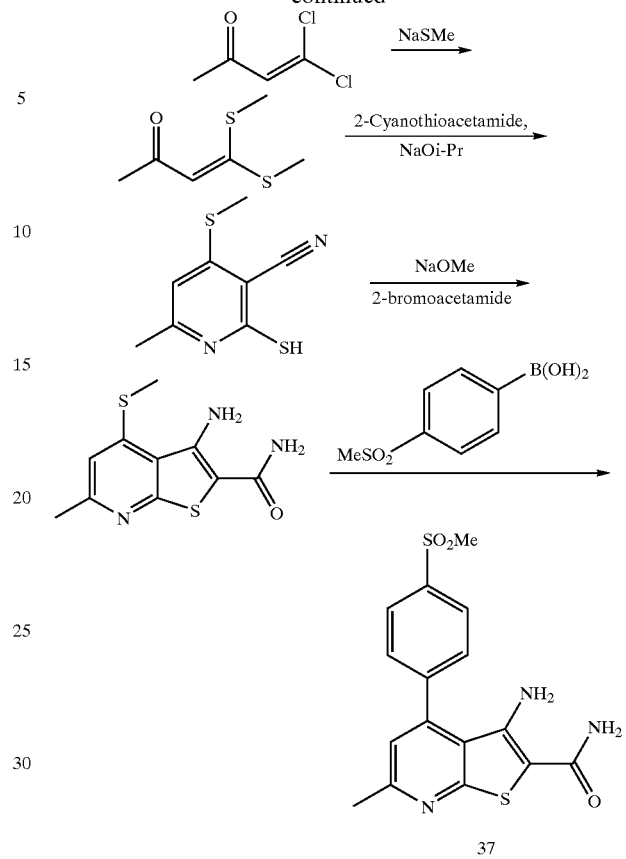

37

Aluminum chloride (4.2 g, 32 mmol) was suspended in methylene chloride (5 mL) and acetyl chloride (2.44 mL, 34 mmol) was added dropwise over 30 min, while the internal temperature was kept below 30° C. Stirring was continued for 15 min, after which vinylidene chloride was added over 10 min at 30° C. After stirring for another 90 min at room temperature, the mixture was poured onto crushed ice. The mixture was stirred for 20 min and the aqueous phase was extracted twice with methylene chloride. The combined organic phases were washed with water. The methylene chloride solution was then cooled to 0° C. and triethylamine (4.21 mL, 30 mmol) was added while stirring the solution. After 30 min 10% HCl was added and the organic phase was washed with 5% HCl, water and brine. The volatiles were evaporated and the residue was distilled over a small path distillation apparatus to yield 3.28 g (78%) of the desired dichlorovinyl ketone.

Sodium thiomethoxide (1.40 g, 20 mmol) was suspended in ether (20 mL) and the above dichlorovinyl ketone (10 mmol), dissolved in ether (10 mL), was added dropwise. The resulting solution was refluxed for 1 h, filtered, and the precipitate washed with ether. The combined filtrates were evaporated to yield 1.4 g (87%) of the desired dimethylthiovinyl ketone.

Sodium (533 mg, 23.2 mmol) was dissolved in isopropanol (50 mL) under heating. 2-Cyanothioacetamide (2.1 g, 21 mmol) was added and the solution was stirred for 5 min of at room temperature. The above dimethylthiovinyl ketone (3.4 g, 21 mmol) was added to the reaction mixture and the solution was refluxed until starting material disappeared (~30 h). The solvent was evaporated and the residue was dissolved in water. The aqueous solution was filtered, acidified to pH 3, and the precipitate was filtered off. The precipitate was washed with ether and then with hexane to give 3.9 g (95%) of the desired thiopyridine.

Sodium methoxide (2.16 g, 40 mmol) was dissolved in MeOH (60 mL) and the above thiopyridine (3.9 g, 20 mmol) was added. After 5 min, 2-bromoacetamide (2.76 g, 20 mmol) was added and the solution was refluxed for 2 h. The MeOH was partly evaporated and the residue was diluted with aqueous sodium bicarbonate solution. The aqueous phase was extracted several times with 10% MeOH/methylene chloride and the combined extracts were dried over magnesium sulfate. The solvent was evaporated and the residue purified by column chromatography on silica gel to give 2.1 g (41%) of the desired thieno[2,3-b]pyridine intermediate.

Dry THF (3 mL) was added to a sealable tube and a stream of Ar was bubbled through the solvent for 5 min. The above thieno[2,3-b]pyridine intermediate (50 mg, 0.2 mmol), 4-methanesulfonylphenylboronic acid (48 mg, 0.24 mmol), tris(dibezylideneacetone)dipalladium(0)-chloroform adduct (4 mg, 4 pmol), tri-2-furylphosphine (7.5 mg, 32 μmol), and copper(I)thiophene-2-carboxylate (50 mg, 0.26 mmol) were added. The tube was sealed and then heated at 65° C. for 24 h. The solution was diluted with CH$_2$Cl$_2$ and the organic phase was extracted with aqueous sodium bicarbonate solution. The aqueous phase was extracted twice with CH$_2$Cl$_2$ and the combined organic phases were washed with brine. The solution was dried over MgSO$_4$, filtered, and evaporated. The residue was purified by column chromatography. All fractions containing product were combined, evaporated and re-purified by preparative TLC to give 23 mg (32%) of the title compound.

Example 38

Synthesis of 3-amino-6-methyl-4-(1-methyl-1H-pyrrol-2-yl)-thieno[2,3-b]pyridine-2-carboxylic acid amide

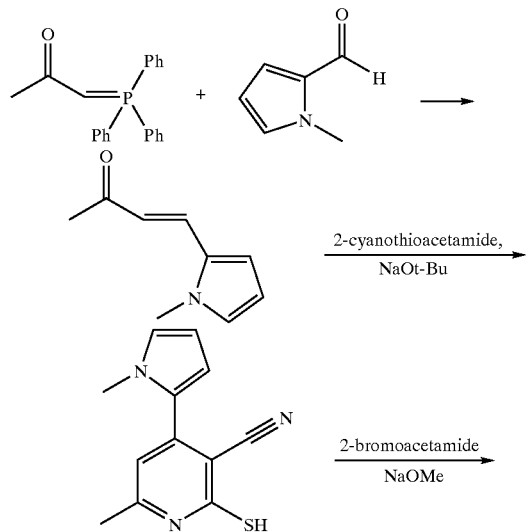

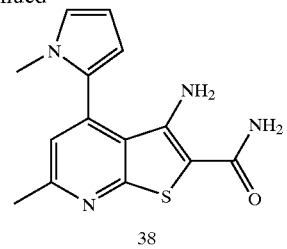

38

1-Methyl-2-pyrrolecarboxaldehyde (500 mg, 4.58 mmol) was dissolved in 10 mL of toluene followed by addition of 1-triphenylphosphoranylidene-2-propanone (1.53 g, 4.81 mmol) and 10 drops of acetic acid. The reaction mixture was heated to 120° C. in a sealed tube for 16 h. The reaction mixture was cooled to room temperature and the solvent was evaporated. The residue was dissolved in EtOAc, and the organic phase was washed with saturated NaHCO$_3$ solution and brine. The organic phase was dried over anhydrous Na$_2$SO$_4$, filtered, and concentrated. The residue was purified by column chromatography on silica gel to yield 565 mg (82.7%) of the vinyl ketone.

To a sealed tube was added 2-cyanothioacetamide (70.6 mg, 0.71 mmol) and sodium t-butoxide (71 mg, 0.74 mmol) in 2-propanol (4 mL). The mixture was stirred at room temperature for 5 min, followed by the addition of above vinyl ketone (100 mg, 0.67 mmol). The mixture was heated at 80° C. for 16 h. The solution was concentrated and the residue was dissolved in water. Dilute HCl was added to adjust the pH to 6. The solid that formed during acidification was filtered and washed with water. The solid was dried under high vacuum to afford 70 mg (45.5%) of the desired thiopyridine intermediate.

The above thiopyridine intermediate (70 mg, 0.31 mmol) was suspended in 2 mL of MeOH, followed by the addition of 2-bromoacetamide (42 mg, 0.3 mmol) and 1.22 mL of 0.5 N sodium methoxide solution in MeOH. The mixture was heated in a sealed tube at 70° C. for 2 h. The reaction mixture was concentrated and the residue was purified by column chromatography on silica gel to yield 36 mg (41%) of the title compound.

Example 39

Synthesis of 3-amino-6-(4-{[(2-carbamoyl-phenylcarbamoyl)-methyl]-amino}-piperidin-1-yl)-4-propyl-thieno[2,3-b]pyridine-2-carboxylic acid amide

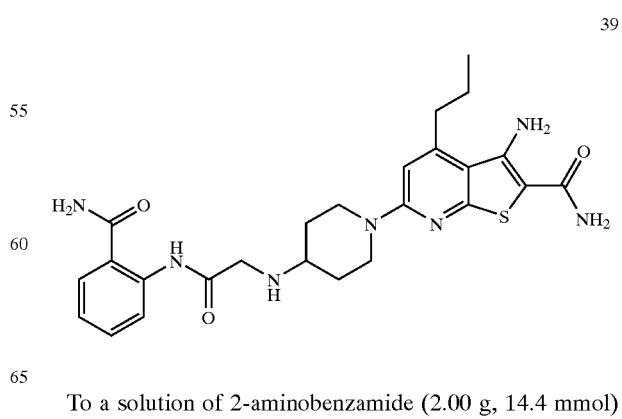

To a solution of 2-aminobenzamide (2.00 g, 14.4 mmol) and triethylamine (2.4 mL, 17 mmol) in dry dioxane (20 mL)

was added bromoacetyl bromide (1.33 mL, 15.0 mmol). This reaction mixture was stirred at room temperature for 1 h then poured into water. The resulting solid was collected by filtration and recrystallized from MeOH to give the diamide intermediate as a brown solid (2.02 g).

The above intermediate (70 mg, 0.21 mmol) and 3-amino-6-(4-amino-piperidin-1-yl)-4-propyl-thieno[2,3-b]pyridine-2-carboxylic acid amide (65 mg, 0.25 mmol), along with triethylamine (0.05 mL, 0.36 mmol), were stirred in 1 mL of DMF for 2 h. The solvent was removed in vacuo. The residue was triturated with water. The resulting solid was collected by filtration and recrystallized from acetonitrile to give the title compound (37 mg) as a pale colored solid.

Example 40

Synthesis of 3-amino-6-{4-[3-(4-carbamoyl-phenoxy)-2-hydroxy-propylamino]-piperidin-1-yl}-4-propyl-thieno[2,3-b]pyridine-2-carboxylic acid amide and potassium carbonate (403 mg, 2.916 mmol) in 7 mL of dry DMF. The reaction mixture was stirred at 70° C. for 18 h. The reaction mixture was filtered and concentrated. The residue was purified by flash chromatography, eluting with 0–5% 2M NH$_3$ in MeOH/CH$_2$Cl$_2$. The product fractions were collected and concentrated to afford 80 mg of 4-oxiranylmethoxy-benzamide as a white solid.

4-Oxiranylmethoxy-benzamide (76 mg, 0.393 mmol) was dissolved in 8 mL of dry DMF, followed by the addition of 4-amino-1-N-boc-piperidine (178 mg, 0.889 mmol). The reaction mixture was stirred at 80° C. for 48 h. The reaction mixture was concentrated and the residue was purified by flash chromatography eluting with 0–5% 2M NH$_3$ in MeOH/CH$_2$Cl$_2$. The product fractions were collected and concentrated to afford 62 mg of 4-[3-(4-carbamoyl-phenoxy)-2-hydroxy-propylamino]-piperidine-1-carboxylic acid tert-butyl ester as a colorless oil.

To a round bottom flask was added the above ester (62 mg, 0.158 mmol) in 5 mL of HCl, 4.0 M in 1,4-dioxane and 2 mL of MeOH. The reaction mixture was stirred at room

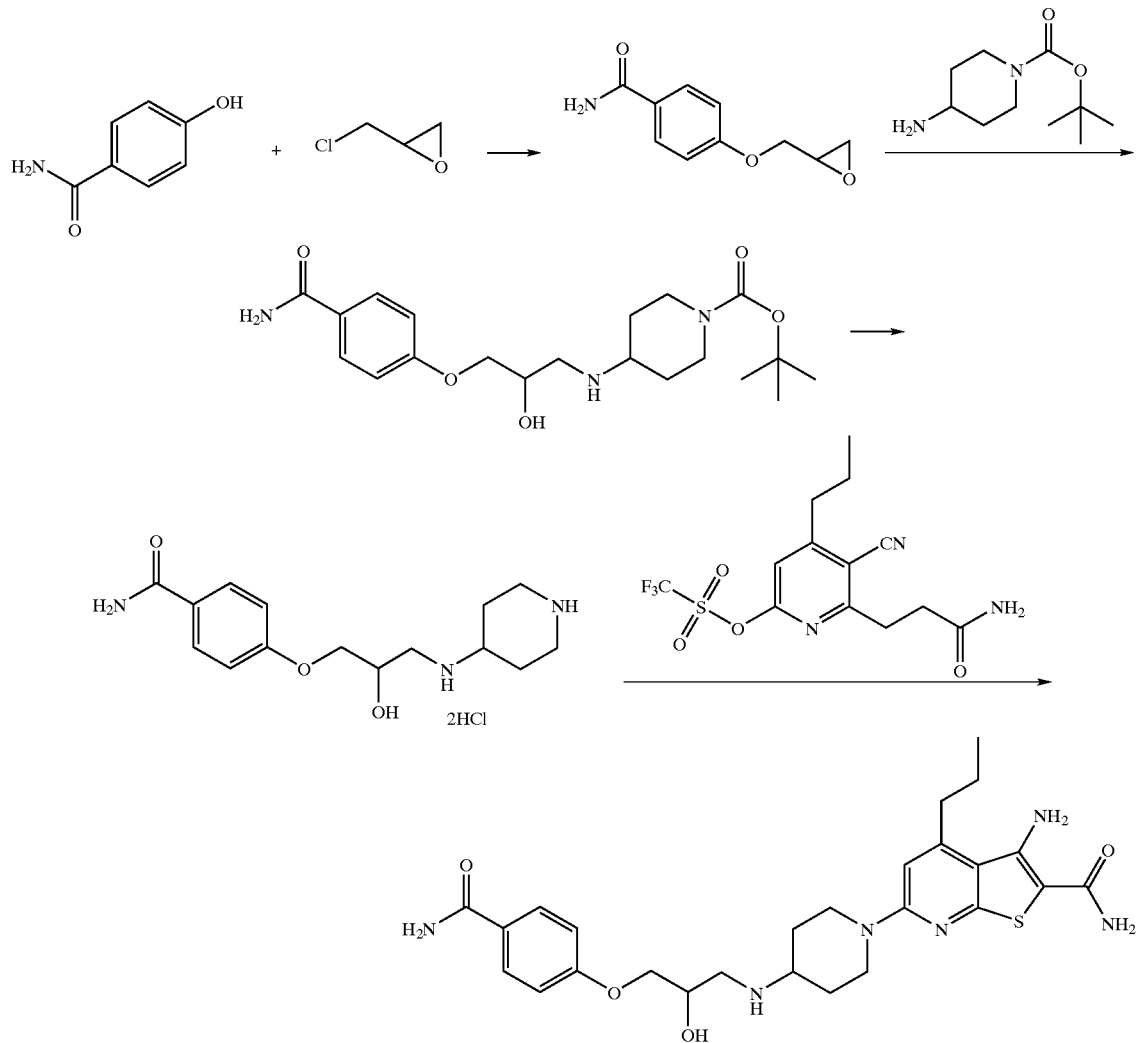

40

To a sealed tube was added 4-hydroxybenzamide (200 mg, 1.458 mmol), epichlorohydrin (135 mg, 1.458 mmol)

temperature for 3 h. The reaction mixture was concentrated by high vacuum pump to afford 57 mg of 4-[2-hydroxy-3-

(piperidin-4-ylamino)-propoxy]-benzamide, hydrogen chloride salt as a white glass-solid product.

To a sealed tube was added trifluoro-methanesulfonic acid 6-(2-carbamoyl-ethyl)-5-cyano-4-propyl-pyridin-2-yl ester (54.2 mg, 0.141 mmol) in 5 mL of dry DMF, followed by the addition of the above hydrohloride salt (57 mg, 0.156 mmol) and N-N-diisopropylethylamine (91.4 mg, 0.707 mmol). The reaction mixture was stirred at 70° C. for 2 h. The reaction was concentrated and to the residue was added sodium methoxide, 0.5 M solution in MeOH (1.41 mL, 0.707 mmol) and 2 mL of MeOH. The reaction mixture was heated at 70° C. for 4 h. The reaction mixture was concentrated and the residue was purified by flash chromatography eluting with 0–10% 2M $NH_3$ in $MeOH/CH_2Cl_2$. The product fractions were collected and concentrated to afford 42 mg (56.4%) of the title compound as a light yellow crystalline solid.

The following compounds were prepared using the procedures described in Example 40 or slight modifications thereof starting from the corresponding epoxide reagents.

3-amino-6-{4-[3-(3-cyano-phenoxy)-2-hydroxy-propylamino]-piperidin-1-yl}-4-propyl-thieno[2,3-b]pyridine-2-carboxylic acid amide

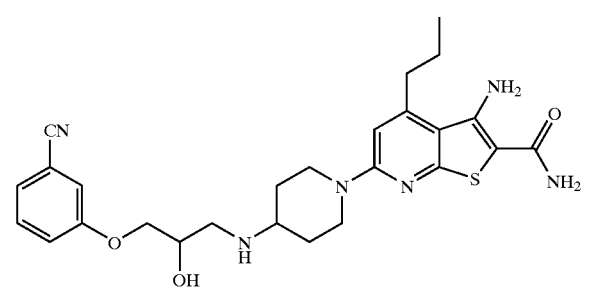

3-amino-6-{4-[3-(4-cyano-phenoxy)-2-hydroxy-propylamino]-piperidin-1-yl}-4-propyl-thieno[2,3-b]pyridine-2-carboxylic acid amide

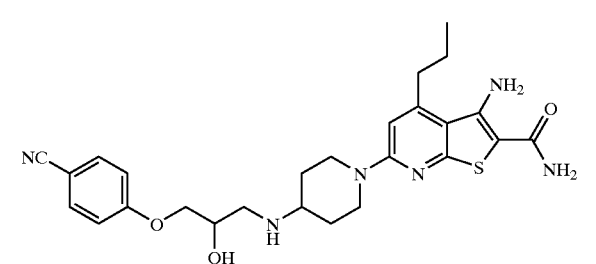

3-amino-6-[4-(R)-2-hydroxy-3-phenoxy-propylamino)-piperidin-1-yl]-4-propyl-thieno[2,3-b]pyridine-2-carboxylic acid amide

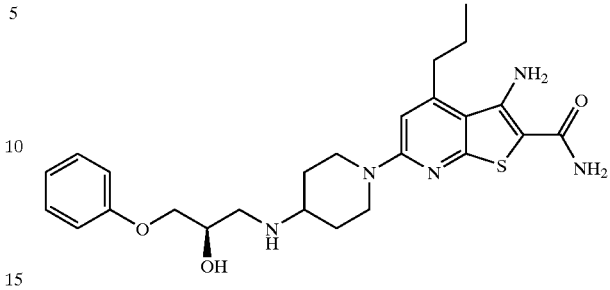

3-amino-6-[4-(S)-2-hydroxy-3-phenoxy-propylamino)-piperidin-1-yl]-4-propyl-thieno[2,3-b]pyridine-2-carboxylic acid amide

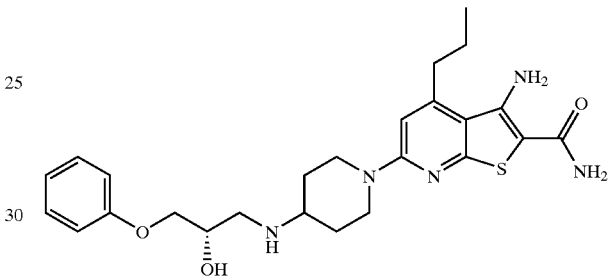

3-amino-6-{4-[3-(4-fluoro-phenoxy)-2-hydroxy-propylamino]-piperidin-1-yl}-4-propyl-thieno[2,3-b]pyridine-2-carboxylic acid amide

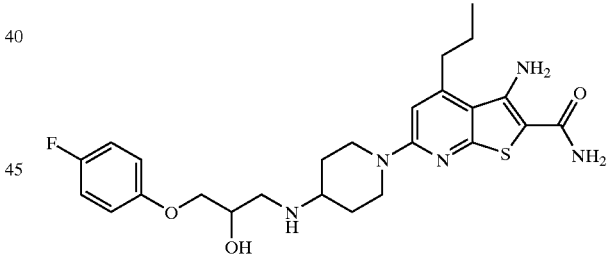

3-amino-6-{4-[2-hydroxy-3-(3-methoxy-phenoxy)-propylamino]-piperidin-1-yl}-4-propyl-thieno[2,3-b]pyridine-2-carboxylic acid amide

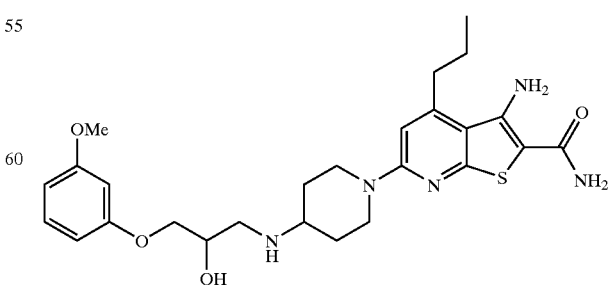

243

3-amino-6-{4-[2-hydroxy-3-(4-trifluoromethyl-phenoxy)-propylamino]-piperidin-1-yl}-4-propyl-thieno[2,3-b]pyridine-2-carboxylic acid amide

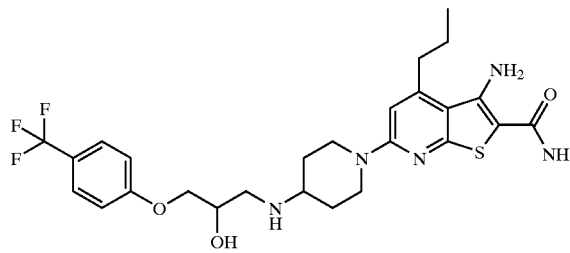

3-amino-6-{4-[2-hydroxy-3-(naphthalene-1-yloxy)-propylamino]-piperidin-1-yl}-4-propyl-thieno[2,3-b]pyridine-2-carboxylic acid amide

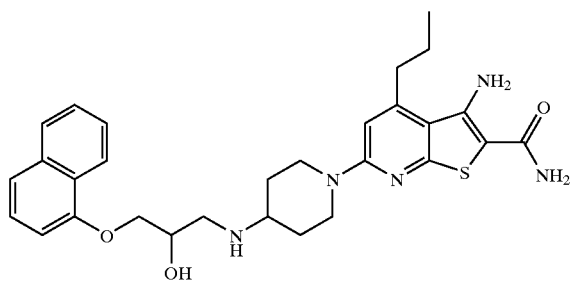

3-amino-6-{4-[2-hydroxy-3-(naphthalene-2-yloxy)-propylamino]-piperidin-1-yl}-4-propyl-thieno[2,3-b]pyridine-2-carboxylic acid amide

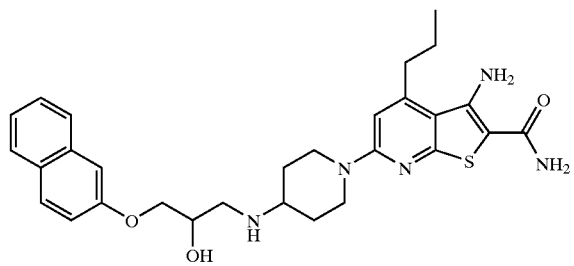

3-amino-6-[4-(3-benzyloxy-2-hydroxy-propylamino)-piperidin-1-yl]-4-propyl-thieno[2,3-b]pyridine-2-carboxylic acid amide

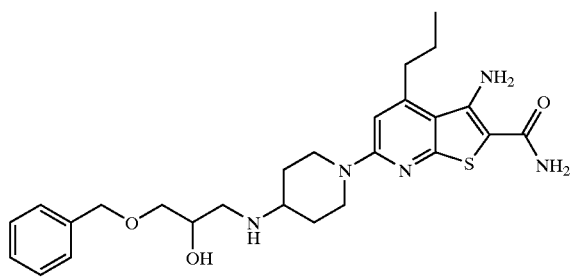

244

3-amino-6-{4-[3-(4-carbamoyl-phenyl)-2-hydroxy-propylamino)-piperidin-1-yl]-4-propyl-thieno[2,3-b]pyridine-2-carboxylic acid amide

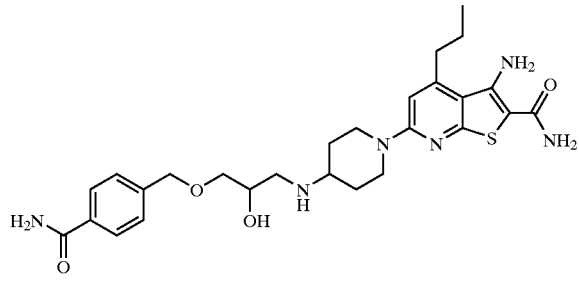

3-amino-6-{4-[3-(3-carbamoyl-phenyl)-2-hydroxy-propylamino)-piperidin-1-yl]-4-propyl-thieno[2,3-b]pyridine-2-carboxylic acid amide

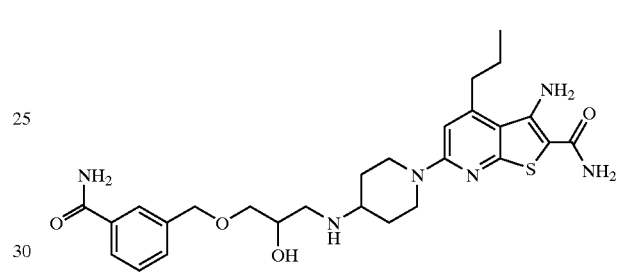

3-amino-6-[4-(2-hydroxy-4-phenyl-butylamino)-piperidin-1-yl]-4-propyl-thieno[2,3-b]pyridine-2-carboxylic acid amide

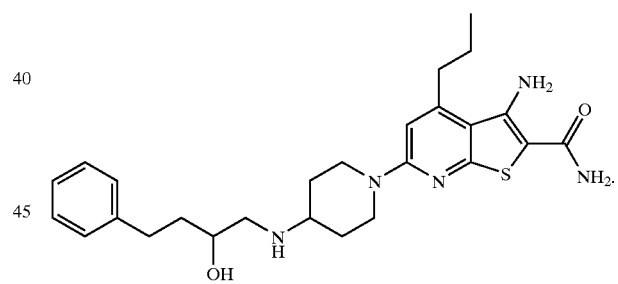

Example 41

Synthesis of 3-amino-6-((S)-3-hydroxy-4-methanesulfonylamino-piperidin-1-yl)-4-propyl-thieno[2,3-b]pyridine-2-carboxylic acid amide

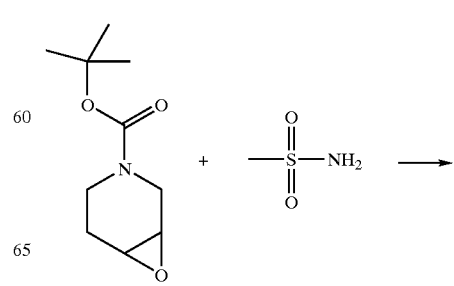

245

-continued

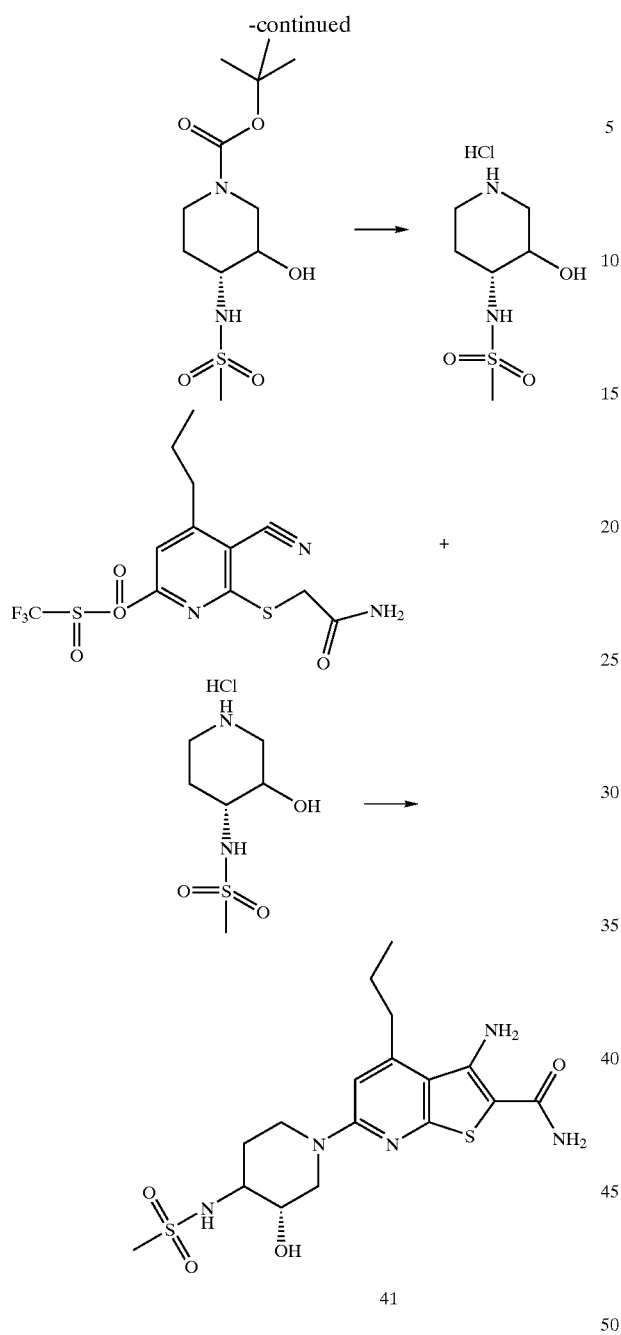

41

A mixture of the 7-oxa-3-aza-bicyclo[4.1.0]heptane-3-carboxylic acid tert-butyl ester (830 mg, 4.2 mmol), methylsulfonamide (1.2 g, 12.5 mmol), potassium carbonate (829 mg, 12.5 mmol), magnesium sulfate (1.5 g, 12.5 mmol) in MeOH (15 mL) was heated under Ar in a pressure tube at 90° C. overnight. The mixture was then cooled to room temperature, diluted with CH$_2$CL$_2$ (10 mL), filtered through diatomaceous earth and concentrated. The crude product was further purified by column chromatography on silica gel using EtOAc as elutant to give 504 mg the desired hydroxypiperidine intermediate.

The above intermediate (118 mg, 0.4 mmol) was dissolved in MeOH (1 mL). To this solution was added 4M HCL (0.2 mL in dioxane) dropwise. The mixture was stirred at room temperature overnight and concentrated. The product thus obtained was dissolved in dioxane, basified with

246

300 microL of triethylamine, and reacted with 144 mg (0.376 mmol) of 2-(3-cyano-4-n-propyl-6-trifluoromethanesulfonylpyridin-2-ylmercapto)acetamide, by the procedure described in Example 26, to provide 73 mg of the title compound.

Example 42

Synthesis of 3-amino-6-(4-hydrazinocarbonyl-piperazin-1-yl)-4-propyl-thieno[2,3-b]pyridine-2-carboxylic acid amide

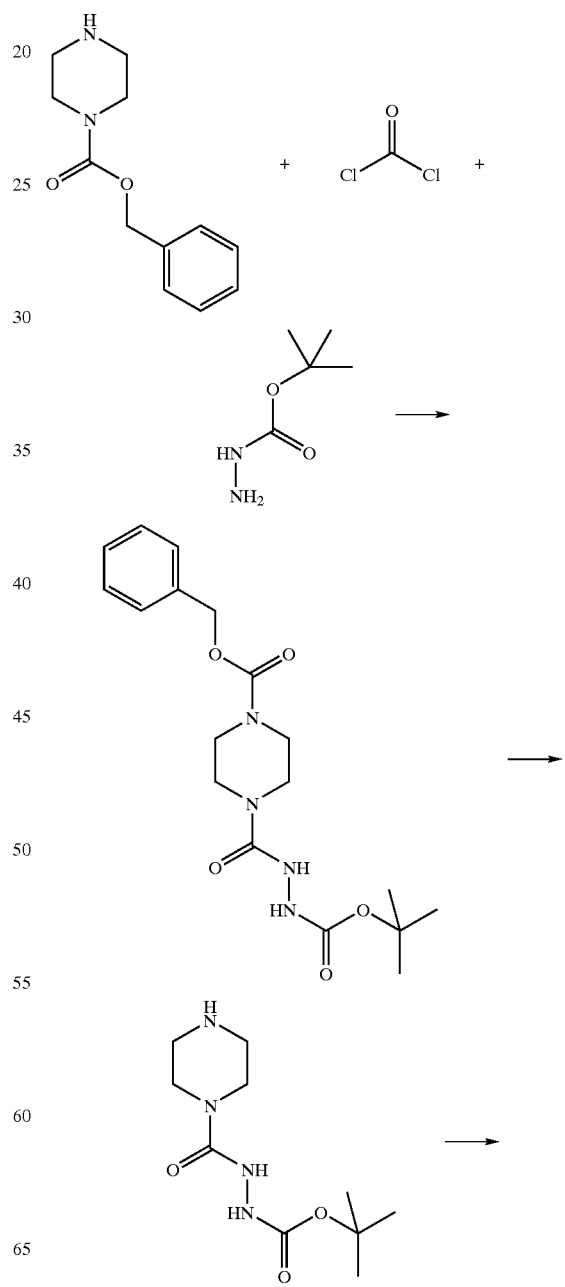

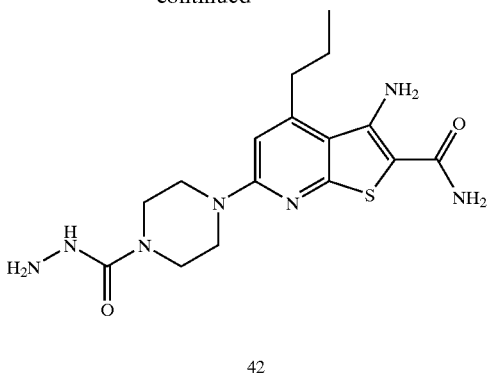

42

To a phosgene solution (20% solution in toluene) at 0° C. was added piperazine-1-carboxylic acid benzyl ester (0.385 mL, 1.996 mmol) and diisopropylethyl amine (0.383 mL, 4.397 mmol) in 5 mL of CH₂Cl₂ dropwise. The resulting pale yellow mixture was stirred 2 h warming to room temperature under Ar. The phosgene solution was removed by vacuum distillation. 20 mL of anhydrous CH₂Cl₂ was added. The reaction vessel was cooled to 0° C. and hydrazinecarboxylic acid tert-butyl ester and diisopropylethyl amine (0.383 mL, 4.397 mmol) was added in one portion. The reaction was warmed to room temperature and stirred for 1 h. The reaction was quenched with 10 mL of saturated NaHCO₃, diluted with 30 mL of EtOAc, then washed with 2×30 mnL of saturated NH₄Cl solution and 30 mL of brine. The organic phase was dried over MgSO₄, filtered and concentrated to provide 720 mg of 4-(N-tert-butoxycarbonyl-hydrazinocarbonyl)-piperazine-1-carboxylic acid benzyl ester as a white solid.

The above benzyl ester (720 mg, 1.913 mmol) was dissolved into 10 ML of EtOH and placed in a round-bottom flask. 10% Pd/C (300 mg) was added and the reaction was placed under 1 atm of H₂ in a balloon. The reaction was allowed to stir overnight, then was filtered through a plug of diatomaceous earth and concentrated to give 465 mg of 4-(N-tert -butoxycarbonyl-hydrazinocarbonyl)-piperazine as a pale white solid.

N'-[4-(3-Amino-2-carbamoyl-4-propyl-thieno[2,3-b]pyridin-6-yl)-piperazine-1-carbonyl]-hydrazinecarboxylic acid tert-butyl ester was prepared from the above intermediate as described in Example 26. Removal of the t-Boc protecting group by dissolving in EtOAc/CH₂Cl₂ and treatment with 4 N HCl in dioxane provided the title compound.

Example 43

Synthesis of 3-amino-6-[4-(1-imino-ethyl)-piperazin-1-yl]-4-propyl-thieno[2,3-b]pyridine-2-carboxylic acid amide

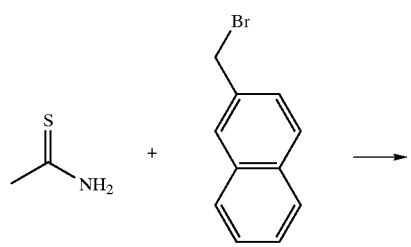

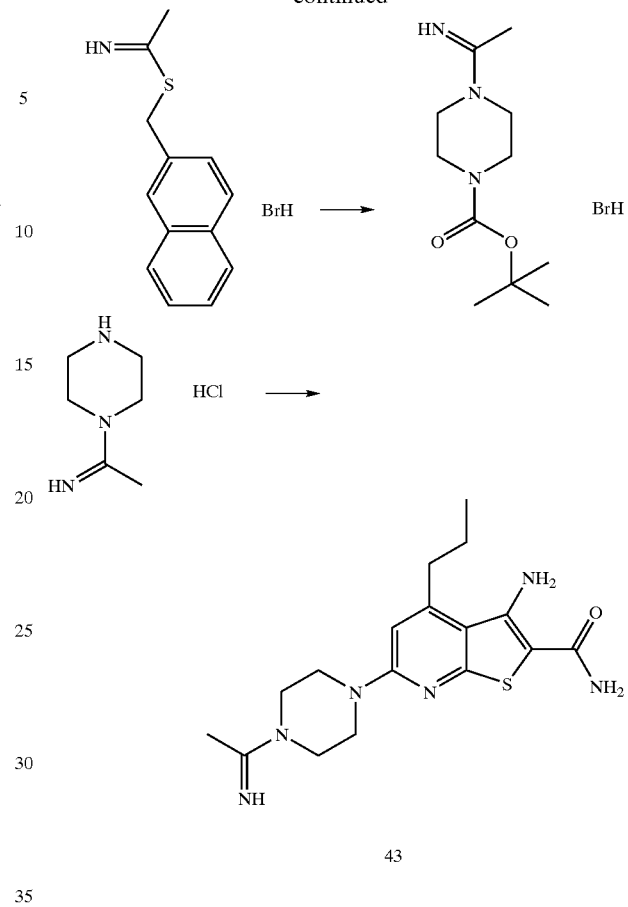

43

Thioacetamide (326.0 mg, 4.339 mmol) and 2-bromomethyl-naphthalene (959.0 mg, 4.337 mmol) were placed in a 50 mL round-bottom flask. 20 mL of CHCl₃ were added and the mixure was refluxed for 3 h at which time a white precipitate formed. The mixture was cooled and the precipitate collected. The precipitate was washed with 20 mL of CH₂Cl₂ and placed under vacuum for drying to give 1.01 g of thioacetimidic acid naphthalen-2-ylmethyl ester hydrobromide salt as a fine white powder.

The above hydrobromide salt (850.0 mg, 2.869 mmol) was placed into a 25 mL round-bottom flask. To this was added 10 mL of EtOH resulting in a suspension. The flask was placed in an ice bath and piperazine-1-carboxylic acid tert-butyl ester (534.4 mg, 2.869 mmol) was added in one portion. The reaction was allowed to warm to room temperature and stirred an additional 3 h. The heterogenous solution was diluted with 40 mL of EtOAc and washed with 2×30 mL of H₂O. The aqueous phase was concentrated to near dryness, azeotroped with 2×20 mL of toluene to give a white solid. The solid was suspended in CH₂Cl₂/hexane and concentrated to dryness. The material was placed under vacuum overnight, affording 769 mg of 4-(1-imino-ethyl)-piperazine-1-carboxylic acid tert-butyl ester hydrobromide salt as a white solid.

The t-Boc protecting group of the above intermediate was removed as described in Example 42 and the resulting intermediate reacted further as described in Example 40 to provide the title compound.

Example 44
Synthesis of 3-amino-6-(4-hydroxy-piperidin-1-yl)-4-(3-hydroxy-propyl)-thieno[2,3-b]pyridine-2-carboxylic acid amide
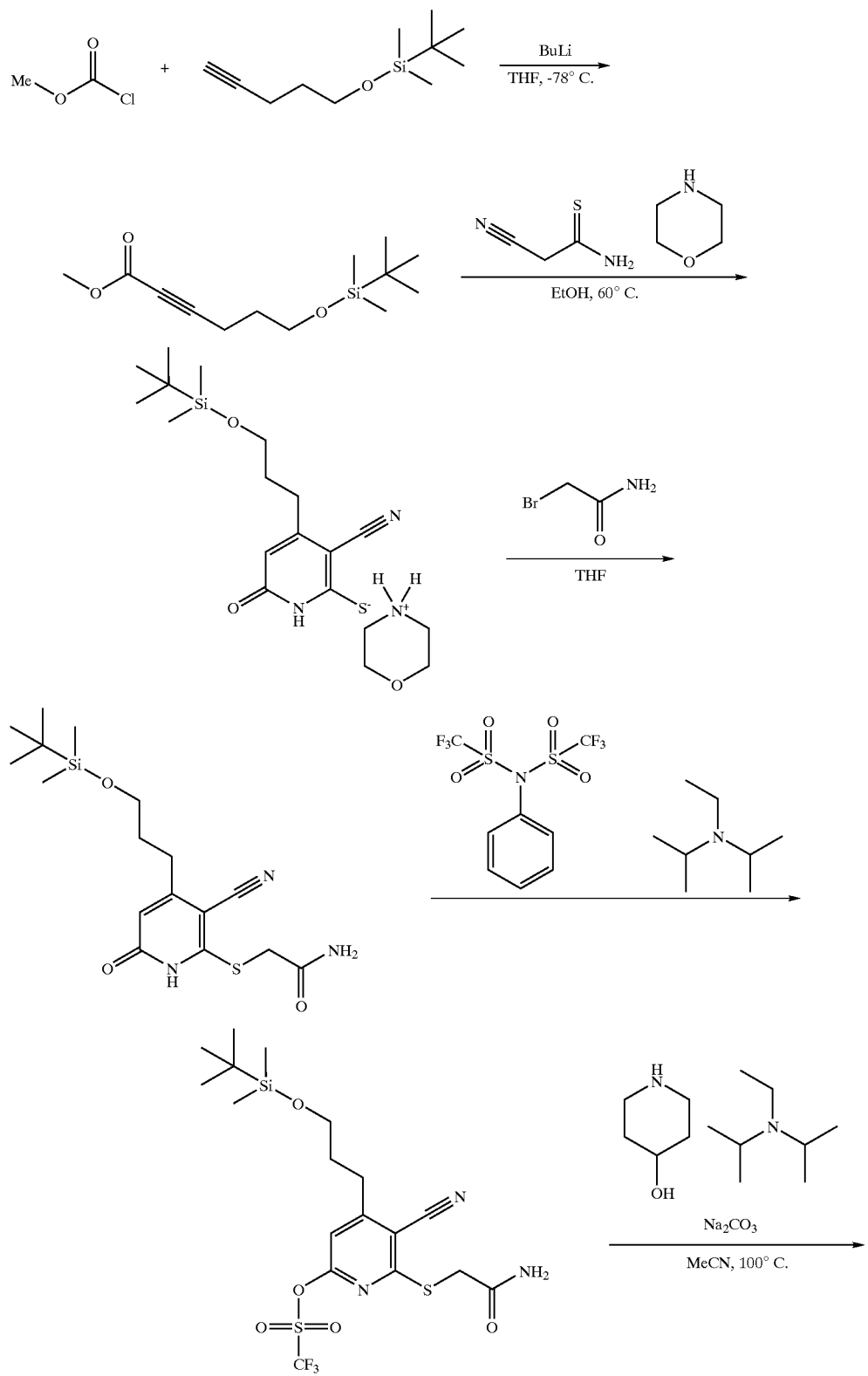

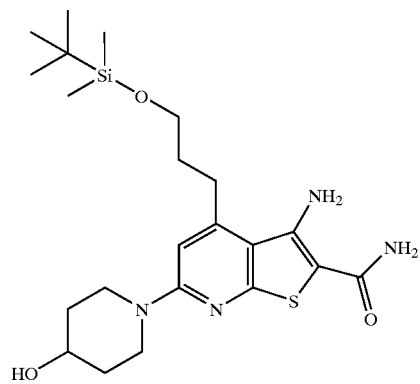 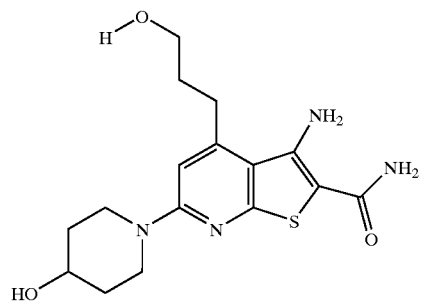

44

To a solution of 7.98 g (40.2 mmol) of t-Butyl-dimethyl-pent-4-ynyloxy-silane (J. A. Marshall and B. S. DeHoff, *J. Org. Chem.*, 1986, 51, 863) in THF (100 mL), cooled to −78° C., was added a solution of n-butyllithium in hexanes (28.0 mL of a 1.6 M solution). The mixture was stirred at −78° C. for 1 h then transferred, via cannula, to a flask containing a solution of 4.5 mL (58 mmol) of methyl chloroformate in THF (100 mL) cooled to −78° C. The reaction was stirred at −78° C. for 2 h then excess base was consumed by addition of a saturated aqueous solution of $NH_4Cl$. The mixture was diluted with $H_2O$ and washed with $Et_2O$. The combined organic phase was dried over anhydrous $Na_2SO_4$ and concentrated under reduced pressure. The crude residue was purified by flash silica gel chromatography using a 5% solution of EtOAc in hexanes as the eluent to provide, after concentration of the solvent, 6.18 g (60%) of the desired ester as a clear oil.

To a solution of 6.18 g (24.1 mmol) of the above ester in EtOH (120 mL) was added 2.2 mL (25 mmol) of morpholine. The mixture was heated at 60° C. for 3 h. The reaction mixture was cooled to room temperature and 2.5 g (25 mmol) of 2-cyanoacetamide was added as a solid in one portion. The reaction mixture was then heated at 60° C. for 15 h then cooled to room temperature and concentrated under reduced pressure. The residue was suspended in $Et_2O$ and washed with $H_2O$. The combined aqueous phase was back extracted with $Et_2O$. The aqueous phase was lyophilized to provide 3.5 g (30.8%) of 4-[3-(t-butyl-dimethyl-silanyloxy)-propyl]-3-cyano-6-oxo-1,6-dihydro-pyridine-2-thiolate morpholine salt, as a yellow powder.

To a solution of 0.940 g (2.28 mmol) of the above morpholine salt in THF (15 mL), cooled to 0° C., was added 0.315 g (0.280 mmol) of 2-bromoacetamide as a solid in one portion. The mixture was stirred and allowed to slowly warm to room temperature over a 2 h period during which time salts precipitated from solution. The mixture was filtered through diatomaceous earth to remove solids and the filter pad was washed with EtOAc. The mixture was concentrated under reduced pressure to provide 0.385 g (44%) of 2-{4-[3-(t-butyl-dimethyl-silanyloxy)-propyl]-3-cyano-6-oxo-1,6-dihydro-pyridin-2-ylsulfanyl}-acetamide as an orange foam.

To a solution of 2.32 g (6.08 mmol) of the above acetamide in THF (25 mL), cooled to 0° C., was added 2.2 g (6.2 mmol) of N-phenyltrifluoromethanesulfonimide and 1.2 mL (6.7 mmol) of N,N-diisopropylethylamine. The mixture was stirred for 3 h as it slowly warmed to room temperature. The mixture was poured into $H_2O$ and washed with EtOAc. The combined organic phase were dried over anhydrous $Na_2SO_4$ and concentrated under reduced pressure. The residue was purified by flash silica gel chromatography using a 0–50% gradient of A (10% MeOH in $CH_2Cl_2$) to B ($CH_2Cl_2$) to provide, after concentration of the eluent, 0.832 g (26%) of the desired trifluoromethanesulfonyl ester as an orange oil.

To a solution of 0.832 g (1.62 mmol) of the above trifluoromethanesulfonyl ester in 1,4-dioxane (30 mL) was added 0.175 g (1.73 mmol) of 4-hydroxypipiridine and 0.32 mL (1.79 mmol) of N,N-diisopropylethylamine. The mixture was heated to 80° C. for 5 h. The reaction was cooled to room temperature and an aqueous solution of $Na_2CO_3$ (8.0 mL of a 2.0 M solution) was added. The mixture was heated to 100° C. for 3 days then cooled to room temperature and diluted with $H_2O$. The mixture was washed with $CH_2Cl_2$ and the combined organic phase was dried over anhydrous $Na_2SO_4$ and concentrated under reduced pressure. The residue was purified by flash silica gel chromatography using a 0–50% gradient of A (10% MeOH in $CH_2Cl_2$) to B($CH_2Cl_2$) to provide, after concentration of the eluent, 0.232 g (31%) of 3-amino-4-[3-(t-butyl-dimethyl-silanyloxy)-propyl]-6-(4-hydroxy-piperidin-1-yl)-thieno[2,3-b]pyridine-2-carboxylic acid amide as a yellow powder.

To a solution of 0.23 g (0.49 mmol) of the above amide in a 1:1 mixture of THF:$H_2O$ (1.0 mL) was added 0.50 mL (8.7 mmol) of glacial acetic acid. The mixture was heated to 50° C. for 15 h then cooled to room temperature and concentrated under reduced pressure which cause a solid to precipitate from solution. The material was collected by filtration and washed with $H_2O$ and $CH_2Cl_2$ then dried under vacuum to provide 0.106 g (61%) of the title compound as a white solid.

Example 45

Synthesis of 3-Amino-6-(4-amino-3,3-dimethyl-piperidin-1-yl)-4-propyl-thieno[2,3-b]pyridine-2-carboxylic acid amide

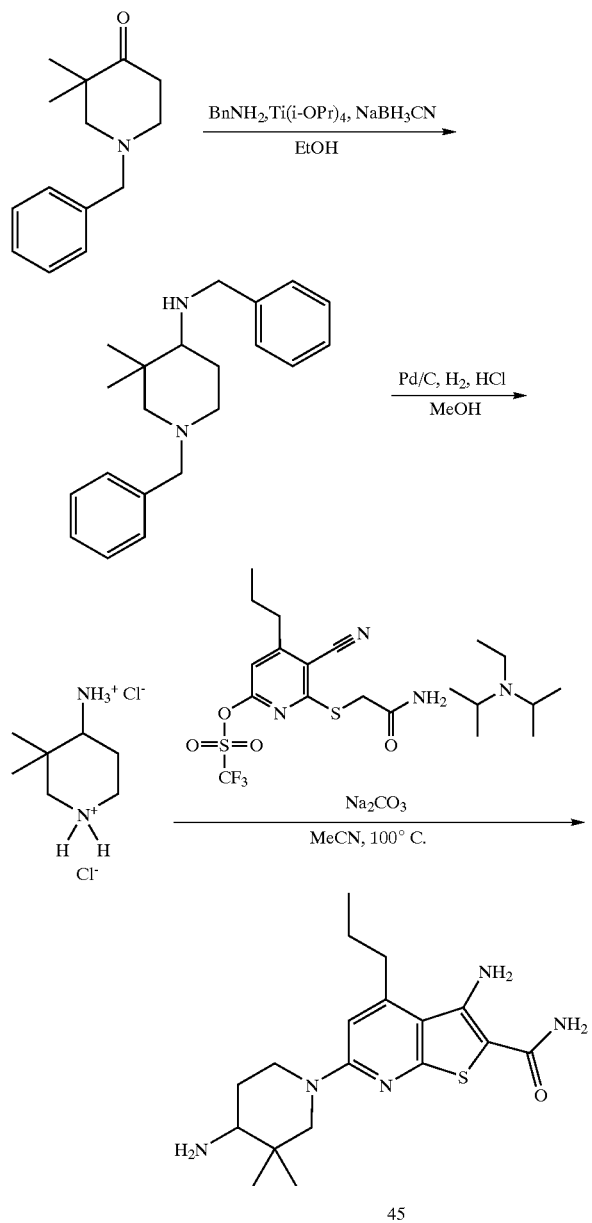

A mixture of 0.10 g (0.46 mmol) of 1-benzyl-3,3-dimethyl-piperidin-4-one, 0.055 mL (0.50 mmol) of benzyl amine, and 0.19 mL (0.64 mmol) of titanium isopropoxide was stirred at room temperature for 1 h. The mixture was diluted with EtOH (1 mL) which caused the yellow solution to turn cloudy. To the reaction was added 0.031 g (0.49 mmol) of sodium cyanoborohydride and the mixture was stirred at room temperature for 20 h. The mixture was diluted with H$_2$O (1 mL) then filtered through diatomaceous earth to remove precipitates. The filter pad was washed with MeOH and the mixture was concentrated under reduced pressure. The residue was purified by flash silica gel chromatography using a 0–40% gradient of A (10% MeOH in CH$_2$Cl$_2$) to B (CH$_2$Cl$_2$) to provide, after concentration of the eluent, 0.069 g (44%) of the desired benzyl amine as a clear oil.

To a solution of 0.069 g (0.22 mmol) of the above benzyl amine in MeOH (5 mL) placed in a heavy walled pressure vessel was added 0.049 g (0.046 mmol) of palladium on carbon and 0.050 mL (0.60 mmol) of concentrated HCl. The mixture was placed under an atmosphere of hydrogen (50 psi) and shaken for 24 h. The mixture was filtered through a plug of diatomaceous earth and the filter pad was washed with MeOH. The organic phase was concentrated under reduced pressure to provide 0.041 g (91%) of the desired 4-amino-3,3-dimethylpiperidine diHCl salt as a white solid.

To a solution of 0.075 g (0.20 mmol) of trifluoromethane-sulfonic acid 6-carbamoylmethylsulfanyl-5-cyano-4-propyl-pyridin-2-yl ester in 1,4-dioxane (5 mL) was added 0.041 g (0.20 mmol) of the above diHCl salt and 0.11 mL (0.61 mmol) of N,N-diisopropylethylamine. The mixture was heated at 60° C. for 15 h then cooled to room temperature and an aqueous solution of Na$_2$CO$_3$ (0.5 mL of a 2M solution) was added. The mixture was heated to 100° C. for 3 d then cooled to room temperature, diluted with H$_2$O and washed with CH$_2$Cl$_2$. The combined organic phase was dried over anhydrous Na$_2$SO$_4$ and concentrated under reduced pressure. The crude residue was purified by flash silica gel chromatography using a 0–50% gradient of A (10% MeOH in CH$_2$Cl$_2$) to B (CH$_2$Cl$_2$) to provide, after concentration of the eluent, 0.019 g (27%) of the title compound as a yellow solid.

Example 46

Synthesis of 3-amino-6-piperidin-4-yl-4-propyl-3a,7a-dihydro-thieno[2,3-b]pyridine-2-carboxylic acid amide dihydrochloride

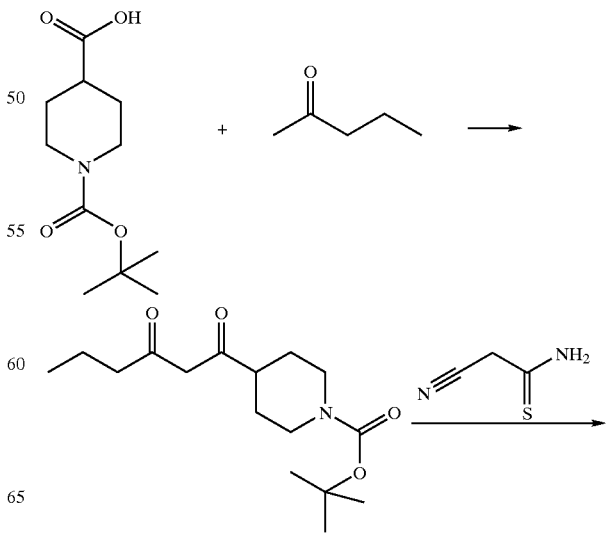

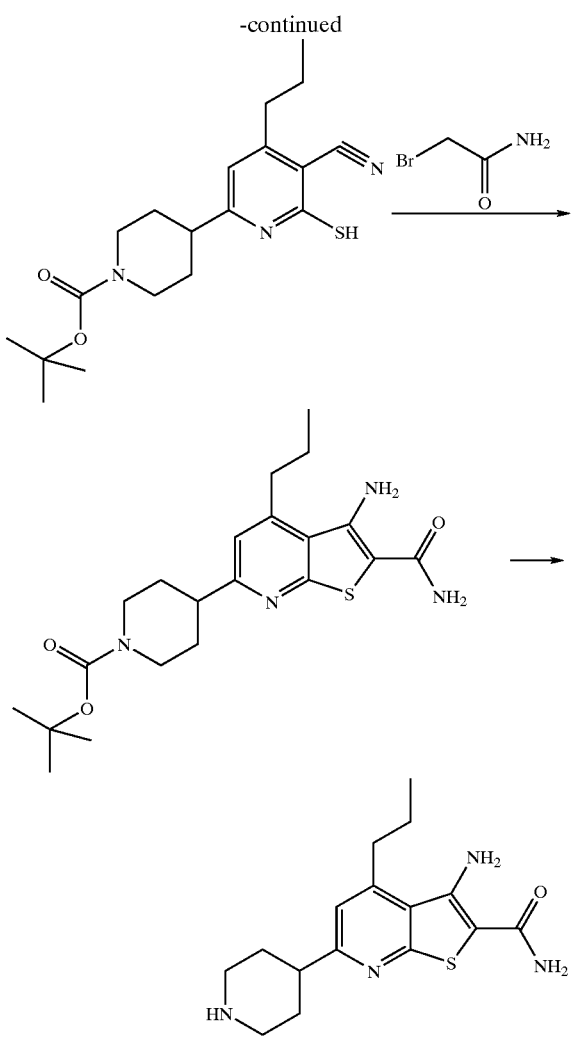

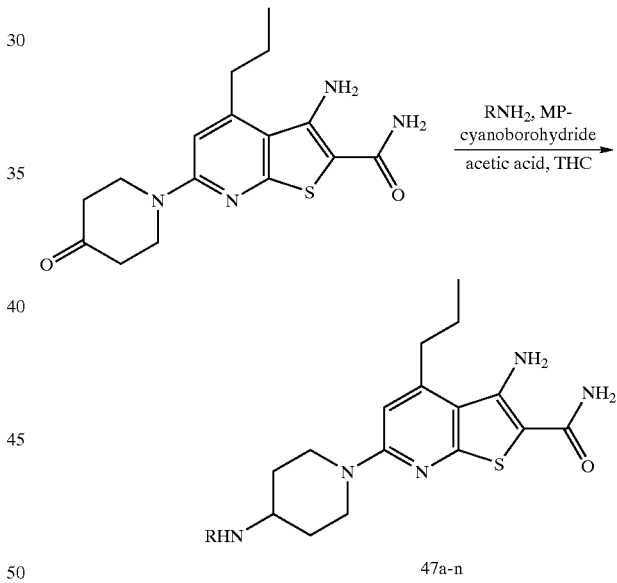

46 dioxane (20 mL) was heated at 80° C. for 2 h. A solution of sodium carbonate (400 mg) in water (7 mL) was added and the reaction was heated at reflux overnight. It was diluted with water (100 mL) and the precipitates were filtered and dried to give 0.85 g of 4-(3-amino-2-carbamoyl-4-propyl-3a,7a-dihydro-thieno[2,3-b]pyridin-6-yl)-piperidine-1-carboxylic acid tert-butyl ester.

To a stirred solution of the above tert-butyl ester (600 mg, 1.43 mmol) in dry dichloromethane (35 mL) was added HCl/dioxane (4 N, 2 mL). Precipitates appeared immediately. It was concentrated and dried in vacuo to give the title compound as the dihydrochloride salt (570 mg).

Example 47

Solid-Phase Reductive Amination

The following general procedure describes the method by which several 3-amino-6-(4-substituted amino-piperidin-1-yl)-4-propyl-thieno[2,3-b]pyridine-2-carboxylic acid amide compounds were made:

47a-n

1-Boc-piperidine-4-carboxylic acid (4.4 g, 19.2 mmol) in oxalyl chloride (50 mL) was heated at reflux for 3 h and then concentrated and dried in vacuo to give the acid chloride, 4-chlorocarbonyl-piperidine-1-carboxylic acid tert-butyl ester.

To a stirred solution of LDA (1.8 M in THF/heptane/ethylbenzene, 21.3 mL, 38.4 mmol) in dry THF (50 mL) at −50° C. was added 2-pentanone (4.1 mL, 38.4 mmol), and after 10 min, a solution of the above acid chloride in dry THF (50 mL) was added. The reaction was allowed warming to room temperature and stirred overnight. It was diluted with 1 N HCl (500 mL), extracted with dichloromethane, washed with saturated sodium bicarbonate and brine, dried over sodium sulfate, concentrated. It was purified by chromatography on silica gel (EtOAc/dichloromethane=1/10) to give the desired diketone intermediate: 4-(3-oxo-hexanoyl)-piperidine-1-carboxylic acid tert-butyl ester (2.1 g).

A stirred mixture of the diketone (2.1 g, 7.1 mmol) and 2-cyanothioacetamide (1.42 g, 14.2 mmol) in EtOH (30 mL) was heated at 70° C. overnight. It was concentrated and chromatography on silica gel (MeOH/dichloromethane=1/10) gave 1.8 g of 5-cyano-6-mercapto-4-propyl-3',4',5',6'-tetrahydro-2'H-[2,4']bipyridinyl-1'-carboxylic acid tert-butyl ester.

A stirred mixture of the above tert-butyl ester (0.9 g, 2.49 mmol) and bromoacetamide (0.38 g, 2.75 mmol) in dry To 3-amino-6-(4-oxo-piperidin-1-yl)-4-propyl-thieno[2,3-b]pyridine-2-carboxylic acid amide was added 1.5–3.00 equivalents of the desired amine, 1.42 solid-supported cyanoborohydride, and 8–9 equivalents acetic acid in THF. The reaction mixture was shaken on an orbital shaker for 15–72 h. The reaction was then filtered, and the solid-supported cyanoborohydride shaken with MeOH for 5–15 min, then filtered. To the combined filtrates was added 5 M $NH_3$ in MeOH and the resulting mixture was concentrated in vacuo. Purification was either via preparatory TLC (5–10% (5 M $NH_3$/MeOH)/EtOAc as eluant) or via flash silica chromatography (2.5–10% (5 M $NH_3$/MeOH)/$CH_2Cl_2$ as eluant) to afford compounds described in the table below:

-continued

| Cpd | R | Percent Yield |
|---|---|---|
| 47a | (structure) | 45% |
| 47b | (structure) | 65% |
| 47c | (structure) | 51% |
| 47d | (structure) | 44% |
| 47e | (structure) | 56% |
| 47f | (structure) | 53% |
| 47g | (structure) | 26% |
| 47h | (structure) | 18% |
| 47i | (structure) | 9% |
| 47j | (structure) | 41% |
| 47k | (structure) | 54% |
| 47l | (structure) | 62% |
| 47m | (structure) | 34% |
| 47n | (structure) | 55% |

Example 48

Solid-Phase Reductive Amination

The following general procedure describes the method by which several amine intermediates were prepared for use in the preparation of 3-amino-6-(4-substituted amino-piperidin-1-yl)-4-propyl-thieno[2,3-b]pyridine-2-carboxylic acid amide compounds using the method in the Example above:

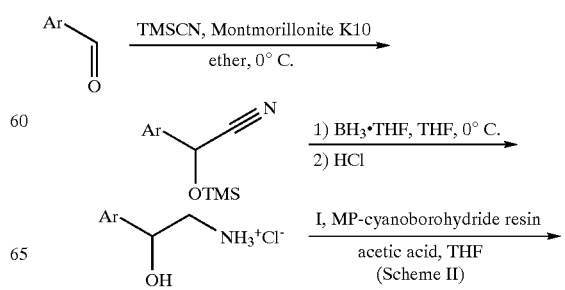
(Scheme II)

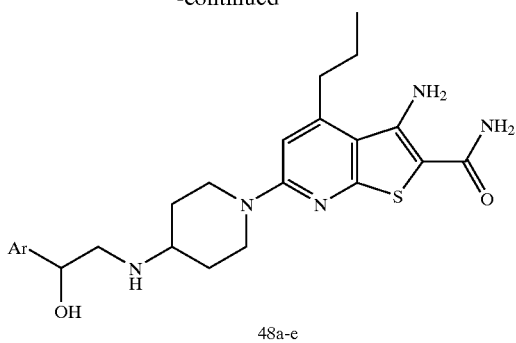

48a-e

The desired aryl aldehyde was dissolved in ether and reacted with trimethylsilyl cyanide (1–2 eq.) at 0° C. using Montmorillonite K 10 (0.1–0.2 eq.) as an acidic catalyst. The reaction stirred 1–3 h, and then was filtered, and the filtrate concentrated in vacuo to afford compounds the corresponding trimethylsilyl ether. The ether was dissolved in THF and added to a solution of borane/THF at 0° C. The reaction stirred for 17–24 h while the cold bath expired. The reaction was cooled back down to 0° C. and quenched with MeOH, then concentrated in vacuo. The residue was taken up in EtOAc/CH$_2$Cl$_2$ and HCl/MeOH or HCl/dioxane was added. The white solid that resulted was isolated either by suction filtration or concentration in vacuo to afford the corresponding hydroxyl amine HCl salts. These HCl salts were then reacted and purified according to the method described in Example 47 to provide compounds 48a–48e shown in the table below:

|     | Ar            | % yield |
| --- | ------------- | ------- |
| 48a | p-MeOPh       | 13%     |
| 48b | p-ClPh        | 17%     |
| 48c | p-MeO$_2$CPh  | 61%     |
| 48d |               | 58%     |
| 48e | m-MeO$_2$CPh  | 52%     |

Example 49

Synthesis of 3-amino-6-(4-hydroxy-piperidin-1-yl)-thieno[2,3-b]pyridine-2,4-dicarboxylic acid 2-amide 4-pyridin-3-ylamide

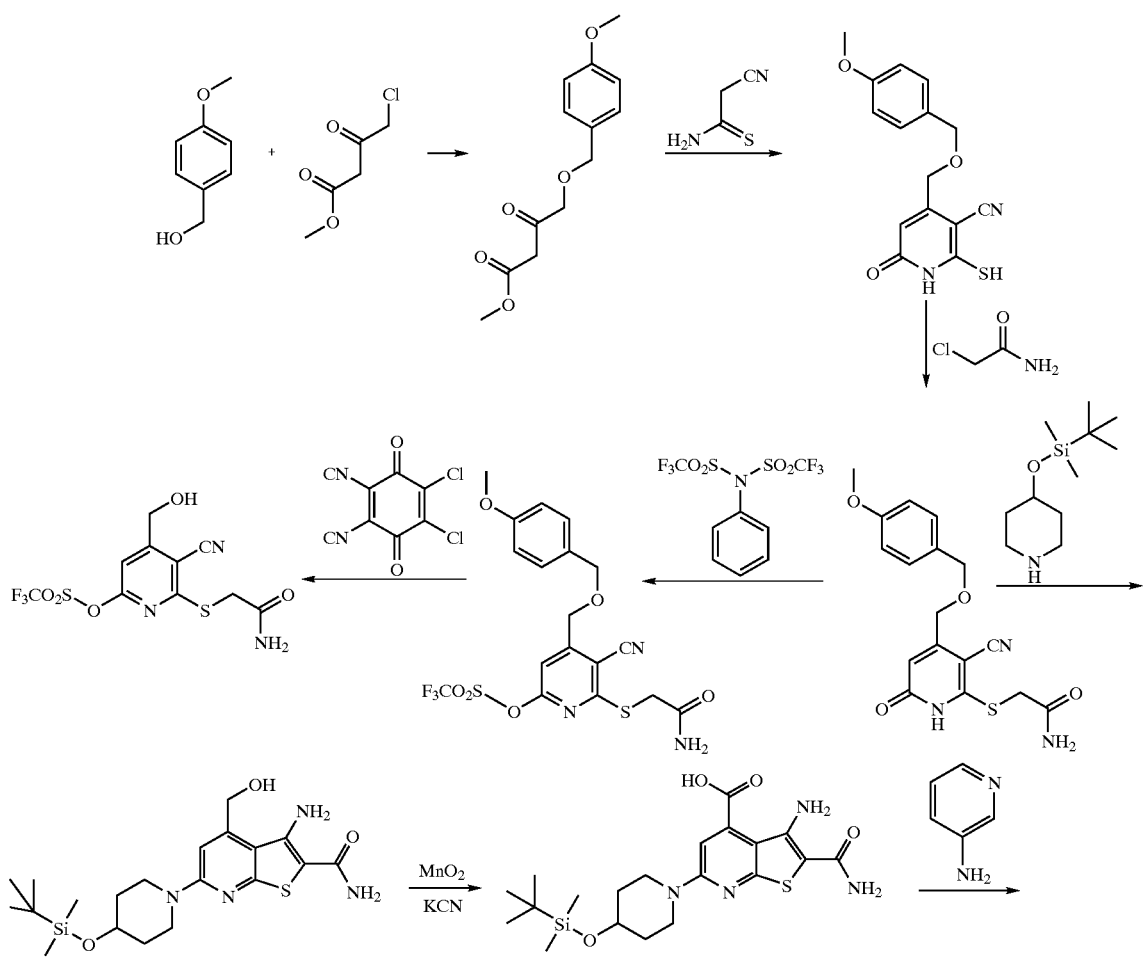

-continued

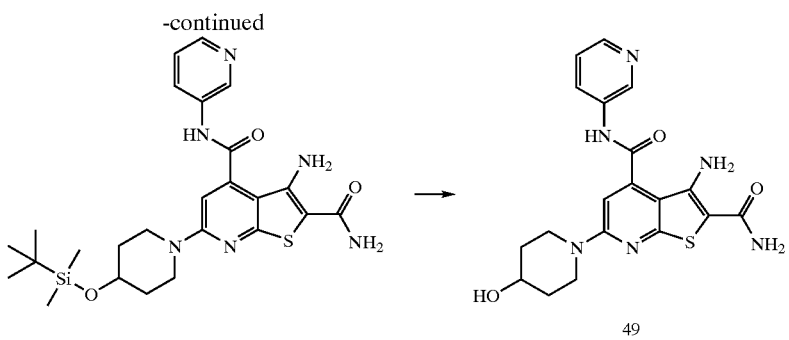

49

4-Methoxybenzyl alcohol (11.0 g, 79.7) was added in portions to a suspension of 6.38 g 60% NaH in 110 mL THF at 400 and the reaction was stirred 30 min under Ar. A solution of 10.00 g methyl 4-chloroacetoacetate in 40 mL THF was dripped in at 40° C. and the reaction was stirred at room temperature overnight. Aqueous NH$_4$Cl was added and the product was extracted into EtOAc, washed with aqueous NH$_4$Cl and brine, dried over MgSO$_4$, filtered, and concentrated to 18.5 g oil. This was flash-chromatographed eluting with 15% acetone/petroleum ether to provide one fraction of 2.99 g oil, that was shown by NMR(CDCl3) to contain showed 80% pure 4-(4-methoxy-benzyloxy)-3-oxo-butyric acid methyl ester. A second fraction of 12.01 g oil was obtained that contained 55% 4-(4-methoxy-benzyloxy)-3-oxo-butyric acid methyl ester by NMR with the rest being mostly unreacted starting material.

4-(4-Methoxy-benzyloxy)-3-oxo-butyric acid methyl ester was converted to 2-[3-cyano-6-trifluorometanesulfonyloxy-4-(4-methoxy-benzyloxymethyl)-pyridin-2-ylsulfanyl]-acetamide by procedures described above in earlier examples.

The above intermediate (9.00 g) was dissolved in 171 mL CH$_2$Cl$_2$ and 9 mL water. 2,3-dichloro-5,6-dicyano-1,4-benzoquinone (DDQ) (12.47 g) was added and the dark suspension was stirred for 6 h then another 4.16 g DDQ was added and the reaction was stirred overnight. The reaction was decanted and the remaining gummy red precipitate was triturated 2× with CH$_2$Cl$_2$ and decanted. The precipitate was dissolved in EtOAc, washed with water (4×) and aqueous NaHCO$_3$, dried and concentrated to a brown solid. This was triturated in CH$_2$Cl$_2$, filtered and dried to provide 4.61 (68%) of the desired hydroxymethylpyridine intermediate as a tan solid.

tert-Butyldimethylsilyl chloride (8.94 g) was added to a solution of 5.00 g 4-hydroxypiperidine in 25 mL DMF and the exothermic reaction was placed in an icebath for 10 min and then 10.10 g imidazole was added and the reaction was stirred at room temperature under Ar overnight. TLC showed mostly starting material. 4-Dimethylaminopyridine (0.60 g) and 7.45 g more tert-butyldimethylsilyl chloride were added and the reaction was stirred overnight. This was poured into aqueous Na$_2$CO$_3$, extracted with EtOAc (3×), washed with water (4×), dried and concentrated to 15.3 g yellow oil. This was flash-chromatographed eluting with 0–10% MeOH/CH$_2$Cl$_2$ to give several fractions of varying purity. The best contained 2.9 g yellow oil that was determined by NMR(CDCl3) to contain 55 mol % 4-(tert-butyl-dimethyl-silanyloxy)-piperidine: 45 mol % tert-butyl-dimethylsilyl chloride.

The crude 4-(tert-butyl-dimethyl-silanyloxy)-piperidine was coupled with the 4-hydroxymethylpyridine intermediate from above by the procedure described in an earlier example to provide 3-amino-6-[4-(tert--butyl-dimethyl-silanyloxy)-piperidin-1-yl]-4-hydroxymethyl-thieno[2,3-b]pyridine-2-carboxylic acid amide A mixture of 400 mg of the above amide, 298 mg KCN, 1.59 g MnO$_2$ and 157 microL acetic acid was suspended in 16 mL MeOH and the reaction was capped and stirred 2 days. The reaction mixture was filtered through diatomaceous earth, concentrated, and flash-chromatographed eluting with 5% MeOH/CH$_2$Cl$_2$ to provide 254 mg (60%) 3-amino-6-[4-(tert-butyl-dimethyl-silanyloxy)-piperidin-1-yl]-2-carbamoyl-thieno[2,3-b]pyridine-4-carboxylic acid methyl ester as determined by NMR(DMDO). Further elution with 25% MeOH/CH2Cl2/1% HOAc brought down 151 mg (36%) of the corresponding carboxylic acid as determined by NMR(DMDO).

81 mg 1-[Dimethylaminopropyl]-3-ethylcarbodiimide hydrochloride was added a solution of 9.5 mg of the above carboxylic acid in 0.5 mL dry DMF at 0° C. After 15 min, 99 mg 3-aminopyridine was added and the reaction was stirred at room temperature overnight. This was diluted with EtOAc, washed with water (4×) and aqueous NH$_4$Cl (3×), dried, concentrated and purified by preparative TLC in 7.5% MeOH/CH$_2$Cl$_2$/0.5% NH$_4$OH. The major band was eluted with 50% MeOH/CH$_2$Cl$_2$ to provide 12.8 mg oil that was shown to be a mixture of 3-amino-6-[4-(tert-butyl-dimethyl-silanyloxy)-piperidin-1-yl]-thieno[2,3-b]pyridine-2,4-dicarboxylic acid 2-amide 4-pyridin-3-ylamide and unreacted starting material by NMR(CD$_3$OD). The mixture was dissolved in 0.5 mL CH$_2$Cl$_2$ and 50 microL HF-pyridine complex was added and the reaction was stirred overnight. The clear solution was decanted off the gummy precipitate that was washed and decanted 2× more with CH$_2$Cl$_2$. The precipitate was dissolved in 10% MeOH/CH$_2$Cl$_2$, neutralized with a drop of concentrated NH$_4$OH, applied to a

3-Amino-6-(4-hydroxy-piperidin-1-yl)-thieno[2,3-b]pyridine-2,4-dicarboxylic acid 2-amide 4-methylamide:

This compound was prepared from the above 3-amino-6-[4-(tert-butyl-dimethyl-silanyloxy)-piperidin-1-yl]-2-carbamoyl-thieno[2,3-b]pyridine-4-carboxylic acid methyl ester by conbining of 10 mg of the ester in 1 mL CH$_2$Cl$_2$ with added 0.5 mL 2M methylamine in THF. The reaction was capped and stirred 2 days. The reaction was concentrated to give 3-amino-6-[4-(tert-butyl-dimethyl-silanyloxy)-piperidin-1-yl]-thieno[2,3-b]pyridine-2,4-dicarboxylic acid 2-amide 4-methylamide as a yellow solid. This was dissolved in 0.5 mL 10% MeOH/CH$_2$Cl$_2$ and 50 microL HF-pyridine complex was added and the reaction was capped and stirred overnight. The reaction was blown down with N$_2$, dissolved in EtOAc, washed with aqueous NaHCO$_3$ and aqueous NH$_4$Cl, dried, concentrated and purified by preparative TLC eluting with 10% MeOH/CH$_2$Cl$_2$. The band was eluted with 25% MeOH/CH$_2$Cl$_2$ to get 2.7 mg (35%) of the title compound as a yellow solid.

The following compounds have been made via a minor modification of the procedures described in Example 49 in which 4-N-Boc aminopiperidine was added to the triflate intermediate and ultimately deprotected and other amines were employed to prepare a variety of amides as R$_1$ substituents.

3-amino-6-(4-amino-piperidin-1-yl)-thieno[2,3-b]pyridine-2,4-dicarboxylic acid diamide

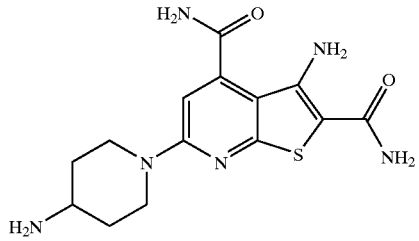

3-amino-6-(4-amino-piperidin-1-yl)-thieno[2,3-b]pyridine-2,4-dicarboxylic acid 2-amide 4-methylamide

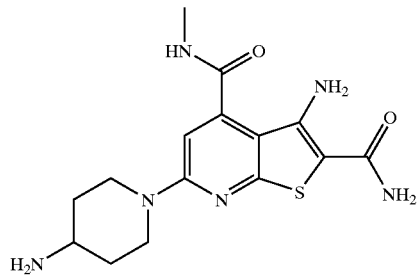

3-amino-6-(4-amino-piperidin-1-yl)-thieno[2,3-b]pyridine-2,4-dicarboxylic acid diamide

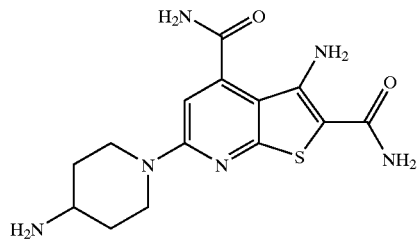

3-amino-6-(4-amino-piperidin-1-yl)-thieno[2,3-b]pyridine-2,4-dicarboxylic acid 2-amide 4-phenylamide

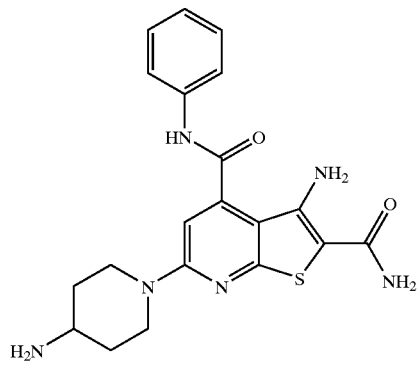

3-amino-6-(4-amino-piperidin-1-yl)-thieno[2,3-b]pyridine-2,4-dicarboxylic acid 2-amide 4-pyridin-4-ylamide

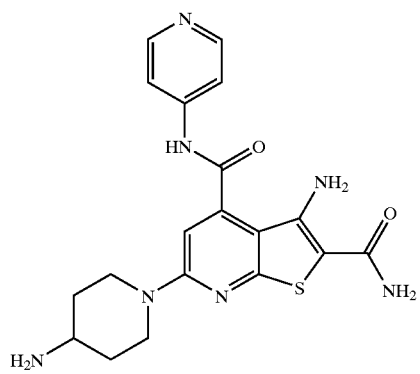

265
3-amino-6-(4-amino-piperidin-1-yl)-thieno[2,3-b]
pyridine-2,4-dicarboxylic acid 2-amide 4-pyridin-3-
ylamide
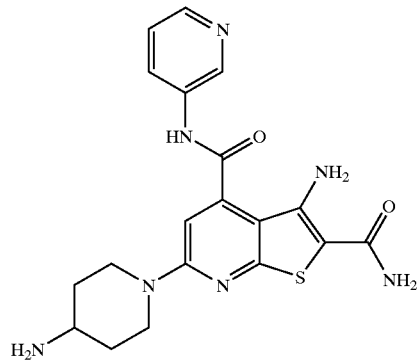
266
3-Amino-6-(4-amino-piperidin-1-yl)-thieno[2,3-b]
pyridine-2,4-dicarboxylic acid 2-amide 4-[(3-
morpholin-4-yl-propyl)-amide]
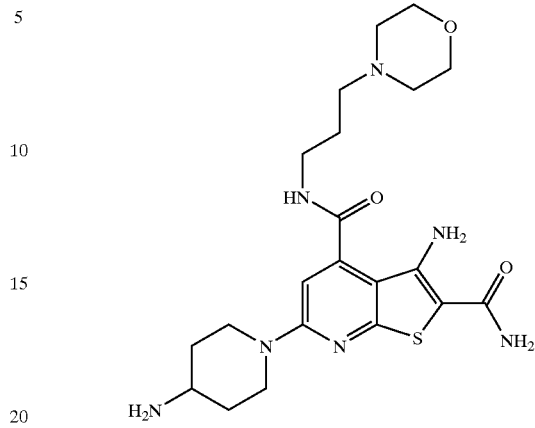
Example 50
Synthesis of 3-Amino-6-(4-amino-piperidin-1-yl-4-
((E)-2-pyridin-4-yl-vinyl)-thieno[2,3-b]pyridine-2-
carboxylic acid amide
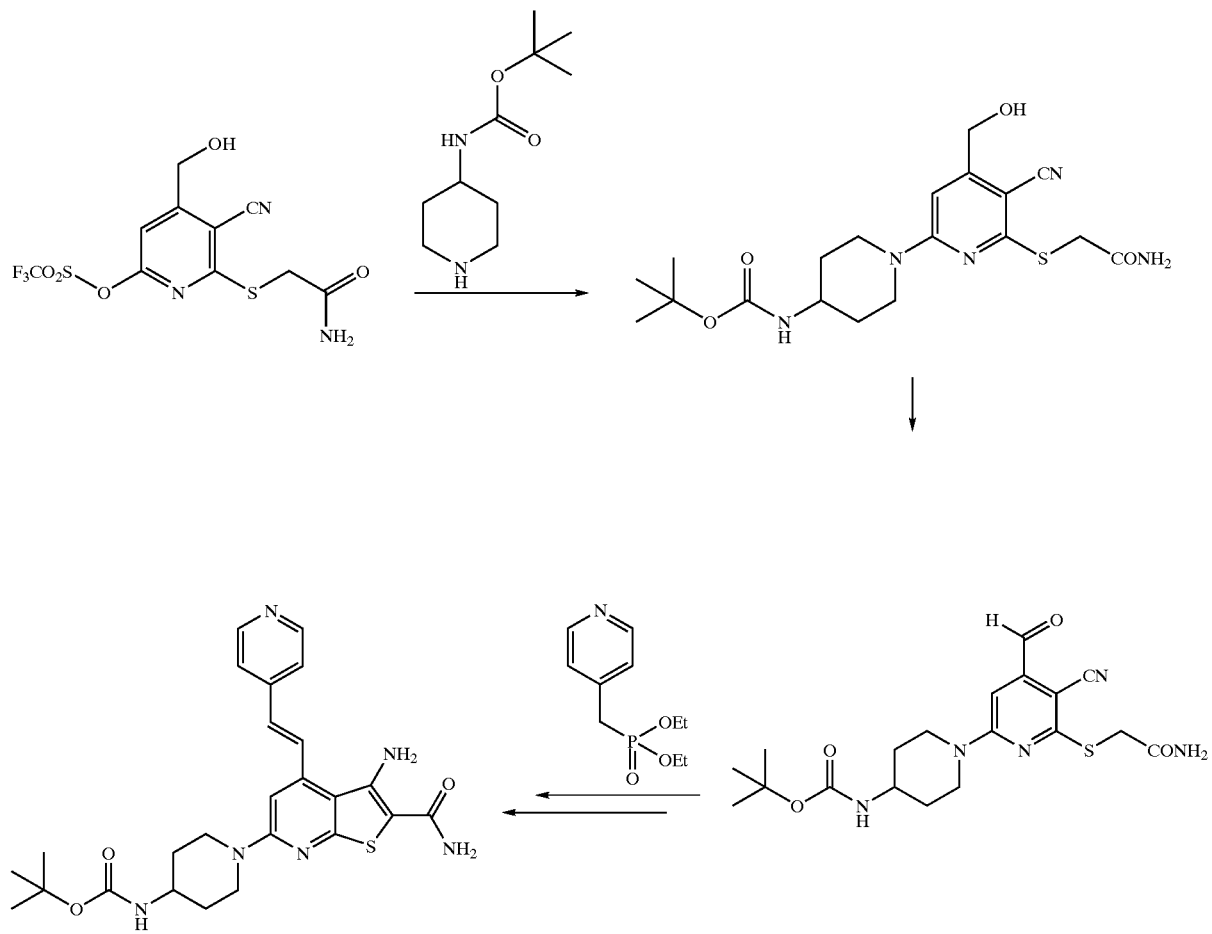

A mixture of 2.00 g (5.39 mmol) 2-[3-cyano-6-trifluoromethanesulfonyloxy-4-(4-methoxy-benzyloxymethyl)-pyridin-2-ylsulfanyl]-acetamide, 1.29 g (6.46 mmol) Boc-4-aminopiperidine and 1.88 mL (10.8 mmol) diisopropylethylamine in 20 mL dioxane was stirred at 80° C. for 1.5 h under Ar giving a brown precipitate. The precipitate was triturated in H₂O/EtOAc, filtered, and washed with H₂O and EtOAc, and dried overnight to give 1.85 g (81%) beige solid.

A yellow solution of 110 mg (0.261 nmmol) of the above product and 166 mg (0.391 mmol) Dess-Martin periodinane in 2 mL DMF was stirred 1.5 h under Ar. H₂O was added and the product was extracted 4× into EtOAc/MeOH, washed 4× H₂O, dried and stripped to 102 mg yellow solid. This was flash-chromatographed eluting with 4% MeOH/CH₂Cl₂ to obtain 56.2 mg (52%) yellow resin. NMR(DMSO) showed the product to be a 50:50 mixture of aldehyde and hydrate.

To convert the aldehyde/hydrate mixture above back into mostly aldehyde, 1.30 g aldehyde/hydrate and 6.50 g NH4Cl was stirred in 25 mL DMF overnight. The reaction was diluted with a large amount of EtOAc/MeOH and washed with H₂O that was re-extracted 3×. The combined organic phase was washed again with H2O, re-extracted 2×, dried over MgSO4, and concentrated in vacuo to give 1.28 g yellow powder. NMR(DMSO) showed 91% aldehyde+9% hydrate+3:1 DMF.

0.953 mL (0.953 mmol) 1 M lithium bis(trimethylsilylamide) was added to a solution of 270 mg (1.18 mmol) pyridine-4-ylmethyl-phosphonic acid diethyl ester (prepared by literature methods) in 4 mL dry THF. After 5 min, this was added dropwise to a solution of 200 mg (0.477 mmol) of the above aldehyde in 4 mL dry DMF and the reaction was stirred overnight under Ar. It was quenched with aq. NH4Cl, diluted with EtOAc, and washed 4× with H₂O, which was re-extracted 3× with EtOAc. The organics were combined, dried and concentrated in vacuo to a solid. This was triturated in Et2O and filtered, affording 123 mg brown solid, after drying, and then re-crystallized from MeOH/Et2O to get 77 mg (33%) orange solid.

0.25 mL 4N HCl in dioxane was added to a suspension of 75 mg (0.152 mmol) of the above product in 2.25 mL 1:1:0.25 EtOAc/CH₂Cl₂/MeOH 0.25 mL, and the reaction was capped and stirred overnight. It was diluted with EtOAc, filtered, the filtrate was diluted with Et2O and re-filtered. The filter cakes were combined and boiled and concentrated in vacuo to dryness 3× in MeOH. The product was suspended in MeOH, Et₂O added, and the product was filtered, washing with Et₂O. The solid was dried in vacuo at 60° C. to get 59.6 mg (78%) of the copper-colored final product: 3-amino-6-(4-amino-piperidin-1-yl)-4-((E)-2-pyridin-4-yl-vinyl)-thieno[2,3-b]pyridine-2-carboxylic acid amide tri-HCl salt. NMR(DMSO) showed the pure trans olefin (J=16 hz) compound. LC-+ESMS MH⁺ 395

4-{(E)-2-[3-Amino-6-(4-amino-piperidin-1-yl)-2-carbamoyl-thieno[2,3b]pyridine-4-yl]-vinyl}-benzoic acid methyl ester

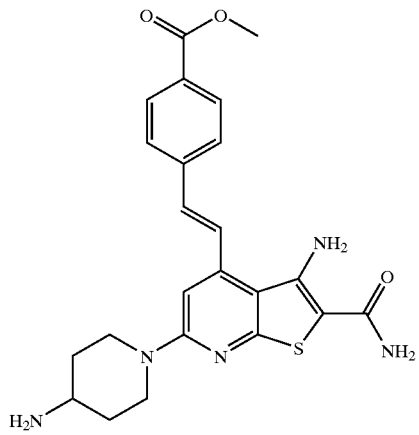

This compound was prepared by a variation of Example 50 in which the corresponding Wittig reagent was added to the common aldehyde intermediate.

Assessment of Biological Properties

The inhibition of IKKα and IKKβ by the compounds of the present invention was determined with the following assay that measures the phosphorylation of the IκBα substrate by the respective kinases. The enzymes used in the assay were N-terminally flag-tagged versions of the human IKKβ or IKKα and the substrate was a GST fusion protein with IκBα (amino acids 1–54).

The reaction mixtures (60 µl) contained 20 mM HEPES pH 7.5, 10 mM MgCl₂, 2 mM MnCl₂, 100 mM NaCl, 100 µM Na₃VO₄, 20 mM β-glycerophosphate, 1 mM DTT, 2% DMSO, 250 nM ATP, 0.4 nM [³³P]ATP (specific activity, 3000 Ci/mmol), IκBα substrate, IKK enzyme and test compound. The reaction mixtures contained either 3.6 µg/ml IKKα and 245 µg/ml IκBα or 0.9 µg/ml IKKβ and 53 µg/ml IκBα.

Reactions were initiated by adding a solution of IκBα substrate and ATP to polypropylene plates containing IKK enzyme that was pre-incubated for 5 minutes with test compound. Then the reaction mixtures were incubated for 1 hour at 25° C., placed on ice and quenched by the addition of 150 µl 10% trichloroacetic acid and 5% disodium pyrophosphate. After mixing, the entire contents of the quenched reaction mixtures were transferred to a pre-wetted Packard UniFilter filtration plate, aspirated and washed 6 times with 250 µl of ddH₂O using the Packard Filtermate Harvester. Filtration plates were then air dried, supplemented with 40 µl of Microscint 20 scintillation fluid and the ³³P-labeled reaction products were quantified using the Packard Top-Count scintillation counter.

Compounds were tested in three-fold serial dilutions and inhibitor concentrations to achieve 50% inhibition of enzyme activity (i.e., IC₅₀) were derived from dose-reponse curves using SAS software (SAS Institute, Cary N.C.). A non-linear regression analysis based on the Hill equation was applied to the percent inhibition versus concentration data. In all cases, compound concentrations were verified by HPLC.

Compounds in the Tables in the Detailed Description of the Invention section were all evaluated in the assay for IKKβ inhibition and had IC₅₀'s of 10 µM or below. Compounds, listed below had IC₅₀'s below 1 µM in this assay:

3-Amino-6-[4-(2-biphenyl-4-yl-2-hydroxy-ethylamino)-piperidin-1-yl]-4-propyl-thieno[2,3-b]pyridine-2-carboxylic acid amide
3-Amino-6-[4-(2-biphenyl-4-yl-2-hydroxy-ethylamino)-piperidin-1-yl]-4-trifluoromethyl-thieno[2,3-b]pyridine-2-carboxylic acid amide
3-Amino-6-{4-[2-hydroxy-2-(4-pyridin-2-yl-phenyl)-ethylamino]-piperidin-1-yl}-4-propyl-thieno[2,3-b]pyridine-2-carboxylic acid amide
3-Amino-6-{4-[2-hydroxy-2-(4-pyridin-2-yl-phenyl)-ethylamino]-piperidin-1-yl}-4-trifluoromethyl-thieno[2,3-b]pyridine-2-carboxylic acid amide
3-Amino-6-{4-[2-hydroxy-2-(4-pyridin-3-yl-phenyl)-ethylamino]-piperidin-1-yl}-4-propyl-thieno[2,3-b]pyridine-2-carboxylic acid amide
3-Amino-6-{4-[2-hydroxy-2-(4-pyridin-3-yl-phenyl)-ethylamino]-piperidin-1-yl}-4-trifluoromethyl-thieno[2,3-b]pyridine-2-carboxylic acid amide
3-Amino-6-{4-[2-hydroxy-2-(4-pyridin-4-yl-phenyl)-ethylamino]-piperidin-1-yl}-4-propyl-thieno[2,3-b]pyridine-2-carboxylic acid amide
3-Amino-6-{4-[2-hydroxy-2-(4-pyridin-4-yl-phenyl)-ethylamino]-piperidin-1-yl}-4-trifluoromethyl-thieno[2,3-b]pyridine-2-carboxylic acid amide
3-Amino-6-{4-[2-hydroxy-2-(3-pyridin-2-yl-phenyl)-ethylamino]-piperidin-1-yl}-4-propyl-thieno[2,3-b]pyridine-2-carboxylic acid amide
3-Amino-6-{4-[2-hydroxy-2-(4-pyrazin-2-yl-phenyl)-ethylamino]-piperidin-1-yl}-4-propyl-thieno[2,3-b]pyridine-2-carboxylic acid amide
3-Amino-6-{4-[2-hydroxy-2-(4-pyrazin-2-yl-phenyl)-ethylamino]-piperidin-1-yl}-4-trifluoromethyl-thieno[2,3-b]pyridine-2-carboxylic acid amide
3-Amino-6-{4-[2-hydroxy-2-(4-pyrimidin-5-yl-phenyl)-ethylamino]-piperidin-1-yl}-4-propyl-thieno[2,3-b]pyridine-2-carboxylic acid amide
3-Amino-6-{4-[2-hydroxy-2-(4-imidazol-1-yl-phenyl)-ethylamino]-piperidin-1-yl}-4-propyl-thieno[2,3-b]pyridine-2-carboxylic acid amide
3-Amino-6-{4-[2-hydroxy-2-(4-thiazol-2-yl-phenyl)-ethylamino]-piperidin-1-yl}-4-propyl-thieno[2,3-b]pyridine-2-carboxylic acid amide
3-Amino-6-{4-[2-hydroxy-2-(4-thiazol-2-yl-phenyl)-ethylamino]-piperidin-1-yl}-4-trifluoromethyl-thieno[2,3-b]pyridine-2-carboxylic acid amide
3-Amino-6-(4-{2-hydroxy-2-[4-(1-methyl-1H-imidazol-2-yl)-phenyl]-ethylamino}-piperidin-1-yl)-4-propyl-thieno[2,3-b]pyridine-2-carboxylic acid amide
3-Amino-6-(4-{2-[4-(1-benzyl-1H-imidazol-2-yl)-phenyl]-2-hydroxy-ethylamino}1-yl)-4-propyl-thieno[2,3-b]pyridine-2-carboxylic acid amide
3-Amino-6-(4-amino-piperidin-1-yl)-4-((E)-2-pyridin-4-yl-vinyl)-thieno[2,3-b]pyridine-2-carboxylic acid amide
4-{(E)-2-[3-Amino-6-(4-amino-piperidin-1-yl)-2-carbamoyl-thieno[2,3-b]pyridin-4-yl]-vinyl}-benzoic acid methyl ester
3-Amino-6-(4-amino-piperidin-1-yl)-4-cyclopropyl-thieno[2,3-b]pyridine-2-carboxylic acid amide
3-Amino-6-(4-amino-piperidin-1-yl)-4-tert-butyl-thieno[2,3-b]pyridine-2-carboxylic acid amide
3-Amino-6-(4-amino-piperidin-1-yl)-4-methyl-thieno[2,3-b]pyridine-2-carboxylic acid amide
3-Amino-6-(4-amino-piperidin-1-yl)-4-ethyl-thieno[2,3-b]pyridine-2-carboxylic acid amide
3-Amino-6-(4-amino-piperidin-1-yl)-4-isopropyl-thieno[2,3-b]pyridine-2-carboxylic acid amide
3-Amino-6-(4-methylamino-piperidin-1-yl)-4-trifluoromethyl-thieno[2,3-b]pyridine-2-carboxylic acid amide
3-Amino-6-(4-methylamino-piperidin-1-yl)-4-methylsulfanyl-thieno[2,3-b]pyridine-2-carboxylic acid amide
3-Amino-6-(4-methylamino-piperidin-1-yl)-4-(2,2,2-trifluoro-ethoxy)-thieno[2,3-b]pyridine-2-carboxylic acid amide
3-Amino-4-difluoromethyl-6-(4-methylamino-piperidin-1-yl)-thieno[2,3-b]pyridine-2-carboxylic acid amide
3-Amino-6-(4-amino-piperidin-1-yl)-thieno[2,3-b]pyridine-2,4-dicarboxylic acid diamide
3-Amino-6-(4-amino-piperidin-1-yl)-thieno[2,3-b]pyridine-2,4-dicarboxylic acid 2-amide 4-methylamide
3-Amino-6-(4-amino-piperidin-1-yl)-thieno[2,3-b]pyridine-2,4-dicarboxylic acid 2-amide 4-phenylamide
3-Amino-6-(4-amino-piperidin-1-yl)-thieno[2,3-b]pyridine-2,4-dicarboxylic acid 2-amide 4-pyridin-4-ylamide
3-Amino-6-(4-amino-piperidin-1-yl)-thieno[2,3-b]pyridine-2,4-dicarboxylic acid 2-amide 4-pyridin-3-ylamide
3-Amino-6-(4-amino-piperidin-1-yl)-thieno[2,3-b]pyridine-2,4-dicarboxylic acid 2-amide 4-pyridin-3-ylamide
3-Amino-6-{4-[2-(4-carbamoyl-phenyl)-ethylamino]-piperidin-1-yl}-4-propyl-thieno[2,3-b]pyridine-2-carboxylic acid amide
3-Amino-6-[4-(2-hydroxy-ethylamino)-piperidin-1-yl]-4-trifluoromethyl-thieno[2,3-b]pyridine-2-carboxylic acid amide
3-Amino-6-(4-cyclopropylamino-piperidin-1-yl)-4-propyl-thieno[2,3-b]pyridine-2-carboxylic acid amide
3-Amino-4-propyl-6-{4-[(1H-tetrazol-5-ylmethyl)-amino]-piperidin-1-yl}-thieno[2,3-b]pyridine-2-carboxylic acid amide
[1-(3-Amino-2-carbamoyl-4-propyl-thieno[2,3-b]pyridin-6-yl)-piperidin-4-ylamino]-acetic acid
3-Amino-6-{4-[3-(3-cyano-phenoxy)-2-hydroxy-propylamino]-piperidin-1-yl}-4-propyl-thieno[2,3-b]pyridine-2-carboxylic acid amide
3-Amino-6-{4-[3-(4-cyano-phenoxy)-2-hydroxy-propylamino]-piperidin-1-yl}-4-propyl-thieno[2,3-b]pyridine-2-carboxylic acid amide
3-Amino-6-[4-((R)-2-hydroxy-3-phenoxy-propylamino)-piperidin-1-yl]-4-propyl-thieno[2,3-b]pyridine-2-carboxylic acid amide
3-Amino-6-[4-((S)-2-hydroxy-3-phenoxy-propylamino)-piperidin-1-yl]-4-propyl-thieno[2,3-b]pyridine-2-carboxylic acid amide
3-Amino-6-{4-[3-(4-fluoro-phenoxy)-2-hydroxy-propylamino]-piperidin-1-yl}-4-propyl-thieno[2,3-b]pyridine-2-carboxylic acid amide
3-Amino-6-{4-[2-hydroxy-3-(3-methoxy-phenoxy)-propylamino]-piperidin-1-yl}-4-propyl-thieno[2,3-b]pyridine-2-carboxylic acid amide
3-Amino-6-{4-[2-hydroxy-3-(4-trifluoromethyl-phenoxy)-propylamino]-piperidin-1-yl}-4-propyl-thieno[2,3-b]pyridine-2-carboxylic acid amide
3-Amino-6-[4-(3-benzyloxy-2-hydroxy-propylamino)-piperidin-1-yl]-4-propyl-thieno[2,3-b]pyridine-2-carboxylic acid amide
3-Amino-6-{4-[2-hydroxy-3-(naphthalen-1-yloxy)-propylamino]-piperidin-1-yl}-4-propyl-thieno[2,3-b]pyridine-2-carboxylic acid amide
3-Amino-6-{4-[2-hydroxy-3-(naphthalen-2-yloxy)-propylamino]-piperidin-1-yl}-4-propyl-thieno[2,3-b]pyridine-2-carboxylic acid amide
3-Amino-6-{4-[3-(4-carbamoyl-phenyl)-2-hydroxy-propylamino]-piperidin-1-yl}-4-propyl-thieno[2,3-b]pyridine-2-carboxylic acid amide
3-Amino-6-{4-[3-(3-carbamoyl-phenyl)-2-hydroxy-propylamino]-piperidin-1-yl}-4-propyl-thieno[2,3-b]pyridine-2-carboxylic acid amide 3-Amino-6-[4-(2-hydroxy-4-phenyl-butylamino)-piperidin-1-yl]-4-propyl-thieno[2,3-b]pyridine-2-carboxylic acid amide
3-Amino-6-[4-(2-hydroxy-3-phenylamino-propylamino)-piperidin-1-yl]-4-propyl-thieno[2,3-b]pyridine-2-carboxylic acid amide
3-Amino-6-{4-[3-(3-carbamoyl-phenylamino)-2-hydroxy-propylamino]-piperidin-1-yl}-4-propyl-thieno[2,3-b]pyridine-2-carboxylic acid amide
3-Amino-6-[4-(2-hydroxy-2-phenylcarbamoyl-ethylamino)-piperidin-1-yl]-4-propyl-thieno[2,3-b]pyridine-2-carboxylic acid amide
3-Amino-6-[4-(2-benzylcarbamoyl-2-hydroxy-ethylamino)-piperidin-1-yl]-4-propyl-thieno[2,3-b]pyridine-2-carboxylic acid amide
3-Amino-6-(4-{[(3-carbamoyl-phenylcarbamoyl)-methyl]-amino}-piperidin-1-yl)-4-propyl-thieno[2,3-b]pyridine-2-carboxylic acid amide
3-Amino-6-(4-{[(2-carbamoyl-phenylcarbamoyl)-methyl]-amino}-piperidin-1-yl)-4-propyl-thieno[2,3-b]pyridine-2-carboxylic acid amide
3-Amino-6-(4-{[(2-hydroxy-ethylcarbamoyl)-methyl]-amino}-piperidin-1-yl)-4-propyl-thieno[2,3-b]pyridine-2-carboxylic acid amide
3-Amino-6-{4-[2-(4-hydroxy-piperidin-1-yl)-2-oxo-ethylamino]-piperidin-1-yl}-4-propyl-thieno[2,3-b]pyridine-2-carboxylic acid amide
3-Amino-6-{4-[2-(4-hydroxy-piperidin-1-yl)-2-oxo-ethylamino]-piperidin-1-yl}-4-propyl-thieno[2,3-b]pyridine-2-carboxylic acid amide
3-Amino-4-propyl-6-{4-[(quinolin-3-ylcarbamoylmethyl)-amhino]-piperidin-1-yl}-thieno[2,3-b]pyridine-2-carboxylic acid amide
3-Amino-6-{4-[(naphthalen-1-ylcarbamoylmethyl)-amino]-piperidin-1-yl}-4-propyl-thieno[2,3-b]pyridine-2-carboxylic acid amide
3-Amino-6-(4-{[(carbamoylmethyl-carbamoyl)-methyl]-amino}-piperidin-1-yl)-4-propyl-thieno[2,3-b]pyridine-2-carboxylic acid amide Selected compounds from the Table in the Detailed Description of the Invention section were evaluated for IKKα inhibition. Compounds listed below had $IC_{50}$'s of 10 µM or below in this assay:

3-Amino-4-furan-2-yl-6-methyl-thieno[2,3-b]pyridine-2-carboxylic acid amide;
3-Amino-4-isopropoxy-thieno[2,3-b]pyridine-2-carboxylic acid amide;
3-Amino-6-methyl-4-(4-nitro-phenyl)-thieno[2,3-b]pyridine-2-carboxylic acid amide;
3-Amino-6-methyl-4-((E)-styryl)-thieno[2,3-b]pyridine-2-carboxylic acid amide;
3-Amino-4-(4-methanesulfonyl-phenyl)-6-methyl-thieno[2,3-b]pyridine-2-carboxylic acid amide;
3-Amino-4-[(E)-2-(4-fluoro-phenyl)-vinyl]-6-methyl-thieno[2,3-b]pyridine-2-carboxylic acid amide;
3-Amino-4-[(E)-2-(4-chloro-phenyl)-vinyl]-6-methyl-thieno[2,3-b]pyridine-2-carboxylic acid amide;
3-Amino-6-(4-methyl-piperazin-1-yl)-4-propyl-thieno[2,3-b]pyridine-2-carboxylic acid amide;
3-Amino-6-piperazin-1-yl-4-propyl-thieno[2,3-b]pyridine-2-carboxylic acid amide;
3-Amino-6-(4-amino-piperidin-1-yl)-4-propyl-thieno[2,3-b]pyridine-2-carboxylic acid amide;
3-Amino-6-((R)-3-amino-pyrrolidin-1-yl)-4-propyl-thieno[2,3-b]pyridine-2-carboxylic acid amide;
3-Amino-6-(4-amino-4-cyano-piperidin-1-yl)-4-propyl-thieno[2,3-b]pyridine-2-carboxylic acid amide;
3-Amino-6-(4-methylamino-piperidin-1-yl)-4-propyl-thieno[2,3-b]pyridine-2-carboxylic acid amide;
3-Amino-6-(4-amino-piperidin-1-yl)-4-methylsulfanyl-thieno[2,3-b]pyridine-2-carboxylic acid amide;
3-Amino-6-(4-amino-piperidin-1-yl)-4-((E)-styryl)-thieno[2,3-b]pyridine-2-carboxylic acid amide; and
3-Amino-6-(4-amino-piperidin-1-yl)-4-(4-nitro-phenyl)-thieno[2,3-b]pyridine-2-carboxylic acid amide.
3-Amino-6-(4-{2-[4-(3-carbamoyl-benzylcarbamoyl)-phenyl]-2-hydroxy-ethylamino}-piperidin-1-yl)-4-propyl-thieno[2,3-b]pyridine-2-carboxylic acid amide
3-Amino-6-[4-(2-hydroxy-2-{4-[(pyridin-3-ylmethyl)-carbamoyl]-phenyl}-ethylamino)-piperidin-1-yl]-4-propyl-thieno[2,3-b]pyridine-2-carboxylic acid amide
3-Amino-6-{4-[2-(4-benzylcarbamoyl-phenyl)-2-hydroxy-ethylamino]-piperidin-1-yl}-4-trifluoromethyl-thieno[2,3-b]pyridine-2-carboxylic acid amide
3-Amino-6-{4-[2-hydroxy-2-(4-methanesulfonylamino-phenyl)-ethylamino]-piperidin-1-yl}-4-propyl-thieno[2,3-b]pyridine-2-carboxylic acid amide
3-Amino-6-{4-[2-(3,4-difluoro-phenyl)-2-hydroxy-ethylamino]-piperidin-1-yl}-4-trifluoromethyl-thieno[2,3-b]pyridine-2-carboxylic acid amide
3-Amino-6-{4-[2-hydroxy-2-(4-pyridin-3-yl-phenyl)-ethylamino]-piperidin-1-yl}-4-propyl-thieno[2,3-b]pyridine-2-carboxylic acid amide
3-Amino-6-{4-[2-hydroxy-2-(4-pyrazin-2-yl-phenyl)-ethylamino]-piperidin-1-yl}-4-trifluoromethyl-thieno[2,3-b]pyridine-2-carboxylic acid amide
3-Amino-6-{4-[2-hydroxy-2-(4-imidazol-1-yl-phenyl)-ethylamino]-piperidin-1-yl}-4-propyl-thieno[2,3-b]pyridine-2-carboxylic acid amide
3-Amino-6-{4-[2-hydroxy-2-(4-thiazol-2-yl-phenyl)-ethylamino]-piperidin-1-yl}-4-propyl-thieno[2,3-b]pyridine-2-carboxylic acid amide
3-Amino-6-{4-[2-hydroxy-2-(4-thiazol-2-yl-phenyl)-ethylamino]-piperidin-1-yl}-4-trifluoromethyl-thieno[2,3-b]pyridine-2-carboxylic acid amide
3-Amino-6-(4-{2-hydroxy-2-[4-(1-methyl-1H-imidazol-2-yl)-phenyl]-ethylamino}-piperidin-1-yl)-4-propyl-thieno[2,3-b]pyridine-2-carboxylic acid amide
3-Amino-6-(4-amino-piperidin-1-yl)-4-((E)-2-pyridin-4-yl-vinyl)-thieno[2,3-b]pyridine-2-carboxylic acid amide
4-{(E)-2-[3-Amino-6-(4-amino-piperidin-1-yl)-2-carbamoyl-thieno[2,3-b]pyridin-4-yl]-vinyl}-benzoic acid methyl ester
3-Amino-6-(4-amino-piperidin-1-yl)-4-cyclopropyl-thieno[2,3-b]pyridine-2-carboxylic acid amide
3-Amino-6-(4-amino-piperidin-1-yl)-4-methyl-thieno[2,3-b]pyridine-2-carboxylic acid amide
3-Amino-6-(4-amino-piperidin-1-yl)-4-ethyl-thieno[2,3-b]pyridine-2-carboxylic acid amide
3-Amino-6-(4-amino-piperidin-1-yl)-4-isopropyl-thieno[2,3-b]pyridine-2-carboxylic acid amide
3-Amino-6-(4-methylamino-piperidin-1-yl)-4-trifluoromethyl-thieno[2,3-b]pyridine-2-carboxylic acid amide
3-Amino-6-(4-methylamino-piperidin-1-yl)-4-methylsulfanyl-thieno[2,3-b]pyridine-2-carboxylic acid amide
3-Amino-6-(4-methylamino-piperidin-1-yl)-4-(2,2,2-trifluoro-ethoxy)-thieno[2,3-b]pyridine-2-carboxylic acid amide
3-Amino-4-difluoromethyl-6-(4-methylamino-piperidin-1-yl)-thieno[2,3-b]pyridine-2-carboxylic acid amide
3-Amino-6-(4-amino-piperidin-1-yl)-thieno[2,3-b]pyridine-2,4-dicarboxylic acid diamide 3-Amino-6-(4-amino-piperidin-1-yl)-thieno[2,3-b]pyridine-2,4-dicarboxylic acid 2-amide 4-methylamide 3-Amino-6-(4-amino-piperidin-1-yl)-thieno[2,3-b]pyridine-2,4-dicarboxylic acid 2-amide 4-phenylamide 3-Amino-6-(4-amino-piperidin-1-yl)-thieno[2,3-b]pyridine-2,4-dicarboxylic acid 2-amide 4-pyridin-4-ylamide 3-Amino-6-(4-amino-piperidin-1-yl)-thieno[2,3-b]pyridine-2,4-dicarboxylic acid 2-amide 4-pyridin-3-ylamide 3-Amino-6-(4-amino-piperidin-1-yl)-thieno[2,3-b]pyridine-2,4-dicarboxylic acid 2-amide 4-[(3-morpholin-4-yl-propyl)-amide]

3-Amino-6-(4-cyclopropylamino-piperidin-1-yl)-4-propyl-thieno[2,3-b]pyridine-2-carboxylic acid amide 3-Amino-4-propyl-6-{4-[(1H-tetrazol-5-ylmethyl)-amino]-piperidin-1-yl}-thieno[2,3-b]pyridine-2-carboxylic acid amide

[1-(3-Amino-2-carbamoyl-4-propyl-thieno[2,3-b]pyridin-6-yl)-piperidin-4-ylamino]-acetic acid 3-Amino-6-{4-[2-(4-hydroxy-piperidin-1-yl)-2-oxo-ethylamino]-piperidin-1-yl}-4-propyl-thieno[2,3-b]pyridine-2-carboxylic acid amide 3-Amino-6-{4-[(naphthalen-1-ylcarbamoylmethyl)-amino]-piperidin-1-yl}-4-propyl-thieno[2,3-b]pyridine-2-carboxylic acid amide.

What is claimed is:

1. A compound according to formula (I):

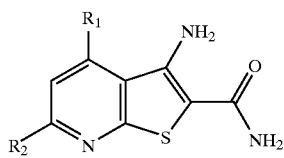

(I)

wherein:

$R_1$ is
(a) phenyl or heteroaryl selected from furanyl, thienyl, pyridyl, pyrrolyl, imidazolyl and benzofuranyl, optionally substituted with one to two $R_3$,
(b) heterocyclyl selected from 1-piperidinyl, 1-piperazinyl, 1-pyrrolidinyl and 4-morpholinyl, optionally substituted with one to two groups selected from $C_{1-6}$alkyl, —$CO_2C_{1-5}$alkyl, phenyl, benzyl, —OH and —C(O)heteroaryl, wherein the heteroaryl is selected from furanyl, thienyl, pyridyl and pyrrolyl,
(c) $R_6(CH_2)_mO$—,
(d) $R_6OCH_2$—,
(e) $R_6(CH_2)_mNH$—,
(f) $R_6(CH_2)_p(CH=CH)_m$— or pyridyl$(CH_2)p(CH=CH)_m$—
(g) $C_{1-6}$alkyl, optionally partially or fully halogenated and optionally substituted with one to two $R_9$,
(h) $C_{3-6}$ cycloalkyl
(i) $C_{1-8}$alkoxy, optionally partially or fully halogenated and optionally substituted with one to two $R_9$,
(j) $C_{1-8}$alkylS(O)$_n$—, optionally partially or fully halogenated and optipnally substituted with one to two $R_9$,
(k) —$N(R_4)(R_5)$, or
(l) —C(O)NHR', wherein R' is $R_6$, pyridyl or —$CH_3$;

$R_2$ is
(a) heterocyclyl$(CH_2)_m$— wherein said heterocycle is selected from piperdinyl, piperazinyl, morpholinyl, azepanyl, pyrrolidinyl, 1,4-diazacyclolheptanyl, azepanyl, 2,5-diazabicyclo[2.2.]heptanyl, oxazepanyl and thiomorpholino and is optionally substituted with one to three $R_7$,
(b) heterocyclylCH$_2$O— wherein the heterocyclyl is selected from 1-piperidinyl, 1-piperazinyl, 4-morpholinyl and 1-pyrrolidinyl, optionally substituted with $C_{1-6}$alkyl;

$R_3$ is chosen from $C_{1-6}$alkyl, $C_{1-6}$alkoxy, hydroxy$C_{1-6}$alkyl, halogen, —CN, —$CO_2H$, —$CO_2C_{1-6}$alkyl, —$S(O)_nC_{1-6}$alkyl, —$NO_2$, —OH, —$CF_3$, —$N(R_4)(R_5)$, —NHC(O)NH$C_{1-6}$alkyl, —C(O)N($R_4$)($R_5$) and phenyl optionally substituted with halogen, $C_{1-6}$alkyl, —CN or $C_{1-6}$alkoxy;

$R_4$ and $R_5$ are independently selected from H, $C_{1-6}$alkyl, —$C_{0-3}$alkyl$C_{3-6}$cycloalkyl, —$C_{0-3}$alkylheteroaryl selected from the list consisting of benzothiophenyl, furanyl, tetrazolyl, pyridyl, —$C_{0-3}$alkylheterocyclyl selected from the list consisting of piperdinyl and morpholinyl, —$C_{0-3}$alkylphenyl($R_6$),-2-methylcyclohexyl, —C(O)$C_{1-6}$alkyl, —$SO_2C_{1-6}$alkyl, phenyl, pyridyl, piperidinyl, phenylethyl optionally substituted with hydroxymethyl, $(CH_3)_3COC(O)$—, —$CH_2CO_2Me$, —$C_{1-6}$alkylOH, —$C_{1-6}$alkylNMe$_2$, or alternatively R4 and R5 with the atom to which they are attached can be fused together to form a heterocyclic ring which may be substituted with an OH group;

$R_6$ is a phenyl group optionally substituted with one to three groups selected from halogen, $C_{1-6}$alkyl, —CN, —$CO_2C_{1-6}$alkyl, —$CO_2H$, —C(O)NR$_4$R$_5$, —CH$_2$N($R_4$)($R_5$), —SO$_2$N($R_4$)($R_5$), —NHSO$_2C_{1-6}$alkyl, —SO$_2C_{1-6}$alkyl, —$NO_2$, —OH, —$NH_2$, —$CF_3$, $OCF_2$, $OCF_3$, OBenzyl, $C_{1-6}$alkoxy, a beteroaryl group selected from the list consisting of pyridyl, pyrazine, imidazolyl and thiazolyl which may be further substituted by an $R_4$ group, phenyl, a heterocyclic group, or alternatively when R6 is phenyl two of its adjacent carbon atoms may be bridged by an —OCH$_2$O— or an —OCF$_2$O— group, or $R_6$ is $C_{3-6}$cycloalkyl, —CH$_2$OH, naphthalene-2-yl, naphthalene-1-yl or 2-thienyl;

$R_7$ is $R_6CH(OH)CH_2NH$—, or $C_{1-6}$alkyl $R_9$ is selected from oxo, —OH, —NR$_4$R$_5$, —CO$_2H$ and $C_{1-6}$alkoxy;

m is 0 or 1;

n is 0, 1 or 2; and p is 0, 1, 2 or 3 or a pharmaceutically acceptable salt, racemate, racemic mixture, single enantioner, diastereomeric mixture or individual diastereomer thereof.

2. The compounds of formula I of claim 1 wherein:

$R_1$ is
(a) phenyl or heteroaryl selected from furanyl, thienyl, pyridyl, pyrrolyl, imidazolyl and benzofuranyl, optionally substituted with one to two $R_3$,
(b) heterocyclyl selected from 1-piperidinyl, 1-piperazinyl, 1-pyrrolidinyl and 4-morpholinyl, optionally substituted with one to two groups selected from $C_{1-6}$alkyl, —$CO_2C_{1-5}$alkyl, phenyl, benzyl, —OH and —C(O)heteroaryl, wherein the heteroaryl is selected from furanyl, thienyl, pyridyl and pyrrolyl,
(c) $R_6(CH_2)_mO$—,
(d) $R_6OCH_2$—,
(e) $R_6(CH_2)_mNH$—,
(f) $R_6(CH_2)_p(CH=CH)_m$— or pyridyl$(CH_2)p(CH=CH)_m$—

(g) $C_{1-6}$alkyl, optionally partially or fully halogenated and optionally substituted with one to two $R_9$,
(h) $C_{3-6}$ cycloalkyl
(i) $C_{1-8}$alkoxy, optionally partially or fully halogenated and optionally substituted with one to two $R_9$,
(j) $C_{1-8}$alkylS(O)$_n$—, optionally partially or fully halogenated and optionally substituted with one to two $R_9$,
(k) —N($R_4$)($R_5$), or
(l) —C(O)NHR', wherein R' is $R_6$, pyridyl or —$H_3$;

$R_2$ is piperdinyl(CH$_2$)$_m$— optionally substituted with one to three $R_7$, $R_3$ is chosen from $C_{1-6}$alkyl, $C_{1-6}$alkoxy, hydroxyC$_{1-6}$alkyl, halogen, —CN, —CO$_2$H, —CO$_2$C$_{1-6}$alkyl, —S(O)$_n$C$_{1-6}$alkyl, —NO$_2$, —OH, —CF$_3$, —N($R_4$)($R_5$), —NHC(O)NHC$_{1-6}$alkyl, —C(O)N($R_4$)($R_5$) and phenyl optionally substituted with halogen, $C_{1-6}$alkyl, —CN or $C_{1-6}$alkoxy;

$R_4$ and $R_5$ are independently selected from, —C$_{0-3}$alkylheteroaryl, —C$_{0-3}$alkylheterocyclyl, —C$_{0-3}$alkylphenyl($R_6$),-2-methylcyclohexyl, —C(O)C$_{1-6}$alkyl, —SO$_2$C$_{1-6}$alkyl, phenyl, pyridyl, piperidinyl, phenylethyl optionally substituted with hydroxymethyl, (CH$_3$)$_3$COC(O)—, —CH$_2$CO$_2$Me, —C$_{1-6}$alkylOH, —C$_{1-6}$alkylNMe$_2$, or alternatively R4 and R5 with the atom to which they are attached can be fused together to form a heterocyclic ring which may be substituted with an OH group;

$R_6$ is a phenyl group substituted with one to three groups selected from $C_{1-6}$ alkyl —CN, —CO$_2$H, —CH$_2$N($R_4$)($R_5$),—SO$_2$N($R_4$)($R_5$), —C(O)NR$_4$R$_5$, NHSO$_2$C$_{1-6}$alkyl, —SO$_2$C$_{1-6}$alkyl, —CF$_3$, OCF$_2$, OCF$_3$, OBenzyl, $C_{2-6}$alkoxy, a heteroaryl group selected from the list consisting of pyridyl, pyrazinyl, imidazolyl and thiazolyl which may be further substituted by an $R_4$ group, phenyl, a heterocyclic group, or alternatively when R6 is phenyl two of its adjacent carbon atoms may be bridged by an —OCH$_2$O— or an —OCF$_2$O— group;

$R_7$ is $R_6$CH(OH)CH$_2$NH—, or $C_{1-6}$alkyl $R_9$ is selected from oxo, —OH, —NR$_4$R$_5$, —CO$_2$H and $C_{1-6}$alkoxy;

m is 0 or 1;
n is 0, 1 or 2; and
p is 0, 1, 2 or 3.

3. The compounds of formula 1 of claim 1 wherein:

$R_1$ is $C_{1-6}$alkyl, optionally partially or fully halogenated and optionally substituted with one to two $R_9$;

$R_2$ is piperdinyl(CH$_2$)$_m$— optionally substituted with one to three $R_7$;

$R_3$ is chosen from $C_{1-6}$alkyl, $C_{1-6}$alkoxy, hydroxyC$_{1-6}$alkyl, halogen, —CN, —CO$_2$H, —CO$_2$C$_{1-6}$alkyl, —S(O)$_n$C$_{1-6}$alkyl, —NO$_2$, —OH, —CF$_3$, —N($R_4$)($R_5$), —NHC(O)NHC$_{1-6}$alkyl, —C(O)N($R_4$)($R_5$) and phenyl optionally substituted with halogen, $C_{1-6}$alkyl, —CN or $C_{1-6}$alkoxy;

$R_4$ and $R_5$ are independently selected from, —C$_{0-3}$alkylheteroaryl, —C$_{0-3}$alkylheterocyclyl, —C$_{0-3}$alkylphenyl($R_6$),-2-methylcyclohexyl, —C(O)C$_{1-6}$alkyl, —SO$_2$C$_{1-6}$alkyl, phenyl, pyridyl, piperidinyl, phenylethyl optionally substituted with hydroxymethyl, (CH$_3$)$_3$COC(O)—, —CH$_2$CO$_2$Me, —C$_{1-6}$alkylOH, —C$_{1-6}$alkylNMe$_2$, or alternatively R4 and R5 with the atom to which they are attached can be fused together to form a heterocyclic ring which may be substituted with an OH group;

$R_6$ is a phenyl group substituted with one to three groups selected from $C_{1-6}$ alkyl —CN, —CO$_2$H, —CH$_2$N($R_4$)($R_5$), —SO$_2$N($R_4$)($R_5$), —C(O)NR$_4$R$_5$, NHSO$_2$C$_{1-6}$alkyl, —SO$_2$C$_{1-6}$alkyl, —CF$_3$, OCF$_2$, OCF$_3$, OBenzyl, $C_{2-6}$alkoxy, a heteroaryl group selected from the list consisiting of pyridyl, pyrazinyl, imidazolyl and thiazolyl which may be further substituted by an $R_4$ group, phenyl, a heterocyclic group, or alternatively when R6 is phenyl two of its adjacent carbon atoms may be bridged by an —OCH$_2$O— or an —OCF$_2$O— group;

$R_7$ is $R_6$CH(OH)CH$_2$NH—, or $C_{1-6}$alkyl $R_9$ is selected from oxo, —OH, —NR$_4$R$_5$, —CO$_2$H and $C_{1-6}$alkoxy;

m is 0 or 1;
n is 0, 1 or 2; and
p is 0, 1, 2 or 3.

4. A compound selected from the list consisting of:

3-Amino-6-{4-[2-(4-benzylcarbamoyl-phenyl)-2-hydroxy-ethylamino]-piperidin-1-yl}-4-trifluoromethyl-thieno[2,3-b]pyridine-2-carboxylic acid amide

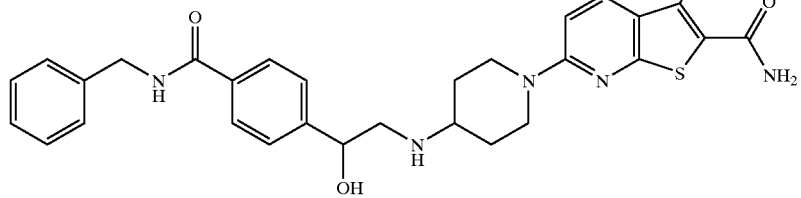

-continued

3-Amino-6-[4-(2-hydroxy-2-naphthalen-2-yl-ethylamino)-piperidin-1-yl]-4-trifluoromethyl-thieno[2,3-b]pyridine-2-carboxylic acid amide

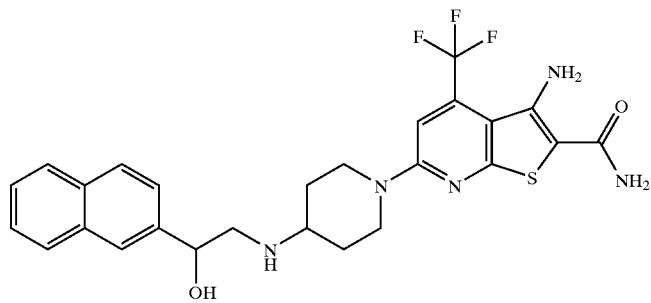

3-Amino-6-{4-[2-(4-cyano-phenyl)-2-hydroxy-ethylamino]-piperidin-1-yl}-4-trifluoromethyl-thieno[2,3-b]pyridine-2-carboxylic acid amide

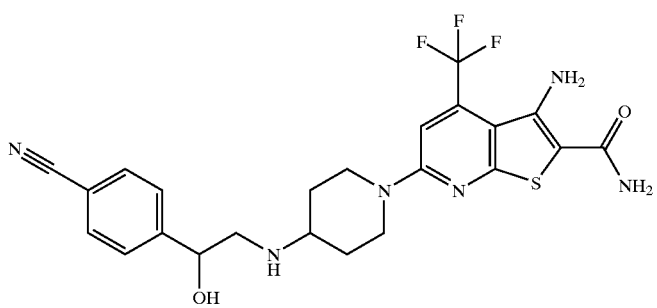

3-Amino-6-{4-[2-hydroxy-2-(4-methanesulfonyl-phenyl)-ethylamino]-piperidin-1-yl}-4-trifluoromethyl-thieno[2,3-b]pyridine-2-carboxylic acid amide

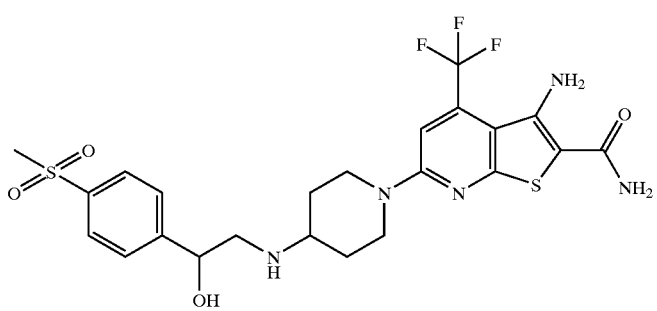

3-Amino-6-[4-((S)-2-hydroxy-2-phenyl-ethylamino)-piperidin-1-yl]-4-trifluoromethyl-thieno[2,3-b]pyridine-2-carboxylic acid amide

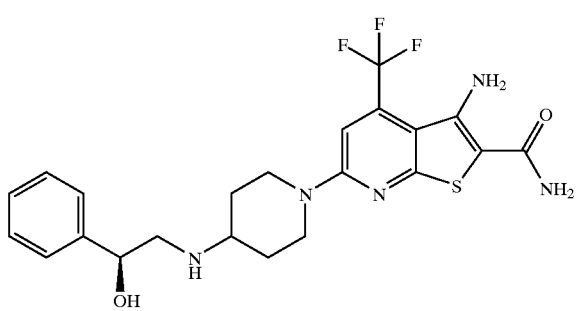

3-Amino-6-[4-((R)-2-hydroxy-2-phenyl-ethylamino)-piperidin-1-yl]-4-trifluoromethyl-thieno[2,3-b]pyridine-2-carboxylic acid amide

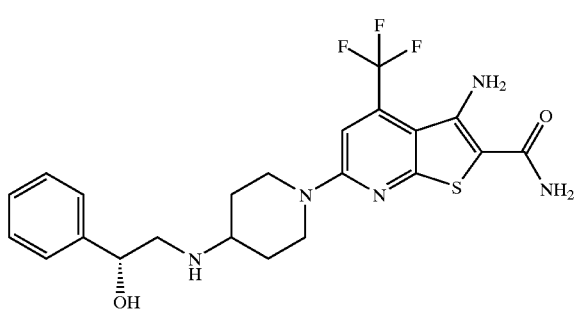

-continued

3-Amino-6-{4-[2-(4-fluoro-phenyl)-2-hydroxy-ethylamino]-piperidin-1-yl}-4-trifluoromethyl-thieno[2,3-b]pyridine-2-carboxylic acid amide

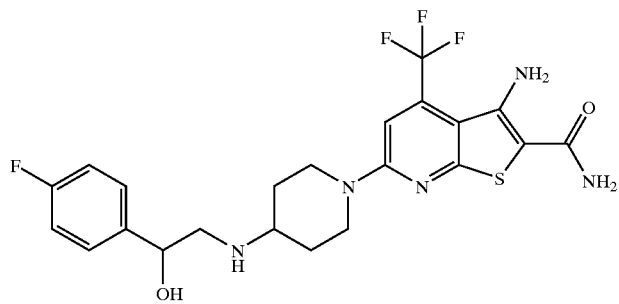

3-Amino-6-{4-[2-(2-fluoro-phenyl)-2-hydroxy-ethylamino]-piperidin-1-yl}-4-trifluoromethyl-thieno[2,3-b]pyridine-2-carboxylic acid amide

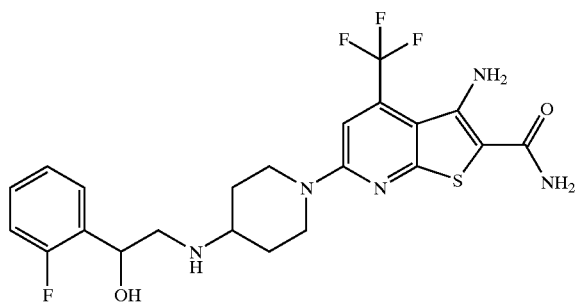

3-Amino-6-{4-[2-(3,4-difluoro-phenyl)-2-hydroxy-ethylamino]-piperidin-1-yl}-4-trifluoromethyl-thieno[2,3-b]pyridine-2-carboxylic acid amide

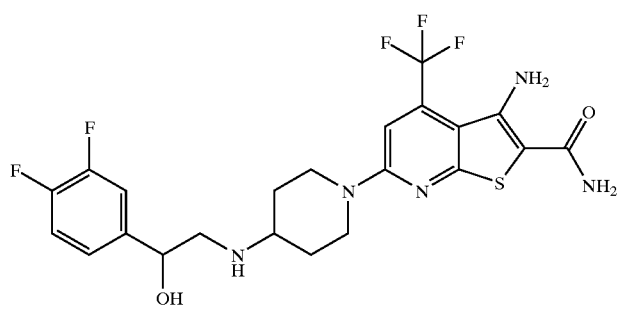

3-Amino-6-{4-[2-(4-difluoromethoxy-phenyl)-2-hydroxy-ethylamino]-piperidin-1-yl}-4-trifluoromethyl-thieno[2,3-b]pyridine-2-carboxylic acid amide

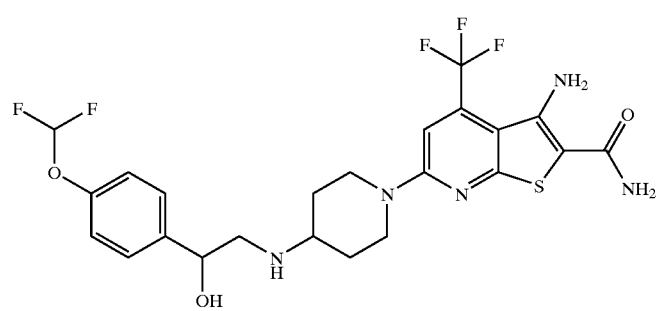

3-Amino-6-{4-[2-hydroxy-2-(4-trifluoromethoxy-phenyl)-ethylamino]-piperidin-1-yl}-4-trifluoromethyl-thieno[2,3-b]pyridine-2-carboxylic acid amide

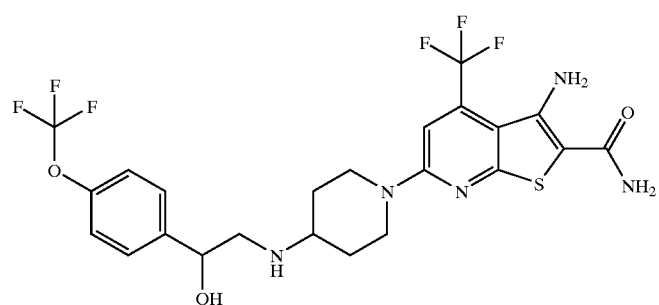

-continued

3-Amino-6-{4-[2-(3,5-difluoro-phenyl)-2-hydroxy-ethylamino]-piperidin-1-yl}-4-trifluoromethyl-thieno[2,3-b]pyridine-2-carboxylic acid amide

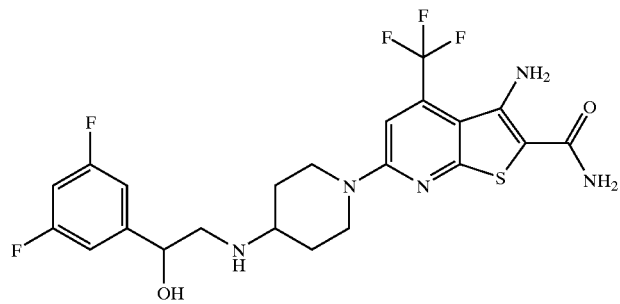

3-Amino-6-{4-[2-(3-fluoro-phenyl)-2-hydroxy-ethylamino]-piperidin-1-yl}-4-trifluoromethyl-thieno[2,3-b]pyridine-2-carboxylic acid amide

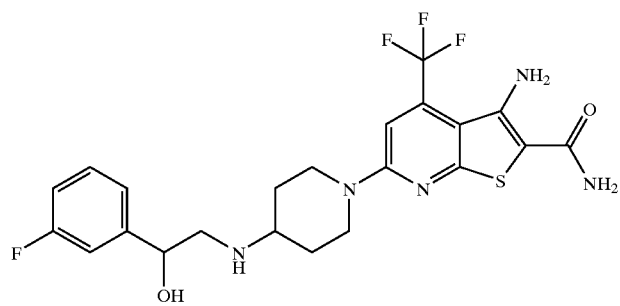

3-Amino-6-{4-[2-hydroxy-2-(3,4,5-trifluoro-phenyl)-ethylamino]-piperidin-1-yl}-4-trifluoromethyl-thieno[2,3-b]pyridine-2-carboxylic acid amide

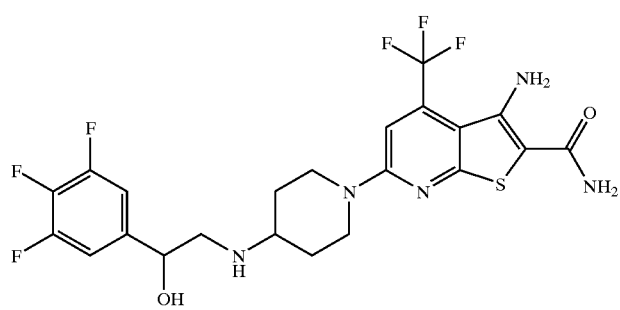

3-Amino-6-{4-[2-hydroxy-2-(4-hydroxy-phenyl)-ethylamino]-piperidin-1-yl}-4-trifluoromethyl-thieno[2,3-b]pyridine-2-carboxylic acid amide

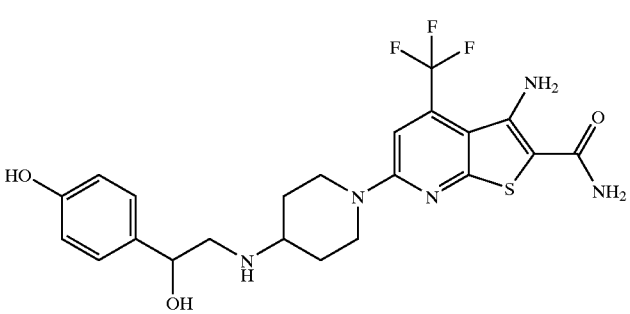

3-Amino-6-{4-[2-(3,4-dimethoxy-phenyl)-2-hydroxy-ethylamino]-piperidin-1-yl}-4-trifluoromethyl-thieno[2,3-b]pyridine-2-carboxylic acid amide

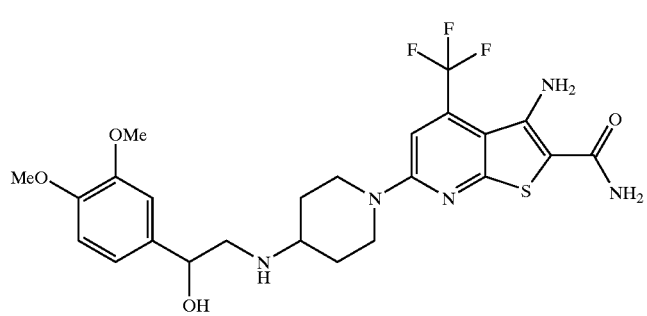

-continued

3-Amino-6-[4-(2-benzo[1,3]dioxol-5-yl-2-hydroxy-ethylamino)-piperidin-1-yl]-4-trifluoromethyl-thieno[2,3-b]pyridine-2-carboxylic acid amide

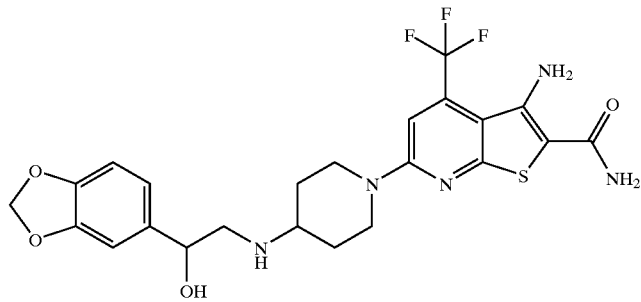

3-Amino-6-[4-(2-benzo[1,3]dioxol-4-yl-2-hydroxy-ethylamino)-piperidin-1-yl]-4-trifluoromethyl-thieno[2,3-b]pyridine-2-carboxylic acid amide

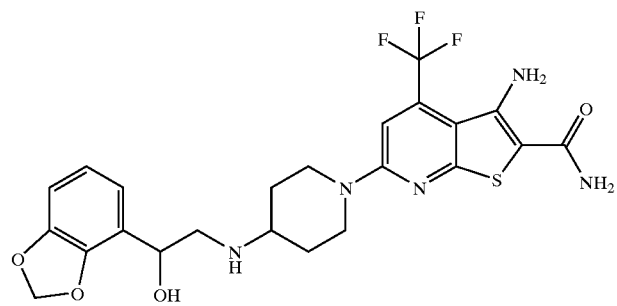

3-Amino-6-{4-[2-(2,2-difluoro-benzo[1,3]dioxol-5-yl)-2-hydroxy-ethylamino]-piperidin-1-yl}-4-trifluoromethyl-thieno[2,3-b]pyridine-2-carboxylic acid amide

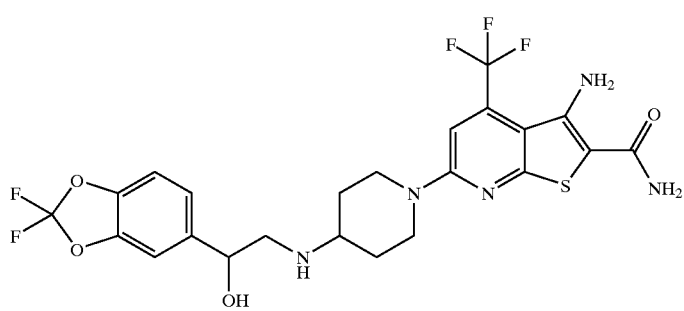

3-Amino-6-{4-[2-(4-benzyloxy-phenyl)-2-hydroxy-ethylamino]-piperidin-1-yl}-4-trifluoromethyl-thieno[2,3-b]pyridine-2-carboxylic acid amide

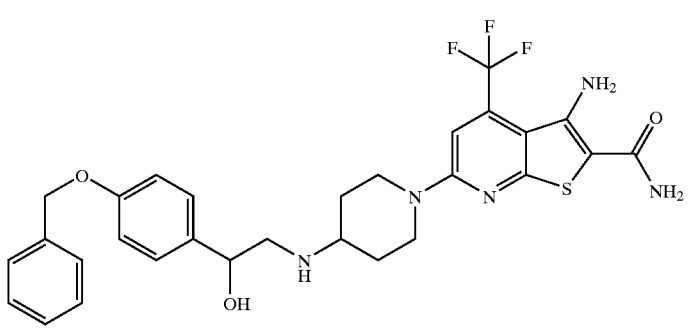

3-Amino-6-{4-[2-hydroxy-2-(4-morpholin-4-yl-phenyl)-ethylamino]-piperidin-1-yl}-4-trifluoromethyl-thieno[2,3-b]pyridine-2-carboxylic acid amide

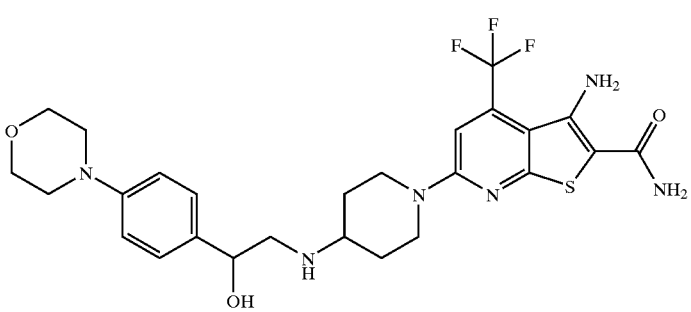

3-Amino-6-[4-(2-biphenyl-4-yl-2-hydroxy-ethylamino)-piperidin-1-yl]-4-trifluoromethyl-thieno[2,3-b]pyridine-2-carboxylic acid amide

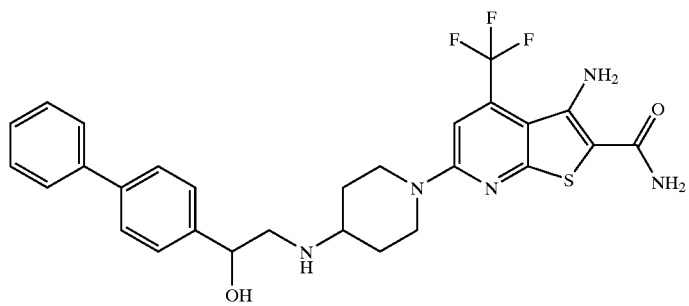

3-Amino-6-{4-[2-hydroxy-2-(4-pyridin-2-yl-phenyl)-ethylamino]-piperidin-1-yl}-4-trifluoromethyl-thieno[2,3-b]pyridine-2-carboxylic acid amide

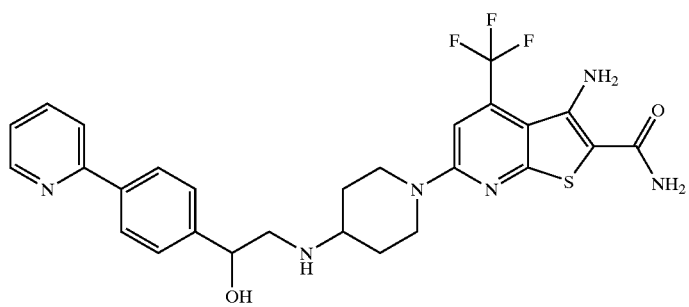

3-Amino-6-{4-[2-hydroxy-2-(4-pyridin-3-yl-phenyl)-ethylamino]-piperidin-1-yl}-4-trifluoromethyl-thieno[2,3-b]pyridine-2-carboxylic acid amide

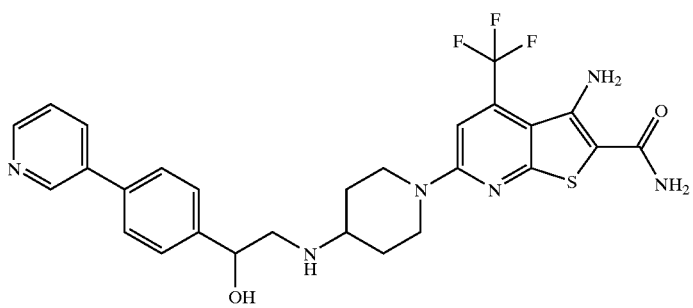

3-Amino-6-{4-[2-hydroxy-2-(4-pyridin-4-yl-phenyl)-ethylamino]-piperidin-1-yl}-4-trifluoromethyl-thieno[2,3-b]pyridine-2-carboxylic acid amide

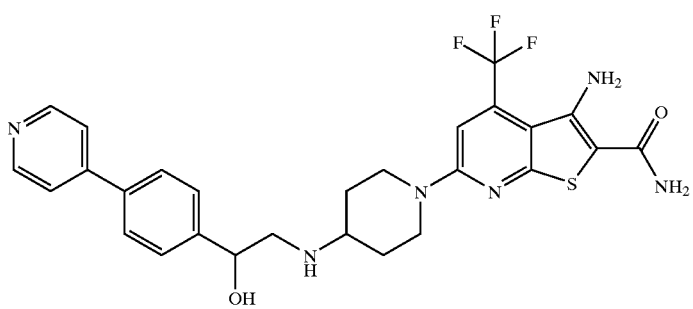

3-Amino-6-{4-[2-hydroxy-2-(4-pyrazin-2-yl-phenyl)-ethylamino]-piperidin-1-yl}-4-trifluoromethyl-thieno[2,3-b]pyridine-2-carboxylic acid amide

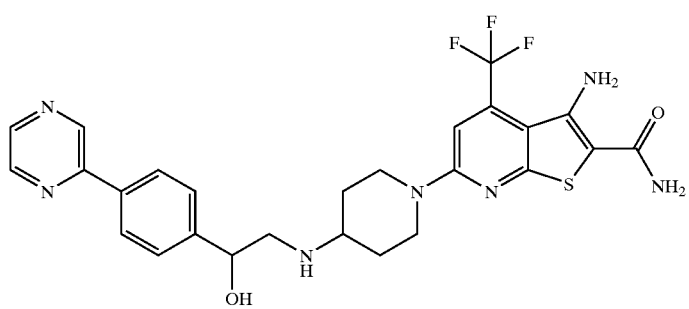

-continued

3-Amino-6-{4-[2-hydroxy-2-(4-thiazol-2-yl-phenyl)-ethylamino]-piperidin-1-yl}-4-trifluoromethyl-thieno[2,3-b]pyridine-2-carboxylic acid amide

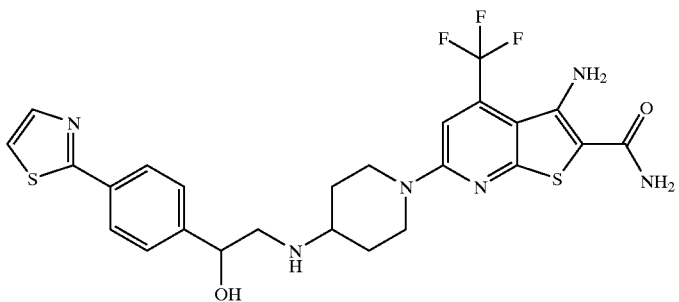

or a pharmaceutically acceptable salt, racemate, racemic mixture, single enantioner, diastereomeric mixture or individual diastereomer thereof.

5. A compound selected from the list consisting of:

3-Amino-6-[4-(2-hydroxy-2-phenyl-ethylamino)-piperidin-1-yl]-4-propyl-thieno[2,3-b]pyridine-2-carboxylic acid amide

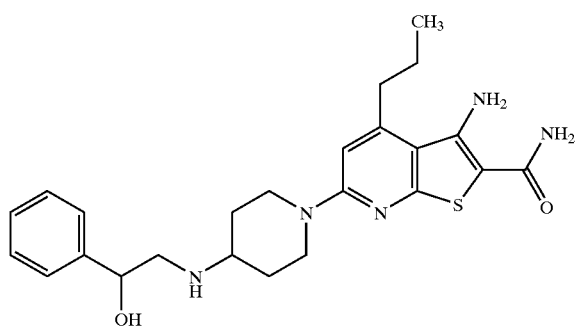

3-Amino-6-[4-((S)-2-hydroxy-2-phenyl-ethylamino)-piperidin-1-yl]-4-propyl-thieno[2,3-b]pyridine-2-carboxylic acid amide

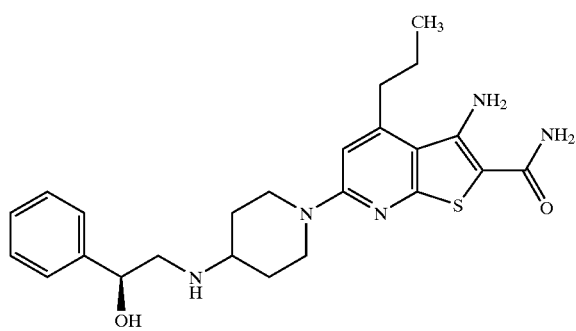

3-Amino-6-[4-((R)-2-hydroxy-2-phenyl-ethylamino)-piperidin-1-yl]-4-propyl-thieno[2,3-b]pyridine-2-carboxylic acid amide

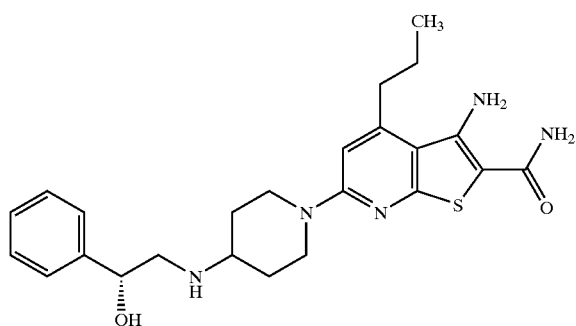

-continued

3-Amino-6-{4-[2-hydroxy-2-(4-nitro-phenyl)-ethylamino]-piperidin-1-yl}-4-propyl-thieno[2,3-b]pyridine-2-carboxylic acid amide

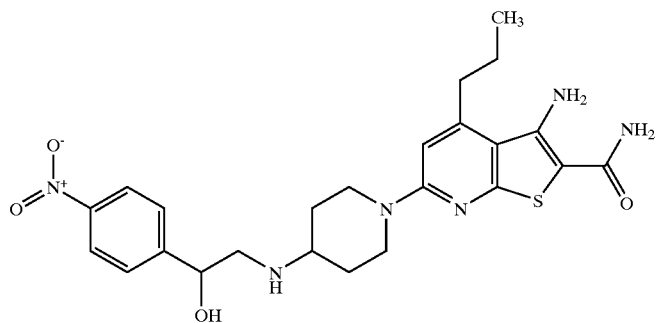

3-Amino-6-{4-[2-hydroxy-2-(3-hydroxy-phenyl)-ethylamino]-piperidin-1-yl}-4-propyl-thieno[2,3-b]pyridine-2-carboxylic acid amide

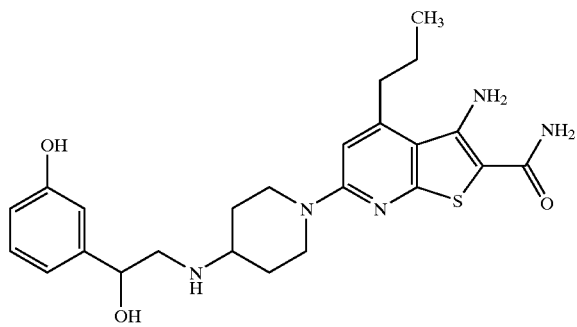

3-Amino-6-{4-[2-hydroxy-2-(4-hydroxy-phenyl)-ethylamino]-piperidin-1-yl}-4-propyl-thieno[2,3-b]pyridine-2-carboxylic acid amide

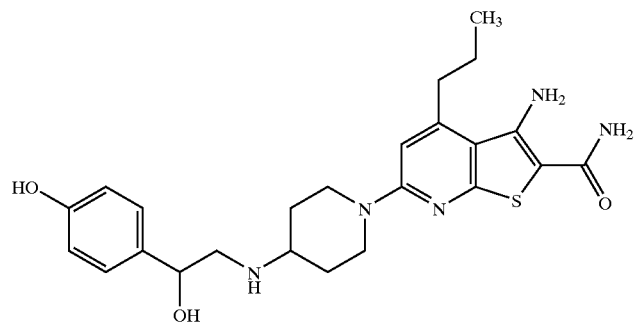

3-Amino-6-{4-[2-(4-amino-phenyl)-2-hydroxy-ethylamino]-piperidin-1-yl}-4-propyl-thieno[2,3-b]pyridine-2-carboxylic acid amide

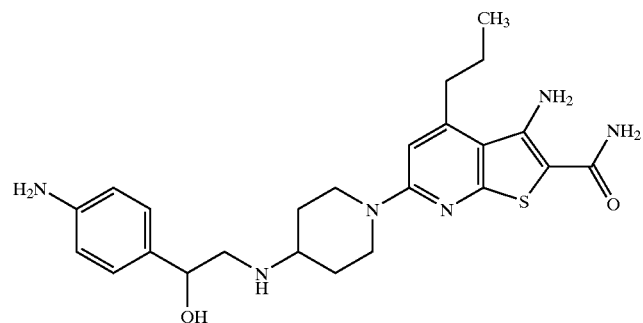

3-Amino-6-{4-[2-hydroxy-2-(4-methoxy-phenyl)-ethylamino]-piperidin-1-yl}-4-propyl-thieno[2,3-b]pyridine-2-carboxylic acid amide

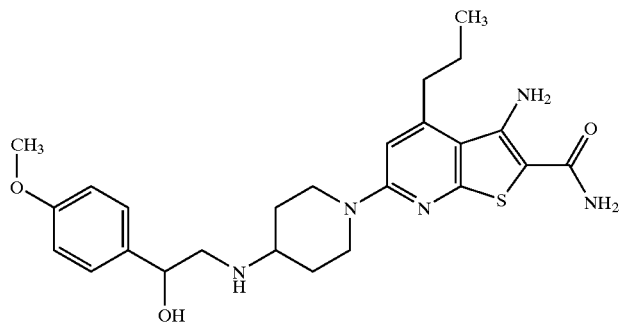

3-Amino-6-{4-[2-(4-chloro-phenyl)-2-hydroxy-ethylamino]-piperidin-1-yl}-4-propyl-thieno[2,3-b]pyridine-2-carboxylic acid amide

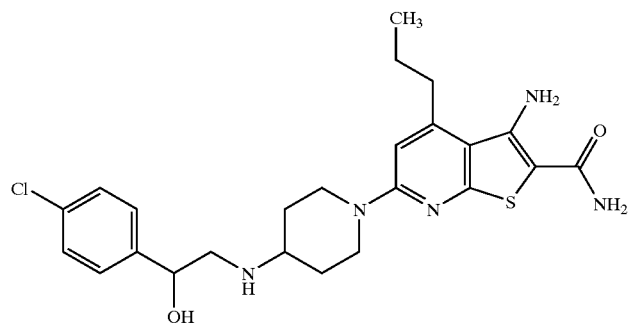

4-{2-[1-(3-Amino-2-carbamoyl-4-propyl-thieno[2,3-b]pyridin-6-yl)-piperidin-4-ylamino]-1-hydroxy-ethyl}-benzoic acid methyl ester

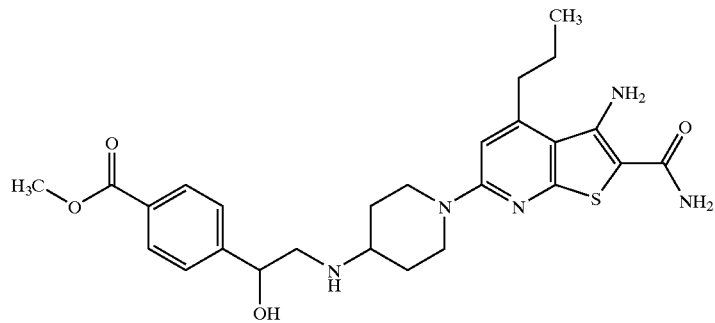

3-{2-[1-(3-Amino-2-carbamoyl-4-propyl-thieno[2,3-b]pyridin-6-yl)-piperidin-4-ylamino]-1-hydroxy-ethyl}-benzoic acid methyl ester

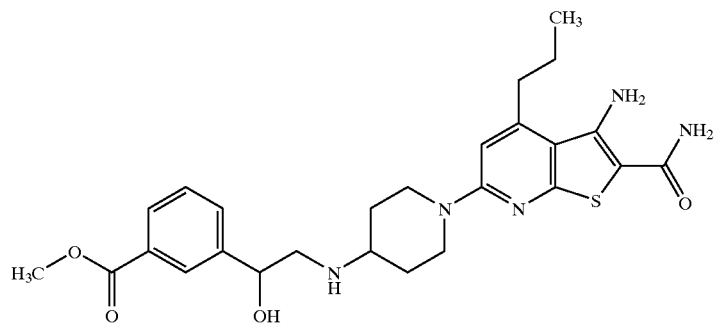

3-Amino-6-{4-[2-(4-carbamoyl-phenyl)-2-hydroxy-ethylamino]-piperidin-1-yl}-4-propyl-thieno[2,3-b]pyridine-2-carboxylic acid amide

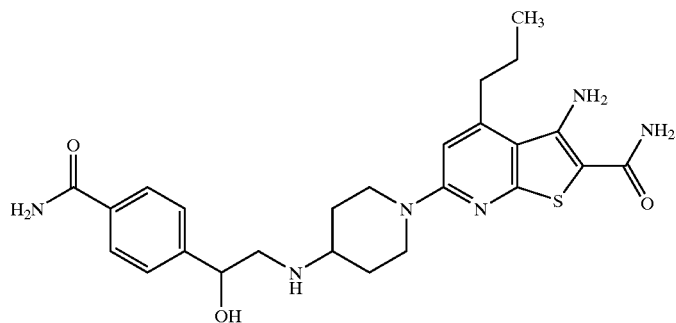

3-Amino-6-[4-(2-hydroxy-2-naphthalen-2-y-ethylamino)-piperidin-1-yl]-4-propyl-thieno[2,3-b]pyridine-2-carboxylic acid amide

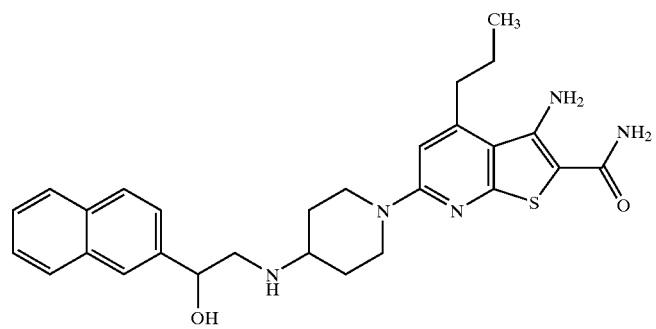

3-Amino-6-[4-(2-hydroxy-2-naphthalen-1-yl-ethylamino)-piperidin-1-yl]-4-propyl-thieno[2,3-b]pyridine-2-carboxylic acid amide

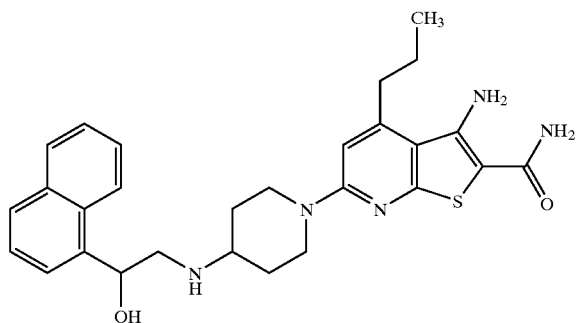

3-Amino-6-{4-[2-hydroxy-2-(4-methylcarbomoyl-phenyl)-ethylamino]-piperidin-1-yl}-4-propyl-thieno[2,3-b]pyridine-2-carboxylic acid amide

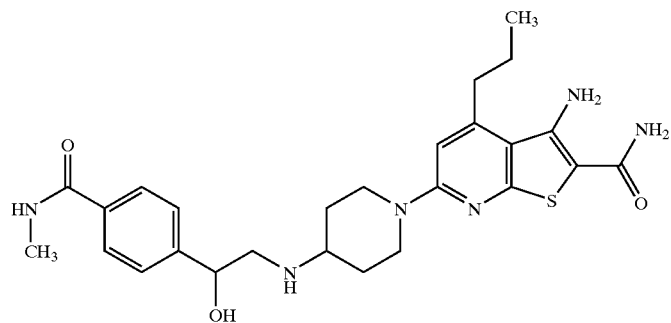

| | |
|---|---|
| 3-Amino-6-{4-[2-(4-dimethylcarbamoyl-phenyl)-2-hydroxy-ethylamino]piperidin-1-yl}-4-propyl-thieno[2,3-b]pyridine-2-carboxylic acid amide | 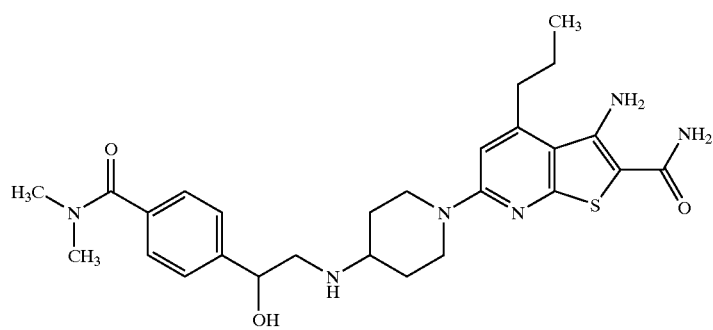 |
| 3-Amino-6-{4-[2-(4-benzylcarbamoyl-phenyl)-2-hydroxy-ethylamino]-piperidin-1-yl}-4-propyl-thieno[2,3-b]pyridine-2-carboxylic acid amide | 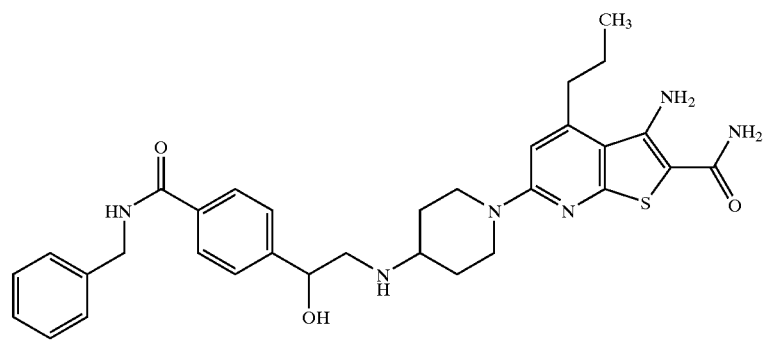 |
| 3-Amino-6-{4-[2-(3-carbamoyl-phenyl)-2-hydroxy-ethylamino]-piperidin-1-yl}-4-propyl-thieno[2,3-b]pyridine-2-carboxylic acid amide | 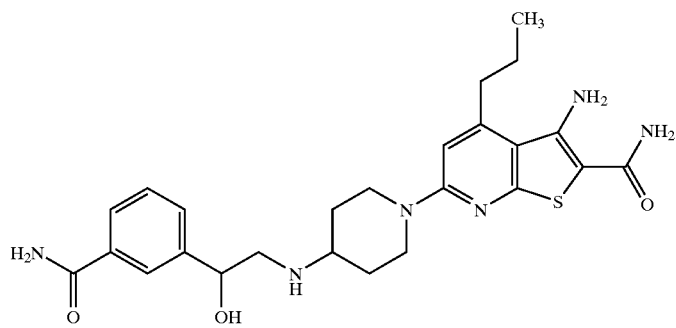 |
| 3-Amino-6-[4-(2-hydroxy-2-thiophen-2-yl-ethylamino)-piperidin-1-yl]-4-propyl-thieno[2,3-b]pyridine-2-carboxylic acid amide | 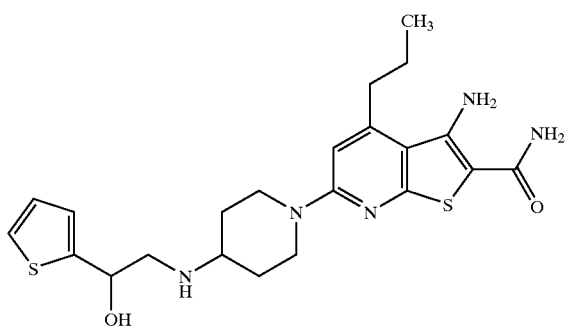 | or a pharmaceutically acceptable salt, racemate, racemic mixture, single enantioner, diastereomeric mixture or individual diastereomer thereof.